(12) United States Patent
Albrecht et al.

(10) Patent No.: US 9,187,835 B2
(45) Date of Patent: *Nov. 17, 2015

(54) ELECTROCHEMICAL SYSTEMS AND METHODS USING METAL AND LIGAND

(75) Inventors: Thomas A. Albrecht, Mountain View, CA (US); Ryan J. Gilliam, San Jose, CA (US); Bryan Boggs, Campbell, CA (US); Kyle Self, San Jose, CA (US); Dennis W. Solas, San Francisco, CA (US); Michael Kostowskyj, Los Gatos, CA (US); Margarete K. Leclerc, Mountain View, CA (US); Alexander Gorer, Los Gatos, CA (US); Michael Joseph Weiss, Los Gatos, CA (US)

(73) Assignee: Calera Corporation, Los Gatos, CA (US)

( * ) Notice: Subject to any disclaimer, the term of this patent is extended or adjusted under 35 U.S.C. 154(b) by 787 days.

This patent is subject to a terminal disclaimer.

(21) Appl. No.: 13/474,599

(22) Filed: May 17, 2012

(65) Prior Publication Data

US 2012/0292197 A1   Nov. 22, 2012

Related U.S. Application Data

(60) Provisional application No. 61/488,079, filed on May 19, 2011, provisional application No. 61/499,499, filed on Jun. 21, 2011, provisional application No. 61/515,474, filed on Aug. 5, 2011, provisional (Continued)

(51) Int. Cl.
*C07C 17/00* (2006.01)
*C07C 315/00* (2006.01)
(Continued)

(52) U.S. Cl.
CPC ... *C25B 1/20* (2013.01); *C25B 1/00* (2013.01); *C25B 1/02* (2013.01); *Y02E 60/366* (2013.01)

(58) Field of Classification Search
CPC .............. C25B 3/02; C25B 3/04; C25B 3/06; C25B 3/08; C25B 3/12; C07C 17/00; C07C 315/00; C08F 14/06
USPC .......... 205/444, 457, 459, 460, 687; 570/101, 570/261; 568/18; 526/344
See application file for complete search history.

(56) References Cited

U.S. PATENT DOCUMENTS 3,214,481 A   10/1965   Heinemann et al.
3,214,482 A   10/1965   Caropreson et al.

(Continued)

FOREIGN PATENT DOCUMENTS

CA   1339833 C   4/1998
EP   0039547 B1   7/1984

(Continued)

OTHER PUBLICATIONS

Yuan et al., "Direct Electrochemical Synthesis and Crystal Structure of a Copper(II) Complex with a Chiral (S)-2-(diphenylmethanol-1-(2-pyridylmethyl)pyrrolidine," Inorganic Chemistry Communications (no month, 2005), vol. 8, pp. 1014-1017.*

(Continued)

*Primary Examiner* — Edna Wong
(74) *Attorney, Agent, or Firm* — Calera Corporation; Vandana Bansal

(57) ABSTRACT

There are provided methods and systems for an electrochemical cell including an anode and a cathode where the anode is contacted with a metal ion that converts the metal ion from a lower oxidation state to a higher oxidation state. The metal ion in the higher oxidation state is reacted with hydrogen gas, an unsaturated hydrocarbon, and/or a saturated hydrocarbon to form products.

26 Claims, 40 Drawing Sheets

Related U.S. Application Data application No. 61/546,461, filed on Oct. 12, 2011, provisional application No. 61/552,701, filed on Oct. 28, 2011, provisional application No. 61/597,404, filed on Feb. 10, 2012, provisional application No. 61/617,390, filed on Mar. 29, 2012.

(51) Int. Cl.
  *C08F 14/06* (2006.01)
  *C25B 1/20* (2006.01)
  *C25B 1/00* (2006.01)
  *C25B 1/02* (2006.01)

(56) References Cited

U.S. PATENT DOCUMENTS

| | | | |
|---|---|---|---|
| 3,437,712 | A | 4/1969 | Knarr et al. |
| 3,461,180 | A | 8/1969 | Heinemann et al. |
| 3,510,532 | A | 5/1970 | Caropreso et al. |
| 3,691,239 | A | 9/1972 | Homer et al. |
| 3,985,794 | A | 10/1976 | Calcagno et al. |
| 4,256,719 | A | 3/1981 | Van Andel |
| 4,324,625 | A | 4/1982 | Cumbo |
| 4,376,019 | A | 3/1983 | Gamlen et al. |
| 4,379,019 | A | 4/1983 | Pool |
| 4,394,227 | A | 7/1983 | Jager et al. |
| 4,834,847 | A | 5/1989 | Mcintyre |
| 4,950,368 | A | 8/1990 | Weinberg et al. |
| 5,296,107 | A | 3/1994 | Harrison |
| 5,595,641 | A | 1/1997 | Traini et al. |
| 5,891,318 | A * | 4/1999 | Freire et al. ................. 205/349 |
| 6,146,787 | A | 11/2000 | Harrup et al. |
| 7,735,274 | B2 | 6/2010 | Constantz et al. |
| 7,744,761 | B2 | 6/2010 | Constantz et al. |
| 7,749,476 | B2 | 7/2010 | Constantz et al. |
| 7,753,618 | B2 | 7/2010 | Constantz et al. |
| 7,754,169 | B2 | 7/2010 | Constantz et al. |
| 7,771,684 | B2 | 8/2010 | Constantz et al. |
| 7,790,012 | B2 | 9/2010 | Kirk et al. |
| 7,815,880 | B2 | 10/2010 | Constantz et al. |
| 7,829,053 | B2 | 11/2010 | Constantz et al. |
| 7,875,163 | B2 | 1/2011 | Gilliam et al. |
| 7,887,694 | B2 | 2/2011 | Constantz et al. |
| 7,906,028 | B2 | 3/2011 | Constantz et al. |
| 7,914,685 | B2 | 3/2011 | Constantz et al. |
| 7,922,809 | B1 | 4/2011 | Constantz et al. |
| 7,931,809 | B2 | 4/2011 | Constantz et al. |
| 7,939,336 | B2 | 5/2011 | Constantz et al. |
| 7,966,250 | B2 | 6/2011 | Constantz et al. |
| 7,993,500 | B2 | 8/2011 | Gilliam et al. |
| 7,993,511 | B2 | 8/2011 | Gilliam et al. |
| 8,006,446 | B2 | 8/2011 | Constantz et al. |
| 8,062,418 | B2 | 11/2011 | Constantz et al. |
| 8,114,214 | B2 | 2/2012 | Constantz et al. |
| 8,137,444 | B2 | 3/2012 | Farsad et al. |
| 2006/0124445 | A1 | 6/2006 | Labrecque et al. |
| 2007/0292762 | A1 | 12/2007 | Johnson |
| 2009/0029199 | A1 | 1/2009 | Tao |
| 2009/0087698 | A1 | 4/2009 | Huth et al. |
| 2009/0202410 | A1 | 8/2009 | Kawatra et al. |
| 2010/0051469 | A1 | 3/2010 | Stolberg |
| 2010/0051859 | A1 | 3/2010 | House et al. |
| 2010/0084280 | A1 | 4/2010 | Gilliam et al. |
| 2010/0132556 | A1 | 6/2010 | Constantz et al. |
| 2010/0135865 | A1 | 6/2010 | Constantz et al. |
| 2010/0135882 | A1 | 6/2010 | Constantz et al. |
| 2010/0144521 | A1 | 6/2010 | Constantz et al. |
| 2010/0150802 | A1 | 6/2010 | Gilliam et al. |
| 2010/0154679 | A1 | 6/2010 | Constantz et al. |
| 2010/0196104 | A1 | 8/2010 | Constantz et al. |
| 2010/0200419 | A1 | 8/2010 | Gilliam et al. |
| 2010/0219373 | A1 | 9/2010 | Seeker et al. |
| 2010/0224503 | A1 | 9/2010 | Kirk et al. |
| 2010/0229725 | A1 | 9/2010 | Farsad et al. |
| 2010/0230293 | A1 | 9/2010 | Gilliam et al. |
| 2010/0230830 | A1 | 9/2010 | Farsad et al. |
| 2010/0236242 | A1 | 9/2010 | Farsad et al. |
| 2010/0239467 | A1 | 9/2010 | Constantz et al. |
| 2010/0239487 | A1 | 9/2010 | Constantz et al. |
| 2010/0258035 | A1 | 10/2010 | Constantz et al. |
| 2010/0258506 | A1 | 10/2010 | Berkowitz et al. |
| 2010/0276299 | A1 | 11/2010 | Kelly et al. |
| 2010/0290967 | A1 | 11/2010 | Detournay et al. |
| 2010/0313793 | A1 | 12/2010 | Constantz et al. |
| 2010/0313794 | A1 | 12/2010 | Constantz et al. |
| 2010/0319586 | A1 | 12/2010 | Blount et al. |
| 2011/0030586 | A1 | 2/2011 | Constantz et al. |
| 2011/0030957 | A1 | 2/2011 | Constantz et al. |
| 2011/0033239 | A1 | 2/2011 | Constantz et al. |
| 2011/0035154 | A1 | 2/2011 | Kendall et al. |
| 2011/0036728 | A1 | 2/2011 | Farsad et al. |
| 2011/0042230 | A1 | 2/2011 | Gilliam et al. |
| 2011/0054084 | A1 | 3/2011 | Constantz et al. |
| 2011/0059000 | A1 | 3/2011 | Constantz et al. |
| 2011/0071309 | A1 | 3/2011 | Constantz et al. |
| 2011/0079515 | A1 | 4/2011 | Gilliam et al. |
| 2011/0083968 | A1 | 4/2011 | Gilliam et al. |
| 2011/0091366 | A1 | 4/2011 | Kendall et al. |
| 2011/0091955 | A1 | 4/2011 | Constantz et al. |
| 2011/0120888 | A1 | 5/2011 | James et al. |
| 2011/0132234 | A1 | 6/2011 | Constantz et al. |
| 2011/0147227 | A1 | 6/2011 | Gilliam et al. |
| 2011/0203489 | A1 | 8/2011 | Constantz et al. |
| 2011/0226989 | A9 | 9/2011 | Seeker et al. |
| 2011/0240916 | A1 | 10/2011 | Constantz et al. |
| 2011/0247336 | A9 | 10/2011 | Farsad et al. |
| 2011/0277474 | A1 | 11/2011 | Constantz et al. |
| 2011/0277670 | A1 | 11/2011 | Self et al. |
| 2012/0292196 | A1 * | 11/2012 | Albrecht et al. ............. 205/351 |
| 2013/0206606 | A1 | 8/2013 | Gilliam et al. |
| 2014/0353146 | A1 | 12/2014 | Gilliam et al. |
| 2015/0038750 | A1 | 2/2015 | Weiss et al. |

FOREIGN PATENT DOCUMENTS

| | | |
|---|---|---|
| EP | 2253600 A1 | 11/2010 |
| FR | 1539499 A | 9/1968 |
| GB | 812680 A | 4/1959 |
| GB | 1019437 A | 2/1966 |
| JP | 57-027129 A | 2/1982 |
| JP | 63-293186 A | 11/1988 |
| JP | H 0238573 B2 | 8/1990 |
| JP | H 0356683 A | 3/1991 |
| JP | 2009-299111 A | 12/2009 |
| WO | WO 2008/018928 A2 | 2/2008 |
| WO | WO 2008/148055 A1 | 12/2008 |
| WO | WO 2009/006295 A2 | 1/2009 |
| WO | WO 2009/086460 A1 | 7/2009 |
| WO | WO 2009/146436 A1 | 12/2009 |
| WO | WO 2009/155378 A1 | 12/2009 |
| WO | WO 2010/006242 A1 | 1/2010 |
| WO | WO 2010/008896 A1 | 1/2010 |
| WO | WO 2010/009273 A1 | 1/2010 |
| WO | WO 2010/030826 A1 | 3/2010 |
| WO | WO 2010/039903 A1 | 4/2010 |
| WO | WO 2010/039909 A1 | 4/2010 |
| WO | WO 2010/048457 A1 | 4/2010 |
| WO | WO 2010/051458 A1 | 5/2010 |
| WO | WO 2010/068924 A1 | 6/2010 |
| WO | WO 2010/074686 A1 | 7/2010 |
| WO | WO 2010/074687 A1 | 7/2010 |
| WO | WO 2010/087823 A1 | 8/2010 |
| WO | WO 2010/091029 A1 | 8/2010 |
| WO | WO 2010/093713 A1 | 8/2010 |
| WO | WO 2010/093716 A1 | 8/2010 |
| WO | WO 2010/101953 A1 | 9/2010 |
| WO | WO 2010/104989 A1 | 9/2010 |
| WO | WO 2010/132863 A1 | 11/2010 |
| WO | WO 2010/136744 A1 | 12/2010 |
| WO | WO 2011/008223 A1 | 1/2011 |
| WO | WO 2011/017609 A1 | 2/2011 |
| WO | WO 2011/038076 A1 | 3/2011 |
| WO | WO 2011/049996 A1 | 4/2011 |
| WO | WO 2011/066293 A1 | 6/2011 |

(56) References Cited

FOREIGN PATENT DOCUMENTS

| | | |
|---|---|---|
| WO | WO 2011/073621 A1 | 6/2011 |
| WO | WO 2011/075680 A1 | 6/2011 |
| WO | WO 2011/081681 A1 | 7/2011 |
| WO | WO 2011/097468 A2 | 8/2011 |
| WO | WO 2011/102868 A1 | 8/2011 |
| WO | WO 2011/116236 A2 | 9/2011 |
| WO | WO 2012/158969 A1 | 11/2012 |

OTHER PUBLICATIONS

Kotora et al., "Selective Additions of Polyhalognated Compounds to Chloro Substituted Ethenes Catalyzed by a Copper Complex," React. Kinet. Catal. Lett. (no month, 1991), vol. 44, No. 2, pp. 415-419.*

Margraf et al., "Copper(II) PMDTA and Copper(II) TMEDA Complexes: Precursors for the Synthesis of Dinuclear Copper(II) Complexes," Inorgancia Chimica Acta (no month, 2005), vol. 358, pp. 1193-1203.*

Acquah, et al. The electrochlorination of aliphatic hydrocarbons. J. Appl. Chem. Biotechnol. 1972; 22:1195-1200.

European search report and opinion dated Feb. 25, 2015 for EP Application No. 12785945.2.

Office action dated Mar. 4, 2015 for U.S. Appl. No. 13/474,598.

Rollin, et al. The electrochemistry of nickel complexes with triphenylphosphine and ethylene in methylpyrrolidinone. Journal of Electroanalytical Chemistry and Interfacial Electrochemistry. 1985; 183(1-2):247-260.

Rorabacher. Electron transfer by copper centers. Chemical Centers. 2004; 104(2):651-698.

U.S. Appl. No. 13/799,131, filed Mar. 13, 2013, Albrecht et al.

Brugger, et al. UV-Vis-NIR spectroscopic study of Cu(II) complexing in LiCl brines between 20° C. and 90° C. Geochimica et Cosmochimica Acta. 2001; 65(16):2691-2708.

Kinoshita, et al. Mass-Transfer Study of Carbon Felt, Flow-Through Electrode. J. Electrochem. Soc. 1982; 129(9):1993-1997.

Langer, et al. Electrogenerative and Voltameiotic Processes. Ind. Eng. Chem. Process Des. Dev. 1979; 18(4):567-579.

Langer, et al. Electrogenerative Chlorination J. Electrochem. Soc. 1970; 117(4):510-511.

Liu, et al. A spectrophotometric study of aqueous copper(I)—chloride complexes in LiCl solutions between 100° C. and 250° C. Geochimica et Cosmochimica Acta. 2002; 66(20):3615-3633.

Lundstrom, et al Redox potential characteristics of cupric chloride solutions. Hydrometallurgy. 2009; 95:285-289.

Powell, et al. Chemical speciation of environmentally significant metals with inorganic ligands. Pure Appl. Chem. 2007; 79(5):895-950.

Ralph, et al. Mass transport in an electrochemical laboratory filterpress reactor and its enhancement by turbulence promoters. Electrochemical Acta. 1996; 41(4):591-603.

U.S. Appl. No. 14/460,697, filed Aug. 15, 2014, Gilliam et al.

International search report and written opinion dated Oct. 15, 2014 for PCT/US2014/048976.

U.S. Appl. No. 14/446,791, filed Jul. 30, 2014, Weiss et al.

International search report and written opinion dated May 23, 2013 for PCT/US2013/031064.

International search report and written opinion dated Aug. 14, 2012 for PCT/US2012/038438.

Benadda, B. et al. 1996. A study of Oxygen Absorption Kinetics in Ionic Cu(I) Aqueous Solutions. Chem. Eng. Technol. 19: 34-38.

Constantz, B. (2009) "The Risk of Implementing New Regulations on Game-Changing Technology: Sequestering CO2 in the Built Environment" AGU, 90(22), Jt. Assem, Suppl., Abstract.

Friend, L. et al. 1974. Liquid-Phase Oxychlorination of Ethylene to Produce Vinyl Chloride. Homogeneous Catalysis. American Chemical Society. Piscataway, N.J. pp. 168-176.

Georgiadou, M. et al. 1998. Modelling of copper etching in aerated chloride solutions. Journal of Applied Electrochemistry. 28: 127-134.

Hine, F. et al. 1970. Mechanism of Oxidation of Cuprous Ion in Hydrochloric Acid Solution by Oxygen. Electrochimica Acta. 15: 769-781.

Jhaveri, A.S., et al. 1967. Kinetics of absorption of oxygen in aqueous solutions of cuprous chloride. Chemical Engineering Science. 22: 1-6.

Spector, M.L. et al. 1967. Olefin Chlorination in Homogeneous Aqueous Copper Chloride Solutions. Industrial & Engineering Chemistry Process Design and Development. 6(3): 327-331.

Office action dated Aug. 6, 2015 for U.S. Appl. No. 13/474,598.

Wikipedia definition of "Aqueous Solution". Accessed Jul. 29, 2015. 2 pages.

Wikipedia definition of "Solvent". Accessed Jul. 29, 2015. 14 pages.

European search report and opinion dated May 11, 2015 for EP Application No. 13769321.4.

Krishnamoorthy, et al. Chlorination of substituted aromatics on graphite anode. Asian Journal of Chemistry. 2002; 14(3-4):1801-1803.

Office action dated Jun. 11, 2015 for U.S. Appl. No. 13/799,131.

Office action dated Jul. 9, 2015 for U.S. Appl. No. 13/474,598.

* cited by examiner

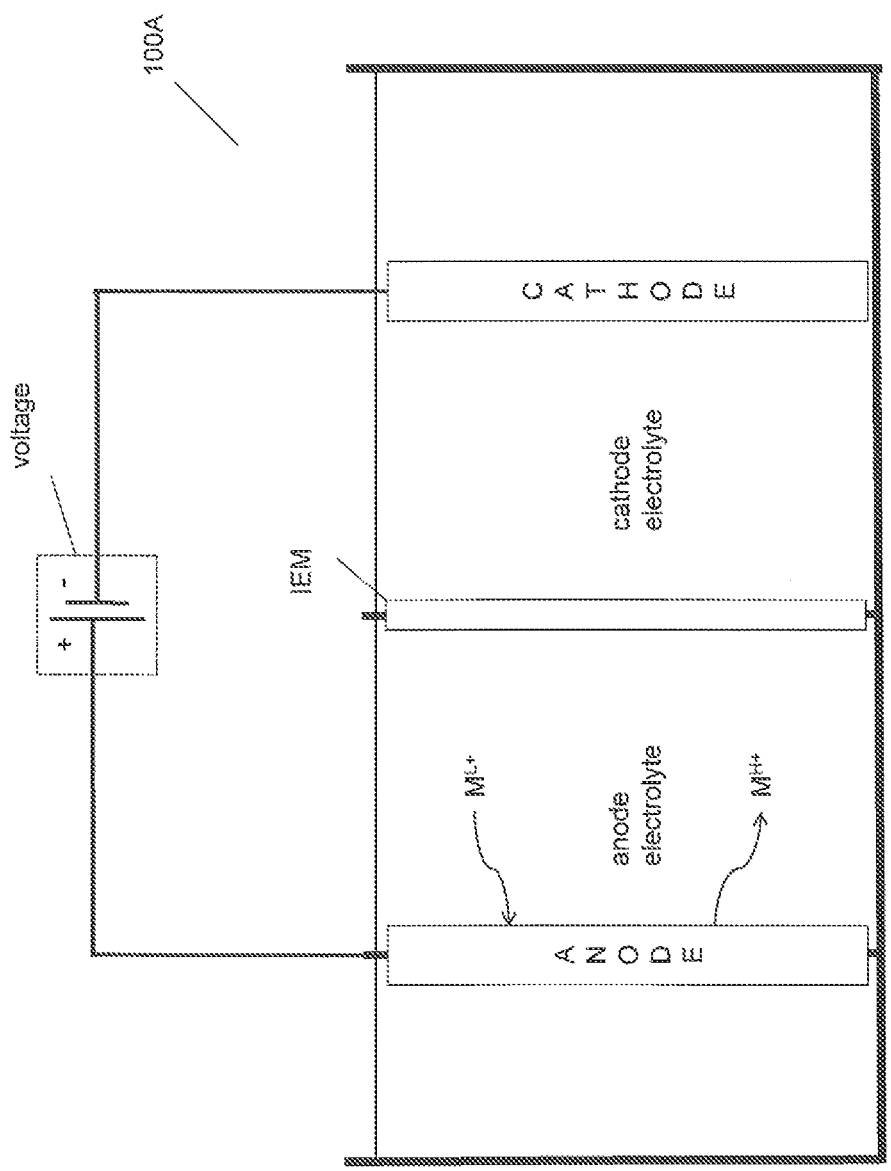

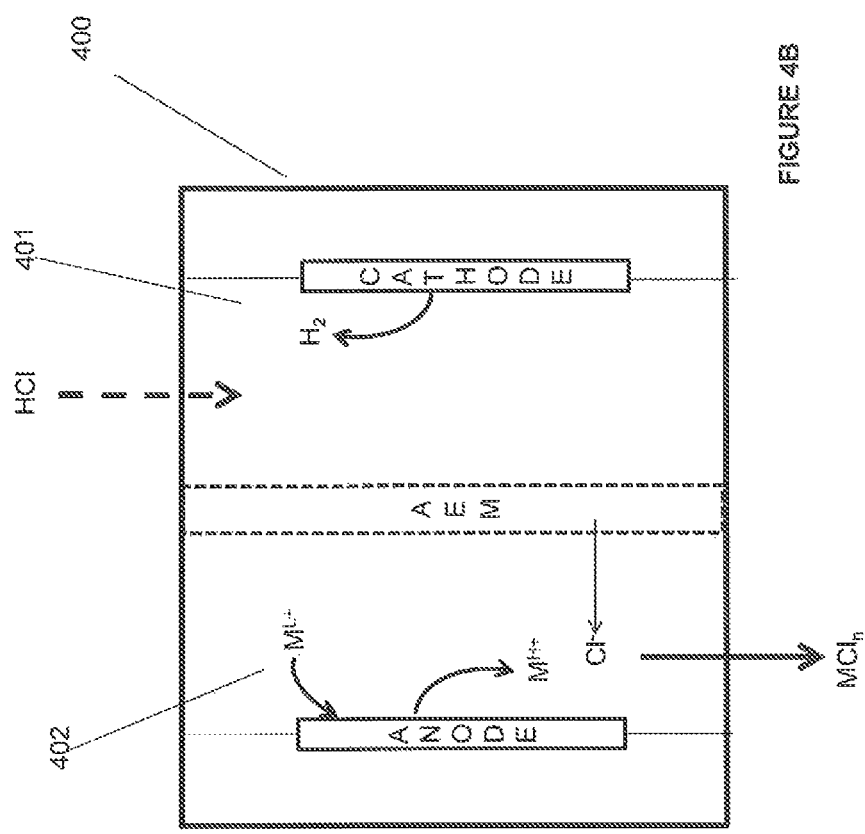

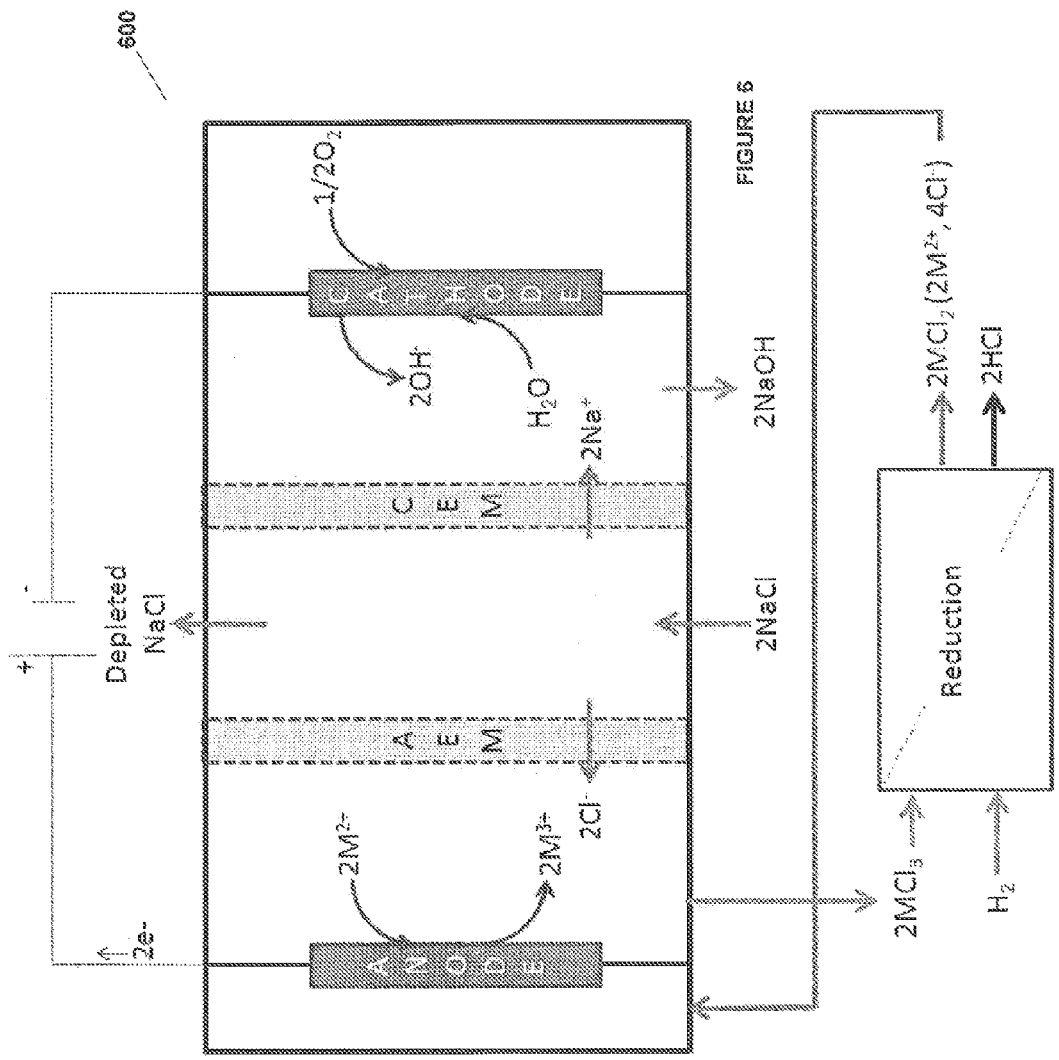

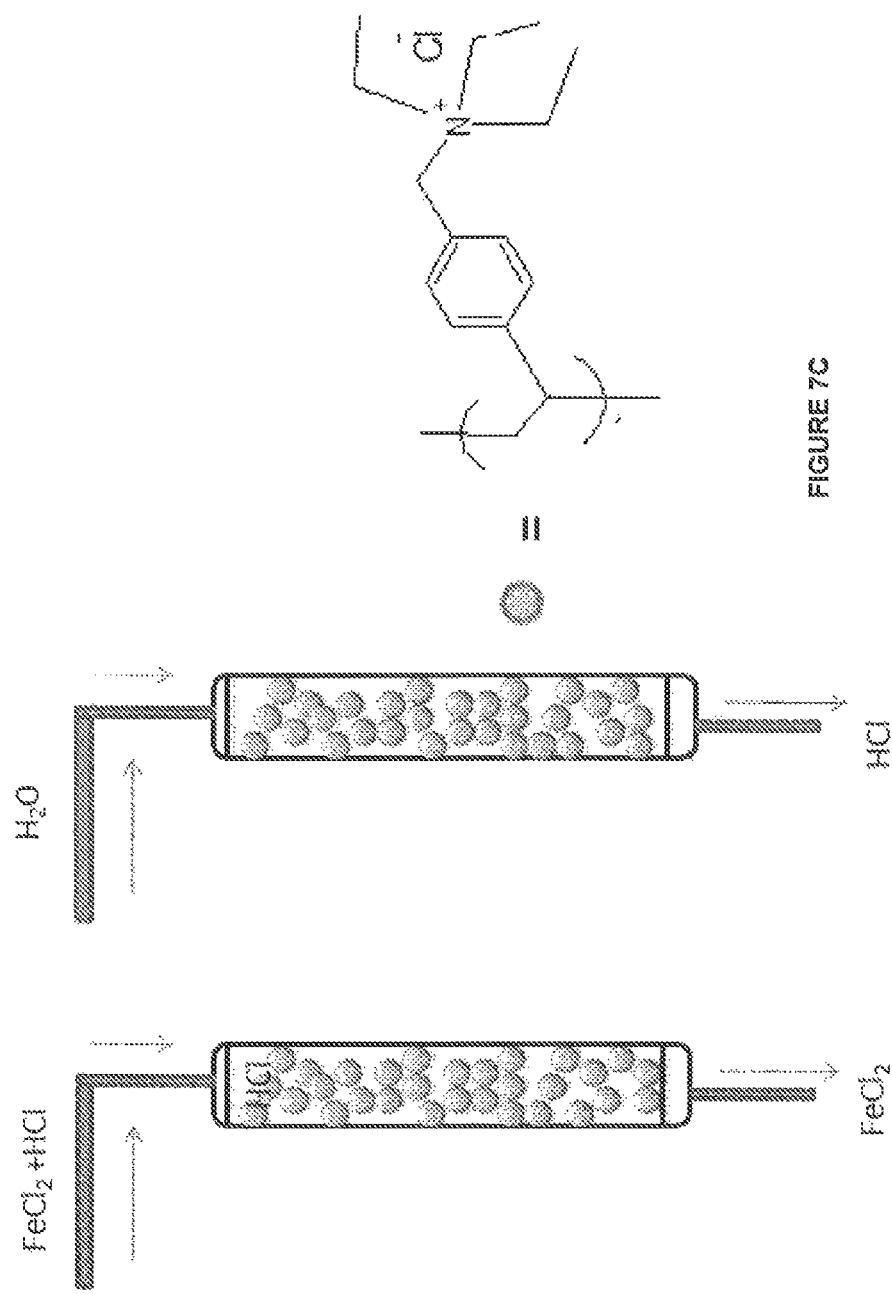

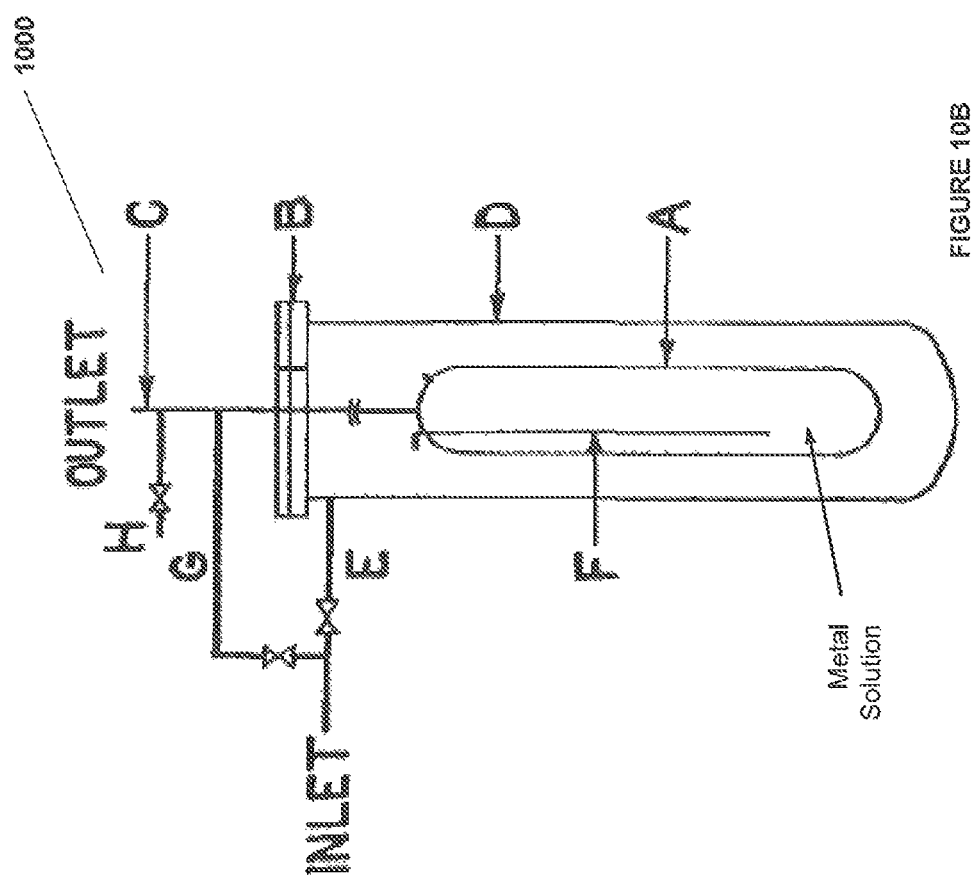

ELECTROCHEMICAL SYSTEMS AND METHODS USING METAL AND LIGAND

CROSS-REFERENCE TO RELATED APPLICATIONS

This application claims priority to U.S. Provisional Patent Application No. 61/488,079, filed May 19, 2011; U.S. Provisional Patent Application No. 61/499,499, filed Jun. 21, 2011; U.S. Provisional Patent Application No. 61/515,474, filed Aug. 5, 2011; U.S. Provisional Patent Application No. 61/546,461, filed Oct. 12, 2011; U.S. Provisional Patent Application No. 61/552,701, filed Oct. 28, 2011; U.S. Provisional Patent Application No. 61/597,404, filed Feb. 10, 2012; and U.S. Provisional Patent Application No. 61/617,390, filed Mar. 29, 2012, all of which are incorporated herein by reference in their entireties in the present disclosure.

BACKGROUND

In many chemical processes, caustic soda may be required to achieve a chemical reaction, e.g., to neutralize an acid, or buffer pH of a solution, or precipitate an insoluble hydroxide from a solution. One method by which the caustic soda may be produced is by an electrochemical system. In producing the caustic soda electrochemically, such as via chlor-alkali process, a large amount of energy, salt, and water may be used.

Polyvinyl chloride, commonly known as PVC, may be the third-most widely-produced plastic, after polyethylene and polypropylene. PVC is widely used in construction because it is durable, cheap, and easily worked. PVC may be made by polymerization of vinyl chloride monomer which in turn may be made from ethylene dichloride. Ethylene dichloride may be made by direct chlorination of ethylene using chlorine gas made from the chlor-alkali process.

The production of chlorine and caustic soda by electrolysis of aqueous solutions of sodium chloride or brine is one of the electrochemical processes demanding high-energy consumption. The total energy requirement is for instance about 2% in the USA and about 1% in Japan of the gross electric power generated, to maintain this process by the chlor-alkali industry. The high energy consumption may be related to high carbon dioxide emission owing to burning of fossil fuels. Therefore, reduction in the electrical power demand needs to be addressed to curtail environment pollution and global warming.

SUMMARY

In one aspect, there is provided a method, comprising contacting an anode with an anode electrolyte wherein the anode electrolyte comprises metal ion; oxidizing the metal ion from a lower oxidation state to a higher oxidation state at the anode; contacting a cathode with a cathode electrolyte; and reacting an unsaturated hydrocarbon or a saturated hydrocarbon with the anode electrolyte comprising the metal ion in the higher oxidation state, in an aqueous medium wherein the aqueous medium comprises more than 5 wt % water.

In one aspect, there is provided a method comprising contacting an anode with an anode electrolyte; oxidizing metal ion from a lower oxidation state to a higher oxidation state at the anode; contacting a cathode with a cathode electrolyte; and adding a ligand to the anode electrolyte wherein the ligand interacts with the metal ion.

In some embodiments of the aforementioned aspects, the method further comprises forming an alkali, water, or hydrogen gas at the cathode. In some embodiments of the aforementioned aspects, the method further comprises forming an alkali at the cathode. In some embodiments of the aforementioned aspects, the method further comprises forming hydrogen gas at the cathode. In some embodiments of the aforementioned aspects, the method further comprises forming water at the cathode. In some embodiments of the aforementioned aspects, the cathode is an oxygen depolarizing cathode that reduces oxygen and water to hydroxide ions. In some embodiments of the aforementioned aspects, the cathode is a hydrogen gas producing cathode that reduces water to hydrogen gas and hydroxide ions. In some embodiments of the aforementioned aspects, the cathode is a hydrogen gas producing cathode that reduces hydrochloric acid to hydrogen gas. In some embodiments of the aforementioned aspects, the cathode is an oxygen depolarizing cathode that reacts hydrochloric acid and oxygen gas to form water In some embodiments of the aforementioned aspects and embodiments, the metal ion includes, but not limited to, iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combination thereof. In some embodiments, the metal ion includes, but not limited to, iron, chromium, copper, and tin. In some embodiments, the metal ion is copper. In some embodiments, the lower oxidation state of the metal ion is 1+, 2+, 3+, 4+, or 5+. In some embodiments, the higher oxidation state of the metal ion is 2+, 3+, 4+, 5+, or 6+. In some embodiments, the metal ion is copper that is converted from $Cu^+$ to $Cu^{2+}$, the metal ion is iron that is converted from $Fe^{2+}$ to $Fe^{3+}$, the metal ion is tin that is converted from $Sn^{2+}$ to $Sn^{4+}$, the metal ion is chromium that is converted from $Cr^{2+}$ to $Cr^{3+}$, the metal ion is platinum that is converted from $Pt^{2+}$ to $Pt^{4+}$, or combination thereof.

In some embodiments of the aforementioned aspects and embodiments, no gas is used or formed at the anode.

In some embodiments of the aforementioned aspects and embodiments, the method further comprises adding a ligand to the anode electrolyte wherein the ligand interacts with the metal ion.

In some embodiments of the aforementioned aspects and embodiments, the method further comprises reacting an unsaturated hydrocarbon or a saturated hydrocarbon with the anode electrolyte comprising the metal ion in the higher oxidation state and the ligand, wherein the reaction is in an aqueous medium.

In some embodiments of the aforementioned aspects and embodiments, the reaction of the unsaturated hydrocarbon or the saturated hydrocarbon with the anode electrolyte comprising the metal ion in the higher oxidation state is halogenation or sulfonation using the metal halide or the metal sulfate in the higher oxidation state resulting in a halohydrocarbon or a sulfohydrocarbon, respectively, and the metal halide or the metal sulfate in the lower oxidation state. In some embodiments, the metal halide or the metal sulfate in the lower oxidation state is re-circulated back to the anode electrolyte.

In some embodiments of the aforementioned aspects and embodiments, the anode electrolyte comprising the metal ion in the higher oxidation state further comprises the metal ion in the lower oxidation state.

In some embodiments of the aforementioned aspects and embodiments, the unsaturated hydrocarbon is compound of formula I resulting in compound of formula II after halogenation or sulfonation:

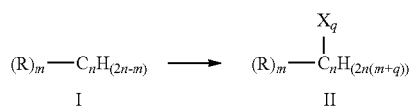

wherein, n is 2-10; m is 0-5; and q is 1-5;

R is independently selected from hydrogen, halogen, —COOR', —OH, and —NR'(R"), where R' and R" are independently selected from hydrogen, alkyl, and substituted alkyl; and X is a halogen selected from chloro, bromo, and iodo; —SO$_3$H; or —OSO$_2$OH.

In some embodiments, m is 0; n is 2; q is 2; and X is chloro. In some embodiments, the compound of formula I is ethylene, propylene, or butylene and the compound of formula II is ethylene dichloride, propylene dichloride or 1,4-dichlorobutane, respectively. In some embodiments, the method further comprises forming vinyl chloride monomer from the ethylene dichloride and forming poly(vinyl chloride) from the vinyl chloride monomer.

In some embodiments of the aforementioned aspects and embodiments, the saturated hydrocarbon is compound of formula III resulting in compound of formula IV after halogenation or sulfonation:

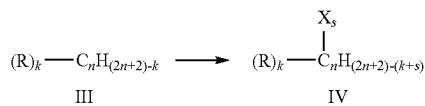

wherein, n is 2-10; k is 0-5; and s is 1-5;

R is independently selected from hydrogen, halogen, —COOR', —OH, and —NR'(R"), where R' and R" are independently selected from hydrogen, alkyl, and substituted alkyl; and X is a halogen selected from chloro, bromo, and iodo; —SO$_3$H; or —OSO$_2$OH.

In some embodiments, the compound of formula III is methane, ethane, or propane.

In some embodiments of the aforementioned aspects and embodiments, the aqueous medium comprises between 5-90 wt % water.

In some embodiments of the aforementioned aspects and embodiments, the ligand results in one or more of the properties including, but not limited to, enhanced reactivity of the metal ion towards the unsaturated hydrocarbon, saturated hydrocarbon, or hydrogen gas, enhanced selectivity of the metal ion towards halogenations of the unsaturated or saturated hydrocarbon, enhanced transfer of the halogen from the metal ion to the unsaturated hydrocarbon, saturated hydrocarbon, or the hydrogen gas, reduced redox potential of the electrochemical cell, enhanced solubility of the metal ion in the aqueous medium, reduced membrane cross-over of the metal ion to the cathode electrolyte in the electrochemical cell, reduced corrosion of the electrochemical cell and/or the reactor, enhanced separation of the metal ion from the acid solution after reaction with hydrogen gas, enhanced separation of the metal ion from the halogenated hydrocarbon solution, and combination thereof.

In some embodiments of the aforementioned aspects and embodiments, the ligand includes, but not limited to, substituted or unsubstituted phosphine, substituted or unsubstituted crown ether, substituted or unsubstituted aliphatic nitrogen, substituted or unsubstituted pyridine, substituted or unsubstituted dinitrile, and combination thereof.

In some embodiments of the aforementioned aspects and embodiments, the ligand is of formula A:

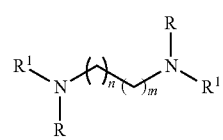

wherein n and m independently are 0-2 and R and R$^1$ independently are H, alkyl, or substituted alkyl.

In some embodiments, the substituted alkyl is alkyl substituted with one or more of a group selected from alkenyl, halogen, amine, and substituted amine.

In some embodiments of the aforementioned aspects and embodiments, the ligand is of formula C:

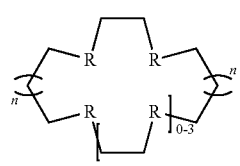

wherein R is independently O, S, P, or N; and n is 0 or 1.

In some embodiments of the aforementioned aspects and embodiments, the ligand is of formula D, or an oxide thereof:

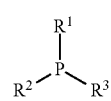

wherein R$^1$, R$^2$, and R$^3$ independently are H, alkyl, substituted alkyl, alkoxy, substituted alkoxy, aryl, substituted aryl, heteroaryl, substituted heteroaryl, amine, substituted amine, cycloalkyl, substituted cycloalkyl, heterocycloalkyl, and substituted heterocycloalkyl.

In some embodiments of the aforementioned aspects and embodiments, the ligand is of formula E:

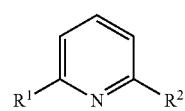

wherein R$^1$ and R$^2$ independently are H, alkyl, substituted alkyl, aryl, substituted aryl, heteroaryl, substituted heteroaryl, amine, substituted amine, cycloalkyl, substituted cycloalkyl, heterocycloalkyl, and substituted heterocycloalkyl.

In some embodiments of the aforementioned aspects and embodiments, the ligand is of formula F:

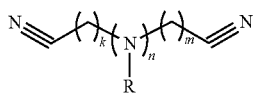

wherein R is hydrogen, alkyl, or substituted alkyl; n is 0-2; m is 0-3; and k is 1-3.

In one aspect, there is provided a system, comprising an anode in contact with an anode electrolyte comprising metal ion wherein the anode is configured to oxidize the metal ion from a lower oxidation state to a higher oxidation state; a cathode in contact with a cathode electrolyte; and a reactor operably connected to the anode chamber and configured to react the anode electrolyte comprising the metal ion in the higher oxidation state with an unsaturated hydrocarbon or saturated hydrocarbon in an aqueous medium wherein the aqueous medium comprises more than 5 wt % water.

In one aspect, there is provided a system, comprising an anode in contact with an anode electrolyte comprising metal ion wherein the anode is configured to oxidize the metal ion from a lower oxidation state to a higher oxidation state; a ligand in the anode electrolyte wherein the ligand is configured to interact with the metal ion; and a cathode in contact with a cathode electrolyte.

In some embodiments of the aforementioned aspects and embodiments, the system further comprises a ligand in the anode electrolyte wherein the ligand is configured to interact with the metal ion.

In some embodiments of the aforementioned system aspects and embodiments, the cathode is a gas-diffusion cathode configured to react oxygen gas and water to form hydroxide ions. In some embodiments of the aforementioned system aspects and embodiments, the cathode is a hydrogen gas producing cathode configured to form hydrogen gas and hydroxide ions by reducing water. In some embodiments of the aforementioned system aspects and embodiments, the cathode is a hydrogen gas producing cathode configured to reduce an acid, such as, hydrochloric acid to hydrogen gas. In some embodiments of the aforementioned system aspects and embodiments, the cathode is a gas-diffusion cathode configured to react hydrochloric acid and oxygen to form water.

In some embodiments of the aforementioned system aspects and embodiments, the anode is configured to not form a gas.

In some embodiments of the aforementioned aspects and embodiments, the system further comprises a precipitator configured to contact the cathode electrolyte with divalent cations to form a carbonate and/or bicarbonate product.

In some embodiments of the aforementioned aspects and embodiments, the system further comprises a reactor operably connected to the anode chamber and configured to react the anode electrolyte comprising the metal ion in the higher oxidation state and the ligand with an unsaturated hydrocarbon or saturated hydrocarbon in an aqueous medium.

In some embodiments of the aforementioned aspects and embodiments, the metal ion is copper. In some embodiments of the aforementioned aspects and embodiments, the unsaturated hydrocarbon is ethylene.

In another aspect, there is provided a method comprising contacting an anode with an anode electrolyte; oxidizing a metal ion from the lower oxidation state to a higher oxidation state at the anode; and contacting a cathode with a cathode electrolyte wherein the cathode is an oxygen depolarizing cathode that reduces oxygen and water to hydroxide ions.

In another aspect, there is provided a method comprising contacting an anode with an anode electrolyte and oxidizing a metal ion from the lower oxidation state to a higher oxidation state at the anode; contacting a cathode with a cathode electrolyte and producing hydroxide ions in the cathode electrolyte; and contacting the cathode electrolyte with a carbon dioxide gas or a solution containing bicarbonate/carbonate ions.

In another aspect, there is provided a method comprising contacting an anode with an anode electrolyte and oxidizing a metal ion from the lower oxidation state to a higher oxidation state at the anode; contacting a cathode with a cathode electrolyte; and preventing migration of the metal ions from the anode electrolyte to the cathode electrolyte by using a size exclusion membrane or an anion exchange membrane.

In another aspect, there is provided a method comprising contacting an anode with an anode electrolyte and oxidizing a metal ion from lower oxidation state to a higher oxidation state at the anode; and contacting a cathode with a cathode electrolyte and producing hydroxide ions and/or hydrogen gas at the cathode; and producing an acid by reacting the metal ion in the higher oxidation state with hydrogen gas.

In another aspect, there is provided a method comprising applying a voltage of less than 2.5 volts; contacting an anode with an anode electrolyte and oxidizing a metal ion from the lower oxidation state to a higher oxidation state at the anode; and contacting a cathode with a cathode electrolyte wherein the cathode produces hydroxide ions, hydrogen gas, or water.

In another aspect, there is provided a method to make green halogenated hydrocarbon, comprising contacting an anode with an anode electrolyte and oxidizing a metal chloride from the lower oxidation state to a higher oxidation state at the anode; contacting a cathode with a cathode electrolyte; and halogenating an unsaturated hydrocarbon with the metal chloride in the higher oxidation state to produce a green halogenated hydrocarbon.

In one aspect, there is provided a method comprising contacting an anode with an anode electrolyte and oxidizing a metal chloride from the lower oxidation state to a higher oxidation state at the anode; contacting a cathode with a cathode electrolyte; halogenating an unsaturated hydrocarbon with the metal chloride in the higher oxidation state; and adding a ligand to the metal chloride wherein the ligand interacts with the metal ion.

Some embodiments of the above described aspects are provided herein. In some embodiments, the cathode is a gas-diffusion cathode. In some embodiments, the cathode forms hydrogen gas by reducing water or hydrochloric acid. In some embodiments, the metal ion is selected from the group consisting of iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combination thereof. In some embodiments, the metal ion is selected from the group consisting of iron, chromium, copper, and tin. In some embodiments, the metal ion is copper. In some embodiments, the metal ion is tin. In some embodiments, the metal ion is chromium. In some embodiments, the metal ion is iron. In some embodiments, the lower oxidation state of the metal ion is 1+, 2+, 3+, 4+, or 5+. In some embodiments, wherein the higher oxidation state of the metal ion is 2+, 3+, 4+, 5+, or 6+. In some embodiments, the metal ion is copper that is converted from $Cu^+$ to $Cu^{2+}$ in the anode chamber. In some embodiments, the metal ion is iron that is converted from $Fe^{2+}$ to $Fe^{3+}$ in the anode chamber. In some embodiments, the metal ion is tin that is converted from $Sn^{2+}$ to $Sn^{4+}$ in the anode chamber. In some embodiments, the metal ion is chromium that is converted from $Cr^{3+}$ to $Cr^{6+}$ in the anode chamber. In some embodiments, the metal ion is chromium that is converted from $Cr^{2+}$ to $Cr^{3+}$ in the anode chamber. In some embodiments, no gas is used or formed at the anode. In some embodiments, no acid is formed in the anode chamber. In some embodiments, the metal ion is in a form of metal halide. In some embodiments, the metal halide with the metal ion in the higher oxidation state optionally comprising the metal halide with the metal ion in the lower oxidation state is contacted with hydrogen gas to form hydrogen halide, such as, but not limited to, hydrogen chloride, hydrochloric acid, hydrogen bromide, hydrobromic acid, hydrogen iodide, or hydroiodic acid, and the metal halide with the metal ion in the lower oxidation state. In some embodiments, the metal halide with the metal ion in the lower oxidation state is re-circulated back to the anode chamber. In some embodiments, the metal halide with metal ion in higher oxidation state optionally comprising the metal halide with the metal ion in the lower oxidation state is contacted with an unsaturated hydrocarbon and/or saturated hydrocarbon to form halohydrocarbon and the metal halide with the metal ion in the lower oxidation state. In some embodiments, the metal halide with the metal ion in the lower oxidation state is re-circulated back to the anode chamber.

In some embodiments, the metal chloride with the metal ion in the higher oxidation state optionally comprising the metal chloride with the metal ion in the lower oxidation state is contacted with hydrogen gas to form hydrochloric acid and the metal chloride with the metal ion in the lower oxidation state. In some embodiments, the metal chloride with the metal ion in the lower oxidation state is re-circulated back to the anode chamber. In some embodiments, the metal chloride with metal ion in higher oxidation state optionally comprising the metal chloride with the metal ion in the lower oxidation state is contacted with an unsaturated hydrocarbon to form chlorohydrocarbon and the metal chloride with the metal ion in the lower oxidation state. In some embodiments, the metal chloride with the metal ion in the lower oxidation state is re-circulated back to the anode chamber. In some embodiments, the unsaturated hydrocarbon is ethylene and the halohydrocarbon such as chlorohydrocarbon is ethylene dichloride. In some embodiments, the methods described herein further include forming vinyl chloride monomer from the ethylene dichloride. In some embodiments, the methods described herein further include forming poly(vinyl chloride) from the vinyl chloride monomer.

In some embodiments, the method further includes contacting the cathode electrolyte with carbon from a source of carbon. In some embodiments, the method further includes contacting the cathode electrolyte with carbon selected from gaseous carbon dioxide from an industrial process or a solution of carbon dioxide from a gas/liquid contactor in contact with the gaseous carbon dioxide from the industrial process. In some embodiments, the method further includes contacting the cathode electrolyte with divalent cations after contacting with the carbon to form carbonate and/or bicarbonate product. In some embodiments, the method includes applying a voltage of between 0.01 to 2.5V between the anode and the cathode.

In some embodiments, the treatment of the metal ion in the higher oxidation state with the unsaturated hydrocarbon is inside the anode chamber. In some embodiments, the treatment of the metal ion in the higher oxidation state with the unsaturated hydrocarbon is outside the anode chamber. In some embodiments, the treatment of the metal ion in the higher oxidation state with the unsaturated hydrocarbon results in a chlorohydrocarbon. In some embodiments, the chlorohydrocarbon is ethylene dichloride. In some embodiments, the method further includes treating the $Cu^{2+}$ ions with ethylene to form ethylene dichloride. In some embodiments, the method further includes treating the ethylene dichloride to form vinyl chloride monomer. In some embodiments, the method further includes treating the vinyl chloride monomer to form poly (vinyl) chloride.

In another aspect, there is provided a system, comprising an anode chamber comprising an anode in contact with a metal ion in an anode electrolyte, wherein the anode chamber is configured to convert the metal ion from a lower oxidation state to a higher oxidation state; and a cathode chamber comprising an oxygen depolarizing cathode in contact with a cathode electrolyte, wherein the cathode chamber is configured to produce an alkali.

In another aspect, there is provided a system, comprising an anode chamber comprising an anode in contact with a metal ion in an anode electrolyte wherein the anode chamber is configured to convert the metal ion from a lower oxidation state to a higher oxidation state; a cathode chamber comprising a cathode in contact with a cathode electrolyte, wherein the cathode chamber is configured to produce an alkali; and a contactor operably connected to the cathode chamber and configured to contact carbon from a source of carbon with the cathode electrolyte.

In another aspect, there is provided a system, comprising an anode chamber comprising an anode in contact with a metal ion in an anode electrolyte wherein the anode chamber is configured to convert the metal ion from a lower oxidation state to a higher oxidation state; and a cathode chamber comprising a cathode in contact with a cathode electrolyte, wherein the cathode chamber is configured to produce an alkali; and a size exclusion membrane and/or an anion exchange membrane configured to prevent migration of the metal ion from the anode electrolyte to the cathode electrolyte.

In another aspect, there is provided a system, comprising an anode in contact with an anode electrolyte wherein the anode is configured to oxidize a metal ion from the lower oxidation state to a higher oxidation state; a cathode in contact with a cathode electrolyte; and a reactor operably connected to the anode chamber and configured to react the metal ion in the higher oxidation state with hydrogen gas to form an acid.

In another aspect, there is provided a system, comprising an anode in contact with an anode electrolyte wherein the anode is configured to oxidize a metal ion from the lower oxidation state to a higher oxidation state; a cathode in contact with a cathode electrolyte; and a reactor operably connected to the anode chamber and configured to react the metal ion in the higher oxidation state with an unsaturated hydrocarbon to form a green halogenated hydrocarbon.

In another aspect, there is provided a system, comprising an anode in contact with an anode electrolyte wherein the anode is configured to oxidize a metal ion from the lower oxidation state to a higher oxidation state; a cathode in contact with a cathode electrolyte; a ligand in the anode electrolyte wherein the ligand is configured to interact with the metal ion; and a reactor operably connected to the anode chamber and configured to react the metal ion in the higher oxidation state with an unsaturated hydrocarbon in the presence of the ligand.

Some embodiments of the above described system aspects are provided herein. In some embodiments, the cathode is a gas-diffusion cathode. In some embodiments, the cathode is configured to form hydrogen gas by reducing water. In some embodiments, the system further includes an oxygen gas delivery system operably connected to the cathode chamber and configured to provide oxygen gas from a source of oxygen gas to the cathode chamber. In some embodiments, the metal ion is in a form of metal chloride. In some embodiments, the system further includes a reactor operably connected to the anode chamber and configured to contact the metal chloride with metal ion in the higher oxidation state with an unsaturated hydrocarbon to form chlorohydrocarbon. In some embodiments, the system further includes a contactor operably connected to the cathode chamber and configured to contact carbon from a source of carbon with the cathode electrolyte. In some embodiments, the system further includes a contactor operably connected to the cathode chamber and configured to contact carbon from a source of carbon with the cathode electrolyte wherein the carbon from the source of carbon is selected from gaseous carbon dioxide from an industrial process or a solution of carbon dioxide from a gas/liquid contactor in contact with the gaseous carbon dioxide from the industrial process. In some embodiments, the system further includes a precipitator to contact the cathode electrolyte with alkaline earth metal ions to form a carbonate and/or bicarbonate product.

In one aspect, there is provided a system including an anode chamber wherein the anode chamber comprises an anode in contact with a metal ion in an anode electrolyte wherein the anode chamber is configured to convert the metal ion from a lower oxidation state to a higher oxidation state and an unsaturated hydrocarbon delivery system configured to deliver the unsaturated hydrocarbon to the anode chamber. In some embodiments, the unsaturated hydrocarbon is ethylene. In some embodiments, the metal ion is copper ion.

BRIEF DESCRIPTION OF THE DRAWINGS

The novel features of the invention are set forth with particularity in the appended claims. A better understanding of the features and advantages of the present invention may be obtained by reference to the following detailed description that sets forth illustrative embodiments, in which the principles of the invention are utilized, and the accompanying drawings of which:

FIG. 1A is an illustration of an embodiment of the invention.
FIG. 4B is an illustration of an embodiment of the invention.
FIG. 6 is an illustration of an embodiment of the invention.
FIG. 7C is an illustration of an embodiment of the invention.
FIG. 10B is an illustration of an embodiment of the invention.

DETAILED DESCRIPTION

Figure 1B:
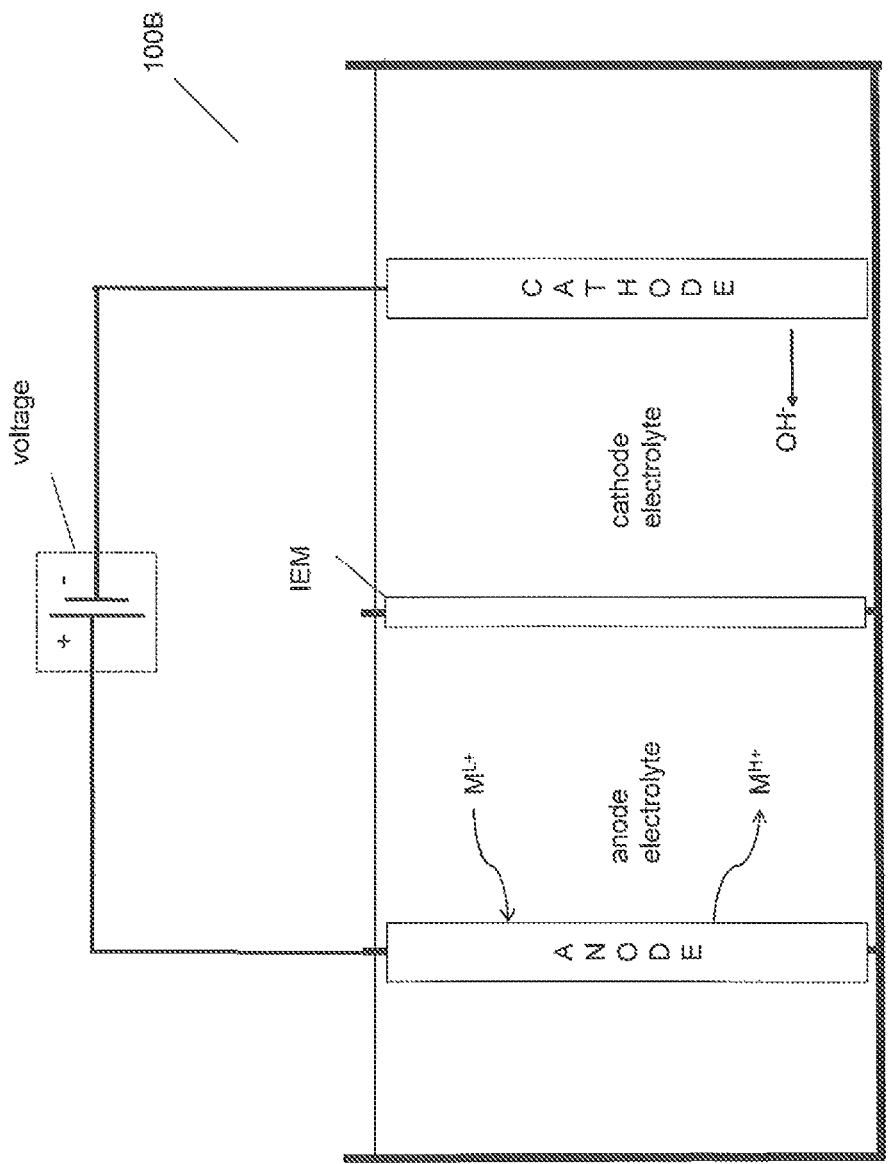
FIG. 1B is an illustration of an embodiment of the invention.

Disclosed herein are systems and methods that relate to the oxidation of a metal ion by the anode in the anode chamber where the metal ion is oxidized from the lower oxidation state to a higher oxidation state.

As can be appreciated by one ordinarily skilled in the art, the present electrochemical system and method can be configured with an alternative, equivalent salt solution, e.g., a potassium chloride solution or sodium chloride solution or a magnesium chloride solution or sodium sulfate solution or ammonium chloride solution, to produce an equivalent alkaline solution, e.g., potassium hydroxide and/or potassium carbonate and/or potassium bicarbonate or sodium hydroxide and/or sodium carbonate and/or sodium bicarbonate or magnesium hydroxide and/or magnesium carbonate in the cathode electrolyte. Accordingly, to the extent that such equivalents are based on or suggested by the present system and method, these equivalents are within the scope of the application.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges that are presented herein with numerical values may be construed as "about" numericals. The "about" is to provide literal support for the exact number that it precedes, as well as a number that is near to or approximately the number that the term precedes. In determining whether a number is near to or approximately a specifically recited number, the near or approximating unrequited number may be a number, which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a," "an," and "the" include plural references unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Compositions, Methods, and Systems

In one aspect, there are provided methods and systems that relate to the oxidation of metal ions from a lower oxidation state to a higher oxidation state in the anode chamber of the electrochemical cell. The metal ions formed with the higher oxidation state may be used as is or are used for commercial purposes such as, but not limited to, chemical synthesis reactions, reduction reactions etc. In one aspect, the electrochemical cells described herein provide an efficient and low voltage system where the metal compound such as metal halide, e.g., metal chloride or a metal sulfate with the higher oxidation state produced by the anode can be used for other purposes, such as, but not limited to, generation of hydrogen chloride, hydrochloric acid, hydrogen bromide, hydrobromic acid, hydrogen iodide, hydroiodic acid, or sulfuric acid from hydrogen gas and/or generation of halohydrocarbons or sulfohydrocarbons from hydrocarbons.

The "halohydrocarbons" or "halogenated hydrocarbon" as used herein, include halo substituted hydrocarbons where halo may be any number of halogens that can be attached to the hydrocarbon based on permissible valency. The halogens include fluoro, chloro, bromo, and iodo. The examples of halohydrocarbons include chlorohydrocarbons, bromohydrocarbons, and iodohydrocarbons. The chlorohydrocarbons include, but not limited to, monochlorohydrocarbons, dichlorohydrocarbons, trichlorohydrocarbons, etc. For metal halides, such as, but not limited to, metal bromide and metal iodide, the metal bromide or metal iodide with the higher oxidation state produced by the anode chamber can be used for other purposes, such as, but not limited to, generation of hydrogen bromide or hydrogen iodide and/or generation of bromo or iodohydrocarbons, such as, but not limited to, monobromohydrocarbons, dibromohydrocarbons, tribromohydrocarbons, monoiodohydrocarbons, diiodohydrocarbons, triiodohydrocarbons, etc. In some embodiments, the metal ion in the higher oxidation state may be sold as is in the commercial market.

The "sulfohydrocarbons" as used herein include hydrocarbons substituted with one or more of $-SO_3H$ or $-OSO_2OH$ based on permissible valency.

The electrochemical cell of the invention may be any electrochemical cell where the metal ion in the lower oxidation state is converted to the metal ion in the higher oxidation state in the anode chamber. In such electrochemical cells, cathode reaction may be any reaction that does or does not form an alkali in the cathode chamber. Such cathode consumes electrons and carries out any reaction including, but not limited to, the reaction of water to form hydroxide ions and hydrogen gas or reaction of oxygen gas and water to form hydroxide ions or reduction of protons from an acid such as hydrochloric acid to form hydrogen gas or reaction of protons from hydrochloric acid and oxygen gas to form water.

In some embodiments, the electrochemical cells may include production of an alkali in the cathode chamber of the cell. The alkali generated in the cathode chamber may be used as is for commercial purposes or may be treated with divalent cations to form divalent cation containing carbonates/bicarbonates. In some embodiments, the alkali generated in the cathode chamber may be used to sequester or capture carbon dioxide. The carbon dioxide may be present in flue gas emitted by various industrial plants. The carbon dioxide may be sequestered in the form of carbonate and/or bicarbonate products. In some embodiments, the metal compound with metal in the higher oxidation state may be withdrawn from the anode chamber and is used for any commercial process that is known to skilled artisan in the art. Therefore, both the anode electrolyte as well as the cathode electrolyte can be used for generating products that may be used for commercial purposes thereby providing a more economical, efficient, and less energy intensive process.

In some embodiments, the metal compound produced by the anode chamber may be used as is or may be purified before reacting with hydrogen gas, unsaturated hydrocarbon, or saturated hydrocarbon for the generation of hydrogen chloride, hydrochloric acid, hydrogen bromide, hydrobromic acid, hydrogen iodide, or hydroiodic acid, sulfuric acid, and/or halohydrocarbon or sulfohydrocarbon, respectively. In some embodiments, the metal compound may be used on-site where hydrogen gas is generated and/or in some embodiments, the metal compound withdrawn from the anode chamber may be transferred to a site where hydrogen gas is generated and hydrogen chloride, hydrochloric acid, hydrogen bromide, hydrobromic acid, hydrogen iodide, or hydroiodic acid are formed from it. In some embodiments, the metal compound may be formed in the electrochemical system and used on-site where an unsaturated hydrocarbon such as, but not limited to, ethylene gas is generated or transferred to and/or in some embodiments, the metal compound withdrawn from the anode chamber may be transferred to a site where an unsaturated hydrocarbon such as, but not limited to, ethylene gas is generated or transferred to and halohydrocarbon, e.g., chlorohydrocarbon is formed from it. In some embodiments, the ethylene gas generating facility is integrated with the electrochemical system of the invention to simultaneously produce the metal compound in the higher oxidation state and the ethylene gas and treat them with each other to form a product, such as ethylene dichloride (EDC). The ethylene dichloride may also be known as 1,2-dichloroethane, dichloroethane, 1,2-ethylene dichloride, glycol dichloride, freon 150, borer sol, brocide, destruxol borer-sol, dichlor-mulsion, dutch oil, or granosan. In some embodiments, the electrochemical system of the invention is integrated with vinyl chloride monomer (VCM) production facility or polyvinylchloride (PVC) production facility such that the EDC formed via the systems and methods of the invention is used in VCM and/or PVC production.

The electrochemical systems and methods described herein provide one or more advantages over conventional electrochemical systems known in the art, including, but not limited to, no requirement of gas diffusion anode; higher cell efficiency; lower voltages; platinum free anode; sequestration of carbon dioxide; green and environment friendly chemicals; and/or formation of various commercially viable products.

The systems and methods of the invention provide an electrochemical cell that produces various products, such as, but not limited to, metal salts formed at the anode, the metal salts used to form various other chemicals, alkali formed at the cathode, alkali used to form various other products, and/or hydrogen gas formed at the cathode. All of such products have been defined herein and may be called "green chemicals" since such chemicals are formed using the electrochemical cell that runs at low voltage or energy and high efficiency. The low voltage or less energy intensive process described herein would lead to lesser emission of carbon dioxide as compared to conventional methods of making similar chemicals or products. In some embodiments, the chemicals or products are formed by the capture of carbon dioxide from flue gas in the alkali generated at the cathode, such as, but not limited to, carbonate and bicarbonate products. Such carbonate and bicarbonate products are "green chemicals" as they reduce the pollution and provide cleaner environment.

Metal

The "metal ion" or "metal" as used herein, includes any metal ion capable of being converted from lower oxidation state to higher oxidation state. Examples of metal ions include, but not limited to, iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combination thereof. In some embodiments, the metal ions include, but not limited to, iron, copper, tin, chromium, or combination thereof. In some embodiments, the metal ion is copper. In some embodiments, the metal ion is tin. In some embodiments, the metal ion is iron. In some embodiments, the metal ion is chromium. In some embodiments, the metal ion is platinum. The "oxidation state" as used herein, includes degree of oxidation of an atom in a substance. For example, in some embodiments, the oxidation state is the net charge on the ion. Some examples of the reaction of the metal ions at the anode are as shown in Table I below (SHE is standard hydrogen electrode). The theoretical values of the anode potential are also shown. It is to be understood that some variation from these voltages may occur depending on conditions, pH, concentrations of the electrolytes, etc and such variations are well within the scope of the invention.

TABLE I

| Anode Reaction | Anode Potential (V vs. SHE) |
|---|---|
| $Ag^+ \rightarrow Ag^{2+} + e^-$ | −1.98 |
| $Co^{2+} \rightarrow Co^{3+} + e^-$ | −1.82 |
| $Pb^{2+} \rightarrow Pb^{4+} + 2e^-$ | −1.69 |
| $Ce^{3+} \rightarrow Ce^{4+} + e^-$ | −1.44 |
| $2Cr^{3+} + 7H_2O \rightarrow Cr_2O_7^{2-} + 14H^+ + 6e^-$ | −1.33 |
| $Tl^+ \rightarrow Tl^{3+} + 2e^-$ | −1.25 |
| $Hg_2^{2+} \rightarrow 2Hg^{2+} + 2e^-$ | −0.91 |
| $Fe^{2+} \rightarrow Fe^{3+} + e^-$ | −0.77 |
| $V^{3+} + H_2O \rightarrow VO^{2+} + 2H^+ + e^-$ | −0.34 |
| $U^{4+} + 2H_2O \rightarrow UO_2^{2+} + 4H^+ + e^-$ | −0.27 |
| $Bi^+ \rightarrow Bi^{3+} + 2e^-$ | −0.20 |
| $Tl^{3+} + H_2O \rightarrow TlO^{2+} + 2H^+ + e^-$ | −0.19 |
| $Cu^+ \rightarrow Cu^{2+} + e^-$ | −0.16 |
| $UO_2^+ \rightarrow UO_2^{2+} + e^-$ | −0.16 |
| $Sn^{2+} \rightarrow Sn^{4+} + 2e^-$ | −0.15 |
| $Ru(NH_3)_6^{2+} \rightarrow Ru(NH_3)_6^{3+} + e^-$ | −0.10 |
| $V^{2+} \rightarrow V^{3+} + e^-$ | +0.26 |
| $Eu^{2+} \rightarrow Eu^{3+} + e^-$ | +0.35 |
| $Cr^{2+} \rightarrow Cr^{3+} + e^-$ | +0.42 |
| $U^{3+} \rightarrow U^{4+} + e^-$ | +0.52 |

The metal ion may be present as a compound of the metal or an alloy of the metal or combination thereof. In some embodiments, the anion attached to the metal is same as the anion of the electrolyte. For example, for sodium or potassium chloride used as an electrolyte, a metal chloride, such as, but not limited to, iron chloride, copper chloride, tin chloride, chromium chloride etc. is used as the metal compound. For example, for sodium or potassium sulfate used as an electrolyte, a metal sulfate, such as, but not limited to, iron sulfate, copper sulfate, tin sulfate, chromium sulfate etc. is used as the metal compound. For example, for sodium or potassium bromide used as an electrolyte, a metal bromide, such as, but not limited to, iron bromide, copper bromide, tin bromide etc. is used as the metal compound.

In some embodiments, the anion of the electrolyte may be partially or fully different from the anion of the metal. For example, in some embodiments, the anion of the electrolyte may be a sulfate whereas the anion of the metal may be a chloride. In such embodiments, it may be desirable to have less concentration of the chloride ions in the electrochemical cell. For example, in some embodiments, the higher concentration of chloride ions in the anode electrolyte, due to chloride of the electrolyte and the chloride of the metal, may result in undesirable ionic species in the anode electrolyte. This may be avoided by utilizing an electrolyte that contains ions other than chloride. In some embodiments, the anode electrolyte may be a combination of ions similar to the metal anion and anions different from the metal ion. For example, the anode electrolyte may be a mix of sulfate ions as well as chloride ions when the metal anion is chloride. In such embodiments, it may be desirable to have sufficient concentration of chloride ions in the electrolyte to dissolve the metal salt but not high enough to cause undesirable ionic speciation.

In some embodiments, the electrolyte and/or the metal compound are chosen based on the desired end product. For example, if HCl is desired from the reaction between the hydrogen gas and the metal compound then metal chloride is used as the metal compound and the sodium chloride is used as an electrolyte. For example, if a brominated hydrocarbon is desired from the reaction between the metal compound and the hydrocarbon, then a metal bromide is used as the metal compound and the sodium or potassium bromide is used as the electrolyte.

In some embodiments, the metal ions used in the electrochemical systems described herein, may be chosen based on the solubility of the metal in the anode electrolyte and/or cell voltages desired for the metal oxidation from the lower oxidation state to the higher oxidation state. For example, the voltage required to oxidize $Cr^{2+}$ to $Cr^{3+}$ may be lower than that required for $Sn^{2+}$ to $Sn^{4+}$, however, the amount of HCl formed by the reaction of the hydrogen gas with the $Cr^{3+}$ may be lower than the HCl formed with $Sn^{4+}$ owing to two chlorine atoms obtained per tin molecule. Therefore, in some embodiments, where the lower cell voltages may be desired, the metal ion oxidation that results in lower cell voltage may be used, such as, but not limited to $Cr^{2+}$. For example, for the reactions where carbon dioxide is captured by the alkali produced by the cathode electrolyte, a lower voltage may be desired. In some embodiments, where a higher amount of the product, such as hydrochloric acid may be desired, the metal ion that results in higher amount of the product albeit relatively higher voltages may be used, such as, but not limited to $Sn^{2+}$. For example, the voltage of the cell may be higher for tin system as compared to the chromium system, however, the concentration of the acid formed with $Sn^{4+}$ may offset the higher voltage of the system. It is to be understood, that the products formed by the systems and methods described herein, such as the acid, halohydrocarbons, sulfohydrocarbons, carbonate, bicarbonates, etc. are still "green" chemicals as they are made by less energy intensive processes as compared to energy input required for conventionally known methods of making the same products.

In some embodiments, the metal ion in the lower oxidation state and the metal ion in the higher oxidation state are both present in the anode electrolyte. In some embodiments, it may be desirable to have the metal ion in both the lower oxidation state and the higher oxidation state in the anode electrolyte. Suitable ratios of the metal ion in the lower and higher oxidation state in the anode electrolyte have been described herein. The mixed metal ion in the lower oxidation state with the metal ion in the higher oxidation state may assist in lower voltages in the electrochemical systems and high yield and selectivity in corresponding catalytic reactions with hydrogen gas or hydrocarbons.

In some embodiments, the metal ion in the anode electrolyte is a mixed metal ion. For example, the anode electrolyte containing the copper ion in the lower oxidation state and the copper ion in the higher oxidation state may also contain another metal ion such as, but not limited to, iron. In some embodiments, the presence of a second metal ion in the anode electrolyte may be beneficial in lowering the total energy of the electrochemical reaction in combination with the catalytic reaction.

Some examples of the metal compounds that may be used in the systems and methods of the invention include, but are not limited to, copper (II) sulfate, copper (II) nitrate, copper (I) chloride, copper (I) bromide, copper (I) iodide, iron (III) sulfate, iron (III) nitrate, iron (II) chloride, iron (II) bromide, iron (II) iodide, tin (II) sulfate, tin (II) nitrate, tin (II) chloride, tin (II) bromide, tin (II) iodide, chromium (III) sulfate, chromium (III) nitrate, chromium (II) chloride, chromium (II) bromide, chromium (II) iodide, zinc (II) chloride, zinc (II) bromide, etc.

Ligands

In some embodiments, an additive such as a ligand is used in conjunction with the metal ion to improve the efficiency of the metal ion oxidation inside the anode chamber and/or improve the catalytic reactions of the metal ion inside/outside the anode chamber such as, but not limited to reactions with hydrogen gas, with unsaturated hydrocarbon, and/or with saturated hydrocarbon. In some embodiments, the ligand is added along with the metal in the anode electrolyte. In some embodiments, the ligand is attached to the metal ion. In some embodiments, the ligand is attached to the metal ion by covalent, ionic and/or coordinate bonds. In some embodiments, the ligand is attached to the metal ion through vanderwaal attractions.

Accordingly, in some embodiments, there are provided methods that include contacting an anode with an anode electrolyte; oxidizing a metal ion from the lower oxidation state to a higher oxidation state at the anode; adding a ligand to the anode electrolyte wherein the ligand interacts with the metal ion; and contacting a cathode with a cathode electrolyte. In some embodiments, there are provided methods that include contacting an anode with an anode electrolyte; oxidizing a metal ion from the lower oxidation state to a higher oxidation state at the anode; adding a ligand to the anode electrolyte wherein the ligand interacts with the metal ion; and contacting a cathode with a cathode electrolyte wherein the cathode produces hydroxide ions, water, and/or hydrogen gas. In some embodiments, there are provided methods that include contacting an anode with an anode electrolyte; oxidizing a metal ion from the lower oxidation state to a higher oxidation state at the anode; adding a ligand to the anode electrolyte wherein the ligand interacts with the metal ion; contacting a cathode with a cathode electrolyte wherein the cathode produces hydroxide ions, water, and/or hydrogen gas; and contacting the anode electrolyte containing the ligand and the metal ion in the higher oxidation state with an unsaturated hydrocarbon, hydrogen gas, saturated hydrocarbon, or combination thereof.

In some embodiments, there are provided methods that include contacting an anode with an anode electrolyte; oxidizing a metal halide from a lower oxidation state to a higher oxidation state at the anode; adding a ligand to the metal halide wherein the ligand interacts with the metal ion; contacting a cathode with a cathode electrolyte wherein the cathode produces hydroxide ions, water, and/or hydrogen gas; and halogenating an unsaturated and/or saturated hydrocarbon with the metal halide in the higher oxidation state. In some embodiments, the metal halide is metal chloride and halogenations reaction is chlorination. In some embodiments, such methods contain a hydrogen gas producing cathode. In some embodiments, such methods contain an oxygen depolarized cathode. In some embodiments, the unsaturated hydrocarbon in such methods is a substituted or an unsubstituted alkene as $C_nH_{2n}$ where n is 2-20 (or alkyne or formula I as described further herein), e.g., ethylene, propylene, butene etc. In some embodiments, the saturated hydrocarbon in such methods is a substituted or an unsubstituted alkane as $C_nH_{2n+2}$ where n is 2-20 (or formula III as described further herein), e.g., methane, ethane, propane, etc. In some embodiments, the metal in such methods is metal chloride such as copper chloride. In some embodiments, such methods result in net energy saving of more than 100 kJ/mol or more than 150 kJ/mol or more than 200 kJ/mol or between 100-250 kJ/mol or the method results in the voltage savings of more than 1V (described below and in FIG. 8C). In some embodiments, the unsaturated hydrocarbon in such methods is $C_2$-$C_5$ alkene such as but not limited to, ethylene, propylene, isobutylene, 2-butene (cis and/or trans), pentene etc. or $C_2$-$C_4$ alkene such as but not limited to, ethylene, propylene, isobutylene, 2-butene (cis and/or trans), etc. In some embodiments, the unsaturated hydrocarbon in such methods is ethylene and the metal ion in such methods is metal chloride such as, copper chloride. In such methods, halogenations of the ethylene forms EDC. In some embodiments, the saturated hydrocarbon in such methods is ethane and the metal ion in such methods is metal chloride such as, platinum chloride or copper chloride. In such methods, halogenation of ethane forms chloroethane or EDC.

In some embodiments, there are provided systems that include an anode in contact with an anode electrolyte wherein the anode is configured to oxidize a metal ion from the lower oxidation state to a higher oxidation state; a ligand in the anode electrolyte wherein the ligand is configured to interact with the metal ion; and a cathode in contact with a cathode electrolyte. In some embodiments, there are provided systems that include an anode in contact with an anode electrolyte wherein the anode is configured to oxidize a metal ion from the lower oxidation state to a higher oxidation state; a ligand in the anode electrolyte wherein the ligand is configured to interact with the metal ion; and a cathode in contact with a cathode electrolyte wherein the cathode is configured to produce hydroxide ions, water, and/or hydrogen gas. In some embodiments, there are provided systems that include an anode in contact with an anode electrolyte wherein the anode is configured to oxidize a metal ion from the lower oxidation state to a higher oxidation state; a ligand in the anode electrolyte wherein the ligand is configured to interact with the metal ion; and a cathode in contact with a cathode electrolyte wherein the cathode is configured to form hydroxide ions, water, and/or hydrogen gas; and a reactor configured to react the anode electrolyte containing the ligand and the metal ion in the higher oxidation state with an unsaturated hydrocarbon, hydrogen gas, saturated hydrocarbon, or combination thereof. In some embodiments, such systems contain an oxygen depolarized cathode. In some embodiments, such systems contain a hydrogen gas producing cathode. In some embodiments, such systems result in net energy saving of more than 100 kJ/mol or more than 150 kJ/mol or more than 200 kJ/mol or between 100-250 kJ/mol or the system results in the voltage savings of more than 1V (described below and in FIG. 8C). In some embodiments, the unsaturated hydrocarbon in such systems is $C_2$-$C_5$ alkene, such as but not limited to, ethylene, propylene, isobutylene, 2-butene (cis and/or trans), pentene etc. or $C_2$-$C_4$ alkene, such as but not limited to, ethylene, propylene, isobutylene, 2-butene (cis and/or trans), etc. In some embodiments, the unsaturated hydrocarbon in such systems is ethylene. In some embodiments, the metal in such systems is metal chloride such as copper chloride. In some embodiments, the unsaturated hydrocarbon in such systems is ethylene and the metal ion in such systems is metal chloride such as, copper chloride. In such systems, halogenations of the ethylene forms EDC. In some embodiments, the saturated hydrocarbon in such systems is ethane and the metal ion in such systems is metal chloride such as, platinum chloride, copper chloride, etc. In such systems, halogenation of ethane forms chloroethane and/or EDC.

In some embodiments, the ligand results in one or more of the following: enhanced reactivity of the metal ion towards the unsaturated hydrocarbon, saturated hydrocarbon, or hydrogen gas, enhanced selectivity of the metal ion towards halogenations of the unsaturated or saturated hydrocarbon, enhanced transfer of the halogen from the metal ion to the unsaturated hydrocarbon, saturated hydrocarbon, or the hydrogen gas, reduced redox potential of the electrochemical cell, enhanced solubility of the metal ion in the aqueous medium, reduced membrane cross-over of the metal ion to the cathode electrolyte in the electrochemical cell, reduced corrosion of the electrochemical cell and/or the reactor, enhanced separation of the metal ion from the acid solution after reaction with hydrogen gas (such as size exclusion membranes), enhanced separation of the metal ion from the halogenated hydrocarbon solution (such as size exclusion membranes), and combination thereof.

In some embodiments, the attachment of the ligand to the metal ion increases the size of the metal ion sufficiently higher to prevent its migration through the ion exchange membranes in the cell. In some embodiments, the anion exchange membrane in the electrochemical cell may be used in conjunction with the size exclusion membrane such that the migration of the metal ion attached to the ligand from the anode electrolyte to the cathode electrolyte, is prevented. Such membranes are described herein below. In some embodiments, the attachment of the ligand to the metal ion increases the solubility of the metal ion in the aqueous medium. In some embodiments, the attachment of the ligand to the metal ion reduces the corrosion of the metals in the electrochemical cell as well as the reactor. In some embodiments, the attachment of the ligand to the metal ion increases the size of the metal ion sufficiently higher to facilitate separation of the metal ion from the acid or from the halogenated hydrocarbon after the reaction. In some embodiments, the presence and/or attachment of the ligand to the metal ion may prevent formation of various halogenated species of the metal ion in the solution and favor formation of only the desired species. For example, the presence of the ligand in the copper ion solution may limit the formation of the various halogenated species of the copper ion, such as, but not limited to, $[CuCl_3]^{2-}$ or $CuCl_2^0$ but favor formation of $Cu^{2+}/Cu^+$ ion. In some embodiments, the presence and/or attachment of the ligand in the metal ion solution reduces the overall voltage of the cell by providing one or more of the advantages described above.

Figure 20:
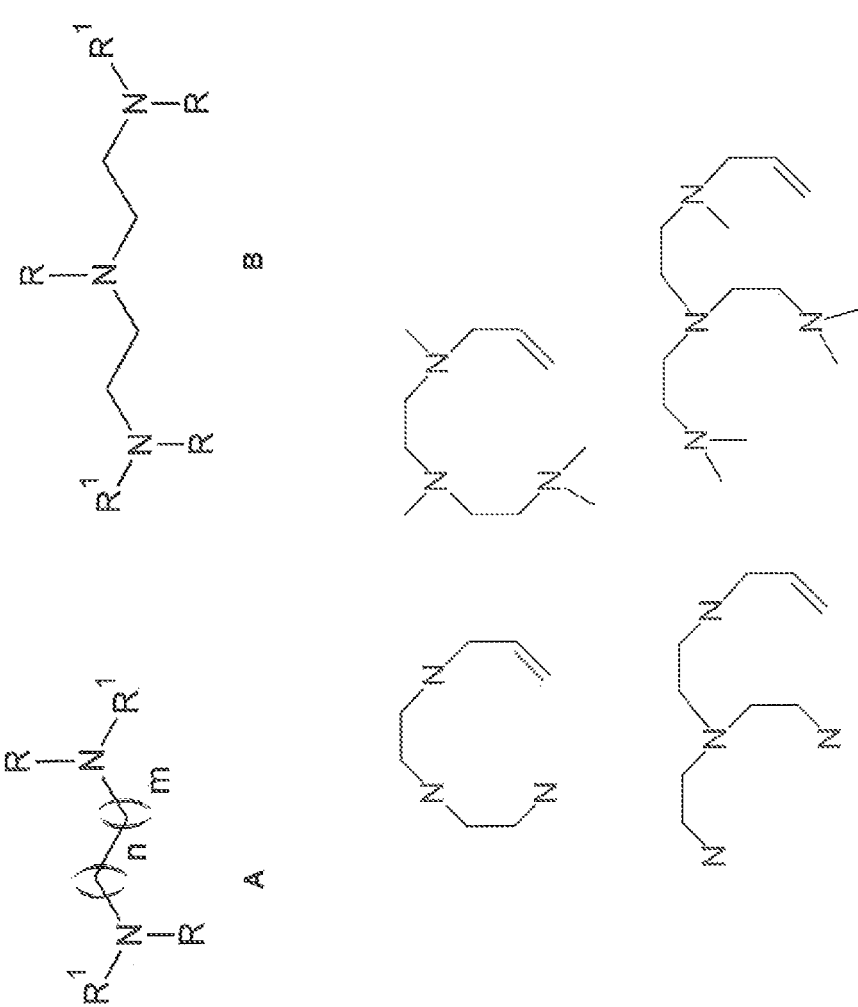
FIG. 20 is an illustrative embodiment as described in Example 6 herein.
Figure 25A:
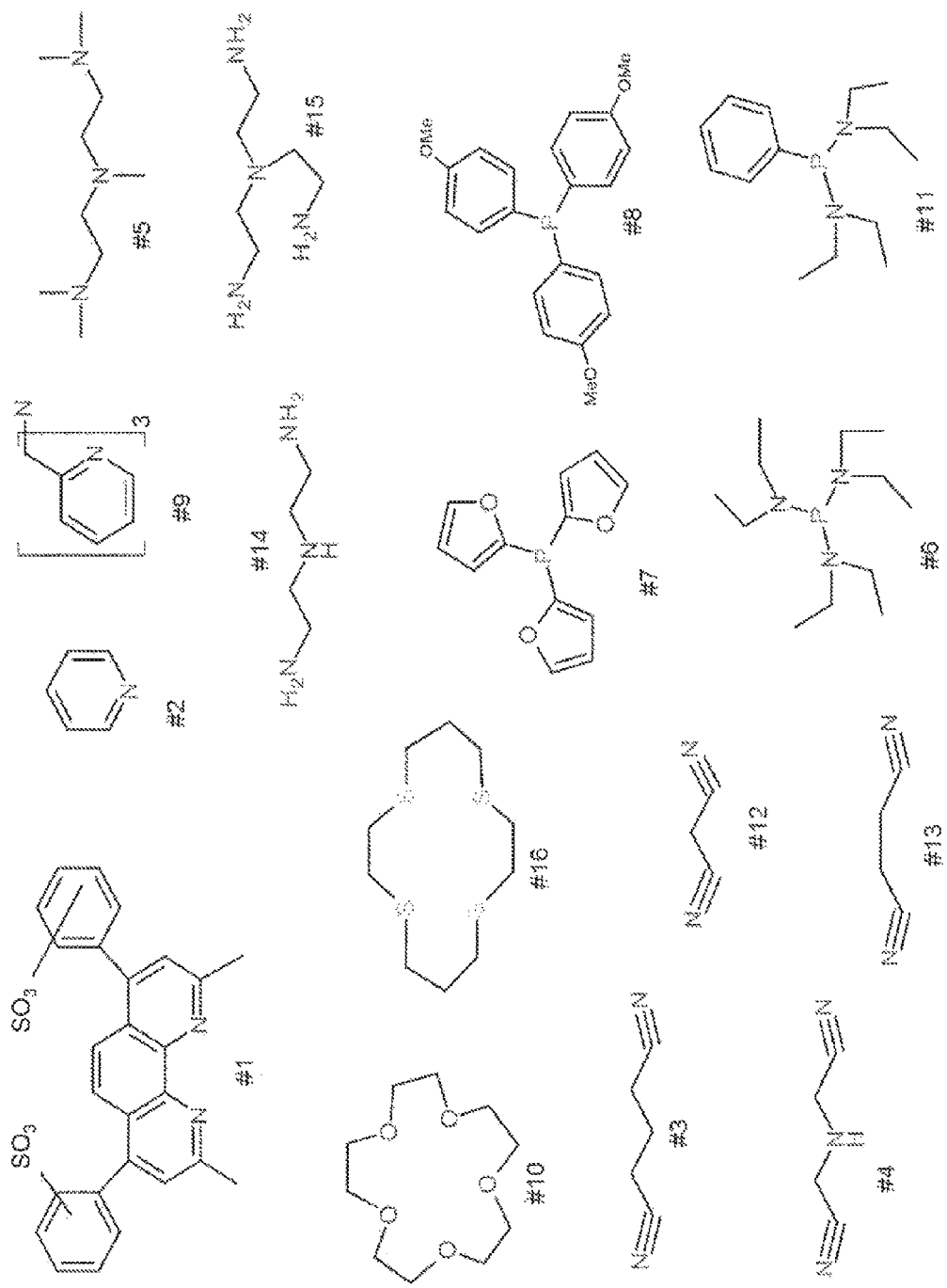
FIG. 25A illustrates few examples of the ligands used in the reaction described in Example 10.
Figure 25B:
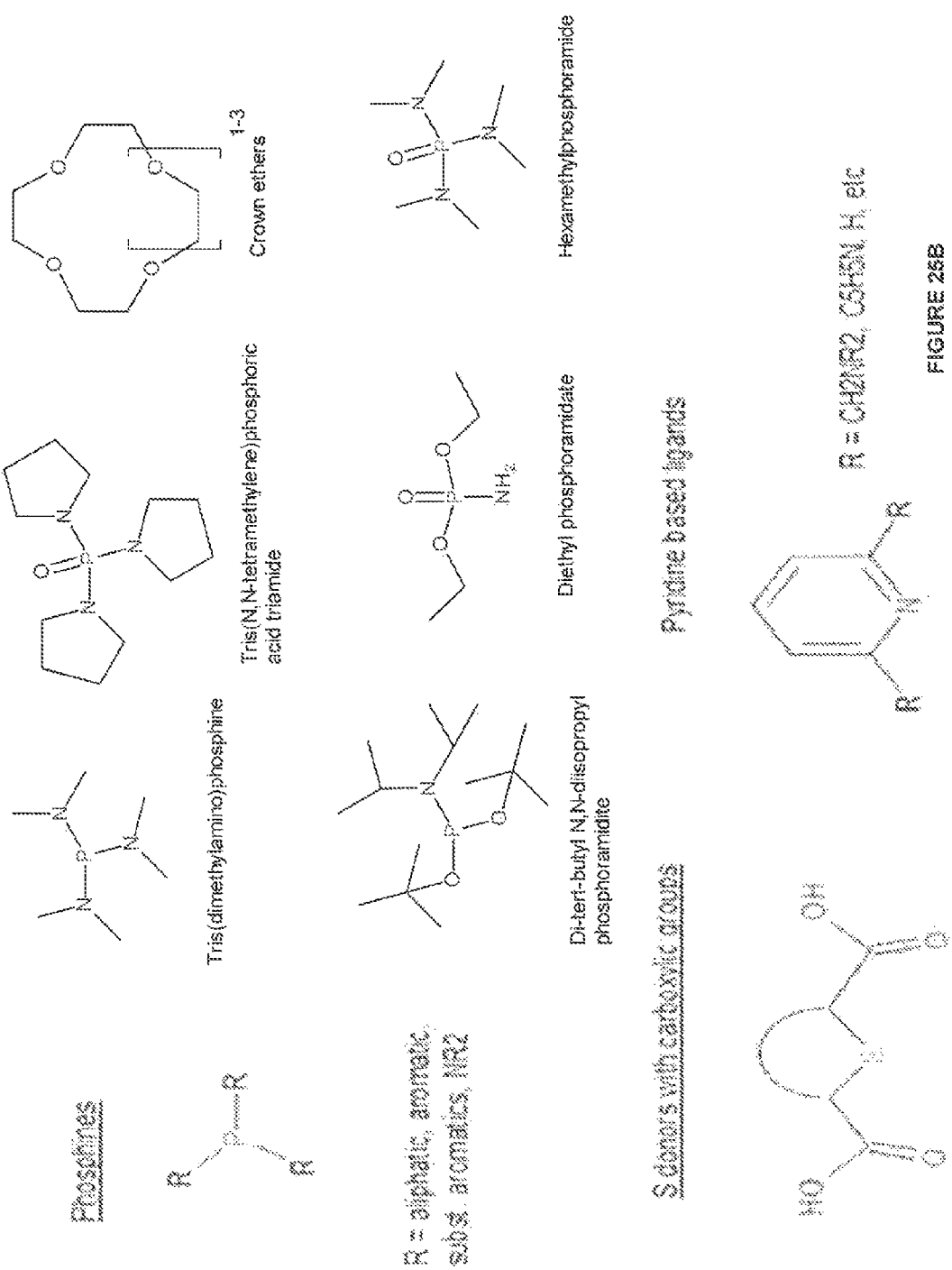
FIG. 25B illustrates few examples of the ligands that can be used in the reaction described in Example 10.

The "ligand" as used herein includes any ligand capable of enhancing the properties of the metal ion. In some embodiments, ligands include, but not limited to, substituted or unsubstituted aliphatic phosphine, substituted or unsubstituted aromatic phosphine, substituted or unsubstituted amino phosphine, substituted or unsubstituted crown ether, substituted or unsubstituted aliphatic nitrogen, substituted or unsubstituted cyclic nitrogen, substituted or unsubstituted aliphatic sulfur, substituted or unsubstituted cyclic sulfur, substituted or unsubstituted heterocyclic, and substituted or unsubstituted heteroaromatic. Some examples of the ligands are illustrated in FIGS. 20, 25A, and 25B.

Substituted or Unsubstituted Aliphatic Nitrogen

In some embodiments, the ligand is a substituted or unsubstituted aliphatic nitrogen of formula A:

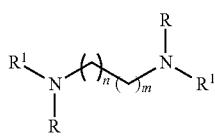

A wherein n and m independently are 0-2 and R and $R^1$ independently are H, alkyl, or substituted alkyl. In some embodiments, alkyl is methyl, ethyl, propyl, i-propyl, butyl, i-butyl, or pentyl. In some embodiments, the substituted alkyl is alkyl substituted with one or more of a group including alkenyl, halogen, amine, substituted amine, and combination thereof. In some embodiments, the substituted amine is substituted with a group selected from hydrogen and/or alkyl. Some examples of the ligands are illustrated in FIG. 20.

In some embodiments, the ligand is a substituted or unsubstituted aliphatic nitrogen of formula B:

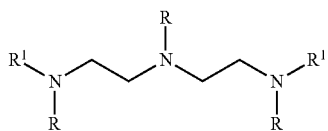

B wherein R and $R^1$ independently are H, alkyl, or substituted alkyl. In some embodiments, alkyl is methyl, ethyl, propyl, i-propyl, butyl, i-butyl, or pentyl. In some embodiments, the substituted alkyl is alkyl substituted with one or more of a group including alkenyl, halogen, amine, substituted amine, and combination thereof. In some embodiments, the substituted amine is substituted with a group selected from hydrogen and/or alkyl.

In some embodiments, the ligand is a substituted or unsubstituted aliphatic nitrogen donor of formula B, wherein R and $R^1$ independently are H, $C_1$-$C_4$ alkyl, or substituted $C_1$-$C_4$ alkyl. In some embodiments, $C_1$-$C_4$ alkyl is methyl, ethyl, propyl, i-propyl, butyl, or i-butyl. In some embodiments, the substituted $C_1$-$C_4$ alkyl is $C_1$-$C_4$ alkyl substituted with one or more of a group including alkenyl, halogen, amine, substituted amine, and combination thereof. In some embodiments, the substituted amine is substituted with a group selected from hydrogen and/or $C_1$-$C_3$ alkyl.

The concentration of the ligand may be chosen based on various parameters, including but not limited to, concentration of the metal ion, solubility of the ligand etc. Some examples of ligands that are substituted or unsubstituted aliphatic nitrogen, are as illustrated in FIG. 20.

Substituted or Unsubstituted Crown Ether with O, S, P or N Heteroatoms

In some embodiments, the ligand is a substituted or unsubstituted crown ether of formula C:

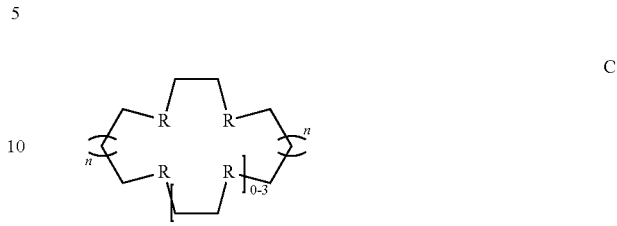

C wherein R is independently O, S, P, or N; and n is 0 or 1.

In some embodiments, the ligand is a substituted or unsubstituted crown ether of formula C, wherein R is O and n is 0 or 1. In some embodiments, the ligand is a substituted or unsubstituted crown ether of formula C, wherein R is S and n is 0 or 1. In some embodiments, the ligand is a substituted or unsubstituted crown ether of formula C, wherein R is N and n is 0 or 1. In some embodiments, the ligand is a substituted or unsubstituted crown ether of formula C, wherein R is P and n is 0 or 1. In some embodiments, the ligand is a substituted or unsubstituted crown ether of formula C, wherein R is O or S, and n is 0 or 1. In some embodiments, the ligand is a substituted or unsubstituted crown ether of formula C, wherein R is O or N, and n is 0 or 1. In some embodiments, the ligand is a substituted or unsubstituted crown ether of formula C, wherein R is N or S, and n is 0 or 1. In some embodiments, the ligand is a substituted or unsubstituted crown ether of formula C, wherein R is N or P, and n is 0 or 1.

Substituted or Unsubstituted Phosphines

In some embodiments, the ligand is a substituted or unsubstituted phosphine of formula D, or an oxide thereof:

D wherein $R^1$, $R^2$, and $R^3$ independently are H, alkyl, substituted alkyl, alkoxy, substituted alkoxy, aryl, substituted aryl, heteroaryl, substituted heteroaryl, amine, substituted amine, cycloalkyl, substituted cycloalkyl, heterocycloalkyl, and substituted heterocycloalkyl.

An example of an oxide of formula D is:

wherein $R^1$, $R^2$, and $R^3$ independently are H, alkyl, substituted alkyl, alkoxy, substituted alkoxy, aryl, substituted aryl, heteroaryl, substituted heteroaryl, amine, substituted amine, cycloalkyl, substituted cycloalkyl, heterocycloalkyl, and substituted heterocycloalkyl.

In some embodiments of the compound of formula D or an oxide thereof, $R^1$, $R^2$, and $R^3$ independently are alkyl and substituted alkyl. In some embodiments of the compound of formula D or an oxide thereof, $R^1$, $R^2$, and $R^3$ independently are alkyl and substituted alkyl wherein the substituted alkyl is substituted with group selected from alkoxy, substituted alkoxy, amine, and substituted amine. In some embodiments of the compound of formula D, or an oxide thereof, $R^1$, $R^2$, and $R^3$ independently are alkyl and substituted alkyl wherein the substituted alkyl is substituted with group selected from alkoxy and amine.

In some embodiments of the compound of formula D or an oxide thereof, $R^1$, $R^2$, and $R^3$ independently are alkoxy and substituted alkoxy. In some embodiments of the compound of formula D or an oxide thereof, $R^1$, $R^2$, and $R^3$ independently are alkoxy and substituted alkoxy wherein the substituted alkoxy is substituted with group selected from alkyl, substituted alkyl, amine, and substituted amine. In some embodiments of the compound of formula D or an oxide thereof, $R^1$, $R^2$, and $R^3$ independently are alkoxy and substituted alkoxy wherein the substituted alkoxy is substituted with group selected from alkyl and amine.

In some embodiments of the compound of formula D or an oxide thereof, $R^1$, $R^2$, and $R^3$ independently are aryl and substituted aryl. In some embodiments of the compound of formula D or an oxide thereof, $R^1$, $R^2$, and $R^3$ independently are aryl and substituted aryl wherein the substituted aryl is substituted with group selected from alkyl, substituted alkyl, alkoxy, substituted alkoxy, amine, and substituted amine. In some embodiments of the compound of formula D or an oxide thereof, $R^1$, $R^2$, and $R^3$ independently are aryl and substituted aryl wherein the substituted aryl is substituted with group selected from alkyl, alkoxy, and amine. In some embodiments of the compound of formula D or an oxide thereof, $R^1$, $R^2$, and $R^3$ independently are aryl and substituted aryl wherein the substituted aryl is substituted with group selected from alkyl and alkoxy.

In some embodiments of the compound of formula D or an oxide thereof, $R^1$, $R^2$, and $R^3$ independently are heteroaryl and substituted heteroaryl. In some embodiments of the compound of formula D or an oxide thereof, $R^1$, $R^2$, and $R^3$ independently are heteroaryl and substituted heteroaryl wherein the substituted heteroaryl is substituted with a group selected from alkyl, substituted alkyl, alkoxy, substituted alkoxy, amine, and substituted amine. In some embodiments of the compound of formula D or an oxide thereof, $R^1$, $R^2$, and $R^3$ independently are heteroaryl and substituted heteroaryl wherein the substituted heteroaryl is substituted with a group selected from alkyl, alkoxy, and amine.

In some embodiments of the compound of formula D or an oxide thereof, $R^1$, $R^2$, and $R^3$ independently are cycloalkyl and substituted cycloalkyl. In some embodiments of the compound of formula D or an oxide thereof, $R^1$, $R^2$, and $R^3$ independently are cycloalkyl and substituted cycloalkyl wherein the substituted cycloalkyl is substituted with a group selected from alkyl, substituted alkyl, alkoxy, substituted alkoxy, amine, and substituted amine. In some embodiments of the compound of formula D or an oxide thereof, $R^1$, $R^2$, and $R^3$ independently are cycloalkyl and substituted cycloalkyl wherein the substituted cycloalkyl is substituted with a group selected from alkyl, alkoxy, and amine.

In some embodiments of the compound of formula D or an oxide thereof, $R^1$, $R^2$, and $R^3$ independently are heterocycloalkyl and substituted heterocycloalkyl. In some embodiments of the compound of formula D or an oxide thereof, $R^1$, $R^2$, and $R^3$ independently are heterocycloalkyl and substituted heterocycloalkyl wherein the substituted heterocycloalkyl is substituted with a group selected from alkyl, substituted alkyl, alkoxy, substituted alkoxy, amine, and substituted amine. In some embodiments of the compound of formula D or an oxide thereof, $R^1$, $R^2$, and $R^3$ independently are heterocycloalkyl and substituted heterocycloalkyl wherein the substituted heterocycloalkyl is substituted with a group selected from alkyl, alkoxy, and amine.

In some embodiments of the compound of formula D or an oxide thereof, $R^1$, $R^2$, and $R^3$ independently are amine and substituted amine. In some embodiments of the compound of formula D or an oxide thereof, $R^1$, $R^2$, and $R^3$ independently are amine and substituted amine wherein the substituted amine is substituted with a group selected from alkyl, substituted alkyl, alkoxy, and substituted alkoxy. In some embodiments of the compound of formula D or an oxide thereof, $R^1$, $R^2$, and $R^3$ independently are amine and substituted amine wherein the substituted amine is substituted with a group selected from alkyl, and alkoxy. In some embodiments of the compound of formula D or an oxide thereof, $R^1$, $R^2$, and $R^3$ independently are amine and substituted amine wherein the substituted amine is substituted with alkyl.

In some embodiments, the ligand is a substituted or unsubstituted phosphine of formula D or an oxide thereof:

$$R^2\underset{\underset{R^3}{}}{\overset{\overset{R^1}{|}}{P}} \quad\quad D$$

wherein $R^1$, $R^2$, and $R^3$ independently are H, alkyl; substituted alkyl substituted with a group selected from alkoxy, substituted alkoxy, amine, and substituted amine; aryl; substituted aryl substituted with a group selected from alkyl, substituted alkyl, alkoxy, substituted alkoxy, amine, and substituted amine; heteroaryl; substituted heteroaryl substituted with a group selected from alkyl, substituted alkyl, alkoxy, substituted alkoxy, amine, and substituted amine; amine; substituted amine substituted with a group selected from alkyl, substituted alkyl, alkoxy, and substituted alkoxy; cycloalkyl; substituted cycloalkyl substituted with a group selected from alkyl, substituted alkyl, alkoxy, substituted alkoxy, amine, and substituted amine; heterocycloalkyl; and substituted heterocycloalkyl substituted with a group selected from alkyl, substituted alkyl, alkoxy, substituted alkoxy, amine, and substituted amine.

In some embodiments, the ligand is a substituted or unsubstituted phosphine of formula D or an oxide thereof:

$$R^2\underset{\underset{R^3}{}}{\overset{\overset{R^1}{|}}{P}} \quad\quad D$$

wherein $R^1$, $R^2$, and $R^3$ independently are H, alkyl; substituted alkyl substituted with a group selected from alkoxy and amine; aryl; substituted aryl substituted with a group selected from alkyl, alkoxy, and amine; heteroaryl; substituted heteroaryl substituted with a group selected from alkyl, alkoxy, and amine; amine; substituted amine substituted with a group selected from alkyl, and alkoxy; cycloalkyl; substituted cycloalkyl substituted with a group selected from alkyl, alkoxy, and amine; heterocycloalkyl; and substituted heterocycloalkyl substituted with a group selected from alkyl, alkoxy, and amine.

Substituted or Unsubstituted Pyridines

In some embodiments, the ligand is a substituted or unsubstituted pyridine of formula E:

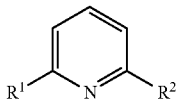

wherein $R^1$ and $R^2$ independently are H, alkyl, substituted alkyl, aryl, substituted aryl, heteroaryl, substituted heteroaryl, amine, substituted amine, cycloalkyl, substituted cycloalkyl, heterocycloalkyl, and substituted heterocycloalkyl.

In some embodiments, the ligand is a substituted or unsubstituted pyridine of formula E:

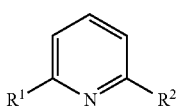

wherein $R^1$ and $R^2$ independently are H, alkyl, substituted alkyl, heteroaryl, substituted heteroaryl, amine, and substituted amine.

In some embodiments, the ligand is a substituted or unsubstituted pyridine of formula E, wherein $R^1$ and $R^2$ independently are H, alkyl, and substituted alkyl wherein substituted alkyl is substituted with a group selected from alkoxy, substituted alkoxy, amine, and substituted amine. In some embodiments, the ligand is a substituted or unsubstituted pyridine of formula E, wherein $R^1$ and $R^2$ independently are H, alkyl, and substituted alkyl wherein substituted alkyl is substituted with a group selected from amine, and substituted amine wherein substituted amine is substituted with an alkyl, heteroaryl or a substituted heteroaryl.

In some embodiments, the ligand is a substituted or unsubstituted pyridine of formula E, wherein $R^1$ and $R^2$ independently are heteroaryl and substituted heteroaryl. In some embodiments, the ligand is a substituted or unsubstituted pyridine of formula E, wherein $R^1$ and $R^2$ independently are heteroaryl and substituted heteroaryl substituted with alkyl, alkoxy or amine.

In some embodiments, the ligand is a substituted or unsubstituted pyridine of formula E, wherein $R^1$ and $R^2$ independently are amine and substituted amine. In some embodiments, the ligand is a substituted or unsubstituted pyridine of formula E, wherein $R^1$ and $R^2$ independently are amine and substituted amine wherein substituted amine is substituted with an alkyl, heteroaryl or a substituted heteroaryl.

In some embodiments, the ligand is a substituted or unsubstituted pyridine of formula E:

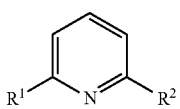

wherein $R^1$ and $R^2$ independently are H; alkyl; substituted alkyl substituted with a group selected from amine and substituted amine; heteroaryl; substituted heteroaryl substituted with alkyl, alkoxy or amine; amine; and substituted amine substituted with an alkyl, heteroaryl or a substituted heteroaryl.

Substituted or Unsubstituted Dinitriles

In some embodiments, the ligand is a substituted or unsubstituted dinitrile of formula F:

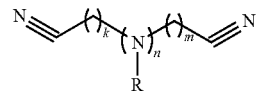

wherein R is hydrogen, alkyl, or substituted alkyl; n is 0-2; m is 0-3; and k is 1-3.

In some embodiments, the ligand is a substituted or unsubstituted dinitrile of formula F, wherein R is hydrogen, alkyl, or substituted alkyl substituted with alkoxy or amine; n is 0-1; m is 0-3; and k is 1-3.

In some embodiments, the ligand is a substituted or unsubstituted dinitrile of formula F, wherein R is hydrogen or alkyl; n is 0-1; m is 0-3; and k is 1-3.

In one aspect, there is provided a composition comprising an aqueous medium comprising a ligand selected from substituted or unsubstituted phosphine, substituted or unsubstituted crown ether, substituted or unsubstituted aliphatic nitrogen, substituted or unsubstituted pyridine, substituted or unsubstituted dinitrile, and combination thereof; and a metal ion.

In one aspect, there is provided a composition comprising an aqueous medium comprising a ligand selected from substituted or unsubstituted phosphine, substituted or unsubstituted crown ether, substituted or unsubstituted aliphatic nitrogen, substituted or unsubstituted pyridine, substituted or unsubstituted dinitrile, and combination thereof; and a metal ion selected from iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combination thereof.

In one aspect, there is provided a composition comprising an aqueous medium comprising a ligand selected from substituted or unsubstituted phosphine, substituted or unsubstituted crown ether, substituted or unsubstituted aliphatic nitrogen, substituted or unsubstituted pyridine, substituted or unsubstituted dinitrile, and combination thereof; a metal ion; and a salt.

In one aspect, there is provided a composition comprising an aqueous medium comprising a ligand selected from substituted or unsubstituted phosphine, substituted or unsubstituted crown ether, substituted or unsubstituted aliphatic nitrogen, substituted or unsubstituted pyridine, substituted or unsubstituted dinitrile, and combination thereof; a metal ion selected from iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combination thereof; and a salt.

In one aspect, there is provided a composition comprising an aqueous medium comprising a ligand selected from substituted or unsubstituted phosphine, substituted or unsubstituted crown ether, substituted or unsubstituted aliphatic nitrogen, substituted or unsubstituted pyridine, substituted or unsubstituted dinitrile, and combination thereof; a metal ion selected from iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combination thereof; and a salt comprising sodium chloride, ammonium chloride, sodium sulfate, ammonium sulfate, calcium chloride, or combination thereof.

In one aspect, there is provided a composition comprising an aqueous medium comprising a ligand selected from substituted or unsubstituted phosphine, substituted or unsubstituted crown ether, substituted or unsubstituted aliphatic nitrogen, substituted or unsubstituted pyridine, substituted or unsubstituted dinitrile, and combination thereof; a metal ion; and a salt comprising sodium chloride, ammonium chloride, sodium sulfate, ammonium sulfate, calcium chloride, or combination thereof.

In one aspect, there is provided a composition comprising an aqueous medium comprising a ligand selected from substituted or unsubstituted phosphine, substituted or unsubstituted crown ether, substituted or unsubstituted aliphatic nitrogen, substituted or unsubstituted pyridine, substituted or unsubstituted dinitrile, and combination thereof; a metal ion; a salt; and an unsaturated or saturated hydrocarbon.

In one aspect, there is provided a composition comprising an aqueous medium comprising a ligand selected from substituted or unsubstituted phosphine, substituted or unsubstituted crown ether, substituted or unsubstituted aliphatic nitrogen, substituted or unsubstituted pyridine, substituted or unsubstituted dinitrile, and combination thereof; a metal ion selected from iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combination thereof; a salt; and an unsaturated or saturated hydrocarbon.

In one aspect, there is provided a composition comprising an aqueous medium comprising a ligand selected from substituted or unsubstituted phosphine, substituted or unsubstituted crown ether, substituted or unsubstituted aliphatic nitrogen, substituted or unsubstituted pyridine, substituted or unsubstituted dinitrile, and combination thereof; a metal ion selected from iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combination thereof; a salt comprising sodium chloride, ammonium chloride, sodium sulfate, ammonium sulfate, calcium chloride, or combination thereof; and an unsaturated or saturated hydrocarbon.

In one aspect, there is provided a composition comprising an aqueous medium comprising a ligand selected from substituted or unsubstituted phosphine, substituted or unsubstituted crown ether, substituted or unsubstituted aliphatic nitrogen, substituted or unsubstituted pyridine, substituted or unsubstituted dinitrile, and combination thereof; a metal ion; a salt comprising sodium chloride, ammonium chloride, sodium sulfate, ammonium sulfate, calcium chloride, or combination thereof; and an unsaturated or saturated hydrocarbon.

In one aspect, there is provided a composition comprising an aqueous medium comprising a ligand selected from substituted or unsubstituted phosphine, substituted or unsubstituted crown ether, substituted or unsubstituted aliphatic nitrogen, substituted or unsubstituted pyridine, substituted or unsubstituted dinitrile, and combination thereof; a metal ion; a salt comprising sodium chloride, ammonium chloride, sodium sulfate, ammonium sulfate, calcium chloride, or combination thereof; and an unsaturated or saturated hydrocarbon selected from ethylene, propylene, butylenes, ethane, propane, butane, and combination thereof.

In one aspect, there is provided a composition comprising an aqueous medium comprising a ligand selected from substituted or unsubstituted phosphine, substituted or unsubstituted crown ether, substituted or unsubstituted aliphatic nitrogen, substituted or unsubstituted pyridine, substituted or unsubstituted dinitrile, and combination thereof; a metal ion selected from iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combination thereof; a salt comprising sodium chloride, ammonium chloride, sodium sulfate, ammonium sulfate, calcium chloride, or combination thereof; and an unsaturated or saturated hydrocarbon selected from ethylene, propylene, butylenes, ethane, propane, butane, and combination thereof.

In some embodiments of the methods and systems provided herein, the ligand is:
sulfonated bathocuprine;
pyridine;
tris(2-pyridylmethyl)amine;
glutaronitrile;
iminodiacetonitrile;
malononitrile;
succininitrile;
tris(diethylamino)phosphine;
tris(dimethylamino)phosphine;
tri(2-furyl)phosphine;
tris(4-methoxyphenyl)phosphine;
bis(diethylamino)phenylphosphine;
tris(N,N-tetramethylene)phosphoric acid triamide;
di-tert-butyl N,N-diisopropyl phosphoramidite;
diethylphosphoramidate;
hexamethylphosphoramide;
diethylenetriamine;
tris(2-aminoethyl)amine;
N,N,N',N',N"-pentamethyldiethylenetriamine;
15-Crown-5;
1,4,8,11-tetrathiacyclotetradecane; and
salt, or stereoisomer thereof.

In some embodiments, there is provided a method of using a ligand, comprising adding a ligand to an anode electrolyte comprising a metal ion solution and resulting in one or more of properties including, but not limited to, enhanced reactivity of the metal ion towards the unsaturated hydrocarbon, saturated hydrocarbon, or hydrogen gas, enhanced selectivity of the metal ion towards halogenations of the unsaturated or saturated hydrocarbon, enhanced transfer of the halogen from the metal ion to the unsaturated hydrocarbon, saturated hydrocarbon, or the hydrogen gas, reduced redox potential of the electrochemical cell, enhanced solubility of the metal ion in the aqueous medium, reduced membrane cross-over of the metal ion to the cathode electrolyte in the electrochemical cell, reduced corrosion of the electrochemical cell and/or the reactor, enhanced separation of the metal ion from the acid solution after reaction with hydrogen gas, enhanced separation of the metal ion from the halogenated hydrocarbon solution, and combination thereof.

In some embodiments, there is provided a method comprising improving an efficiency of an electrochemical cell wherein the electrochemical cell comprises an anode in contact with an anode electrolyte comprising a metal ion where the anode oxidizes the metal ion from a lower oxidation state to a higher oxidation state. In some embodiments, the efficiency relates to the voltage applied to the electrochemical cell.

As used herein, "alkenyl" refers to linear or branched hydrocarbyl having from 2 to 10 carbon atoms and in some embodiments from 2 to 6 carbon atoms or 2 to 4 carbon atoms and having at least 1 site of vinyl unsaturation (>C=C<). For example, ethenyl, propenyl, 1,3-butadienyl, and the like.

As used herein, "alkoxy" refers to —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

As used herein, "alkyl" refers to monovalent saturated aliphatic hydrocarbyl groups having from 1 to 10 carbon atoms and, in some embodiments, from 1 to 6 carbon atoms. "$C_x$-$C_y$ alkyl" refers to alkyl groups having from x to y carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

As used herein, "amino" or "amine" refers to the group —$NH_2$.

As used herein, "aryl" refers to an aromatic group of from 6 to 14 carbon atoms and no ring heteroatoms and having a single ring (e.g., phenyl) or multiple condensed (fused) rings (e.g., naphthyl or anthryl).

As used herein, "cycloalkyl" refers to a saturated or partially saturated cyclic group of from 3 to 14 carbon atoms and no ring heteroatoms and having a single ring or multiple rings including fused, bridged, and spiro ring systems. Examples of cycloalkyl groups include, for instance, cyclopropyl, cyclobutyl, cyclopentyl, cyclooctyl, and cyclohexenyl.

As used herein, "halo" or "halogen" refers to fluoro, chloro, bromo, and iodo.

As used herein, "heteroaryl" refers to an aromatic group of from 1 to 6 heteroatoms selected from the group consisting of oxygen, nitrogen, and sulfur and includes single ring (e.g. furanyl) and multiple ring systems (e.g. benzimidazol-2-yl and benzimidazol-6-yl). The heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, quinazolinonyl, benzimidazolyl, benzisoxazolyl, or benzothienyl.

As used herein, "heterocycloalkyl" refers to a saturated or partially saturated cyclic group having from 1 to 5 heteroatoms selected from the group consisting of nitrogen, sulfur, or oxygen and includes single ring and multiple ring systems including fused, bridged, and spiro ring systems. The heterocyclyl includes, but is not limited to, tetrahydropyranyl, piperidinyl, N-methylpiperidin-3-yl, piperazinyl, N-methylpyrrolidin-3-yl, 3-pyrrolidinyl, 2-pyrrolidon-1-yl, morpholinyl, and pyrrolidinyl.

As used herein, "substituted alkoxy" refers to —O-substituted alkyl wherein substituted alkyl is as defined herein.

As used herein, "substituted alkyl" refers to an alkyl group having from 1 to 5 and, in some embodiments, 1 to 3 or 1 to 2 substituents selected from the group consisting of alkenyl, halogen, —OH, —COOH, amino, substituted amino, wherein said substituents are as defined herein.

As used herein, "substituted amino" or "substituted amine" refers to the group —$NR^{10}R^{11}$ where $R^{10}$ and $R^{11}$ are independently selected from the group consisting of hydrogen, alkyl, substituted alkyl, aryl, substituted aryl, heteroaryl, and substituted heteroaryl.

As used herein, "substituted aryl" refers to aryl groups which are substituted with 1 to 8 and, in some embodiments, 1 to 5, 1 to 3, or 1 to 2 substituents selected from the group consisting of alkyl, substituted alkyl, alkoxy, substituted alkoxy, amine, substituted amine, alkenyl, halogen, —OH, and —COOH, wherein said substituents are as defined herein.

As used herein, "substituted cycloalkyl" refers to a cycloalkyl group, as defined herein, having from 1 to 8, or 1 to 5, or in some embodiments 1 to 3 substituents selected from the group consisting of alkyl, substituted alkyl, alkoxy, substituted alkoxy, amine, substituted amine, alkenyl, halogen, —OH, and —COOH, wherein said substituents are as defined herein.

As used herein, "substituted heteroaryl" refers to heteroaryl groups that are substituted with from 1 to 5, or 1 to 3, or 1 to 2 substituents selected from the group consisting of the substituents defined for substituted aryl.

As used herein, "substituted heterocycloalkyl" refers to heterocyclic groups, as defined herein, that are substituted with from 1 to 5 or in some embodiments 1 to 3 of the substituents as defined for substituted cycloalkyl.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substitutions is three. Similarly, it is understood that the above definitions are not intended to include impermissible substitution patterns (e.g., methyl substituted with 5 chloro groups). Such impermissible substitution patterns are well known to the skilled artisan.

In some embodiments, the concentration of the ligand in the electrochemical cell is dependent on the concentration of the metal ion in the lower and/or the higher oxidation state. In some embodiments, the concentration of the ligand is between 0.25M-5M; or between 0.25M-4M; or between 0.25M-3M; or between 0.5M-5M; or between 0.5M-4M; or between 0.5M-3M; or between 0.5M-2.5M; or between 0.5M-2M; or between 0.5M-1.5M; or between 0.5M-1M; or between 1M-2M; or between 1.5M-2.5M; or between 1.5M-2M.

In some embodiments, the ratio of the concentration of the ligand and the concentration of the Cu(I) ion is between 1:1 to 4:1; or between 1:1 to 3:1; or between 1:1 to 2:1; or is 1:1; or 2:1, or 3:1, or 4:1.

In some embodiments, the solution used in the catalytic reaction, i.e., the reaction of the metal ion in the higher oxidation state with the unsaturated or saturated hydrocarbon, and the solution used in the electrochemical reaction, contain the concentration of the metal ion in the higher oxidation state, such as Cu(II), between 4.5M-7M, the concentration of the metal ion in the lower oxidation state, such as Cu(I), between 0.25M-1.5M, and the concentration of the ligand between 0.25M-6M. In some embodiments, the concentration of the sodium chloride in the solution may affect the solubility of the ligand and/or the metal ion; the yield and selectivity of the catalytic reaction; and/or the efficiency of the electrochemical cell. Accordingly, in some embodiments, the concentration of sodium chloride in the solution is between 1M-3M. In some embodiments, the solution used in the catalytic reaction, i.e., the reaction of the metal ion in the higher oxidation state with the unsaturated or saturated hydrocarbon, and the solution used in the electrochemical reaction, contain the concentration of the metal ion in the higher oxidation state, such as Cu(II), between 4.5M-7M, the concentration of the metal ion in the lower oxidation state, such as Cu(I), between 0.25M-1.5M, the concentration of the ligand between 0.25M-6M, and the concentration of sodium chloride between 1M-3M.

Electrochemical Methods and Systems

In one aspect, there are provided methods including contacting an anode with a metal ion in an anode electrolyte in an anode chamber; converting the metal ion from a lower oxidation state to a higher oxidation state in the anode chamber; and contacting a cathode with a cathode electrolyte in a cathode chamber. In one aspect, there are provided methods including contacting an anode with a metal ion in an anode electrolyte in an anode chamber; converting the metal ion from a lower oxidation state to a higher oxidation state in the anode chamber; contacting a cathode with a cathode electrolyte in a cathode chamber; and forming an alkali, water, and/or hydrogen gas in the cathode chamber. In one aspect, there are provided methods including contacting an anode with a metal ion in an anode electrolyte in an anode chamber; converting the metal ion from a lower oxidation state to a higher oxidation state in the anode chamber; and treating the metal ion in the higher oxidation state with an unsaturated or saturated hydrocarbon. In some embodiments, the treatment of the metal ion in the higher oxidation state with the unsaturated or saturated hydrocarbon results in the formation of halohydrocarbons. In some embodiments, the treatment of the metal ion in the higher oxidation state with an unsaturated or saturated hydrocarbon, is inside the anode chamber. In some embodiments, the treatment of the metal ion in the higher oxidation state with an unsaturated or saturated hydrocarbon, is outside the anode chamber. In some embodiments, the cathode is an oxygen depolarized cathode.

Some embodiments of the electrochemical cells are as illustrated in the figures and described herein. It is to be understood that the figures are for illustration purposes only and that variations in the reagents and set up are well within the scope of the invention. All the electrochemical methods and systems described herein do not produce chlorine gas as is found in the chlor-alkali systems. All the systems and methods related to the halogenation or sulfonation of the unsaturated or saturated hydrocarbon, do not use oxygen gas in the catalytic reactor.

In some embodiments, there are provided methods that include contacting an anode with a metal ion in an anode electrolyte in an anode chamber; converting or oxidizing the metal ion from a lower oxidation state to a higher oxidation state at the anode; and contacting a cathode with a cathode electrolyte in a cathode chamber; and forming an alkali, water, and/or hydrogen gas at the cathode. In some embodiments, there are provided methods that include contacting an anode with a metal ion in an anode electrolyte in an anode chamber; oxidizing the metal ion from a lower oxidation state to a higher oxidation state at the anode; contacting a cathode with a cathode electrolyte in a cathode chamber; forming an alkali, water, and/or hydrogen gas at the cathode; and contacting the anode electrolyte comprising metal ion in the higher oxidation state with an unsaturated and/or saturated hydrocarbon to form halogenated hydrocarbon, or contacting the anode electrolyte comprising metal ion in the higher oxidation state with hydrogen gas to form an acid, or combination of both.

In some embodiments, there are provided systems that include an anode chamber comprising an anode in contact with a metal ion in an anode electrolyte, wherein the anode chamber is configured to convert the metal ion from a lower oxidation state to a higher oxidation state; and a cathode chamber comprising a cathode in contact with a cathode electrolyte. In another aspect, there are provided systems including an anode chamber containing an anode in contact with a metal ion in an anode electrolyte, wherein the anode chamber is configured to convert the metal ion from a lower oxidation state to a higher oxidation state; and a cathode chamber containing a cathode in contact with a cathode electrolyte, wherein the cathode chamber is configured to produce an alkali, water, and/or hydrogen gas. In some embodiments, there are provided systems that include an anode chamber comprising an anode in contact with a metal ion in an anode electrolyte, wherein the anode is configured to convert the metal ion from a lower oxidation state to a higher oxidation state; and a cathode chamber comprising a cathode in contact with a cathode electrolyte wherein the cathode is configured to form an alkali, water, and/or hydrogen gas in the cathode electrolyte; and a reactor operably connected to the anode chamber and configured to contact the anode electrolyte comprising metal ion in the higher oxidation state with an unsaturated and/or saturated hydrocarbon and/or hydrogen gas to form halogenated hydrocarbon or acid, respectively. In another aspect, there are provided systems including an anode chamber comprising an anode in contact with a metal ion in an anode electrolyte wherein the anode chamber is configured to convert the metal ion from a lower oxidation state to a higher oxidation state and an unsaturated and/or saturated hydrocarbon delivery system configured to deliver the unsaturated and/or saturated hydrocarbon to the anode chamber wherein the anode chamber is also configured to convert the unsaturated and/or saturated hydrocarbon to halogenated hydrocarbon.

As illustrated in FIG. 1A, the electrochemical system 100A includes an anode chamber with an anode in contact with an anode electrolyte where the anode electrolyte contains metal ions in lower oxidation state (represented as $M^{L+}$) which are converted by the anode to metal ions in higher oxidation state (represented as $M^{H+}$). The metal ion may be in the form of a sulfate, chloride, bromide, or iodide.

As used herein "lower oxidation state" represented as L+ in $M^{L+}$ includes the lower oxidation state of the metal. For example, lower oxidation state of the metal ion may be 1+, 2+, 3+, 4+, or 5+. As used herein "higher oxidation state" represented as H+ in $M^{H+}$ includes the higher oxidation state of the metal. For example, higher oxidation state of the metal ion may be 2+, 3+, 4+, 5+, or 6+.

The electron(s) generated at the anode are used to drive the reaction at the cathode. The cathode reaction may be any reaction known in the art. The anode chamber and the cathode chamber may be separated by an ion exchange membrane (IBM) that may allow the passage of ions, such as, but not limited to, sodium ions in some embodiments to the cathode electrolyte if the anode electrolyte is sodium chloride or sodium sulfate etc. containing metal halide. Some reactions that may occur at the cathode include, but not limited to, reaction of water to form hydroxide ions and hydrogen gas, reaction of oxygen gas and water to form hydroxide ions, reduction of HCl to form hydrogen gas; or reaction of HCl and oxygen gas to form water.

As illustrated in FIG. 1B, the electrochemical system 100B includes a cathode chamber with a cathode in contact with the cathode electrolyte that forms hydroxide ions in the cathode electrolyte. The electrochemical system 100B also includes an anode chamber with an anode in contact with the anode electrolyte where the anode electrolyte contains metal ions in lower oxidation state (represented as $M^{L+}$) which are converted by the anode to metal ions in higher oxidation state (represented as $M^{H+}$). The electron(s) generated at the anode are used to drive the reaction at the cathode. The anode chamber and the cathode chamber are separated by an ion exchange membrane (IEM) that allows the passage of sodium ions to the cathode electrolyte if the anode electrolyte is sodium chloride, sodium bromide, sodium iodide, sodium sulfate, ammonium chloride etc. or an equivalent solution containing the metal halide. In some embodiments, the ion exchange membrane allows the passage of anions, such as, but not limited to, chloride ions, bromide ions, iodide ions, or sulfate ions to the anode electrolyte if the cathode electrolyte is e.g., sodium chloride, sodium bromide, sodium iodide, or sodium sulfate or an equivalent solution. The sodium ions combine with hydroxide ions in the cathode electrolyte to form sodium hydroxide. The anions combine with metal ions to form metal halide or metal sulfate. It is to be understood that the hydroxide forming cathode, as illustrated in FIG. 1B is for illustration purposes only and other cathodes such as, cathode reducing HCl to form hydrogen gas or cathode reacting both HCl and oxygen gas to form water, are equally applicable to the systems. Such cathodes have been described herein.

In some embodiments, the electrochemical systems of the invention include one or more ion exchange membranes. Accordingly, in some embodiments, there are provided methods that include contacting an anode with a metal ion in an anode electrolyte in an anode chamber; oxidizing the metal ion from a lower oxidation state to a higher oxidation state at the anode; contacting a cathode with a cathode electrolyte in a cathode chamber; forming an alkali, water, and/or hydrogen gas at the cathode; and separating the cathode and the anode by at least one ion exchange membrane. In some embodiments, there are provided methods that include contacting an anode with a metal ion in an anode electrolyte in an anode chamber; oxidizing the metal ion from a lower oxidation state to a higher oxidation state at the anode; contacting a cathode with a cathode electrolyte in a cathode chamber; forming an alkali, water, and/or hydrogen gas at the cathode; separating the cathode and the anode by at least one ion exchange membrane; and contacting the anode electrolyte comprising metal ion in the higher oxidation state with an unsaturated and/or saturated hydrocarbon to form halogenated hydrocarbon, or contacting the anode electrolyte comprising metal ion in the higher oxidation state with hydrogen gas to form an acid, or combination of both. In some embodiments, the ion exchange membrane is a cation exchange membrane (CEM), an anion exchange membrane (AEM); or combination thereof.

In some embodiments, there are provided systems that include an anode chamber comprising an anode in contact with a metal ion in an anode electrolyte, wherein the anode is configured to convert the metal ion from a lower oxidation state to a higher oxidation state; a cathode chamber comprising a cathode in contact with a cathode electrolyte, wherein the cathode is configured to produce an alkali, water, and/or hydrogen gas; and at least one ion exchange membrane separating the cathode and the anode. In some embodiments, there are provided systems that include an anode chamber comprising an anode in contact with a metal ion in an anode electrolyte, wherein the anode is configured to convert the metal ion from a lower oxidation state to a higher oxidation state; a cathode chamber comprising a cathode in contact with a cathode electrolyte, wherein the cathode is configured to produce an alkali, water, and/or hydrogen gas; at least one ion exchange membrane separating the cathode and the anode; and a reactor operably connected to the anode chamber and configured to contact the anode electrolyte comprising metal ion in the higher oxidation state with an unsaturated and/or saturated hydrocarbon and/or hydrogen gas to form a halogenated hydrocarbon and acid, respectively. In some embodiments, the ion exchange membrane is a cation exchange membrane (CEM), an anion exchange membrane (AEM); or combination thereof.

Figure 2:
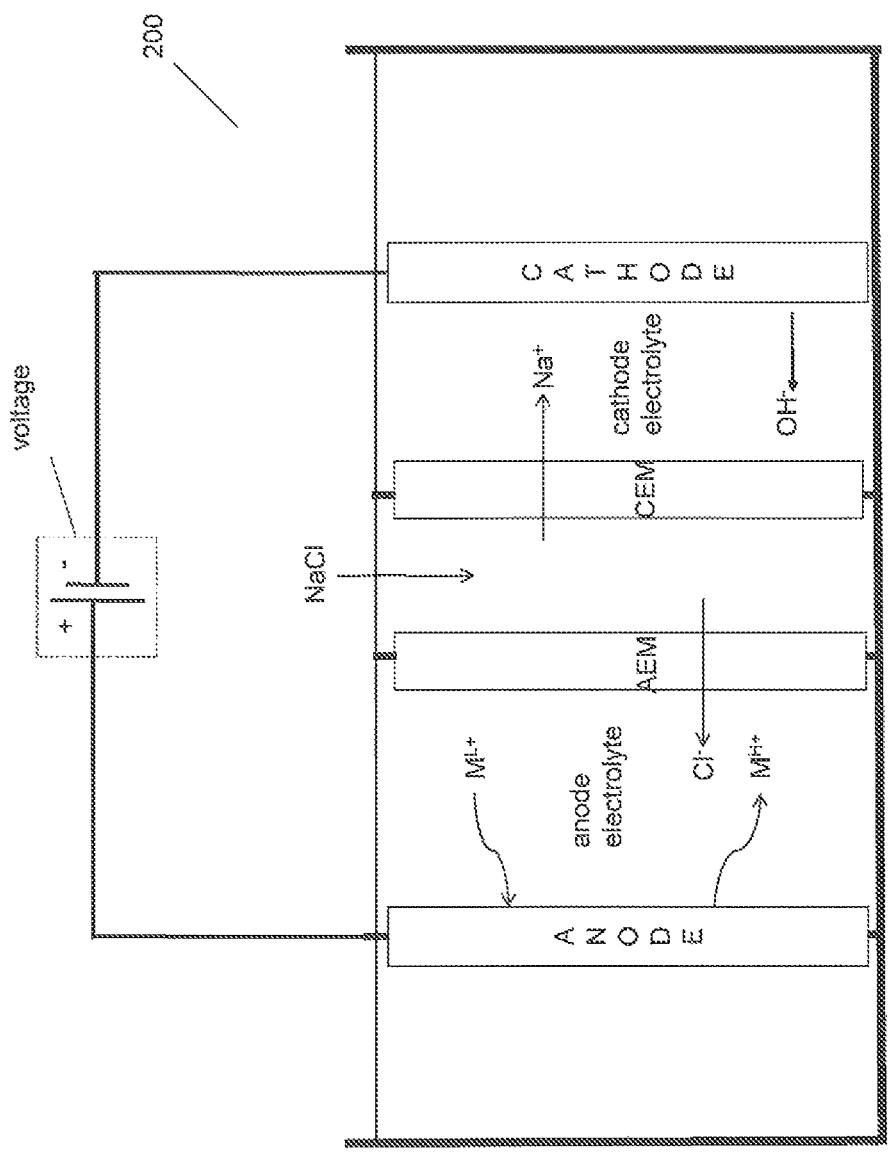
FIG. 2 is an illustration of an embodiment of the invention.

As illustrated in FIG. 2, the electrochemical system 200 includes a cathode in contact with a cathode electrolyte and an anode in contact with an anode electrolyte. The cathode forms hydroxide ions in the cathode electrolyte and the anode converts metal ions from lower oxidation state ($M^{L+}$) to higher oxidation state ($M^{H+}$). The anode and the cathode are separated by an anion exchange membrane (AEM) and a cation exchange membrane (CEM). A third electrolyte (e.g., sodium chloride, sodium bromide, sodium iodide, sodium sulfate, ammonium chloride, or combination thereof or an equivalent solution) is disposed between the AEM and the CEM. The sodium ions from the third electrolyte pass through CEM to form sodium hydroxide in the cathode chamber and the halide anions such as, chloride, bromide or iodide ions, or sulfate anions, from the third electrolyte pass through the AEM to form a solution for metal halide or metal sulfate in the anode chamber. The metal halide or metal sulfate formed in the anode electrolyte is then delivered to a reactor for reaction with hydrogen gas or an unsaturated or saturated hydrocarbon to generate hydrogen chloride, hydrochloric acid, hydrogen bromide, hydrobromic acid, hydrogen iodide, or hydroiodic acid and/or halohydrocarbons, respectively. The third electrolyte, after the transfer of the ions, can be withdrawn from the middle chamber as depleted ion solution. For example, in some embodiments when the third electrolyte is sodium chloride solution, then after the transfer of the sodium ions to the cathode electrolyte and transfer of chloride ions to the anode electrolyte, the depleted sodium chloride solution may be withdrawn from the middle chamber. The depleted salt solution may be used for commercial purposes or may be transferred to the anode and/or cathode chamber as an electrolyte or concentrated for re-use as the third electrolyte. In some embodiments, the depleted salt solution may be useful for preparing desalinated water. It is to be understood that the hydroxide forming cathode, as illustrated in FIG. 2 is for illustration purposes only and other cathodes such as, cathode reducing HCl to form hydrogen gas or cathode reacting both HCl and oxygen gas to form water, are equally applicable to the systems and have been described further herein.

Figure 3A:
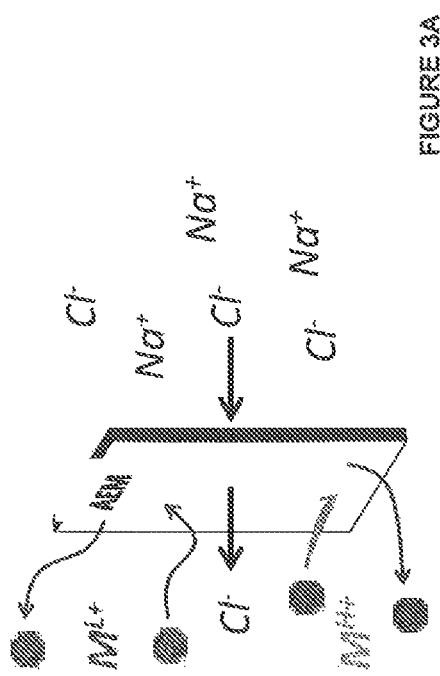
FIG. 3A is an illustration of an embodiment of the invention.
Figure 3B:
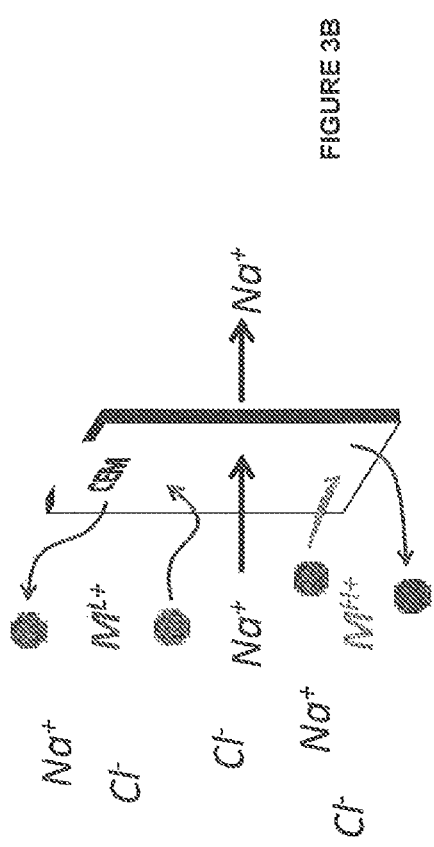
FIG. 3B is an illustration of an embodiment of the invention.

In some embodiments, the two ion exchange membranes, as illustrated in FIG. 2, may be replaced by one ion exchange membrane as illustrated in FIG. 1A or 1B. In some embodiments, the ion exchange membrane is an anion exchange membrane, as illustrated in FIG. 3A. In such embodiments, the cathode electrolyte may be a sodium halide, sodium sulfate or an equivalent solution and the AEM is such that it allows the passage of anions to the anode electrolyte but prevents the passage of metal ions from the anode electrolyte to the cathode electrolyte. In some embodiments, the ion exchange membrane is a cation exchange membrane, as illustrated in FIG. 3B. In such embodiments, the anode electrolyte may be a sodium halide, sodium sulfate or an equivalent solution containing the metal halide solution or an equivalent solution and the CEM is such that it allows the passage of sodium cations to the cathode electrolyte but prevents the passage of metal ions from the anode electrolyte to the cathode electrolyte. In some embodiments, the use of one ion exchange membrane instead of two ion exchange membranes may reduce the resistance offered by multiple IEMs and may facilitate lower voltages for running the electrochemical reaction. Some examples of the suitable anion exchange membranes are provided herein.

In some embodiments, the cathode used in the electrochemical systems of the invention, is a hydrogen gas producing cathode. Accordingly, in some embodiments, there are provided methods that include contacting an anode with a metal ion in an anode electrolyte in an anode chamber; oxidizing the metal ion from a lower oxidation state to a higher oxidation state at the anode; contacting a cathode with a cathode electrolyte in a cathode chamber; forming an alkali and hydrogen gas at the cathode. In some embodiments, there are provided methods that include contacting an anode with a metal ion in an anode electrolyte in an anode chamber; oxidizing the metal ion from a lower oxidation state to a higher oxidation state at the anode; contacting a cathode with a cathode electrolyte in a cathode chamber; forming an alkali and hydrogen gas at the cathode; and contacting the anode electrolyte comprising metal ion in the higher oxidation state with an unsaturated or saturated hydrocarbon to form halogenated hydrocarbon, or contacting the anode electrolyte comprising metal ion in the higher oxidation state with hydrogen gas to form an acid, or combination of both. In some embodiments, the method further includes separating the cathode and the anode by at least one ion exchange membrane. In some embodiments, the ion exchange membrane is a cation exchange membrane (CEM), an anion exchange membrane (AEM); or combination thereof. In some embodiments, the above recited method includes an anode that does not form a gas. In some embodiments, the method includes an anode that does not use a gas.

In some embodiments, there are provided systems that include an anode chamber comprising an anode in contact with a metal ion in an anode electrolyte, wherein the anode is configured to convert the metal ion from a lower oxidation state to a higher oxidation state; and a cathode chamber comprising a cathode in contact with a cathode electrolyte, wherein the cathode is configured to produce an alkali and hydrogen gas. In some embodiments, there are provided systems that include an anode chamber comprising an anode in contact with a metal ion in an anode electrolyte, wherein the anode is configured to convert the metal ion from a lower oxidation state to a higher oxidation state; and a cathode chamber comprising a cathode in contact with a cathode electrolyte, wherein the cathode is configured to produce an alkali and hydrogen gas; and a reactor operably connected to the anode chamber and configured to contact the anode electrolyte comprising metal ion in the higher oxidation state with an unsaturated or saturated hydrocarbon and/or hydrogen gas to form a halogenated hydrocarbon and acid, respectively. In some embodiments, the system is configured to not produce a gas at the anode. In some embodiments, the system is configured to not use a gas at the anode. In some embodiments, the system further includes at least one ion exchange membrane separating the cathode and the anode. In some embodiments, the ion exchange membrane is a cation exchange membrane (CEM), an anion exchange membrane (AEM); or combination thereof.

Figure 4A:
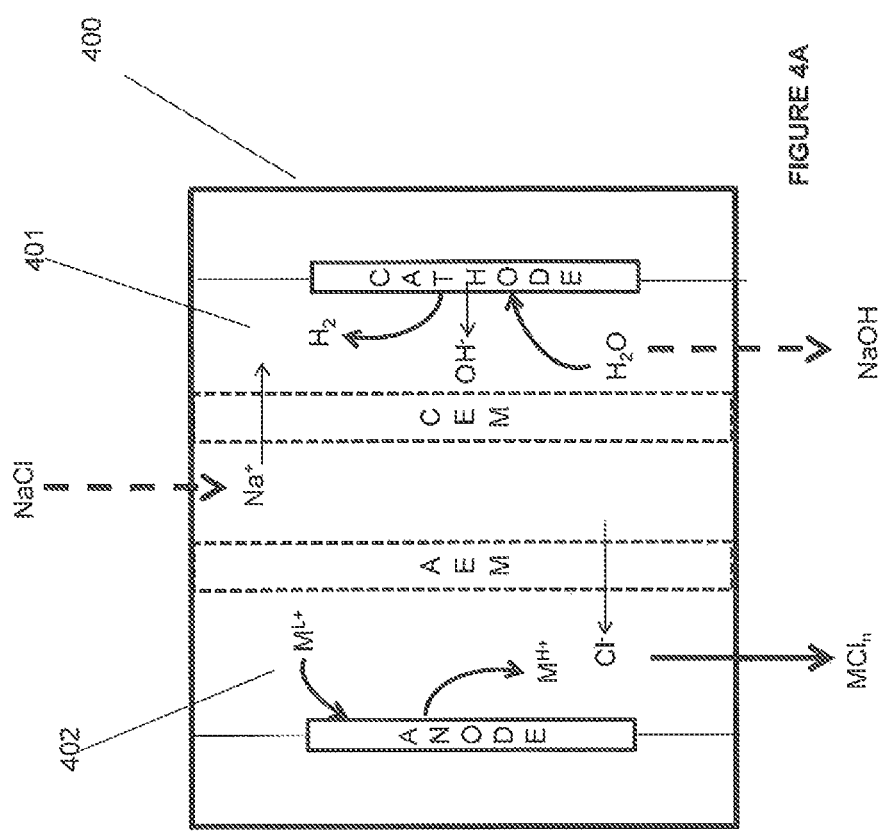
FIG. 4A is an illustration of an embodiment of the invention.

For example, as illustrated in FIG. 4A, the electrochemical system 400 includes a cathode in contact with the cathode electrolyte 401 where the hydroxide is formed in the cathode electrolyte. The system 400 also includes an anode in contact with the anode electrolyte 402 that converts metal ions in the lower oxidation state ($M^{L+}$) to metal ions in the higher oxidation states ($M^{H+}$). Following are the reactions that take place at the cathode and the anode:

$H_2O + e^- \rightarrow \frac{1}{2}H_2 + OH^-$ (cathode)

$M^{L+} \rightarrow M^{H+} + xe^-$ (anode where $x=1-3$)

For example, $Fe^{2+} \rightarrow Fe^{3+} + e^-$ (anode)

$Cr^{2+} \rightarrow Cr^{3+} + e^-$ (anode)

$Sn^{2+} \rightarrow Sn^{4+} + 2e^-$ (anode)

$Cu^+ \rightarrow Cu^{2+} + e^-$ (anode)

As illustrated in FIG. 4A, the electrochemical system 400 includes a cathode that forms hydroxide ions and hydrogen gas at the cathode. The hydrogen gas may be vented out or captured and stored for commercial purposes. In some embodiments, the hydrogen released at the cathode may be subjected to halogenations or sulfonation (including sulfation) with the metal halide or metal sulfate formed in the anode electrolyte to form hydrogen chloride, hydrochloric acid, hydrogen bromide, hydrobromic acid, hydrogen iodide, hydroiodic acid, or sulfuric acid. Such reaction is described in detail herein. The $M^{H+}$ formed at the anode combines with chloride ions to form metal chloride in the higher oxidation state such as, but not limited to, $FeCl_3$, $CrCl_3$, $SnCl_4$, or $CuCl_2$ etc. The hydroxide ion formed at the cathode combines with sodium ions to form sodium hydroxide.

It is to be understood that chloride ions in this application are for illustration purposes only and that other equivalent ions such as, but not limited to, sulfate, bromide or iodide are also well within the scope of the invention and would result in corresponding metal halide or metal sulfate in the anode electrolyte. It is also to be understood that $MCl_n$ shown in the figures illustrated herein, is a mixture of the metal ion in the lower oxidation state as well as the metal ion in the higher oxidation state. The integer n in $MCl_n$ merely represents the metal ion in the lower and higher oxidation state and may be from 1-5 or more depending on the metal ion. For example, in some embodiments, where copper is the metal ion, the $MCl_n$ may be a mixture of $CuCl$ and $CuCl_2$. This mixture of copper ions in the anode electrolyte may be then contacted with the hydrogen gas, unsaturated hydrocarbon, and/or saturated hydrocarbon to form respective products.

In some embodiments, the cathode used in the electrochemical systems of the invention, is a hydrogen gas producing cathode that does not form an alkali. Accordingly, in some embodiments, there are provided methods that include contacting an anode with a metal ion in an anode electrolyte in an anode chamber; oxidizing the metal ion from a lower oxidation state to a higher oxidation state at the anode; contacting a cathode with a cathode electrolyte in a cathode chamber; forming hydrogen gas at the cathode. In some embodiments, there are provided methods that include contacting an anode with a metal ion in an anode electrolyte in an anode chamber; oxidizing the metal ion from a lower oxidation state to a higher oxidation state at the anode; contacting a cathode with a cathode electrolyte in a cathode chamber; forming hydrogen gas at the cathode; and contacting the anode electrolyte comprising metal ion in the higher oxidation state with an unsaturated or saturated hydrocarbon to form halogenated hydrocarbon, or contacting the anode electrolyte comprising metal ion in the higher oxidation state with hydrogen gas to form an acid, or combination of both. In some embodiments, the method further includes separating the cathode and the anode by at least one ion exchange membrane. In some embodiments, the ion exchange membrane is a cation exchange membrane (CEM), an anion exchange membrane (AEM); or combination thereof. In some embodiments, the above recited method includes an anode that does not form a gas. In some embodiments, the method includes an anode that does not use a gas.

In some embodiments, there are provided systems that include an anode chamber comprising an anode in contact with a metal ion in an anode electrolyte, wherein the anode is configured to convert the metal ion from a lower oxidation state to a higher oxidation state; and a cathode chamber comprising a cathode in contact with a cathode electrolyte, wherein the cathode is configured to produce hydrogen gas. In some embodiments, there are provided systems that include an anode chamber comprising an anode in contact with a metal ion in an anode electrolyte, wherein the anode is configured to convert the metal ion from a lower oxidation state to a higher oxidation state; and a cathode chamber comprising a cathode in contact with a cathode electrolyte, wherein the cathode is configured to produce hydrogen gas; and a reactor operably connected to the anode chamber and configured to contact the anode electrolyte comprising metal ion in the higher oxidation state with an unsaturated or saturated hydrocarbon and/or hydrogen gas to form a halogenated hydrocarbon and acid, respectively. In some embodiments, the system is configured to not produce a gas at the anode. In some embodiments, the system is configured to not use a gas at the anode. In some embodiments, the system further includes at least one ion exchange membrane separating the cathode and the anode. In some embodiments, the ion exchange membrane is a cation exchange membrane (CEM), an anion exchange membrane (AEM); or combination thereof.

For example, as illustrated in FIG. 4B, the electrochemical system 400 includes a cathode in contact with the cathode electrolyte 401 where the hydrochloric acid delivered to the cathode electrolyte is transformed to hydrogen gas in the cathode electrolyte. The system 400 also includes an anode in contact with the anode electrolyte 402 that converts metal ions in the lower oxidation state ($M^{L+}$) to metal ions in the higher oxidation states ($M^{H+}$). Following are the reactions that take place at the cathode and the anode:

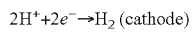
$2H^+ + 2e^- \rightarrow H_2$ (cathode)

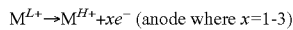
$M^{L+} \rightarrow M^{H+} + xe^-$ (anode where $x=1\text{-}3$)

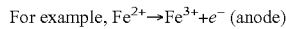
For example, $Fe^{2+} \rightarrow Fe^{3+} + e^-$ (anode)

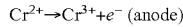
$Cr^{2+} \rightarrow Cr^{3+} + e^-$ (anode)

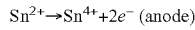
$Sn^{2+} \rightarrow Sn^{4+} + 2e^-$ (anode)

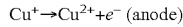
$Cu^+ \rightarrow Cu^{2+} + e^-$ (anode)

As illustrated in FIG. 4B, the electrochemical system 400 includes a cathode that forms hydrogen gas at the cathode. The hydrogen gas may be vented out or captured and stored for commercial purposes. In some embodiments, the hydrogen released at the cathode may be subjected to halogenations or sulfonation (including sulfation) with the metal halide or metal sulfate formed in the anode electrolyte to form hydrogen chloride, hydrochloric acid, hydrogen bromide, hydrobromic acid, hydrogen iodide, hydroiodic acid, or sulfuric acid. Such reaction is described in detail herein. The $M^{H+}$ formed at the anode combines with chloride ions to form metal chloride in the higher oxidation state such as, but not limited to, $FeCl_3$, $CrCl_3$, $SnCl_4$, or $CuCl_2$ etc. The hydroxide ion formed at the cathode combines with sodium ions to form sodium hydroxide.

It is to be understood that one AEM in FIG. 4B is for illustration purposes only and the system can be designed to have CEM with HCl delivered into the anode electrolyte and the hydrogen ions passing through the CEM to the cathode electrolyte. In some embodiments, the system illustrated in FIG. 4B may contain both AEM and CEM with the middle chamber containing a chloride salt. It is also to be understood that $MCl_n$ shown in the figures illustrated herein, is a mixture of the metal ion in the lower oxidation state as well as the metal ion in the higher oxidation state. The integer n in $MCl_n$ merely represents the metal ion in the lower and higher oxidation state and may be from 1-5 or more depending on the metal ion. For example, in some embodiments, where copper is the metal ion, the $MCl_n$ may be a mixture of CuCl and $CuCl_2$. This mixture of copper ions in the anode electrolyte may be then contacted with the hydrogen gas, unsaturated hydrocarbon, and/or saturated hydrocarbon to form respective products.

In some embodiments, the cathode in the electrochemical systems of the invention may be a gas-diffusion cathode. In some embodiments, the cathode in the electrochemical systems of the invention may be a gas-diffusion cathode forming an alkali at the cathode. In some embodiments, there are provided methods that include contacting an anode with a metal ion in an anode electrolyte; oxidizing the metal ion from a lower oxidation state to a higher oxidation state at the anode; and contacting a gas-diffusion cathode with a cathode electrolyte. In some embodiments, the gas-diffusion cathode is an oxygen depolarized cathode (ODC). In some embodiments: the method includes forming an alkali at the ODC. In some embodiments, there are provided methods that include contacting an anode with an anode electrolyte, oxidizing a metal ion from the lower oxidation state to a higher oxidation state at the anode; and contacting a cathode with a cathode electrolyte wherein the cathode is an oxygen depolarizing cathode that reduces oxygen and water to hydroxide ions. In some embodiments, there are provided methods that include contacting an anode with a metal ion in an anode electrolyte in an anode chamber; oxidizing the metal ion from a lower oxidation state to a higher oxidation state at the anode; contacting a gas-diffusion cathode with a cathode electrolyte in a cathode chamber; forming an alkali at the cathode; and contacting the anode electrolyte comprising the metal ion in the higher oxidation state with an unsaturated and/or saturated hydrocarbon to form halogenated hydrocarbon, or contacting the anode electrolyte comprising the metal ion in the higher oxidation state with hydrogen gas to form an acid, or combination of both. In some embodiments, the gas-diffusion cathode does not form a gas. In some embodiments, the method includes an anode that does not form a gas. In some embodiments, the method includes an anode that does not use a gas. In some embodiments, the method further includes separating the cathode and the anode by at least one ion exchange membrane. In some embodiments, the ion exchange membrane is a cation exchange membrane (CEM), an anion exchange membrane (AEM); or combination thereof.

In some embodiments, there are provided systems that include an anode chamber comprising an anode in contact with a metal ion in an anode electrolyte, wherein the anode is configured to convert or oxidize the metal ion from a lower oxidation state to a higher oxidation state; and a cathode chamber comprising a gas-diffusion cathode in contact with a cathode electrolyte, wherein the cathode is configured to produce an alkali. In some embodiments, the gas-diffusion cathode is an oxygen depolarized cathode (ODC). In some embodiments, there are provided systems that include an anode chamber comprising an anode in contact with a metal ion in an anode electrolyte, wherein the anode is configured to convert the metal ion from a lower oxidation state to a higher oxidation state; and a cathode chamber comprising a gas-diffusion cathode in contact with a cathode electrolyte, wherein the cathode is configured to produce an alkali; and a reactor operably connected to the anode chamber and configured to contact the anode electrolyte comprising the metal ion in the higher oxidation state with an unsaturated and/or saturated hydrocarbon and/or hydrogen gas to form a halogenated hydrocarbon and acid, respectively. In some embodiments, the system is configured to not produce a gas at the gas-diffusion cathode. In some embodiments, the system is configured to not produce a gas at the anode. In some embodiments, the system is configured to not use a gas at the anode. In some embodiments, the system further includes at least one ion exchange membrane separating the cathode and the anode. In some embodiments, the ion exchange membrane is a cation exchange membrane (CEM), an anion exchange membrane (AEM); or combination thereof.

As used herein, the "gas-diffusion cathode," or "gas-diffusion electrode," or other equivalents thereof include any electrode capable of reacting a gas to form ionic species. In some embodiments, the gas-diffusion cathode, as used herein, is an oxygen depolarized cathode (ODC). Such gas-diffusion cathode may be called gas-diffusion electrode, oxygen consuming cathode, oxygen reducing cathode, oxygen breathing cathode, oxygen depolarized cathode, and the like.

Figure 5A:
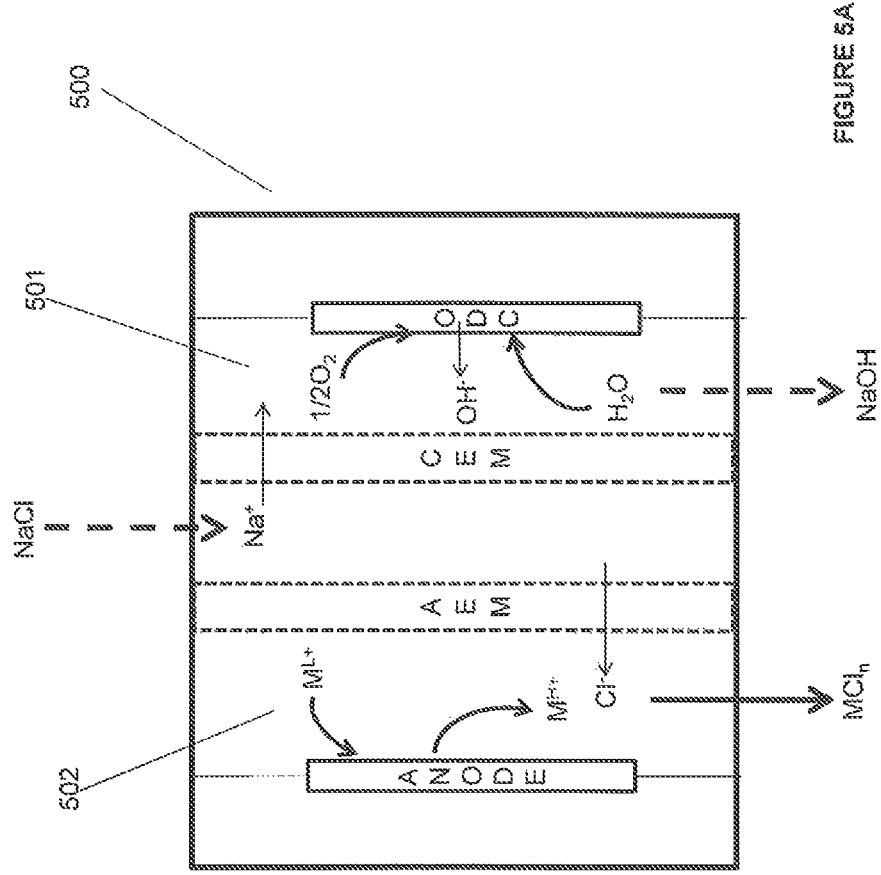
FIG. 5A is an illustration of an embodiment of the invention.

In some embodiments, as illustrated in FIG. 5A, the combination of the gas diffusion cathode (e.g., ODC) and the anode in the electrochemical cell may result in the generation of alkali in the cathode chamber. In some embodiments, the electrochemical system 500 includes a gas diffusion cathode in contact with a cathode electrolyte 501 and an anode in contact with an anode electrolyte 502. The anode and the cathode are separated by an anion exchange membrane (AEM) and a cation exchange membrane (CEM). A third electrolyte (e.g., sodium halide or sodium sulfate) is disposed between the AEM and the CEM. Following are the reactions that may take place at the anode and the cathode.

$$H_2O + \tfrac{1}{2}O_2 + 2e^- \rightarrow 2OH^- \text{ (cathode)}$$

$$M^{L+} \rightarrow M^{H+} + xe^- \text{ (anode where } x=1\text{-}3\text{)}$$

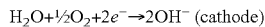

For example, $2Fe^{2+} \rightarrow 2Fe^{3+} + 2e^-$ (anode)

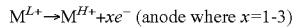

$2Cr^{2+} \rightarrow 2Cr^{3+} + 2e^-$ (anode)

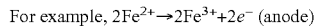

$Sn^{2+} \rightarrow Sn^{4+} + 2e^-$ (anode)

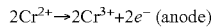

$2Cu^+ \rightarrow 2Cu^{2+} + 2e^-$ (anode)

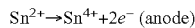

The $M^{H+}$ formed at the anode combines with chloride ions to form metal chloride $MCl_n$ such as, but not limited to, $FeCl_3$, $CrCl_3$, $SnCl_4$, or $CuCl_2$ etc. The hydroxide ion formed at the cathode reacts with sodium ions to form sodium hydroxide. The oxygen at the cathode may be atmospheric air or any commercial available source of oxygen.

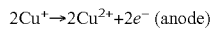

The methods and systems containing the gas-diffusion cathode or the ODC, as described herein and illustrated in FIG. 5A, may result in voltage savings as compared to methods and systems that include the hydrogen gas producing cathode (as illustrated in FIG. 4A). The voltage savings in-turn may result in less electricity consumption and less carbon dioxide emission for electricity generation. This may result in the generation of greener chemicals such as sodium hydroxide, halogentated hydrocarbons and/or acids, that are formed by the efficient and energy saving methods and systems of the invention. In some embodiments, the electrochemical cell with ODC has a theoretical voltage savings of more than 0.5V, or more than 1V, or more than 1.5V, or between 0.5-1.5V, as compared to the electrochemical cell with no ODC or as compared to the electrochemical cell with hydrogen gas producing cathode. In some embodiments, this voltage saving is achieved with a cathode electrolyte pH of between 7-15, or between 7-14, or between 6-12, or between 7-12, or between 7-10.

The overall cell potential can be determined through the combination of Nernst equations for each half cell reaction:

$$E = E° - RT \ln(Q)/nF$$

where, $E°$ is the standard reduction potential, R is the universal gas constant (8.314 J/mol K), T is the absolute temperature, n is the number of electrons involved in the half cell reaction, F is Faraday's constant (96485 J/V mol), and Q is the reaction quotient so that:

$$E_{total} = E_{anode} - E_{cathode}$$

When metal in the lower oxidation state is oxidized to metal in the higher oxidation state at the anode as follows:

$$Cu^+ \rightarrow Cu^{2+} + 2e^-$$

$E_{anode}$ based on varying concentration of copper II species may be between 0.159-0.75V.

When water is reduced to hydroxide ions and hydrogen gas at the cathode (as illustrated in FIG. 4A) as follows:

$$2H_2O + 2e^- = H_2 + 2OH^-,$$

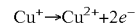

$E_{cathode} = -0.059$ $pH_c$, where $pH_c$ is the pH of the cathode electrolyte=14

$$E_{cathode} = -0.83$$

$E_{total}$ then is between 0.989 to 1.53, depending on the concentration of copper ions in the anode electrolyte.

When water is reduced to hydroxide ions at ODC (as illustrated in FIG. 5A) as follows:

$$2H_2O + O_2 + 4e^- \rightarrow 4OH^-$$

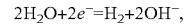

$E_{cathode} = 1.224 - 0.059$ $pH_c$, where $pH_c = 14$ $$E_{cathode} = 0.4V$$

$E_{total}$ then is between $-0.241$ to $0.3V$ depending on the concentration of copper ions in the anode electrolyte.

Therefore, the use of ODC in the cathode chamber brings the theoretical voltage savings in the cathode chamber or the theoretical voltage savings in the cell of about 1.5V or between 0.5-2V or between 0.5-1.5V or between 1-1.5V, as compared to the electrochemical cell with no ODC or as compared to the electrochemical cell with hydrogen gas producing cathode.

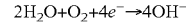

Accordingly, in some embodiments, there are provided methods that include contacting an anode with a metal ion in an anode electrolyte; contacting an oxygen depolarizing cathode with a cathode electrolyte; applying a voltage to the anode and the cathode; forming an alkali at the cathode; converting the metal ion from a lower oxidation state to a higher oxidation state at the anode; and saving a voltage of more than 0.5V or between 0.5-1.5V as compared to the hydrogen gas producing cathode or as compared to the cell with no ODC. In some embodiments, there are provided systems that include an anode chamber comprising an anode in contact with a metal ion in an anode electrolyte, wherein the anode is configured to convert the metal ion from a lower oxidation state to a higher oxidation state; and a cathode chamber comprising an oxygen depolarizing cathode in contact with a cathode electrolyte, wherein the cathode is configured to produce an alkali, wherein the system provides a voltage savings of more than 0.5V or between 0.5-1.5V as compared to the system with the hydrogen gas producing cathode or as compared to the system with no ODC. In some embodiments, the voltage savings is a theoretical voltage saving which may change depending on the ohmic resistances in the cell.

While the methods and systems containing the gas-diffusion cathode or the ODC result in voltage savings as compared to methods and systems containing the hydrogen gas producing cathode, both the systems i.e. systems containing the ODC and the systems containing hydrogen gas producing cathode of the invention, show significant voltage savings as compared to chlor-alkali system conventionally known in the art. The voltage savings in-turn may result in less electricity consumption and less carbon dioxide emission for electricity generation. This may result in the generation of greener chemicals such as sodium hydroxide, halogentated hydrocarbons and/or acids, that are formed by the efficient and energy saving methods and systems of the invention. For example, the voltage savings is beneficial in production of the halogenated hydrocarbons, such as EDC, which is typically formed by reacting ethylene with chlorine gas generated by the high voltage consuming chlor-alkali process. In some embodiments, the electrochemical system of the invention (2 or 3-compartment cells with hydrogen gas producing cathode or ODC) has a theoretical voltage savings of more than 0.5V, or more than 1V, or more than 1.5V, or between 0.5-3V, as compared to chlor-alkali process. In some embodiments, this voltage saving is achieved with a cathode electrolyte pH of between 7-15, or between 7-14, or between 6-12, or between 7-12, or between 7-10.

For example, theoretical $E_{anode}$ in the chlor-alkali process is about 1.36V undergoing the reaction as follows:

$$2Cl^- \rightarrow Cl_2 + 2e^-,$$

Theoretical $E_{cathode}$ in the chlor-alkali process is about −0.83V (at pH>14) undergoing the reaction as follows:

$$2H_2O + 2e^- = H_2 + 2OH^-$$

Theoretical $E_{total}$ for the chlor-alkali process then is 2.19V. Theoretical $E_{total}$ for the hydrogen gas producing cathode in the system of the invention is between 0.989 to 1.53V and $E_{total}$ for ODC in the system of the invention then is between −0.241 to 0.3V, depending on the concentration of copper ions in the anode electrolyte. Therefore, the electrochemical systems of the invention bring the theoretical voltage savings in the cathode chamber or the theoretical voltage savings in the cell of greater than 3V or greater than 2V or between 0.5-2.5V or between 0.5-2.0V or between 0.5-1.5V or between 0.5-1.0V or between 1-1.5V or between 1-2V or between 1-2.5V or between 1.5-2.5V, as compared to the chlor-alkali system.

In some embodiments, the electrochemical cell may be conditioned with a first electrolyte and may be operated with a second electrolyte. For example, in some embodiments, the electrochemical cell and the AEM, CEM or combination thereof are conditioned with sodium sulfate as the electrolyte and after the stabilization of the voltage with sodium sulfate, the cell may be operated with sodium chloride as the electrolyte. An illustrative example of such stabilization of the electrochemical cell is described in Example 13 herein. Accordingly, in some embodiments, there are provided methods that include contacting an anode with a first anode electrolyte in an anode chamber; contacting a cathode with a cathode electrolyte in a cathode chamber; separating the cathode and the anode by at least one ion exchange membrane; conditioning the ion exchange membrane with the first anode electrolyte in the anode chamber; contacting the anode with a second anode electrolyte comprising metal ion; oxidizing the metal ion from a lower oxidation state to a higher oxidation state at the anode; and forming an alkali, water, and/or hydrogen gas at the cathode. In some embodiments, the first anode electrolyte is sodium sulfate and the second anode electrolyte is sodium chloride. In some embodiments, the method further comprises contacting the second anode electrolyte comprising metal ion in the higher oxidation state with an unsaturated and/or saturated hydrocarbon to form halogenated hydrocarbon, or contacting the second anode electrolyte comprising metal ion in the higher oxidation state with hydrogen gas to form an acid, or combination of both. In some embodiments, the ion exchange membrane is a cation exchange membrane (CEM), an anion exchange membrane (AEM); or combination thereof.

In some embodiments, the cathode in the electrochemical systems of the invention may be a gas-diffusion cathode that reacts HCl and oxygen gas to form water. In some embodiments, there are provided methods that include contacting an anode with a metal ion in an anode electrolyte; oxidizing the metal ion from a lower oxidation state to a higher oxidation state at the anode; and contacting a gas-diffusion cathode with a cathode electrolyte. In some embodiments, the gas-diffusion cathode is an oxygen depolarized cathode (ODC). In some embodiments, the method includes reacting HCl and oxygen gas to form water at the ODC. In some embodiments, there are provided methods that include contacting an anode with an anode electrolyte, oxidizing a metal ion from the lower oxidation state to a higher oxidation state at the anode; and contacting a cathode with a cathode electrolyte wherein the cathode is an oxygen depolarizing cathode that reacts oxygen and HCl to form water. In some embodiments, there are provided methods that include contacting an anode with a metal ion in an anode electrolyte in an anode chamber; oxidizing the metal ion from a lower oxidation state to a higher oxidation state at the anode; contacting a gas-diffusion cathode with a cathode electrolyte in a cathode chamber; forming water at the cathode from HCl and oxygen gas; and contacting the anode electrolyte comprising the metal ion in the higher oxidation state with an unsaturated and/or saturated hydrocarbon to form halogenated hydrocarbon, or contacting the anode electrolyte comprising the metal ion in the higher oxidation state with hydrogen gas to form an acid, or combination of both. In some embodiments, the gas-diffusion cathode does not form a gas. In some embodiments, the method includes an anode that does not form a gas. In some embodiments, the method includes an anode that does not use a gas. In some embodiments, the method further includes separating the cathode and the anode by at least one ion exchange membrane. In some embodiments, the ion exchange membrane is a cation exchange membrane (CEM), an anion exchange membrane (AEM); or combination thereof.

In some embodiments, there are provided systems that include an anode chamber comprising an anode in contact with a metal ion in an anode electrolyte, wherein the anode is configured to convert or oxidize the metal ion from a lower oxidation state to a higher oxidation state; and a cathode chamber comprising a gas-diffusion cathode in contact with a cathode electrolyte, wherein the cathode is configured to produce water from HCl. In some embodiments, the gas-diffusion cathode is an oxygen depolarized cathode (ODC). In some embodiments, there are provided systems that include an anode chamber comprising an anode in contact with a metal ion in an anode electrolyte, wherein the anode is configured to convert the metal ion from a lower oxidation state to a higher oxidation state; and a cathode chamber comprising a gas-diffusion cathode in contact with a cathode electrolyte, wherein the cathode is configured to produce water from HCl; and a reactor operably connected to the anode chamber and configured to contact the anode electrolyte comprising the metal ion in the higher oxidation state with an unsaturated and/or saturated hydrocarbon and/or hydrogen gas to form a halogenated hydrocarbon and acid, respectively. In some embodiments, the system is configured to not produce a gas at the gas-diffusion cathode. In some embodiments, the system is configured to not produce a gas at the anode. In some embodiments, the system is configured to not use a gas at the anode. In some embodiments, the system further includes at least one ion exchange membrane separating the cathode and the anode. In some embodiments, the ion exchange membrane is a cation exchange membrane (CEM), an anion exchange membrane (AEM); or combination thereof.

Figure 5B:
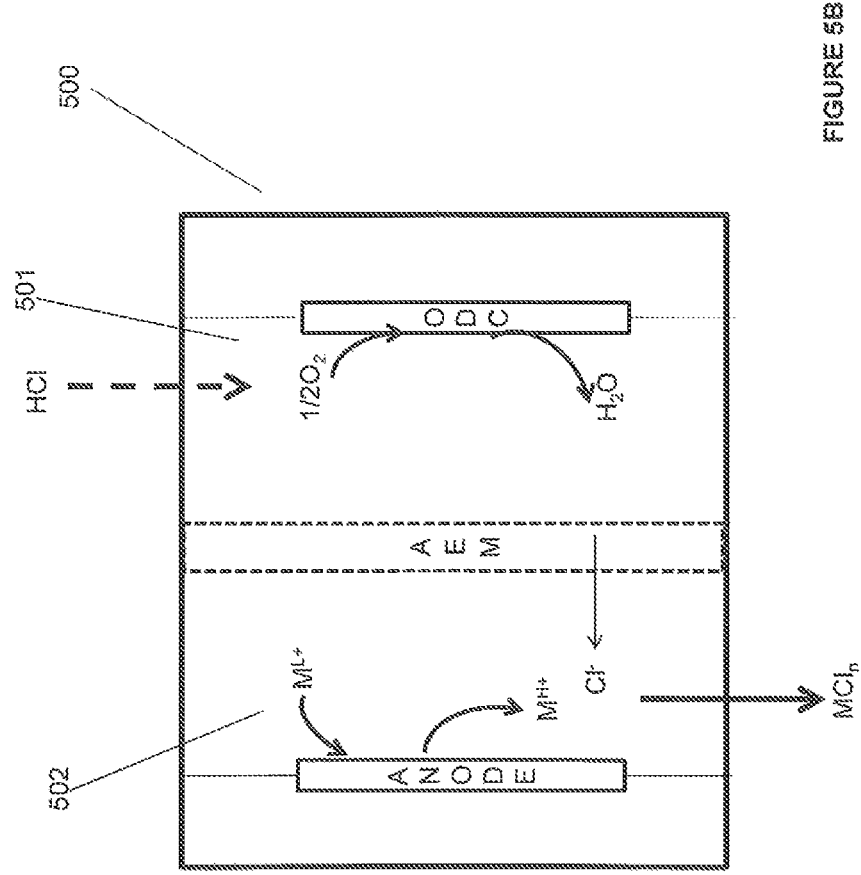
FIG. 5B is an illustration of an embodiment of the invention.

In some embodiments, as illustrated in FIG. 5B, the combination of the gas diffusion cathode (e.g., ODC) and the anode in the electrochemical cell may result in the generation of water in the cathode chamber. In some embodiments, the electrochemical system 500 includes a gas diffusion cathode in contact with a cathode electrolyte 501 and an anode in contact with an anode electrolyte 502. Following are the reactions that may take place at the anode and the cathode.

$$2H^+ + \tfrac{1}{2}O_2 + 2e^- \rightarrow H_2O \text{ (cathode)}$$

$$M^{L+} \rightarrow M^{H+} + xe^- \text{ (anode where } x=1\text{-}3)$$

For example, $2Fe^{2+} \rightarrow 2Fe^{3+} + 2e^-$ (anode)

$$2Cr^{2+} \rightarrow 2Cr^{3+} + 2e^- \text{ (anode)}$$

$$Sn^{2+} \rightarrow Sn^{4+} + 2e^- \text{ (anode)}$$

$$2Cu^+ \rightarrow 2Cu^{2+} + 2e^- \text{ (anode)}$$

The $M^{H+}$ formed at the anode combines with chloride ions to form metal chloride $MCl_n$ such as, but not limited to, $FeCl_3$, $CrCl_3$, $SnCl_4$, or $CuCl_2$ etc. The oxygen at the cathode may be atmospheric air or any commercial available source of oxygen. It is to be understood that one AEM in FIG. 5B is for illustration purposes only and the system can be designed to have CEM with HCl delivered into the anode electrolyte and the hydrogen ions passing through the CEM to the cathode electrolyte. In some embodiments, the system illustrated in FIG. 5B may contain both AEM and CEM with the middle chamber containing a chloride salt.

Figure 5C:
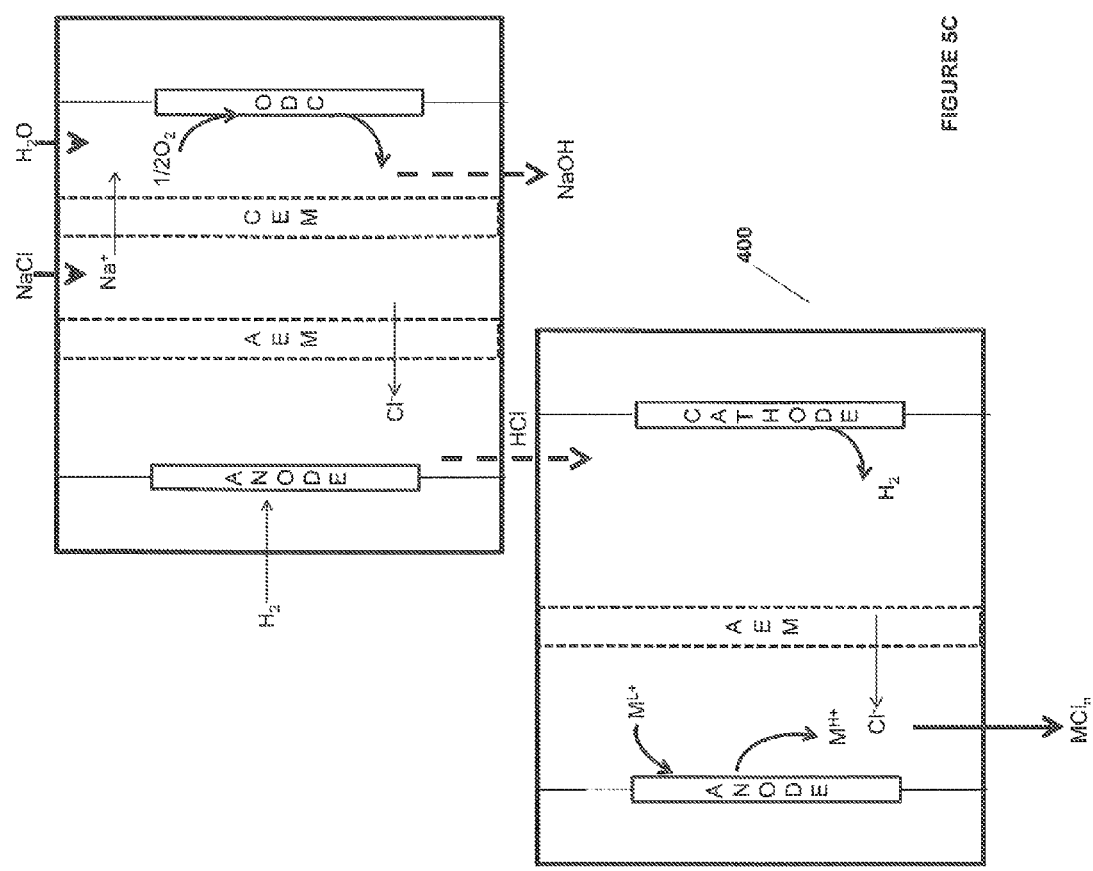
FIG. 5C is an illustration of an embodiment of the invention.

In some embodiments, the electrochemical systems of the invention may be combined with other electrochemical cells for an efficient and low energy intensive system. For example, in some embodiments, as illustrated in FIG. 5C, the electrochemical system 400 of FIG. 4B may be combined with another electrochemical cell such that the hydrochloric acid formed in the other electrochemical cell is administered to the cathode electrolyte of the system 400. The electrochemical system 400 may be replaced with system 100A (FIG. 1A), 100B (FIG. 1B), 200 (FIG. 2), 400 (FIG. 4A), 500 (FIGS. 5A and 5B), except that the cathode compartment is modified to receive HCl from another electrochemical cell and oxidize it to form hydrogen gas. The chloride ions migrate from the cathode electrolyte to anode electrolyte through the AEM. This may result in an overall improvement in the voltage of the system, e.g., the theoretical cell voltage of the system may be between 0.1-0.7V. In some embodiments, when the cathode is an ODC, the theoretical cell voltage may be between −0.5 to −1V. The electrochemical cells producing HCl in the anode electrolyte have been described in U.S. patent application Ser. No. 12/503,557, filed Jul. 15, 2009, which is incorporated herein by reference in its entirety. Other sources of HCl are well known in the art. An example of HCl source from VCM production process and its integration into the electrochemical system of the invention, is illustrated in FIG. 8B below.

In some embodiments of the methods and systems described herein, a size exclusion membrane (SEM) is used in conjunction with or in place of anion exchange membrane (AEM). In some embodiments, the AEM is surface coated with a layer of SEM. In some embodiments, the SEM is bonded or pressed against the AEM. The use of SEM with or in place of AEM can prevent migration of the metal ion or ligand attached metal ion from the anolyte to the catholyte owing to the large size of the metal ion alone or attached to the ligand. This can further prevent fouling of CEM or contamination of the catholyte with the metal ion. It is to be understood that this use of SEM in combination with or in place of AEM will still facilitate migration of chloride ions from the third electrolyte into the anolyte. In some embodiments, there are provided methods that include contacting an anode with an anode electrolyte; oxidizing a metal ion from the lower oxidation state to a higher oxidation state at the anode; contacting a cathode with a cathode electrolyte; and preventing migration of the metal ions from the anode electrolyte to the cathode electrolyte by using a size exclusion membrane. In some embodiments, this method further includes a cathode that produces alkali in the cathode electrolyte, or an oxygen depolarized cathode that produces alkali in the cathode electrolyte or an oxygen depolarized cathode that produces water in the cathode electrolyte or a cathode that produces hydrogen gas. In some embodiments, this method further includes contacting the anode electrolyte comprising the metal ion in the higher oxidation state with an unsaturated or saturated hydrocarbon to form halogenated hydrocarbon, or contacting the anode electrolyte comprising the metal ion in the higher oxidation state with hydrogen gas to form an acid, or combination of both. In some embodiments, the unsaturated hydrocarbon in such methods is ethylene. In some embodiments, the metal ion in such methods is copper chloride. In some embodiments, the unsaturated hydrocarbon in such methods is ethylene and the metal ion is copper chloride. An example of halogenated hydrocarbon that can be formed from ethylene is ethylene dichloride, EDC.

In some embodiments, there are provided systems that include an anode in contact with an anode electrolyte and configured to oxidize a metal ion from the lower oxidation state to a higher oxidation state; a cathode in contact with a cathode electrolyte; and a size exclusion membrane disposed between the anode and the cathode and configured to prevent migration of the metal ions from the anode electrolyte to the cathode electrolyte. In some embodiments, this system further includes a cathode that is configured to produce alkali in the cathode electrolyte or produce water in the cathode electrolyte or produce hydrogen gas. In some embodiments, this system further includes an oxygen depolarized cathode that is configured to produce alkali and/or water in the cathode electrolyte. In some embodiments, this system further includes a hydrogen gas producing cathode. In some embodiments, this system further includes a reactor operably connected to the anode chamber and configured to contact the anode electrolyte comprising the metal ion in the higher oxidation state with an unsaturated or saturated hydrocarbon to form halogenated hydrocarbon, or to contact the anode electrolyte comprising the metal ion in the higher oxidation state with hydrogen gas to form an acid, or combination of both. In some embodiments, the unsaturated hydrocarbon in such systems is ethylene. In some embodiments, the metal ion in such systems is copper chloride. In some embodiments, the unsaturated hydrocarbon in such systems is ethylene and the metal ion is copper chloride. An example of halogenated hydrocarbon that can be formed from ethylene is EDC.

In some embodiments, the size exclusion membrane as defined herein above and herein, fully prevents the migration of the metal ion to the cathode chamber or the middle chamber with the third electrolyte or reduces the migration by 100%; or by 99%; or by 95% or by 75%; or by 50%; or by 25%; or between 25-50%; or between 50-75%; or between 50-95%.

In some embodiments, the AEM used in the methods and systems of the invention, is resistant to the organic compounds (such as ligands or hydrocarbons) such that AEM does not interact with the organics and/or the AEM does not react or absorb metal ions. This can be achieved, for example only, by using a polymer that does not contain a free radical or anion available for reaction with organics or with metal ions. For example only, a fully quaternized amine containing polymer may be used as an AEM. Other examples of AEM have been described herein.

In some embodiments, the metal formed with a higher oxidation state in the anode electrolyte is subjected to reactions that may result in corresponding oxidized products (halogenated hydrocarbon and/or acid) as well as the metal in the reduced lower oxidation state. The metal ion in the lower oxidation state may then be re-circulated back to the electrochemical system for the generation of the metal ion in the higher oxidation state. Such reactions to re-generate the metal ion in the lower oxidation state from the metal ion in the higher oxidation state, include, but are not limited to, reactions with hydrogen gas or hydrocarbons as described herein.

Reaction with Hydrogen Gas, Unsaturated Hydrocarbon, and Saturated Hydrocarbon

In some embodiments, there are provided methods that include contacting an anode with a metal ion in an anode electrolyte in an anode chamber; converting or oxidizing the metal ion from a lower oxidation state to a higher oxidation state at the anode; and treating the metal ion in the higher oxidation state with hydrogen gas. In some embodiments of the method, the method includes contacting a cathode with a cathode electrolyte and forming an alkali in the cathode electrolyte. In some embodiments of the method, the method includes contacting a cathode with a cathode electrolyte and forming an alkali and/or hydrogen gas at the cathode. In some embodiments of the method, the method includes contacting a cathode with a cathode electrolyte and forming an alkali, water, and/or hydrogen gas at the cathode. In some embodiments of the method, the method includes contacting a gas-diffusion cathode with a cathode electrolyte and forming an alkali at the cathode. In some embodiments, there are provided methods that include contacting an anode with a metal ion in an anode electrolyte in an anode chamber; converting the metal ion from a lower oxidation state to a higher oxidation state at the anode; contacting a cathode with a cathode electrolyte; forming an alkali, water or hydrogen gas at the cathode; and treating the metal ion in the higher oxidation state in the anode electrolyte with hydrogen gas from the cathode. In some embodiments, there are provided methods that include contacting an anode with a metal ion in an anode electrolyte in an anode chamber; converting the metal ion from a lower oxidation state to a higher oxidation state at the anode; contacting an oxygen depolarized cathode with a cathode electrolyte; forming an alkali or water at the cathode; and treating the metal ion in the higher oxidation state in the anode electrolyte with hydrogen gas. In some embodiments, there are provided methods that include contacting an anode with a metal ion in an anode electrolyte in an anode chamber; converting the metal ion from a lower oxidation state to a higher oxidation state at the anode; contacting a cathode with a cathode electrolyte; forming water or hydrogen gas at the cathode; and treating the metal ion in the higher oxidation state in the anode electrolyte with hydrogen gas. In some embodiments, the treatment of the hydrogen gas with the metal ion in the higher oxidation state may be inside the cathode chamber or outside the cathode chamber. In some embodiments, the above recited methods include forming hydrogen chloride, hydrochloric acid, hydrogen bromide, hydrobromic acid, hydrogen iodide, hydroiodic acid and/or sulfuric acid by treating the metal ion in the higher oxidation state with the hydrogen gas. In some embodiments, the treatment of the metal ion in the higher oxidation state with the hydrogen gas results in forming hydrogen chloride, hydrochloric acid, hydrogen bromide, hydrobromic acid, hydrogen iodide, hydroiodic acid, and/or sulfuric acid and the metal ion in the lower oxidation state. In some embodiments, the metal ion in the lower oxidation state is re-circulated back to the anode chamber. In some embodiments, the mixture of the metal ion in the lower oxidation state and the acid is subjected to acid retardation techniques to separate the metal ion in the lower oxidation state from the acid before the metal ion in the lower oxidation state is re-circulated back to the anode chamber.

In some embodiments of the above recited methods, the method does not produce chlorine gas at the anode.

In some embodiments, there are provided systems that include an anode chamber including an anode in contact with a metal ion in an anode electrolyte wherein the anode is configured to convert the metal ion from a lower oxidation state to a higher oxidation state; and a reactor operably connected to the anode chamber and configured to react the anode electrolyte comprising the metal ion in the higher oxidation state with hydrogen gas. In some embodiments of the systems, the system includes a cathode chamber including a cathode with a cathode electrolyte wherein the cathode is configured to form an alkali in the cathode electrolyte. In some embodiments of the systems, the system includes a cathode chamber including a cathode with a cathode electrolyte wherein the cathode is configured to form hydrogen gas in the cathode electrolyte. In some embodiments of the systems, the system includes a cathode chamber including a cathode with a cathode electrolyte wherein the cathode is configured to form an alkali and hydrogen gas in the cathode electrolyte. In some embodiments of the systems, the system includes a gas-diffusion cathode with a cathode electrolyte wherein the cathode is configured to form an alkali in the cathode electrolyte. In some embodiments of the systems, the system includes a gas-diffusion cathode with a cathode electrolyte wherein the cathode is configured to form water in the cathode electrolyte. In some embodiments, there are provided systems that include an anode chamber including an anode with a metal ion in an anode electrolyte wherein the anode is configured to convert the metal ion from a lower oxidation state to a higher oxidation state in the anode chamber; a cathode chamber including a cathode with a cathode electrolyte wherein the cathode is configured to form an alkali and/or hydrogen gas in the cathode electrolyte; and a reactor operably connected to the anode chamber and configured to react the anode electrolyte comprising the metal ion in the higher oxidation state with the hydrogen gas from the cathode. In some embodiments, the reactor is operably connected to the anode chamber and configured to react the anode electrolyte comprising the metal ion in the higher oxidation state with the hydrogen gas from the cathode of the same electrochemical cell or with the external source of hydrogen gas. In some embodiments, the treatment of the hydrogen gas with the metal ion in the higher oxidation state may be inside the cathode chamber or outside the cathode chamber. In some embodiments, the above recited systems include forming hydrogen chloride, hydrochloric acid, hydrogen bromide, hydrobromic acid, hydrogen iodide, hydroiodic acid, and/or sulfuric acid by reacting or treating the metal ion in the higher oxidation state with the hydrogen gas. In some embodiments, the treatment of the metal ion in the higher oxidation state with the hydrogen gas results in forming hydrogen chloride, hydrochloric acid, hydrogen bromide, hydrobromic acid, hydrogen iodide, hydroiodic acid, and/or sulfuric acid and the metal ion in the lower oxidation state. In some embodiments, the system is configured to form the metal ion in the lower oxidation state from the metal ion in the higher oxidation state with the hydrogen gas and re-circulate the metal ion in the lower oxidation state back to the anode chamber. In some embodiments, the system is configured to separate the metal ion in the lower oxidation state from the acid using acid retardation techniques such as, but not limited to, ion exchange resin, size exclusion membranes, and acid dialysis, etc.

In some embodiments of the above recited systems, the anode in the system is configured to not produce chlorine gas.

In some embodiments, the metal formed with a higher oxidation state in the anode electrolyte of the electrochemical systems of FIGS. 1A, 1B, 2, 3A, 3B, 4A, 4B, 5A and 5B may be reacted with hydrogen gas to from corresponding products based on the anion attached to the metal. For example, the metal chloride, metal bromide, metal iodide, or metal sulfate may result in corresponding hydrogen chloride, hydrochloric acid, hydrogen bromide, hydrobromic acid, hydrogen iodide, hydroiodic acid, or sulfuric acid, respectively, after reacting the hydrogen gas with the metal halide or metal sulfate. In some embodiments, the hydrogen gas is from an external source. In some embodiments, such as illustrated in FIG. 4A or 4B, the hydrogen gas reacted with the metal halide or metal sulfate, is the hydrogen gas formed at the cathode. In some embodiments, the hydrogen gas is obtained from a combination of the external source and the hydrogen gas formed at the cathode. In some embodiments, the reaction of metal halide or metal sulfate with the hydrogen gas results in the generation of the above described products as well as the metal halide or metal sulfate in the lower oxidation state. The metal ion in the lower oxidation state may then be re-circulated back to the electrochemical system for the generation of the metal ion in the higher oxidation state.

An example of the electrochemical system of FIG. 5A is as illustrated in FIG. 6. It is to be understood that the system 600 of FIG. 6 is for illustration purposes only and other metal ions with different oxidations states (e.g., chromium, tin etc.) and other electrochemical systems forming products other than alkali such as, water (as in FIG. 5B) or hydrogen gas (as in FIG. 4A or 4B), in the cathode chamber, are equally applicable to the system. In some embodiments, as illustrated in FIG. 6, the electrochemical system 600 includes an oxygen depolarized cathode that produces hydroxide ions from water and oxygen. The system 600 also includes an anode that converts metal ions from 2+ oxidation state to 3+ oxidation state (or from 2+ oxidation state to 4+ oxidation state, such as Sn, etc.). The $M^{3+}$ ions combine with chloride ions to form $MCl_3$. The metal chloride $MCl_3$ is then reacted with hydrogen gas to undergo reduction of the metal ion to lower oxidation state to form $MCl_2$. The $MCl_2$ is then re-circulated back to the anode chamber for conversion to $MCl_3$. Hydrochloric acid is generated in the process which may be used for commercial purposes or may be utilized in other processes as described herein. In some embodiments, the HCl produced by this method can be used for the dissolution of minerals to generate divalent cations that can be used in carbonate precipitation processes, as described herein. In some embodiments, the metal halide or metal sulfate in FIG. 6 may be reacted with the unsaturated or saturated hydrocarbon to form halohydrocarbon or sulfohydrocarbon, as described herein (not shown in the figures). In some embodiments, the cathode is not a gas-diffusion cathode but is a cathode as described in FIG. 4A or 4B. In some embodiments, the system 600 may be applied to any electrochemical system that produces alkali.

Figure 7A:
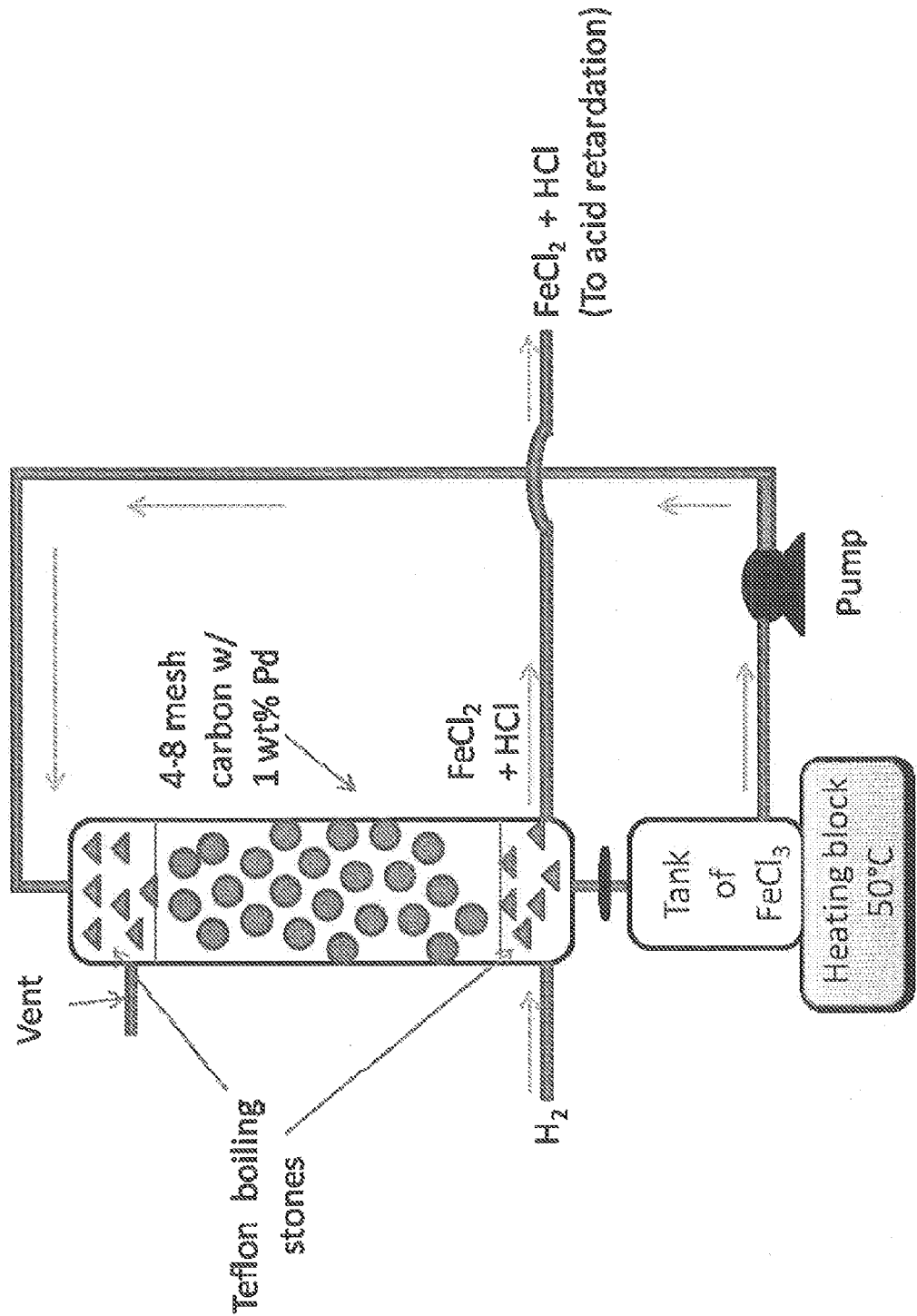
FIG. 7A is an illustration of an embodiment of the invention.

Some examples of the reactors that carry out the reaction of the metal compound with the hydrogen gas are provided herein. As an example, a reactor such as a reaction tower for the reaction of metal ion in the higher oxidation state (formed as shown in the figures) with hydrogen gas is illustrated in FIG. 7A. In some embodiments, as illustrated in FIG. 7A, the anolyte is passed through the reaction tower. The gas containing hydrogen is also delivered to the reaction tower. The excess of hydrogen gas may vent from the reaction tower which may be collected and transferred back to the reaction tower. Inside the reaction tower, the anolyte containing metal ions in higher oxidation state (illustrated as $FeCl_3$) may react with the hydrogen gas to form HCl and metal ions in lower oxidation state, i.e., reduced form illustrated as $FeCl_2$. The reaction tower may optionally contain activated charcoal or carbon or alternatively, the activated carbon may be present outside the reaction tower. The reaction of the metal ion with hydrogen gas may take place on the activated carbon from which the reduced anolyte may be regenerated or the activated carbon may simply act as a filter for removing impurities from the gases. The reduced anolyte containing HCl and the metal ions in lower oxidation state may be subjected to acid recovery using separation techniques or acid retardation techniques known in the art including, but not limited to, ion exchange resin, size exclusion membranes, and acid dialysis, etc. to separate HCl from the anolyte. In some embodiments, the ligands, described herein, may facilitate the separation of the metal ion from the acid solution due to the large size of the ligand attached to the metal ion. The anolyte containing the metal ion in the lower oxidation state may be re-circulated back to the electrochemical cell and HCl may be collected.

Figure 7B:
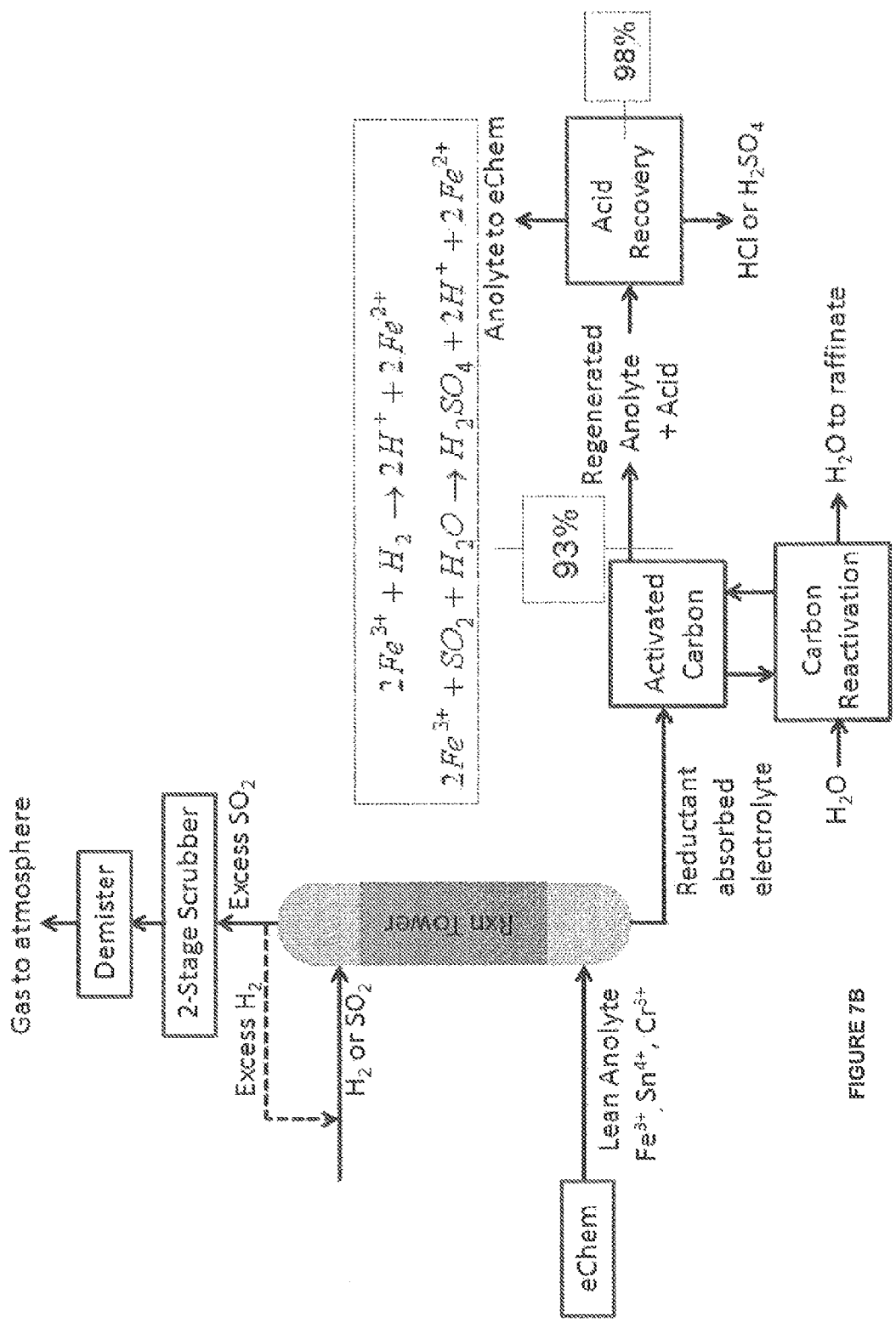
FIG. 7B is an illustration of an embodiment of the invention.

As another example of the reactor, the reaction of metal ion in the higher oxidation state (formed as shown in the figures) with hydrogen gas is also illustrated in FIG. 7B. As illustrated in FIG. 7B, the anolyte from the anode chamber containing the metal ions in the higher oxidation state, such as, but not limited to, $Fe^{3+}$, $Sn^{4+}$, $Cr^{3+}$, etc. may be used to react with hydrogen gas to form HCl or may be used to scrub the $SO_2$ containing gas to form clean gas or sulfuric acid. In some embodiments, it is contemplated that NOx gases may be reacted with the metal ions in the higher oxidation state to form nitric acid. In some embodiments, as illustrated in FIG. 7B, the anolyte is passed through a reaction tower. The gas containing hydrogen, $SO_2$, and/or NOx is also delivered to the reaction tower. The excess of hydrogen gas may vent from the reaction tower which may be collected and transferred back to the reaction tower. The excess of $SO_2$ may be passed through a scrubber before releasing the cleaner gas to the atmosphere. Inside the reaction tower, the anolyte containing metal ions in higher oxidation state may react with the hydrogen gas and/or $SO_2$ to form HCl and/or $H_2SO_4$ and metal ions in lower oxidation state, i.e., reduced form. The reaction tower may optionally contain activated charcoal or carbon or alternatively, the activated carbon may be present outside the reaction tower. The reaction of the metal ion with hydrogen gas or $SO_2$ gas may take place on the activated carbon from which the reduced anolyte may be regenerated or the activated carbon may simply act as a filter for removing impurities from the gases. The reduced anolyte containing HCl and/or $H_2SO_4$ and the metal ions in lower oxidation state may be subjected to acid recovery using separation techniques known in the art including, but not limited to, ion exchange resin, size exclusion membranes, and acid dialysis, etc. to separate HCl and/or $H_2SO_4$ from the anolyte. In some embodiments, the ligands, described herein, may facilitate the separation of the metal ion from the acid solution due to the large size of the ligand attached to the metal ion. The anolyte containing the metal ion in the lower oxidation state may be re-circulated back to the electrochemical cell and HCl and/or $H_2SO_4$ may be collected. In some embodiments, the reaction inside the reaction tower may take place from 1-10 hr at a temperature of 50-100° C.

An example of an ion exchange resin to separate out the HCl from the metal containing anolyte is as illustrated in FIG. 7C. As illustrated in FIG. 7C, the separation process may include a preferential adsorption/absorption of a mineral acid to an anion exchange resin. In the first step, the anolyte containing HCl and/or $H_2SO_4$ is passed through the ion exchange resin which adsorbs HCl and/or $H_2SO_4$ and then separates out the anolyte. The HCl and/or $H_2SO_4$ can be regenerated back from the resin by washing the resin with water. Diffusion dialysis can be another method for separating acid from the anolyte. In some embodiments, the ligands described herein, may facilitate the separation of the metal ion from the acid solution due to the large size of the ligand attached to the metal ion.

In some embodiments, the hydrochloric acid generated in the process is partially or fully used to dissolve scrap iron to form $FeCl_2$ and hydrogen gas. The $FeCl_2$ generated in the process may be re-circulated back to the anode chamber for conversion to $FeCl_3$. In some embodiments, the hydrogen gas may be used in the hydrogen fuel cell. The fuel cell in turn can be used to generate electricity to power the electrochemical described herein. In some embodiments, the hydrogen gas is transferred to the electrochemical systems described in U.S. Provisional Application No. 61/477,097, which is incorporated herein by reference in its entirety.

Figure 11:
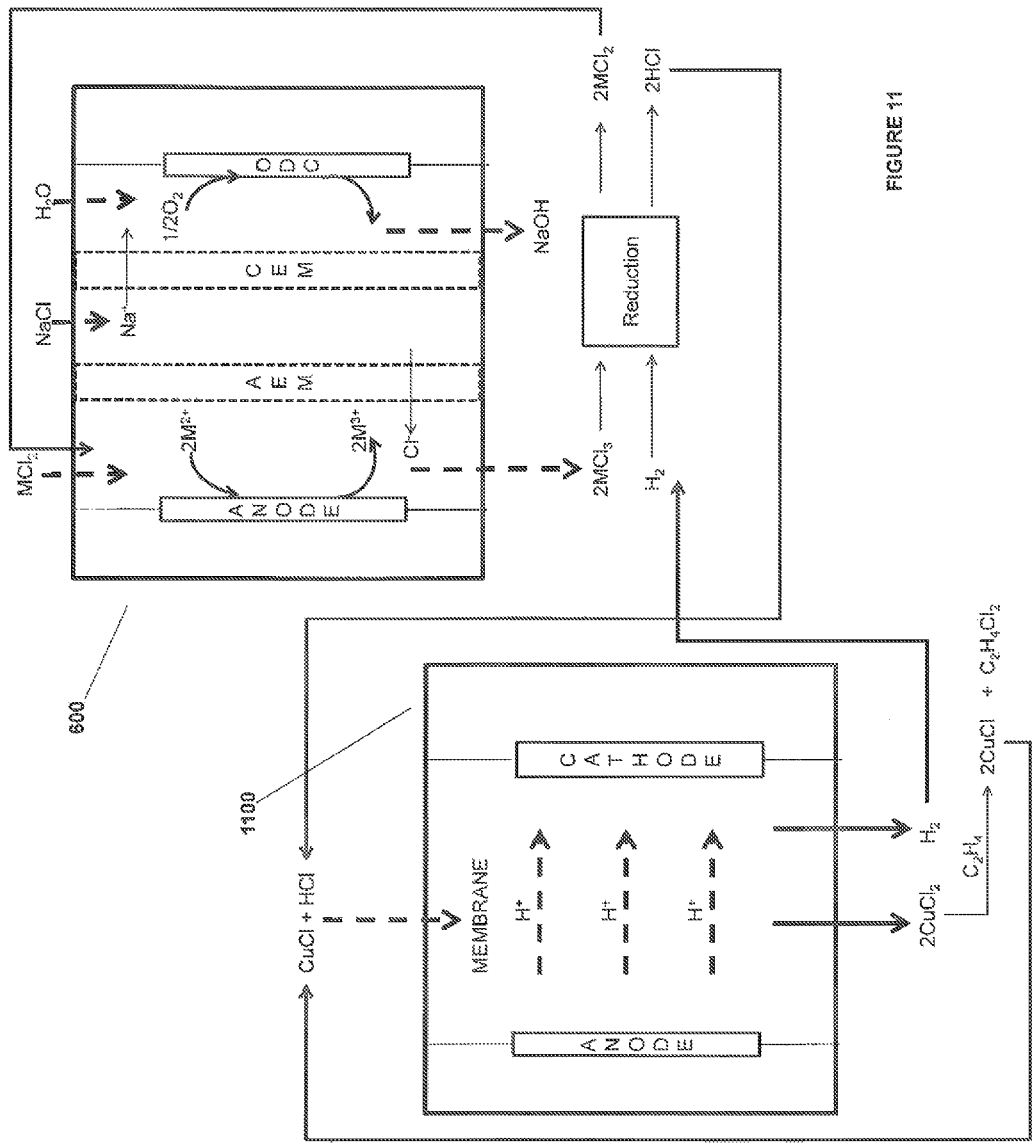
FIG. 11 is an illustration of an embodiment of the invention.

In some embodiments, the hydrochloric acid with or without the metal ion in the lower oxidation state is subjected to another electrochemical process to generate hydrogen gas and the metal ion in the higher oxidation state. Such a system is as illustrated in FIG. 11.

In some embodiments, the hydrochloric acid generated in the process is used to generate ethylene dichloride as illustrated below:

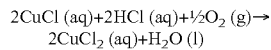

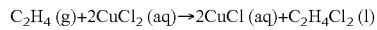

In some embodiments, the metal formed with a higher oxidation state in the anode electrolyte of the electrochemical systems of FIGS. 1A, 1B, 2, 3A, 3B, 4A, 4B, 5A, 5B, and 5C may be reacted with unsaturated hydrocarbons to from corresponding halohydrocarbons or sulfohydrocarbons based on the anion attached to the metal. For example, the metal chloride, metal bromide, metal iodide, or metal sulfate etc. may result in corresponding chlorohydrocarbons, bromohydrocarbons, iodohydrocarbons, or sulfohydrocarbons, after the reaction of the unsaturated hydrocarbons with the metal halide or metal sulfate. In some embodiments, the reaction of metal halide or metal sulfate with the unsaturated hydrocarbons results in the generation of the above described products as well as the metal halide or metal sulfate in the lower oxidation state. The metal ion in the lower oxidation state may then be re-circulated back to the electrochemical system for the generation of the metal ion in the higher oxidation state.

The "unsaturated hydrocarbon" as used herein, includes a hydrocarbon with unsaturated carbon or hydrocarbon with at least one double and/or at least one triple bond between adjacent carbon atoms. The unsaturated hydrocarbon may be linear, branched, or cyclic (aromatic or non-aromatic). For example, the hydrocarbon may be olefinic, acetylenic, non-aromatic such as cyclohexene, aromatic group or a substituted unsaturated hydrocarbon such as, but not limited to, halogenated unsaturated hydrocarbon. The hydrocarbons with at least one double bond may be called olefins or alkenes and may have a general formula of an unsubstituted alkene as $C_nH_{2n}$ where n is 2-20 or 2-10 or 2-8, or 2-5. In some embodiments, one or more hydrogens on the alkene may be further substituted with other functional groups such as but not limited to, halogen (including chloro, bromo, iodo, and fluoro), carboxylic acid (—COOH), hydroxyl (—OH), amines, etc. The unsaturated hydrocarbons include all the isomeric forms of unsaturation, such as, but not limited to, cis and trans isomers, E and Z isomers, positional isomers etc.

In some embodiments, the unsaturated hydrocarbon in the methods and systems provided herein, is of formula I which after halogenation or sulfonation (including sulfation) results in the compound of formula II:

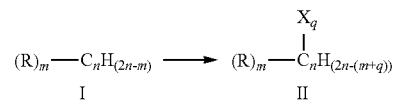

wherein, n is 2-10; m is 0-5; and q is 1-5;

R is independently selected from hydrogen, halogen, —COOR', —OH, and —NR'(R"), where R' and R" are independently selected from hydrogen, alkyl, and substituted alkyl; and X is a halogen selected from fluoro, chloro, bromo, and iodo; —$SO_3H$; or —$OSO_2OH$.

It is to be understood that R substitutent(s) can be on one carbon atom or on more than 1 carbon atom depending on the number of R and carbon atoms. For example only, when n is 3 and m is 2, the substituents R can be on the same carbon atom or on two different carbon atoms.

In some embodiments, the unsaturated hydrocarbon in the methods and systems provided herein, is of formula I which after halogenation results in the compound of formula II, wherein, n is 2-10; m is 0-5; and q is 1-5; R is independently selected from hydrogen, halogen, —COOR', —OH, and —NR'(R"), where R' and R" are independently selected from hydrogen, alkyl, and substituted alkyl; and X is a halogen selected from chloro, bromo, and iodo.

In some embodiments, the unsaturated hydrocarbon in the methods and systems provided herein, is of formula I which after halogenation results in the compound of formula II, wherein, n is 2-5; m is 0-3; and q is 1-4; R is independently selected from hydrogen, halogen, —COOR', —OH, and —NR'(R"), where R' and R" are independently selected from hydrogen and alkyl; and X is a halogen selected from chloro and bromo.

In some embodiments, the unsaturated hydrocarbon in the methods and systems provided herein, is of formula I which after halogenation results in the compound of formula II, wherein, n is 2-5; m is 0-3; and q is 1-4; R is independently selected from hydrogen, halogen, and —OH, and X is a halogen selected from chloro and bromo.

It is to be understood that when m is more than 1, the substituents R can be on the same carbon atom or on a different carbon atoms. Similarly, it is to be understood that when q is more than 1, the substituents X can be on the same carbon atom or on different carbon atoms.

In some embodiments for the above described embodiments of formula I, m is 0 and q is 1-2. In such embodiments, X is chloro.

Examples of substituted or unsubstituted alkenes, including formula I, include, but not limited to, ethylene, chloro ethylene, bromo ethylene, iodo ethylene, propylene, chloro propylene, hydroxyl propylene, 1-butylene, 2-butylene (cis or trans), isobutylene, 1,3-butadiene, pentylene, hexene, cyclopropylene, cyclobutylene, cyclohexene, etc. The hydrocarbons with at least one triple bond may be called alkynes and may have a general formula of an unsubstituted alkyne as $C_nH_{2n-2}$ where n is 2-10 or 2-8, or 2-5. In some embodiments, one or more hydrogens on the alkyne may be further substituted with other functional groups such as but not limited to, halogen, carboxylic acid, hydroxyl, etc.

In some embodiments, the unsaturated hydrocarbon in the methods and systems provided herein, is of formula IA which after halogenation or sulfonation (including sulfation) results in the compound of formula IIA:

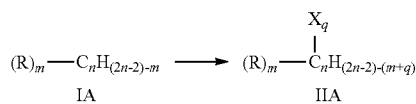

wherein, n is 2-10; m is 0-5; and q is 1-5;

R is independently selected from hydrogen, halogen, —COOR', —OH, and —NR'(R"), where R' and R" are independently selected from hydrogen, alkyl, and substituted alkyl; and X is a halogen selected from fluoro, chloro, bromo, and iodo; —$SO_3H$; or —$OSO_2OH$.

Examples of substituted or unsubstituted alkynes include, but not limited to, acetylene, propyne, chloro propyne, bromo propyne, butyne, pentyne, hexyne, etc.

It is to be understood that R substitutent(s) can be on one carbon atom or on more than 1 carbon atom depending on the number of R and carbon atoms. For example only, when n is 3 and m is 2, the substituents R can be on the same carbon atom or on two different carbon atoms.

In some embodiments, there are provided methods that include contacting an anode with a metal ion in an anode electrolyte in an anode chamber; converting or oxidizing the metal ion from a lower oxidation state to a higher oxidation state at the anode; and treating the anode electrolyte comprising the metal ion in the higher oxidation state with an unsaturated hydrocarbon. In some embodiments of the method, the method includes contacting a cathode with a cathode electrolyte and forming an alkali at the cathode. In some embodiments of the method, the method includes contacting a cathode with a cathode electrolyte and forming an alkali, water, and/or hydrogen gas at the cathode. In some embodiments of the method, the method includes contacting a gas-diffusion cathode with a cathode electrolyte and forming an alkali or water at the cathode. In some embodiments, there are provided methods that include contacting an anode with a metal ion in an anode electrolyte in an anode chamber; converting the metal ion from a lower oxidation state to a higher oxidation state at the anode; contacting a cathode with a cathode electrolyte; forming an alkali, water, and/or hydrogen gas at the cathode; and treating the anode electrolyte comprising the metal ion in the higher oxidation state with an unsaturated hydrocarbon. In some embodiments, there are provided methods that include contacting an anode with a metal ion in an anode electrolyte in an anode chamber; converting the metal ion from a lower oxidation state to a higher oxidation state at the anode; contacting a gas-diffusion cathode with a cathode electrolyte; forming an alkali or water at the cathode; and treating the anode electrolyte comprising the metal ion in the higher oxidation state with an unsaturated hydrocarbon. In some embodiments, there are provided methods that include contacting an anode with a metal ion in an anode electrolyte in an anode chamber; converting the metal ion from a lower oxidation state to a higher oxidation state at the anode; contacting a gas-diffusion cathode with a cathode electrolyte; forming an alkali at the cathode; and treating the anode electrolyte comprising the metal ion in the higher oxidation state with an unsaturated hydrocarbon. In some embodiments, the treatment of the unsaturated hydrocarbon with the metal ion in the higher oxidation state may be inside the cathode chamber or outside the cathode chamber. In some embodiments, the treatment of the metal ion in the higher oxidation state with the unsaturated hydrocarbon results in chloro, bromo, iodo, or sulfohydrocarbons and the metal ion in the lower oxidation state. In some embodiments, the metal ion in the lower oxidation state is re-circulated back to the anode chamber.

In some embodiments of the above described methods, the anode does not produce chlorine gas. In some embodiments of the above described methods, the treatment of the unsaturated hydrocarbon with the metal ion in the higher oxidation state does not require oxygen gas and/or chlorine gas. In some embodiments of the above described methods, the anode does not produce chlorine gas and the treatment of the unsaturated hydrocarbon with the metal ion in the higher oxidation state does not require oxygen gas and/or chlorine gas.

In some embodiments, there are provided systems that include an anode chamber including an anode in contact with a metal ion in an anode electrolyte wherein the anode is configured to convert the metal ion from a lower oxidation state to a higher oxidation state; and a reactor operably connected to the anode chamber and configured to react the anode electrolyte comprising the metal ion in the higher oxidation state with unsaturated hydrocarbon. In some embodiments of the systems, the system includes a cathode chamber including a cathode with a cathode electrolyte wherein the cathode is configured to form an alkali, water, and/or hydrogen gas in the cathode electrolyte. In some embodiments of the systems, the system includes a cathode chamber including a cathode with a cathode electrolyte wherein the cathode is configured to form an alkali and/or hydrogen gas in the cathode electrolyte. In some embodiments of the systems, the system includes a gas-diffusion cathode with a cathode electrolyte wherein the cathode is configured to form an alkali or water in the cathode electrolyte. In some embodiments, there are provided systems that include an anode chamber including an anode with a metal ion in an anode electrolyte wherein the anode is configured to convert the metal ion from a lower oxidation state to a higher oxidation state in the anode chamber; a cathode chamber including a cathode with a cathode electrolyte wherein the cathode is configured to form an alkali, water or hydrogen gas in the cathode electrolyte; and a reactor operably connected to the anode chamber and configured to react the anode electrolyte comprising the metal ion in the higher oxidation state with an unsaturated hydrocarbon. In some embodiments, there are provided systems that include an anode chamber including an anode with a metal ion in an anode electrolyte wherein the anode is configured to convert the metal ion from a lower oxidation state to a higher oxidation state in the anode chamber; a cathode chamber including a gas-diffusion cathode with a cathode electrolyte wherein the cathode is configured to form an alkali in the cathode electrolyte; and a reactor operably connected to the anode chamber and configured to react the anode electrolyte comprising the metal ion in the higher oxidation state with an unsaturated hydrocarbon. In some embodiments, the treatment of the unsaturated hydrocarbon with the metal ion in the higher oxidation state may be inside the cathode chamber or outside the cathode chamber. In some embodiments, the treatment of the metal ion in the higher oxidation state with the unsaturated hydrocarbon results in chloro, bromo, iodo, or sulfohydrocarbons and the metal ion in the lower oxidation state. In some embodiments, the system is configured to form the metal ion in the lower oxidation state from the metal ion in the higher oxidation state with the unsaturated hydrocarbon and re-circulate the metal ion in the lower oxidation state back to the anode chamber.

In some embodiments, the unsaturated hydrocarbon in the aforementioned method and system embodiments and as described herein is of formula I or is C2-C10 alkene or C2-C5 alkene. In some embodiments of the methods and systems described as above, the unsaturated hydrocarbon in the aforementioned embodiments and as described herein is, ethylene. The halohydrocarbon formed from such unsaturated hydrocarbon is of formula II (as described herein), e.g., ethylene dichloride, chloroethanol, butyl chloride, dichlorobutane, chlorobutanol, etc. In some embodiments of the methods and systems described as above, the metal ion is a metal ion described herein, such as, but not limited to, copper, iron, tin, or chromium.

In some embodiments of the above described systems, the anode is configured to not produce chlorine gas. In some embodiments of the above described systems, the reactor configured to react the unsaturated hydrocarbon with the metal ion in the higher oxidation state, is configured to not require oxygen gas and/or chlorine gas. In some embodiments of the above described methods, the anode is configured to not produce chlorine gas and the reactor is configured to not require oxygen gas and/or chlorine gas.

Figure 8A:
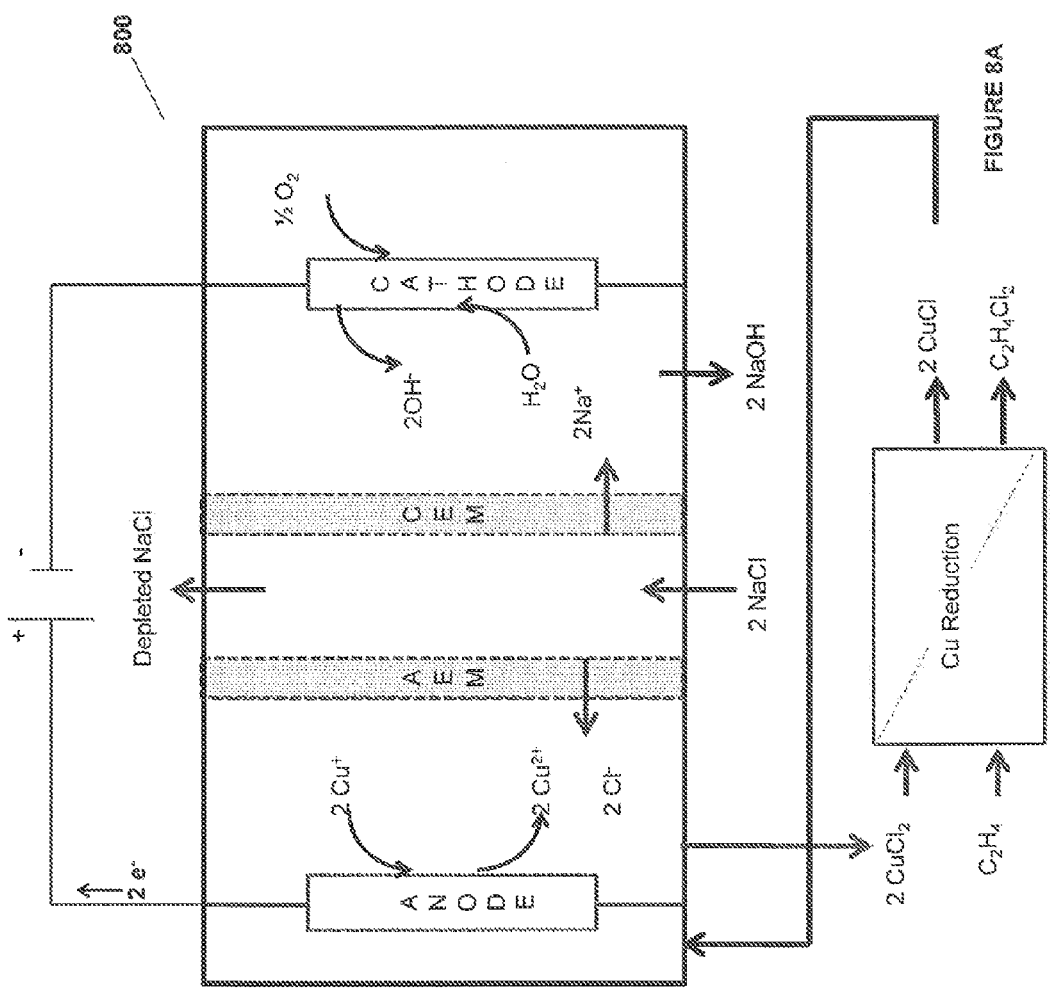
FIG. 8A is an illustration of an embodiment of the invention.
Figure 8B:
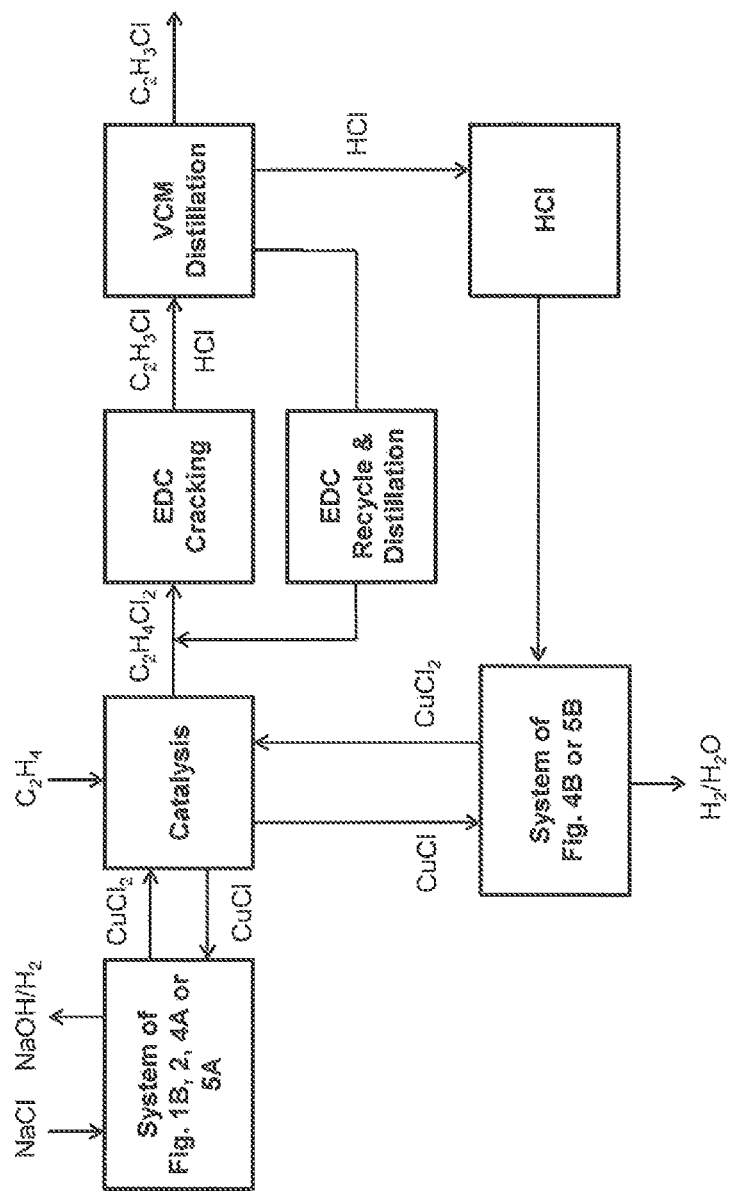
FIG. 8B is an illustration of an embodiment of the invention.

An example of the electrochemical system of FIG. 5A, is as illustrated in FIG. 8A. It is to be understood that the system 800 of FIG. 8A is for illustration purposes only and other metal ions with different oxidations states, other unsaturated hydrocarbons, and other electrochemical systems forming products other than alkali, such as water or hydrogen gas in the cathode chamber, are equally applicable to the system. The cathode of FIG. 4A or 4B may also be substituted in FIG. 8A. In some embodiments, as illustrated in FIG. 8A, the electrochemical system 800 includes an oxygen depolarized cathode that produces hydroxide ions from water and oxygen. The system 800 also includes an anode that converts metal ions from 1+ oxidation state to 2+ oxidation state. The $Cu^{2+}$ ions combine with chloride ions to form $CuCl_2$. The metal chloride $CuCl_2$ can be then reacted with an unsaturated hydrocarbon, such as, but not limited to, ethylene to undergo reduction of the metal ion to lower oxidation state to form CuCl and dichlorohydrocarbon, such as, but not limited to, ethylene dichloride. The CuCl is then re-circulated back to the anode chamber for conversion to $CuCl_2$.

The ethylene dichloride formed by the methods and systems of the invention can be used for any commercial purposes. In some embodiments, the ethylene dichloride is subjected to vinyl chloride monomer (VCM) formation through the process such as cracking/purification. The vinyl chloride monomer may be used in the production of polyvinylchloride. In some embodiments, the hydrochloric acid formed during the conversion of EDC to VCM may be separated and reacted with acetylene to further form VCM.

In some embodiments, the HCl generated in the process of VCM formation may be circulated to one or more of the electrochemical systems described herein where HCl is used in the cathode or anode electrolyte to form hydrogen gas or water at the cathode. As in FIG. 8B, an integrated electrochemical system of the invention is illustrated in combination with the VCM/PVC synthesis. Any of the electrochemical systems of the invention such as system illustrated in FIG. 1B, 2, 4A or 5A may be used to form $CuCl_2$ which when reacted with ethylene results in EDC. The cracking of EDC with subsequent processing of VCM produces HCl which may be circulated to any of the electrochemical systems of FIG. 4B or 5B to further form $CuCl_2$. It is to be understood that the whole process may be conducted with only system of FIG. 4B or 5B (i.e. with no incorporation of systems of FIG. 1B, 2, 4A or 5A).

In some embodiments, the chlorination of ethylene in an aqueous medium with metal chloride in the higher oxidation state, results in ethylene dichloride, chloroethanol, or combination thereof. In some embodiments of the methods and systems described herein, there is a formation of more than 10 wt %; or more than 20 wt %, or more than 30 wt %, or more than 40 wt %, or more than 50 wt %, or more than 60 wt %, or more than 70 wt %, or more than 80 wt %, or more than 90 wt %, or more than 95 wt %, or about 99 wt %, or between about 10-99 wt %, or between about 10-95 wt %, or between about 15-95 wt %, or between about 25-95 wt %, or between about 50-95 wt %, or between about 50-99 wt % ethylene dichloride, or between about 50-99.9 wt % ethylene dichloride, or between about 50-99.99 wt % ethylene dichloride, from ethylene. In some embodiments, the remaining weight percentage is of chloroethanol. In some embodiments, no chloroethanol is formed in the reaction. In some embodiments, less than 0.001 wt % or less than 0.01 wt % or less than 0.1 wt % or less than 0.5 wt % or less than 1 wt % or less than 5 wt % or less than 10 wt % or less than 20 wt % of chloroethanol is formed with the remaining EDC in the reaction. In some embodiments, less than 0.001 wt % or less than 0.01 wt % or less than 0.1 wt % or less than 0.5 wt % or less than 1 wt % or less than 5 wt % of metal ion is present in EDC product. In some embodiments, less than 0.001 wt % or less than 0.01 wt % or less than 0.1 wt % of chloroethanol and/or metal ion is present in the EDC product.

In some embodiments, the EDC product containing the metal ion may be subjected to washing step which may include rinsing with an organic solvent or passing the EDC product through a column to remove the metal ions. In some embodiments, the EDC product may be purified by distillation where any of the side products such as chloral ($CCl_3CHO$) and/or chloral hydrate (2,2,2-trichloroethane-1, 1-diol), if formed, may be separated.

In some embodiments, the unsaturated hydrocarbon is propene. In some embodiments, the metal ion in the higher oxidation state such as $CuCl_2$ is treated with propene to result in propane dichloride ($C_3H_6Cl_2$) or dichloropropane (DCP) which can be used to make allyl chloride ($C_3H_5Cl$). In some embodiments, the unsaturated hydrocarbon is butane or butylene. In some embodiments, the metal ion in the higher oxidation state such as $CuCl_2$ is treated with butene to result in butane dichloride ($C_4H_8Cl_2$) or dichlorobutene ($C_4H_6Cl_2$) which can be used to make chloroprene ($C_4H_5Cl$). In some embodiments, the unsaturated hydrocarbon is benzene. In some embodiments, the metal ion in the higher oxidation state such as $CuCl_2$ is treated with benzene to result in chlorobenzene. In some embodiments, the metal ion in the higher oxidation state such as $CuCl_2$ is treated with acetylene to result in chloroacetylene, dichloroacetylene, vinyl chloride, dichloroethene, tetrachloroethene, or combination thereof. In some embodiments, the unsaturated hydrocarbon is treated with metal chloride in higher oxidation state to form a product including, but not limited to, ethylene dichloride, chloroethanol, chloropropene, propylene oxide (further dehydrochlorinated), allyl chloride, methyl chloride, trichloroethylene, tetrachloroethene, chlorobenzene, 1,2-dichloroethane, 1,1,2-trichloroethane, 1,1,2,2-tetrachloroethane, pentachloroethane, 1,1-dichloroethene, chlorophenol, chlorinated toluene, etc.

In some embodiments, the yield of the halogenated hydrocarbon from unsaturated hydrocarbon, e.g. the yield of EDC from ethylene or yield of DCP from propylene, or dichlorobutene from butene, using the metal ions is more than 90% or more than 95% or between 90-95% or between 90-99% or between 90-99.9% by weight. In some embodiments, the selectivity of the halogenated hydrocarbon from unsaturated hydrocarbon, e.g. the yield of EDC from ethylene or yield of DCP from propylene, or dichlorobutene from butene, using the metal ions is more than 80% or more than 90% or between 80-99% by weight. In some embodiments, the STY (space time yield) of the halogenated hydrocarbon from unsaturated hydrocarbon, e.g. the yield of EDC from ethylene or yield of DCP from propylene, or dichlorobutene from butene, using the metal ions is more than 3 or more than 4 or more than 5 or between 3-5 or between 3-6 or between 3-8.

In some embodiments, the metal formed with a higher oxidation state in the anode electrolyte of the electrochemical systems of FIGS. 1A, 1B, 2, 3A, 3B, 4A, 4B, 5A, and 5B may be reacted with saturated hydrocarbons to from corresponding halohydrocarbons or sulfohydrocarbons based on the anion attached to the metal. For example, the metal chloride, metal bromide, metal iodide, or metal sulfate etc. may result in corresponding chlorohydrocarbons, bromohydrocarbons, iodohydrocarbons, or sulfohydrocarbons, after the reaction of the saturated hydrocarbons with the metal halide or metal sulfate. In some embodiments, the reaction of metal halide or metal sulfate with the saturated hydrocarbons results in the generation of the above described products as well as the metal halide or metal sulfate in the lower oxidation state. The metal ion in the lower oxidation state may then be re-circulated back to the electrochemical system for the generation of the metal ion in the higher oxidation state.

The "saturated hydrocarbon" as used herein, includes a hydrocarbon with no unsaturated carbon or hydrocarbon. The hydrocarbon may be linear, branched, or cyclic. For example, the hydrocarbon may be substituted or unsubstituted alkanes and/or substituted or unsubstituted cycloalkanes. The hydrocarbons may have a general formula of an unsubstituted alkane as $C_nH_{2n+2}$ where n is 2-20 or 2-10 or 2-8, or 2-5. In some embodiments, one or more hydrogens on the alkane or the cycloalkanes may be further substituted with other functional groups such as but not limited to, halogen (including chloro, bromo, iodo, and fluoro), carboxylic acid (—COOH), hydroxyl (—OH), amines, etc.

In some embodiments, the saturated hydrocarbon in the methods and systems provided herein, is of formula III which after halogenation or sulfonation (including sulfation) results in the compound of formula IV:

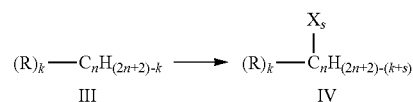

wherein, n is 2-10; k is 0-5; and s is 1-5;

R is independently selected from hydrogen, halogen, —COOR', —OH, and —NR'(R"), where R' and R" are independently selected from hydrogen, alkyl, and substituted alkyl; and X is a halogen selected from fluoro, chloro, bromo, and iodo; —$SO_3H$; or —$OSO_2OH$.

It is to be understood that R substitutent(s) can be on one carbon atom or on more than 1 carbon atom depending on the number of R and carbon atoms. For example only, when n is 3 and k is 2, the substituents R can be on the same carbon atom or on two different carbon atoms.

In some embodiments, the saturated hydrocarbon in the methods and systems provided herein, is of formula III which after halogenation results in the compound of formula IV:

wherein, n is 2-10; k is 0-5; and s is 1-5;

R is independently selected from hydrogen, halogen, —COOR', —OH, and —NR'(R"), where R' and R" are independently selected from hydrogen, alkyl, and substituted alkyl; and X is a halogen selected from chloro, bromo, and iodo.

In some embodiments, the saturated hydrocarbon in the methods and systems provided herein, is of formula III which after halogenation results in the compound of formula IV:

wherein, n is 2-5; k is 0-3; and s is 1-4;

R is independently selected from hydrogen, halogen, —COOR', —OH, and —NR'(R"), where R' and R" are independently selected from hydrogen and alkyl; and X is a halogen selected from chloro and bromo.

In some embodiments, the saturated hydrocarbon in the methods and systems provided herein, is of formula III which after halogenation results in the compound of formula IV:

wherein, n is 2-5; k is 0-3; and s is 1-4;

R is independently selected from hydrogen, halogen, and —OH, and

X is a halogen selected from chloro and bromo.

It is to be understood that when k is more than 1, the substituents R can be on the same carbon atom or on a different carbon atoms. Similarly, it is to be understood that when s is more than 1, the substituents X can be on the same carbon atom or on different carbon atoms.

In some embodiments for the above described embodiments of formula III, k is 0 and s is 1-2. In such embodiments, X is chloro.

Examples of substituted or unsubstituted alkanes, e.g. of formula III, include, but not limited to, methane, ethane, chloroethane, bromoethane, iodoethane, propane, chloropropane, hydroxypropane, butane, chlorobutane, hydroxybutane, pentane, hexane, cyclohexane, cyclopentane, chlorocyclopentane, etc.

In some embodiments, there are provided methods that include contacting an anode with a metal ion in an anode electrolyte in an anode chamber; converting or oxidizing the metal ion from a lower oxidation state to a higher oxidation state at the anode; and treating the anode electrolyte comprising the metal ion in the higher oxidation state with a saturated hydrocarbon. In some embodiments of the method, the method includes contacting a cathode with a cathode electrolyte and forming an alkali at the cathode. In some embodiments of the method, the method includes contacting a cathode with a cathode electrolyte and forming an alkali and hydrogen gas at the cathode. In some embodiments of the method, the method includes contacting a cathode with a cathode electrolyte and forming hydrogen gas at the cathode. In some embodiments of the method, the method includes contacting a gas-diffusion cathode with a cathode electrolyte and forming an alkali at the cathode. In some embodiments of the method, the method includes contacting a gas-diffusion cathode with a cathode electrolyte and forming water at the cathode. In some embodiments, there are provided methods that include contacting an anode with a metal ion in an anode electrolyte in an anode chamber; converting the metal ion from a lower oxidation state to a higher oxidation state at the anode; contacting a cathode with a cathode electrolyte; forming an alkali, water, and/or hydrogen gas at the cathode; and treating the anode electrolyte comprising the metal ion in the higher oxidation state with a saturated hydrocarbon. In some embodiments, there are provided methods that include contacting an anode with a metal ion in an anode electrolyte in an anode chamber; converting the metal ion from a lower oxidation state to a higher oxidation state at the anode; contacting a gas-diffusion cathode with a cathode electrolyte; forming an alkali or water at the cathode; and treating the anode electrolyte comprising the metal ion in the higher oxidation state with a saturated hydrocarbon. In some embodiments, the treatment of the saturated hydrocarbon with the metal ion in the higher oxidation state may be inside the cathode chamber or outside the cathode chamber. In some embodiments, the treatment of the metal ion in the higher oxidation state with the saturated hydrocarbon results in halogenated hydrocarbon or sulfohydrocarbon, such as, chloro, bromo, iodo, or sulfohydrocarbons and the metal ion in the lower oxidation state. In some embodiments, the metal ion in the lower oxidation state is re-circulated back to the anode chamber. In some embodiments, the saturated hydrocarbon in the aforementioned embodiments and as described herein is of formula III (as described herein) or is C2-C10 alkane or C2-C5 alkane. In some embodiments, the saturated hydrocarbon in the aforementioned embodiments and as described herein is, methane. In some embodiments, the saturated hydrocarbon in the aforementioned embodiments and as described herein is, ethane. In some embodiments, the saturated hydrocarbon in the aforementioned embodiments and as described herein is, propane. The halohydrocarbon formed from such saturated hydrocarbon is of formula IV (as described herein), e.g., chloromethane, dichloromethane, chloroethane, dichloroethane, chloropropane, dichloropropane, etc.

In some embodiments of the above described methods, the metal ion used is platinum, palladium, copper, iron, tin, and chromium. In some embodiments of the above described methods, the anode does not produce chlorine gas. In some embodiments of the above described methods, the treatment of the saturated hydrocarbon with the metal ion in the higher oxidation state does not require oxygen gas and/or chlorine gas. In some embodiments of the above described methods, the anode does not produce chlorine gas and the treatment of the saturated hydrocarbon with the metal ion in the higher oxidation state does not require oxygen gas and/or chlorine gas.

In some embodiments, there are provided systems that include an anode chamber including an anode in contact with a metal ion in an anode electrolyte wherein the anode is configured to convert the metal ion from a lower oxidation state to a higher oxidation state; and a reactor operably connected to the anode chamber and configured to react the anode electrolyte comprising the metal ion in the higher oxidation state with a saturated hydrocarbon. In some embodiments of the systems, the system includes a cathode chamber including a cathode with a cathode electrolyte wherein the cathode is configured to form an alkali at the cathode. In some embodiments of the systems, the system includes a cathode chamber including a cathode with a cathode electrolyte wherein the cathode is configured to form hydrogen gas at the cathode. In some embodiments of the systems, the system includes a cathode chamber including a cathode with a cathode electrolyte wherein the cathode is configured to form an alkali and hydrogen gas at the cathode. In some embodiments of the systems, the system includes a gas-diffusion cathode with a cathode electrolyte wherein the cathode is configured to form an alkali at the cathode. In some embodiments of the systems, the system includes a gas-diffusion cathode with a cathode electrolyte wherein the cathode is configured to form water at the cathode. In some embodiments, there are provided systems that include an anode chamber including an anode with a metal ion in an anode electrolyte wherein the anode is configured to convert the metal ion from a lower oxidation state to a higher oxidation state in the anode chamber; a cathode chamber including a cathode with a cathode electrolyte wherein the cathode is configured to form an alkali, water, and hydrogen gas in the cathode electrolyte; and a reactor operably connected to the anode chamber and configured to react the anode electrolyte comprising the metal ion in the higher oxidation state with saturated hydrocarbon. In some embodiments, there are provided systems that include an anode chamber including an anode with a metal ion in an anode electrolyte wherein the anode is configured to convert the metal ion from a lower oxidation state to a higher oxidation state in the anode chamber; a cathode chamber including a gas-diffusion cathode with a cathode electrolyte wherein the cathode is configured to form an alkali or water in the cathode electrolyte; and a reactor operably connected to the anode chamber and configured to react the anode electrolyte comprising the metal ion in the higher oxidation state with saturated hydrocarbon. In some embodiments, the treatment of the saturated hydrocarbon with the metal ion in the higher oxidation state may be inside the cathode chamber or outside the cathode chamber. In some embodiments, the treatment of the metal ion in the higher oxidation state with the saturated hydrocarbon results in chloro, bromo, iodo, or sulfohydrocarbons and the metal ion in the lower oxidation state. In some embodiments, the system is configured to form the metal ion in the lower oxidation state from the metal ion in the higher oxidation state with the saturated hydrocarbon and re-circulate the metal ion in the lower oxidation state back to the anode chamber.

In some embodiments of the methods and systems described as above, the metal ion is a metal ion described herein, such as, but not limited to, platinum, palladium, copper, iron, tin, or chromium.

In some embodiments of the above described systems, the anode is configured to not produce chlorine gas. In some embodiments of the above described systems, the reactor configured to react the saturated hydrocarbon with the metal ion in the higher oxidation state, is configured to not require oxygen gas and/or chlorine gas. In some embodiments of the above described methods, the anode is configured to not produce chlorine gas and the reactor is configured to not require oxygen gas and/or chlorine gas.

It is to be understood that the example of the electrochemical system illustrated in FIG. 8A can be configured for saturated hydrocarbons by replacing the unsaturated hydrocarbon with a saturated hydrocarbon. Accordingly, suitable metal ions may be used such as platinum chloride, palladium chloride, copper chloride etc.

In some embodiments, the chlorination of ethane in an aqueous medium with metal chloride in the higher oxidation state, results in ethane chloride, ethane dichloride, or combination thereof. In some embodiments of the methods and systems described herein, there is a formation of more than 10 wt %; or more than 20 wt %, or more than 30 wt %, or more than 40 wt %, or more than 50 wt %, or more than 60 wt %, or more than 70 wt %, or more than 80 wt %, or more than 90 wt %, or more than 95 wt %, or about 99 wt %, or between about 10-99 wt %, or between about 10-95 wt %, or between about 15-95 wt %, or between about 25-95 wt %, or between about 50-95 wt %, or between about 50-99 wt %, or between about 50-99.9 wt %, or between about 50-99.99 wt % chloroethane, from ethane. In some embodiments, the remaining weight percentage is of chloroethanol and/or ethylene dichloride: In some embodiments, no chloroethanol is formed in the reaction. In some embodiments, less than 0.001 wt % or less than 0.01 wt % or less than 0.1 wt % or less than 0.5 wt % or less than 1 wt % or less than 5 wt % or less than 10 wt % or less than 20 wt % of chloroethanol is formed with the remaining product in the reaction. In some embodiments, less than 0.001 wt % or less than 0.01 wt % or less than 0.1 wt % or less than 0.5 wt % or less than 1 wt % or less than 5 wt % of metal ion is present in the product. In some embodiments, less than 0.001 wt % or less than 0.01 wt % or less than 0.1 wt % of chloroethanol and/or metal ion is present in the product.

In some embodiments, the yield of the halogenated hydrocarbon from saturated hydrocarbon, e.g. the yield of chloroethane or EDC from ethane, using the metal ions is more than 90% or more than 95% or between 90-95% or between 90-99% or between 90-99.9% by weight. In some embodiments, the selectivity of the halogenated hydrocarbon from saturated hydrocarbon, e.g. the yield of chloroethane or EDC from ethane, using the metal ions is more than 80% or more than 90% or between 80-99% by weight. In some embodiments, the STY (space time yield) of the halogenated hydrocarbon from saturated hydrocarbon is more than 3 or more than 4 or more than 5 or between 3-5 or between 3-6 or between 3-8.

The products, such as, but not limited to, halogenated hydrocarbon, acid, carbonate, and/or bicarbonate formed by the methods and systems of the invention are greener than the same products formed by the methods and systems conventionally known in the art. There are provided methods to make green halogenated hydrocarbon, that include contacting an anode with an anode electrolyte; oxidizing a metal chloride from the lower oxidation state to a higher oxidation state at the anode; contacting a cathode with a cathode electrolyte; and halogenating an unsaturated or saturated hydrocarbon with the metal chloride in the higher oxidation state to produce a green halogenated hydrocarbon. In some embodiments, there is provided a green halogenated hydrocarbon formed by the methods described herein. There are also provided system that include an anode in contact with an anode electrolyte wherein the anode is configured to oxidize a metal ion from the lower oxidation state to a higher oxidation state; a cathode in contact with a cathode electrolyte; and a reactor operably connected to the anode chamber and configured to react the metal ion in the higher oxidation state with an unsaturated or saturated hydrocarbon to form a green halogenated hydrocarbon.

The term "greener" or "green" or grammatical equivalent thereof, as used herein, includes any chemical or product formed by the methods and systems of the invention that has higher energy savings or voltage savings as compared to the same chemical or product formed by the methods known in the art. For example, chlor-alkali is a process that typically is used to make chlorine gas, which chlorine gas is then used to chlorinate ethylene to form EDC. The amount of energy required to make EDC from the chlor-alkali process is higher than the amount of energy required to make EDC from the metal oxidation process of the invention. Therefore, the EDC produced by the methods and systems of the invention is greener than the EDC produced by the chlor-alkali process. Such savings in energy is illustrated in FIG. 8C which illustrates the activation barriers for carrying out the methods of the invention compared to the activation barriers for the chlor-alkali process.

Figure 8C:
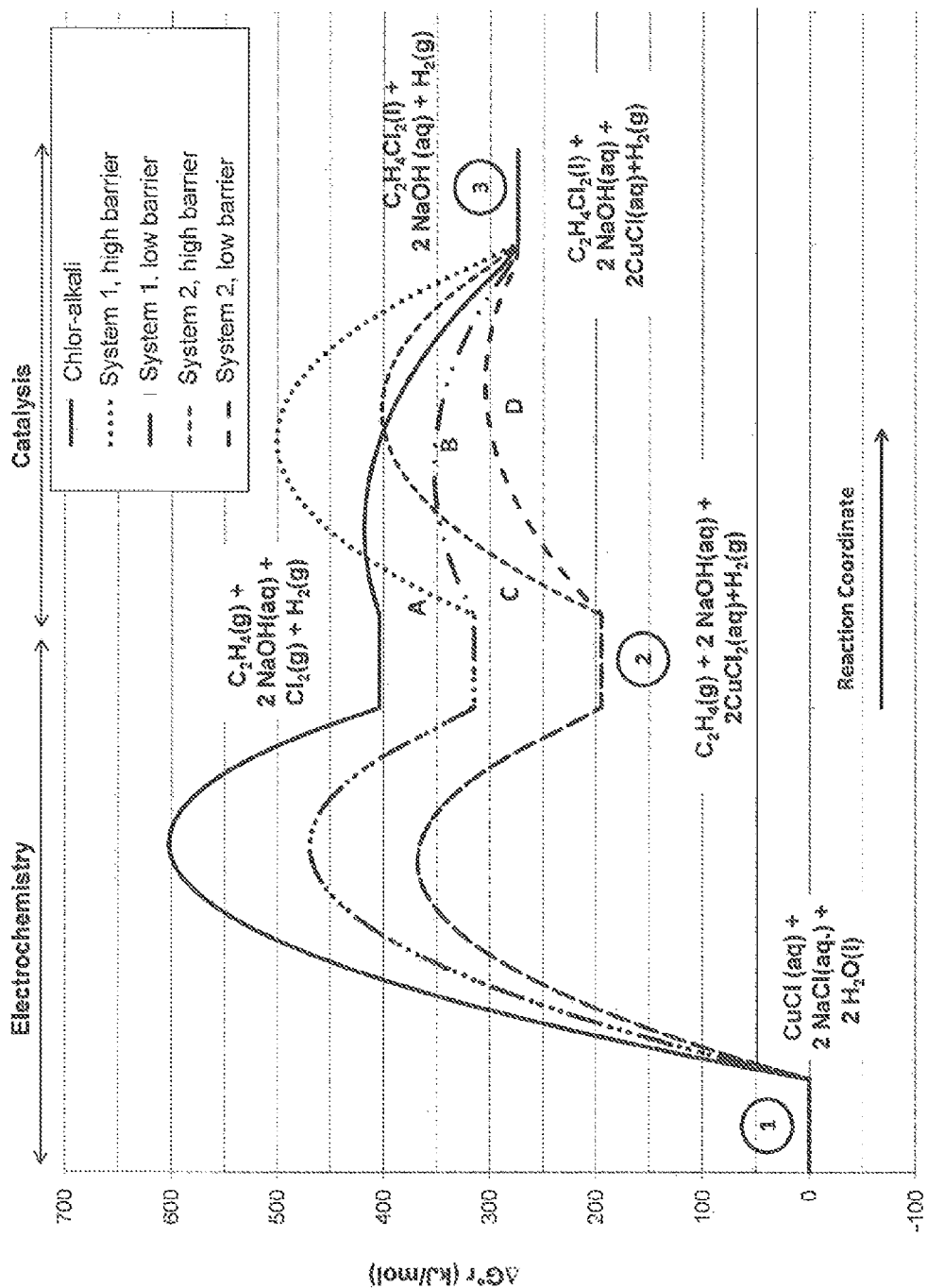
FIG. 8C is an illustration of an embodiment of the invention.

As illustrated in FIG. 8C, a comparison is made between the energy required to make EDC from the chlor-alkali process and the energy required to make the EDC from the methods and systems of the invention. The process of making EDC is illustrated in two parts. An electrochemistry part, where the copper oxidation takes place in System 1 and System 2 of the invention compared to chlorine generation taking place in the chlor-alkali process. A catalysis part, where copper (II) chloride (generated by electrochemistry) chlorinates ethylene in System 1 and 2 and chlorine gas (generated by the chlor-alkali process) chlorinates ethylene (conventionally known) to form EDC. In System 1, the electrochemical reaction is carried out in the absence of ligand and in System 2, the electrochemical reaction is carried out in the presence of the ligand. In System 1, System 2, and the chlor-alkali process, the cathode is a hydrogen gas producing cathode and the current density for the electrochemical reaction is 300 mA/cm$^2$. As illustrated in FIG. 8C, for the electrochemical reaction, there is an energy saving of more than 125 kJ/mol for System 1 over chlor-alkali process and energy savings of more than 225 kJ/mol for System 2 over the chlor-alkali process. Therefore, there can be an energy savings of up to 300 kJ/mol; or up to 250 kJ/mol; or between 50-300 kJ/mol; or between 50-250 kJ/mol; or between 100-250 kJ/mol; or between 100-200 kJ/mol, to make the green halogenated hydrocarbon, such as, but not limited to, EDC, by methods and systems of the invention as compared to conventional process such as chlor-alkali process to make EDC. This converts to a saving of more than 1 megawatthour/ton of EDC or between 1-21 megawatthour/ton of EDC for Systems 1 and 2 compared to the chlor-alkali process. It also correlates to the voltage saving of more than 1V or between 1-2V (1V×2 electrons is approx. 200 kJ/mol) as compared to the chlor-alkali process.

As also illustrated in FIG. 8C, the catalyst part of the reaction has a theoretical low barrier for each System 1 and 2 and a high barrier for the two Systems 1 and 2. The catalyst reaction in System 1 and System 2 can happen at the point of low barrier or at the point of high barrier or anywhere in between, depending on conditions, such as, but not limited to, concentration, size of the reactor, flow rates etc. Even if there is some energy input for the catalysis reaction in System 1 and 2, it will be offset by the significant energy saving in the electrochemical reaction such that there is a net energy saving of up to 100 kJ/mol; or more than 100 kJ/mol; or between 50-100 kJ/mol; or between 0-100 kJ/mol. This converts to up to or more than 1 megawatthr/ton of EDC or voltage saving of 0-1V or more than 1V; or between 1-2V as compared to chlor-alkali process. It is to be understood that the chlor-alkali process, System 1 and System 2 are all carried out in the aqueous medium. The electrochemical cell or the catalysis system running on an organic solvent (e.g., with some or all of the water from electrochemical cell removed by azeotropic distillation) would require even higher energy than the conventional method and would not be yielding a green halogenated hydrocarbon.

Also further illustrated in FIG. 8C, is the savings in energy in System 2 which is with the use of the ligand as compared to System 1 which is without the use of the ligand.

Accordingly, there are provided methods to make green halogenated hydrocarbon, that include contacting an anode with an anode electrolyte; oxidizing a metal chloride from the lower oxidation state to a higher oxidation state at the anode; contacting a cathode with a cathode electrolyte; and halogenating an unsaturated or saturated hydrocarbon with the metal chloride in the higher oxidation state to produce a green halogenated hydrocarbon wherein the method results in net energy saving of more than 100 kJ/mol or more than 150 kJ/mol or more than 200 kJ/mol or between 100-250 kJ/mol or between 50-100 kJ/mol or between 0-100 kJ/mol or the method results in the voltage savings of more than 1V or between 0-1V or between 1-2V or between 0-2V. There are also provided system that include an anode in contact with an anode electrolyte wherein the anode is configured to oxidize a metal ion from the lower oxidation state to a higher oxidation state; a cathode in contact with a cathode electrolyte; and a reactor operably connected to the anode chamber and configured to react the metal ion in the higher oxidation state with an unsaturated or saturated hydrocarbon to form a green halogenated hydrocarbon wherein the system results in net energy saving of more than 100 kJ/mol or more than 150 kJ/mol or more than 200 kJ/mol or between 100-250 kJ/mol or between 50-100 kJ/mol or between 0-100 kJ/mol or the system results in the voltage savings of more than 1V or between 0-1V or between 1-2V or between 0-2V.

All the electrochemical systems and methods described herein are carried out in more than 5 wt % water or more than 6 wt % water or aqueous medium. In one aspect, the methods and systems provide an advantage of conducting the metal oxidation reaction in the electrochemical cell and reduction reaction outside the cell, all in an aqueous medium. Applicants surprisingly and unexpectedly found that the use of aqueous medium, in the halogenations or sulfonation of the unsaturated or saturated hydrocarbon or hydrogen gas, not only resulted in high yield and selectivity of the product (shown in examples herein) but also resulted in the generation of the reduced metal ion with lower oxidation state in the aqueous medium which could be re-circulated back to the electrochemical system. In some embodiments, since the electrochemical cell runs efficiently in the aqueous medium, no removal or minimal removal of water (such as through azeotropic distillation) is required from the anode electrolyte containing the metal ion in the higher oxidation state which is reacted with the unsaturated or saturated hydrocarbon or hydrogen gas in the aqueous medium. Therefore, the use of the aqueous medium in both the electrochemical cell and the catalysis system provides efficient and less energy intensive integrated systems and methods of the invention.

Accordingly in some embodiments, there is provided a method including contacting an anode with an anode electrolyte wherein the anode electrolyte comprises metal ion, oxidizing the metal ion from a lower oxidation state to a higher oxidation state at the anode, contacting a cathode with a cathode electrolyte, and reacting an unsaturated or saturated hydrocarbon with the anode electrolyte comprising the metal ion in the higher oxidation state in an aqueous medium wherein the aqueous medium comprises more than 5 wt % water or more than 5.5 wt % or more than 6 wt % or between 5-90 wt % or between 5-95 wt % or between 5-99 wt % water or between 5.5-90 wt % or between 5.5-95 wt % or between 5.5-99 wt % water or between 6-90 wt % or between 6-95 wt % or between 6-99 wt % water. In some embodiments, there is provided a method including contacting an anode with an anode electrolyte wherein the anode electrolyte comprises metal ion, oxidizing a metal halide or a metal sulfate from the lower oxidation state to a higher oxidation state at the anode, contacting a cathode with a cathode electrolyte, and halogenating or sulfonating an unsaturated or saturated hydrocarbon with the metal halide or a metal sulfate in the higher oxidation state in an aqueous medium wherein the aqueous medium comprises more than 5 wt % or more than 5.5 wt % or more than 6 wt % or between 5-90 wt % or between 5-95 wt % or between 5-99 wt % water or between 5.5-90 wt % or between 5.5-95 wt % or between 5.5-99 wt % water or between 6-90 wt % or between 6-95 wt % or between 6-99 wt % water. The unsaturated hydrocarbons (such as formula I), saturated hydrocarbons (such as formula III), the halogenated hydrocarbons (such as formula II and IV), the metal ions, etc. have all been described in detail herein.

In some embodiments, there is provided a method including contacting an anode with an anode electrolyte, oxidizing a metal halide or a metal sulfate from the lower oxidation state to a higher oxidation state at the anode, contacting a cathode with a cathode electrolyte, and contacting the metal halide or a metal sulfate in the higher oxidation state with hydrogen gas in an aqueous medium to form an acid, such as, hydrochloric acid or sulfuric acid wherein the aqueous medium comprises more than 5 wt % water or more than 5.5 wt % or more than 6 wt % or between 5-90 wt % or between 5-95 wt % or between 5-99 wt % water or between 5.5-90 wt % or between 5.5-95 wt % or between 5.5-99 wt % water or between 6-90 wt % or between 6-95 wt % or between 6-99 wt % water. In some embodiments, the cathode produces hydroxide ions.

In some embodiments of the above described methods, the cathode produces water, alkali, and/or hydrogen gas. In some embodiments of the above described methods, the cathode is an ODC producing water. In some embodiments of the above described methods, the cathode is an ODC producing alkali. In some embodiments of the above described methods, the cathode produces hydrogen gas. In some embodiments of the above described methods, the cathode is an oxygen depolarizing cathode that reduces oxygen and water to hydroxide ions; the cathode is a hydrogen gas producing cathode that reduces water to hydrogen gas and hydroxide ions; the cathode is a hydrogen gas producing cathode that reduces hydrochloric acid to hydrogen gas; or the cathode is an oxygen depolarizing cathode that reacts hydrochloric acid and oxygen gas to form water.

In some embodiments of the above described methods, the metal ion is any metal ion described herein. In some embodiments of the above described methods, the metal ion is selected from the group consisting of iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combination thereof. In some embodiments, the metal ion is selected from the group consisting of iron, chromium, copper, and tin. In some embodiments, the metal ion is copper. In some embodiments, the lower oxidation state of the metal ion is 1+, 2+, 3+, 4+, or 5+. In some embodiments, the higher oxidation state of the metal ion is 2+, 3+, 4+, 5+, or 6+.

In some embodiments, the method further includes recirculating at least a portion of the metal ion in the lower oxidation state back to the electrochemical cell. In some embodiments, the method does not conduct azeotropic distillation of the water before reacting the metal ion in the higher oxidation state with the unsaturated or saturated hydrocarbon.

In some embodiments, the above described methods do not produce chlorine gas at the anode. In some embodiments, the above described methods do not require oxygen gas and/or chlorine gas for the chlorination of unsaturated or saturated hydrocarbon to halogenated hydrocarbon.

In some embodiments, there is provided a system, comprising an anode in contact with an anode electrolyte comprising metal ion wherein the anode is configured to oxidize the metal ion from the lower oxidation state to a higher oxidation state; a cathode in contact with a cathode electrolyte; and a reactor operably connected to the anode chamber and configured to react the anode electrolyte comprising the metal ion in the higher oxidation state with an unsaturated hydrocarbon or saturated hydrocarbon in an aqueous medium wherein the aqueous medium comprises more than 5 wt % water or more than 5.5 wt % or more than 6 wt % or between 5-90 wt % or between 5-95 wt % or between 5-99 wt % water or between 5.5-90 wt % or between 5.5-95 wt % or between 5.5-99 wt % water or between 6-90 wt % or between 6-95 wt % or between 6-99 wt % water. In some embodiments, there is provided a system including an anode in contact with an anode electrolyte and configured to oxidize a metal halide or a metal sulfate from the lower oxidation state to a higher oxidation state at the anode, a cathode in contact with a cathode electrolyte, and a reactor operably connected to the anode chamber and configured to halogenate or sulfonate an unsaturated or saturated hydrocarbon with the metal halide or a metal sulfate in the higher oxidation state in an aqueous medium wherein the aqueous medium comprises more than 5 wt % water or more than 5.5 wt % or more than 6 wt % or between 5-90 wt % or between 5-95 wt % or between 5-99 wt % water or between 5.5-90 wt % or between 5.5-95 wt % or between 5.5-99 wt % water or between 6-90 wt % or between 6-95 wt % or between 6-99 wt % water.

In some embodiments, there is provided a system including an anode in contact with an anode electrolyte and configured to oxidize a metal halide or a metal sulfate from the lower oxidation state to a higher oxidation state at the anode, a cathode in contact with a cathode electrolyte, and a reactor operably connected to the anode chamber and configured to contact the metal halide or a metal sulfate in the higher oxidation state with hydrogen gas in an aqueous medium to form an acid, such as, hydrochloric acid or sulfuric acid wherein the aqueous medium comprises more than 5 wt % water or more than 5.5 wt % or more than 6 wt % or between 5-90 wt % or between 5-95 wt % or between 5-99 wt % water or between 5.5-90 wt % or between 5.5-95 wt % or between 5.5-99 wt % water or between 6-90 wt % or between 6-95 wt % or between 6-99 wt % water.

In some embodiments of the above described systems, the cathode is configured to produce hydroxide ions. In some embodiments of the above described systems, the cathode is configured to produce hydrogen gas. In some embodiments of the above described systems, the cathode is configured to produce water. In some embodiments of the above described systems, the cathode is ODC. In some embodiments of such methods and systems, no azeotropic distillation of water is required to reduce the amount of water in the anode electrolyte. In some embodiments, the system further includes a separator operably connected to the reactor that separates the product such as acid or the halogenated hydrocarbon from the metal ion in the lower oxidation state. In some embodiments, the system further includes a recirculation system operably connected to the separator and the anode chamber of the electrochemical system configured to recirculate at least a portion of the metal ion in the lower oxidation state from the separator back to the electrochemical cell. Such recirculation system may be a conduit, pipe, tube etc. that may be used to transfer the solutions. Appropriate control valves and computer control systems may be associated with such recirculation systems.

In some embodiments, the above described systems are configured to not produce chlorine gas at the anode. In some embodiments, the above described systems are configured to not require oxygen gas and/or chlorine gas for the chlorination of unsaturated or saturated hydrocarbon to halogenated hydrocarbon.

In some embodiments, the electrochemical systems and methods described herein include the aqueous medium containing more than 5 wt % water. In some embodiments, the aqueous medium includes more than 5 wt % water; or more than 6 wt %; or more than 8 wt % water; or more than 10 wt % water; or more than 15 wt % water; or more than 20 wt % water; or more than 25 wt % water; or more than 50 wt % water; or more than 60 wt % water; or more than 70 wt % water; or more than 80 wt % water; or more than 90 wt % water; or about 99 wt % water; or between 5-100 wt % water; or between 5-99 wt % water; or between 5-90 wt % water; or between 5-80 wt % water; or between 5-70 wt % water; or between 5-60 wt % water; or between 5-50 wt % water; or between 5-40 wt % water; or between 5-30 wt % water; or between 5-20 wt % water; or between 5-10 wt % water; or between 6-100 wt % water; or between 6-99 wt % water; or between 6-90 wt % water; or between 6-80 wt % water; or between 6-70 wt % water; or between 6-60 wt % water; or between 6-50 wt % water; or between 6-40 wt % water; or between 6-30 wt % water; or between 6-20 wt % water; or between 6-10 wt % water; or between 8-100 wt % water; or between 8-99 wt % water; or between 8-90 wt % water; or between 8-80 wt % water; or between 8-70 wt % water; or between 8-60 wt % water; or between 8-50 wt % water; or between 8-40 wt % water; or between 8-30 wt % water; or between 8-20 wt % water; or between 8-10 wt % water; or between 10-100 wt % water; or between 10-75 wt % water; or between 10-50 wt % water; or between 20-100 wt % water; or between 20-50 wt % water; or between 50-100 wt % water; or between 50-75 wt % water; or between 50-60 wt % water; or between 70-100 wt % water; or between 70-90 wt % water; or between 80-100 wt % water. In some embodiments, the aqueous medium may comprise a water soluble organic solvent.

In some embodiments of the methods and systems described herein, the amount of total metal ion in the anode electrolyte or the amount of copper in the anode electrolyte or the amount of iron in the anode electrolyte or the amount of chromium in the anode electrolyte or the amount of tin in the anode electrolyte or the amount of platinum or the amount of metal ion that is contacted with the unsaturated or saturated hydrocarbon is between 1-12M; or between 1-11M; or between 1-10M; or between 1-9M; or between 1-8M; or between 1-7M; or between 1-6M; or between 1-5M; or between 1-4M; or between 1-3M; or between 1-2M; or between 2-12M; or between 2-11M; or between 2-10M; or between 2-9M; or between 2-8M; or between 2-7M; or between 2-6M; or between 2-5M; or between 2-4M; or between 2-3M; or between 3-12M; or between 3-11M; or between 3-10M; or between 3-9M; or between 3-8M; or between 3-7M; or between 3-6M; or between 3-5M; or between 3-4M; or between 4-12M; or between 4-11M; or between 4-10M; or between 4-9M; or between 4-8M; or between 4-7M; or between 4-6M; or between 4-5M; or between 5-12M; or between 5-11M; or between 5-10M; or between 5-9M; or between 5-8M; or between 5-7M; or between 5-6M; or between 6-12M; or between 6-11M; or between 6-10M; or between 6-9M; or between 6-8M; or between 6-7M; or between 7-12M; or between 7-11M; or between 7-10M; or between 7-9M; or between 7-8M; or between 8-12M; or between 8-11M; or between 8-10M; or between 8-9M; or between 9-12M; or between 9-11M; or between 9-10M; or between 10-12M; or between 10-11M; or between 11-12M. In some embodiments, the amount of total ion in the anode electrolyte, as described above, is the amount of the metal ion in the lower oxidation state plus the amount of the metal ion in the higher oxidation state; or the total amount of the metal ion in the higher oxidation state; or the total amount of the metal ion in the lower oxidation state.

In some embodiments of the methods and systems described herein, the anode electrolyte containing the metal ion may contain a mixture of the metal ion in the lower oxidation state and the metal ion in the higher oxidation state. In some embodiments, it may be desirable to have a mix of the metal ion in the lower oxidation state and the metal ion in the higher oxidation state in the anode electrolyte. In some embodiments, the anode electrolyte that is contacted with the unsaturated or saturated hydrocarbon contains the metal ion in the lower oxidation state and the metal ion in the higher oxidation state. In some embodiments, the metal ion in the lower oxidation state and the metal ion in the higher oxidation state are present in a ratio such that the reaction of the metal ion with the unsaturated or saturated hydrocarbon to form metal halo or sulfohydrocarbon takes place. In some embodiments, the ratio of the metal ion in the higher oxidation state to the metal ion in the lower oxidation state is between 20:1 to 1:20, or between 14:1 to 1:2; or between 14:1 to 8:1; or between 14:1 to 7:1: or between 2:1 to 1:2; or between 1:1 to 1:2; or between 4:1 to 1:2; or between 7:1 to 1:2.

In some embodiments of the methods and systems described herein, the anode electrolyte in the electrochemical systems and methods of the invention contains the metal ion in the higher oxidation state in the range of 4-7M, the metal ion in the lower oxidation state in the range of 0.1-2M and sodium chloride in the range of 1-3M. The anode electrolyte may optionally contain 0.01-0.1M hydrochloric acid. In some embodiments of the methods and systems described herein, the anode electrolyte reacted with the hydrogen gas or the unsaturated or saturated hydrocarbon contains the metal ion in the higher oxidation state in the range of 4-7M, the metal ion in the lower oxidation state in the range of 0.1-2M and sodium chloride in the range of 1-3M. The anode electrolyte may optionally contain 0.01-0.1M hydrochloric acid.

In some embodiments of the methods and systems described herein, the anode electrolyte may contain another cation in addition to the metal ion. Other cation includes, but is not limited to, alkaline metal ions and/or alkaline earth metal ions, such as but not limited to, lithium, sodium, calcium, magnesium, etc. The amount of the other cation added to the anode electrolyte may be between 0.01-5M; or between 0.01-1M; or between 0.05-1M; or between 0.5-2M; or between 1-5M.

In some embodiments of the methods and systems described herein, the anode electrolyte may contain an acid. The acid may be added to the anode electrolyte to bring the pH of the anolyte to 1 or 2 or less. The acid may be hydrochloric acid or sulfuric acid.

The systems provided herein include a reactor operably connected to the anode chamber. The reactor is configured to contact the metal chloride in the anode electrolyte with the hydrogen gas or the unsaturated or saturated hydrocarbon. The reactor may be any means for contacting the metal chloride in the anode electrolyte with the hydrogen gas or the unsaturated or saturated hydrocarbon. Such means or such reactor are well known in the art and include, but not limited to, pipe, duct, tank, series of tanks, container, tower, conduit, and the like. Some examples of such reactors are described in FIGS. 7A, 7B, 10A, and 10B herein. The reactor may be equipped with one or more of controllers to control temperature sensor, pressure sensor, control mechanisms, inert gas injector, etc. to monitor, control, and/or facilitate the reaction. In some embodiments, the reaction between the metal chloride with metal ion in higher oxidation state and the unsaturated or saturated hydrocarbon, are carried out in the reactor at the temperature of between 100-200° C. or between 100-175° C. or between 150-175° C. and pressure of between 100-500 psig or between 100-400 psig or between 100-300 psig or between 150-350 psig. In some embodiments, the components of the reactor are lined with Teflon to prevent corrosion of the components. Some examples of the reactors for carrying out the reaction of the metal ion in the higher oxidation state with the hydrogen gas are illustrated in FIGS. 7A and 7B.

In some embodiments, the unsaturated or saturated hydrocarbon may be administered to the anode chamber where the metal halide or metal sulfate with metal in the higher oxidation state reacts with the unsaturated or saturated hydrocarbon to form respective products inside the anode chamber. In some embodiments, the unsaturated or saturated hydrocarbon may be administered to the anode chamber where the metal chloride with metal in the higher oxidation state reacts with the unsaturated or saturated hydrocarbon to form chlorohydrocarbon. Such systems include the unsaturated or saturated hydrocarbon delivery system which is operably connected to the anode chamber and is configured to deliver the unsaturated or saturated hydrocarbon to the anode chamber. The unsaturated or saturated hydrocarbon may be a solid, liquid, or a gas. The unsaturated or saturated hydrocarbon may be supplied to the anode using any means for directing the unsaturated or saturated hydrocarbon from the external source to the anode chamber. Such means for directing the unsaturated or saturated hydrocarbon from the external source to the anode chamber or the unsaturated or saturated hydrocarbon delivery system are well known in the art and include, but not limited to, pipe, tanks, duct, conduit, and the like. In some embodiments, the system or the unsaturated or saturated hydrocarbon delivery system includes a duct that directs the unsaturated or saturated hydrocarbon from the external source to the anode. It is to be understood that the unsaturated or saturated hydrocarbon may be directed to the anode from the bottom of the cell, top of the cell or sideways. In some embodiments, the unsaturated or saturated hydrocarbon gas is directed to the anode in such a way that the unsaturated or saturated hydrocarbon gas is not in direct contact with the anolyte. In some embodiments, the unsaturated or saturated hydrocarbon may be directed to the anode through multiple entry ports. The source of unsaturated or saturated hydrocarbon that provides unsaturated or saturated hydrocarbon to the anode chamber, in the methods and systems provided herein, includes any source of unsaturated or saturated hydrocarbon known in the art. Such sources include, without limitation, commercial grade unsaturated or saturated hydrocarbon and/or unsaturated or saturated hydrocarbon generating plants, such as, petrochemical refinery industry.

In some embodiments, there are provided methods and systems where the electrochemical cells of the invention are set up on-site where unsaturated or saturated hydrocarbon is generated, such as refinery for carrying out the halogenations, such as chlorination of the unsaturated or saturated hydrocarbon. In some embodiments, the metal ion containing anolyte from the electrochemical system is transported to the refinery where the unsaturated or saturated hydrocarbon is formed for carrying out the halogenations, such as chlorination of the unsaturated or saturated hydrocarbon. In some embodiments, the methods and systems of the invention can utilize the ethylene gas from the refineries without the need for the filtration or cleaning of the ethylene gas. Typically, the ethylene gas generating plants scrub the gas to get rid of the impurities. In some embodiments of the methods and systems of the invention, such pre-scrubbing of the gas is not needed and can be avoided.

Figure 9:
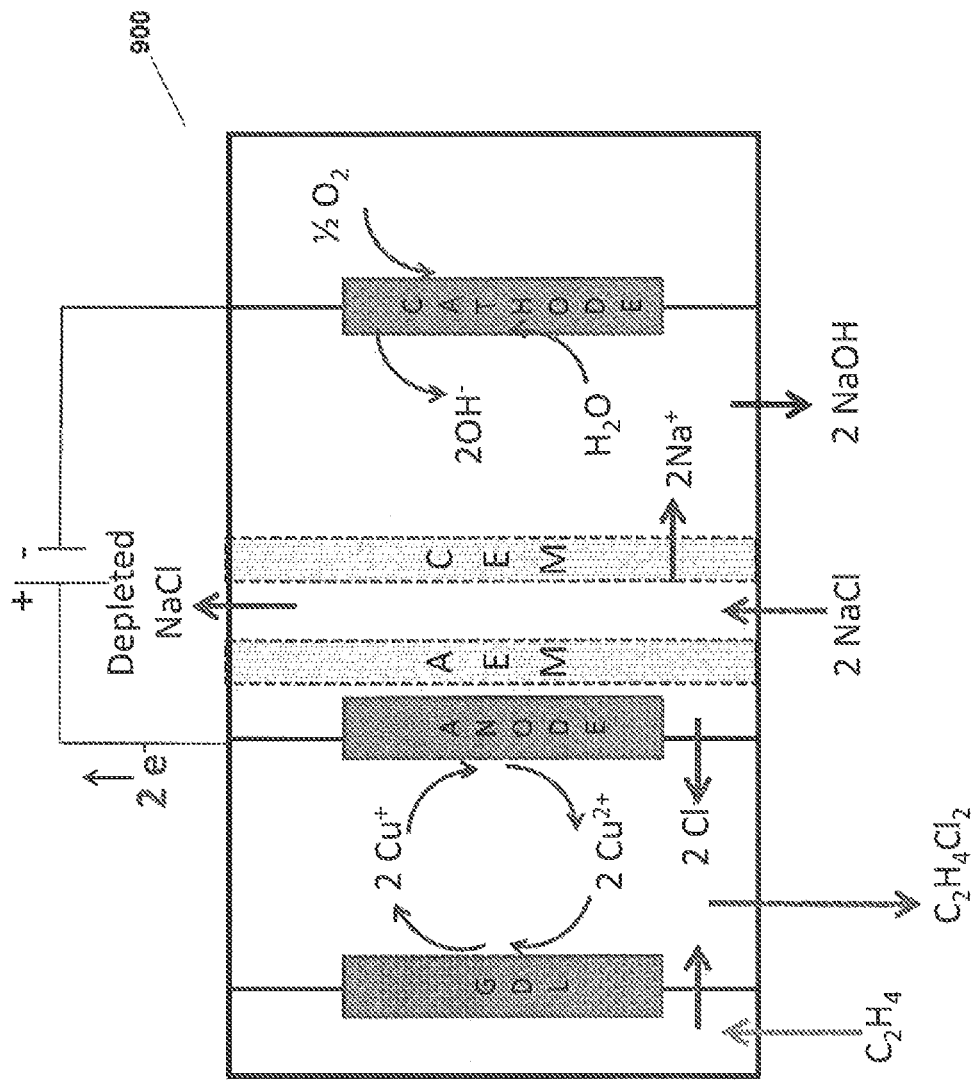
FIG. 9 is an illustration of an embodiment of the invention.

In some embodiments, the metal generation and the halogenations, such as chlorination reaction takes place in the same anode chamber. An illustrative example of such embodiment is depicted in FIG. 9. It is to be understood that the system 900 of FIG. 9 is for illustration purposes only and other metal ions with different oxidations states, other unsaturated or saturated hydrocarbons, other electrochemical systems forming products other than alkali, such as water or hydrogen gas in the cathode chamber, and other unsaturated or saturated hydrocarbon gases, are equally applicable to the system. In some embodiments, as illustrated in FIG. 9, the electrochemical system 900 includes an anode situated near the AEM. The system 900 also includes a gas diffusion layer (GDL). The anode electrolyte is in contact with the anode on one side and the GDL on the other side. In some embodiments, the anode may be situated to minimize the resistance from the anolyte, for example, the anode may be situated close to AEM or bound to AEM. In some embodiments, the anode converts metal ions from the lower oxidation state to the metal ions in the higher oxidation states. For example, the anode converts metal ions from 1+ oxidation state to 2+ oxidation state. The $Cu^{2+}$ ions combine with chloride ions to form $CuCl_2$. The ethylene gas is pressurized into a gaseous chamber on one side of the GDL. The ethylene gas then diffuses through the gas diffusion layer and reacts with metal chloride in the higher oxidation state to form chlorohydrocarbon, such as ethylene dichloride. The metal chloride $CuCl_2$ in turn undergoes reduction to lower oxidation state to form CuCl. In some embodiments, the anode electrolyte may be withdrawn and the ethylene dichloride may be separated from the anode electrolyte using separation techniques well known in the art, including, but not limited to, filtration, vacuum distillation, fractional distillation, fractional crystallization, ion exchange resin, etc. In some embodiments, the ethylene dichloride may be denser than the anode electrolyte and may form a separate layer inside the anode chamber. In such embodiments, the ethylene dichloride may be removed from the bottom of the cell. In some embodiments, the gaseous chamber on one side of GDL may be vented to remove the gas. In some embodiments, the anode chamber may be vented to remove the gaseous ethylene or gaseous byproducts. The system 900 also includes an oxygen depolarized cathode that produces hydroxide ions from water and oxygen. The hydroxide ions may be subjected to any of the carbonate precipitation processes described herein. In some embodiments, the cathode is not a gas-diffusion cathode but is a cathode as described in FIG. 4A or 4B. In some embodiments, the system 900 may be applied to any electrochemical system that produces alkali.

In some embodiments of the system and method described herein, no gas is formed at the cathode. In some embodiments of the system and method described herein, hydrogen gas is formed at the cathode. In some embodiments of the system and method described herein, no gas is formed at the anode. In some embodiments of the system and method described herein, no gas is used at the anode other than the gaseous unsaturated or saturated hydrocarbon.

Figure 10A:
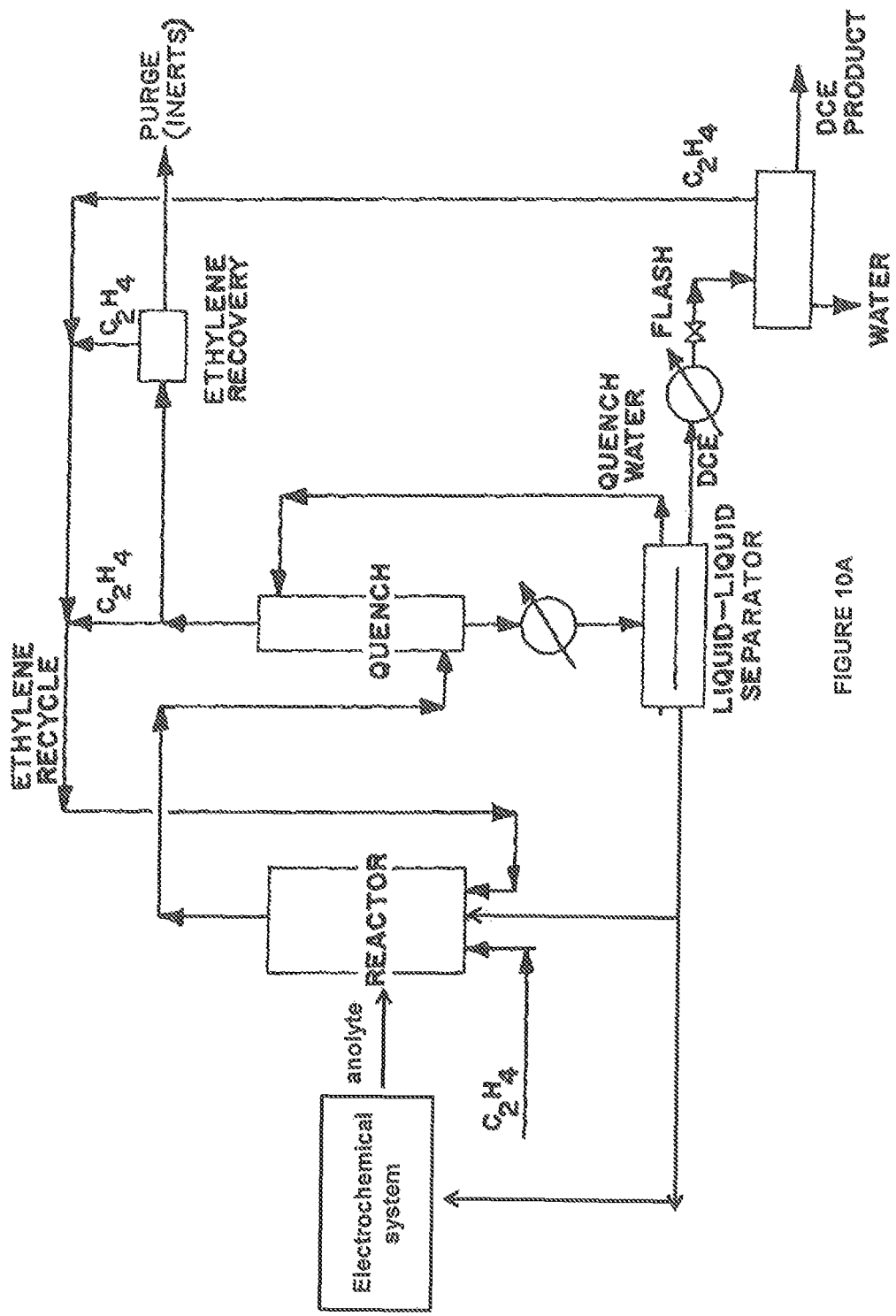
FIG. 10A is an illustration of an embodiment of the invention.

Another illustrative example of the reactor that is connected to the electrochemical system is illustrated in FIG. 10A. As illustrated in FIG. 10A, the anode chamber of the electrochemical system (electrochemical system can be any electrochemical system described herein) is connected to a reactor which is also connected to a source of unsaturated or saturated hydrocarbon, an example illustrated as ethylene ($C_2H_4$) in FIG. 10A. In some embodiments, the electrochemical system and the reactor are inside the same unit and are connected inside the unit. The anode electrolyte, containing the metal ion in the higher oxidation state optionally with the metal ion in the lower oxidation state, along with ethylene are fed to a prestressed (e.g., brick-lined) reactor. The chlorination of ethylene takes place inside the reactor to form ethylene dichloride (EDC or dichloroethane DCE) and the metal ion in the lower oxidation state. The reactor may operate in the range of 340-360° F. and 200-300 psig. Other reactor conditions, such as, but not limited to, metal ion concentration, ratio of metal ion in the lower oxidation state to the metal ion in the higher oxidation state, partial pressures of DCE and water vapor can be set to assure high selectivity operation. Reaction heat may be removed by vaporizing water. In some embodiments, a cooling surface may not be required in the reactor and thus no temperature gradients or close temperature control may be needed. The reactor effluent gases may be quenched with water (shown as "quench" reactor in FIG. 10A) in the prestressed (e.g., brick-lined) packed tower. The liquid leaving the tower may be cooled further and separated into the aqueous phase and DCE phase. The aqueous phase may be split part being recycled to the tower as quench water and the remainder may be recycled to the reactor or the electrochemical system. The DCE product may be cooled further and flashed to separate out more water and dissolved ethylene. This dissolved ethylene may be recycled as shown in FIG. 10A. The uncondensed gases from the quench tower may be recycled to the reactor, except for the purge stream to remove inerts. The purge stream may go through the ethylene recovery system to keep the over-all utilization of ethylene high, e.g., as high as 95%. Experimental determinations may be made of flammability limits for ethylene gas at actual process temperature, pressure and compositions. The construction material of the plant may include prestressed brick linings, Hastealloys B and C, inconel, dopant grade titanium (e.g. AKOT, Grade II), tantalum, Kynar, Teflon, PEEK, glass, or other polymers or plastics. The reactor may also be designed to continuously flow the anode electrolyte in and out of the reactor.

Another illustrative example of the reactor that is connected to the electrochemical system is as illustrated in FIG. 10B. As illustrated in FIG. 10B, the reactor system 1000 is a glass vessel A, suspended from the top portion of a metal flange B, connected to an exit line C, by means of a metal ball socket welded to the head of the flange. The glass reactor is encased in an electrically heated metal shell, D. The heat input and the temperature may be controlled by an automatic temperature regulator. The hydrocarbon may be introduced into the metal shell through an opening E and through the glass tube F, which may be fitted with a fritted glass foot. This arrangement may provide for pressure equalization on both sides of the glass reactor. The hydrocarbon may come into contact with the metal solution (metal in higher oxidation state) at the bottom of the reactor and may bubble through the medium. The volatile products, water vapor, and/or unreacted hydrocarbon may leave via line C, equipped optionally with valve H which may reduce the pressure to atmosphere. The exiting gases may be passed through an appropriate trapping system to remove the product. The apparatus may also be fitted with a bypass arrangement G, which permits the passage of the gas through the pressure zone without passing through the aqueous metal medium. In some embodiments, the reduced metal ions in lower oxidation state that are left in the vessel, are subjected to electrolysis, as described herein, to regenerate the metal ions in the higher oxidation state.

An illustrative embodiment of the invention is as shown in FIG. 11. As illustrated in FIG. 11, the electrochemical system 600 of FIG. 6 (or alternatively system 400 of FIG. 4A) may be integrated with CuCl—HCl electrochemical system 1100 (also illustrated as system in FIG. 4B). In the CuCl—HCl electrochemical system 1100, the input at the anode is CuCl and HCl which results in $CuCl_2$ and hydrogen ions. The hydrogen ions pass through a proton exchange membrane to the cathode where it forms hydrogen gas. In some embodiments, chloride conducting membranes may also be used. In some embodiments, it is contemplated that the CuCl—HCl cell may run at 0.5V or less and the system 600 may run at 0V or less. Some deviations from the contemplated voltage may occur due to resistance losses.

In one aspect, in the systems and methods provided herein, the $CuCl_2$ formed in the anode electrolyte may be used for copper production. For example, the $CuCl_2$ formed in the systems and methods of the invention may be used for leaching process to extract copper from the copper minerals. For example only, chalcopyrite is a copper mineral which can be leached in chloride milieu with the help of an oxidizer, $Cu^{2+}$. Divalent copper may leach the copper of chalcopyrite and other sulfides. Other minerals such as iron, sulfur, gold, silver etc. can be recovered once copper is leached out. In some embodiments, $CuCl_2$ produced by the electrochemical cells described herein, may be added to the copper mineral concentrate. The $Cu^{2+}$ ions may oxidize the copper mineral and form CuCl. The CuCl solution from the concentrate may be fed back to the anode chamber of the electrochemical cell described herein which may convert CuCl to $CuCl_2$. The $CuCl_2$ may be then fed back to the mineral concentrate to further oxidize the copper mineral. Once the copper is leached out, the silver may be cemented out along with further precipitation of zinc, lead etc. The copper may be then precipitated out as copper oxide by treatment with alkali which alkali may be produced by the cathode chamber of the electrochemical cell. After the precipitation of copper as oxide, the filtrate NaCl may be returned to the electrochemical cell. The hydrogen gas generated at the cathode may be used for the reduction of the copper oxide to form metallic copper (at high temp.). The molten copper may be cast into copper products like copper wire rod. This method can be used for low grade ores or for various types of copper minerals. The electrochemical plant may be fitted close to the quarry or close to the concentrator eliminating transportation cost for waste products and allowing transportation of valuable metal products only.

The processes and systems described herein may be batch processes or systems or continuous flow processes or systems.

The reaction of the hydrogen gas or the unsaturated or saturated hydrocarbon with the metal ion in the higher oxidation state, as described in the aspects and embodiments herein, is carried out in the aqueous medium. In some embodiments, such reaction may be in a non-aqueous liquid medium which may be a solvent for the hydrocarbon or hydrogen gas feedstock. The liquid medium or solvent may be aqueous or non-aqueous. Suitable non-aqueous solvents being polar and non-polar aprotic solvents, for example dimethylformamide (DMF), dimethylsulphoxide (DMSO), halogenated hydrocarbons, for example only, dichloromethane, carbon tetrachloride, and 1,2-dichloroethane, and organic nitriles, for example, acetonitrile. Organic solvents may contain a nitrogen atom capable of forming a chemical bond with the metal in the lower oxidation state thereby imparting enhanced stability to the metal ion in the lower oxidation state. In some embodiments, acetonitrile is the organic solvent.

In some embodiments, when the organic solvent is used for the reaction between the metal ion in the higher oxidation state with the hydrogen gas or hydrocarbon, the water may need to be removed from the metal containing medium. As such, the metal ion obtained from the electrochemical systems described herein may contain water. In some embodiments, the water may be removed from the metal ion containing medium by azeotropic distillation of the mixture. In some embodiments, the solvent containing the metal ion in the higher oxidation state and the hydrogen gas or the unsaturated or saturated hydrocarbon may contain between 5-90%; or 5-80%; or 5-70%; or 5-60%; or 5-50%; or 5-40%; or 5-30%; or 5-20%; or 5-10% by weight of water in the reaction medium. The amount of water which may be tolerated in the reaction medium may depend upon the particular halide carrier in the medium, the tolerable amount of water being greater, for example, for copper chloride than for ferric chloride. Such azeotropic distillation may be avoided when the aqueous medium is used in the reactions.

In some embodiments, the reaction of the metal ion in the higher oxidation state with the hydrogen gas or the unsaturated or saturated hydrocarbon may take place when the reaction temperature is above 50° C. up to 350° C. In aqueous media, the reaction may be carried out under a super atmospheric pressure of up to 1000 psi or less to maintain the reaction medium in liquid phase at a temperature of from 50° C. to 200° C., typically from about 120° C. to about 180° C.

In some embodiments, the reaction of the metal ion in the higher oxidation state with the unsaturated or saturated hydrocarbon may include a halide carrier. In some embodiments, the ratio of halide ion:total metal ion in the higher oxidation state is 1:1; or greater than 1:1; or 1.5:1; or greater than 2:1 and or at least 3:1. Thus, for example, the ratio in cupric halide solutions in concentrated hydrochloric acid may be about 2:1 or 3:1. In some embodiments, owing to the high rate of usage of the halide carrier it may be desired to use the metal halides in high concentration and to employ saturated or near-saturated solutions of the metal halides. If desired, the solutions may be buffered to maintain the pH at the desired level during the halogenation reaction.

In some embodiments, a non-halide salt of the metal may be added to the solution containing metal ion in the higher oxidation state. The added metal salt may be soluble in the metal halide solution. Examples of suitable salts for incorporating in cupric chloride solutions include, but are not limited to, copper sulphate, copper nitrate and copper tetrafluoroborate. In some embodiments a metal halide may be added that is different from the metal halide employed in the methods and systems. For example, ferric chloride may be added to the cupric chloride systems at the time of halogenations of the unsaturated hydrocarbon.

The unsaturated or saturated hydrocarbon feedstock may be fed to the halogenation vessel continuously or intermittently. Efficient halogenation may be dependent upon achieving intimate contact between the feedstock and the metal ion in solution and the halogenation reaction may be carried out by a technique designed to improve or maximize such contact. The metal ion solution may be agitated by stirring or shaking or any desired technique, e.g. the reaction may be carried out in a column, such as a packed column, or a tricklebed reactor or reactors described herein. For example, where the unsaturated or saturated hydrocarbon is gaseous, a counter-current technique may be employed wherein the unsaturated or saturated hydrocarbon is passed upwardly through a column or reactor and the metal ion solution is passed downwardly through the column or reactor. In addition to enhancing contact of the unsaturated or saturated hydrocarbon and the metal ion in the solution, the techniques described herein may also enhance the rate of dissolution of the unsaturated or saturated hydrocarbon in the solution, as may be desirable in the case where the solution is aqueous and the water-solubility of the unsaturated or saturated hydrocarbon is low. Dissolution of the feedstock may also be assisted by higher pressures.

Mixtures of saturated, unsaturated hydrocarbons and/or partially halogenated hydrocarbons may be employed. In some embodiments, partially-halogenated products of the process of the invention which are capable of further halogenation may be recirculated to the reaction vessel through a product-recovery stage and, if appropriate, a metal ion in the lower oxidation state regeneration stage. In some embodiments, the halogenation reaction may continue outside the halogenation reaction vessel, for example in a separate regeneration vessel, and care may need to be exercised in controlling the reaction to avoid over-halogenation of the unsaturated or saturated hydrocarbon.

In some embodiments, the electrochemical systems described herein are set up close to the plant that produces the unsaturated or saturated hydrocarbon or that produces hydrogen gas. In some embodiments, the electrochemical systems described herein are set up close to the PVC plant. For example, in some embodiments, the electrochemical system is within the radius of 100 miles near the ethylene gas, hydrogen gas, vinyl chloride monomer, and/or PVC plant. In some embodiments, the electrochemical systems described herein are set up inside or outside the ethylene plant for the reaction of the ethylene with the metal ion. In some embodiments, the plants described as above are retrofitted with the electrochemical systems described herein. In some embodiments, the anode electrolyte containing the metal ion in the higher oxidation state is transported to the site of the plants described above. In some embodiments, the anode electrolyte containing the metal ion in the higher oxidation state is transported to within 100 miles of the site of the plants described above. In some embodiments, the electrochemical systems described herein are set up close to the plants as described above as well as close to the source of divalent cations such that the alkali generated in the cathode electrolyte is reacted with the divalent cations to form carbonate/bicarbonate products. In some embodiments, the electrochemical systems described herein are set up close to the plants as described above, close to the source of divalent cations and/or the source of carbon dioxide such that the alkali generated in the cathode electrolyte is able to sequester carbon dioxide to form carbonate/bicarbonate products. In some embodiments, the carbon dioxide generated by the refinery that forms the unsaturated or saturated hydrocarbon is used in the electrochemical systems or is used in the precipitation of carbonate/bicarbonate products. Accordingly, in some embodiments, the electrochemical systems described herein are set up close to the plants as described above, close to the source of divalent cations and/or the source of carbon dioxide such as, refineries producing the unsaturated or saturated hydrocarbon, such that the alkali generated in the cathode electrolyte is able to sequester carbon dioxide to form carbonate/bicarbonate products.

Any number of halo or sulfohydrocarbons may be generated from the reaction of the metal chloride in the higher oxidation state with the unsaturated or saturated hydrocarbons, as described herein. The chlorohydrocarbons may be used in chemical and/or manufacturing industries. Chlorohydrocarbons may be used as chemical intermediates or solvents. Solvent uses include a wide variety of applications, including metal and fabric cleaning, extraction of fats and oils, and reaction media for chemical synthesis.

In some embodiments, the unsaturated hydrocarbon such as ethylene is reacted with the metal chloride in the higher oxidation state to form ethylene dichloride. Ethylene dichloride may be used for variety of purposes including, but not limited to, making chemicals involved in plastics, rubber and synthetic textile fibers, such as, but not limited to, vinyl chloride, tri- and tetra-chloroethylene, vinylidene chloride, trichloroethane, ethylene glycol, diaminoethylene, polyvinyl chloride, nylon, viscose rayon, styrene-butadiene rubber, and various plastics; as a solvent used as degreaser and paint remover; as a solvent for resins, asphalt, bitumen, rubber, fats, oils, waxes, gums, photography, photocopying, cosmetics, leather cleaning, and drugs; fumigant for grains, orchards, mushroom houses, upholstery, and carpet; as a pickling agent; as a building block reagent as an intermediate in the production of various organic compounds such as, ethylenediamine; as a source of chlorine with elimination of ethene and chloride; as a precursor to 1,1,1-trichloroethane which is used in dry cleaning; as an anti-knock additive in leaded fuels; used in extracting spices such as annatto, paprika and turmeric; as a diluent for pesticide; in paint, coatings, and adhesives; and combination thereof.

In the methods and systems described herein, in some embodiments, no hydrochloric acid is formed in the anode chamber. In the methods and systems described herein, in some embodiments, no gas is formed at the anode. In the methods and systems described herein, in some embodiments, no gas is used at the anode. In the methods and systems described herein, in some embodiments, hydrogen gas is formed at the cathode. In the methods and systems described herein, in some embodiments, no hydrogen gas is formed at the cathode.

In some embodiments, a wire is connected between the cathode and the anode for the current to pass through the cell. In such embodiments, the cell may act as a battery and the current generated through the cell may be used to generate alkali which is withdrawn from the cell. In some embodiments, the resistance of the cell may go up and the current may go down. In such embodiments, a voltage may be applied to the electrochemical cell. The resistance of the cell may increase for various reasons including, but not limited to, corrosion of the electrodes, solution resistance, fouling of membrane, etc. In some embodiments, current may be drawn from the cell using an amperic load.

In some embodiments, the systems provided herein result in low to zero voltage systems that generate alkali as compared to chlor-alkali process or chlor-alkali process with ODC or any other process that oxidizes metal ions from lower oxidation state to the higher oxidation state in the anode chamber. In some embodiments, the systems described herein run at voltage of less than 2V; or less than 1.2V; or less than 1.1V; or less than 1V; or less than 0.9V; or less than 0.8V; or less than 0.7V; or less than 0.6V; or less than 0.5V; or less than 0.4V; or less than 0.3V; or less than 0.2V; or less than 0.1V; or at zero volts; or between 0-1.2V; or between 0-1V; or between 0-0.5 V; or between 0.5-1V; or between 0.5-2V; or between 0-0.1 V; or between 0.1-1V; or between 0.1-2V; or between 0.01-0.5V; or between 0.01-1.2V; or between 1-1.2V; or between 0.2-1V; or 0V; or 0.5V; or 0.6V; or 0.7V; or 0.8V; or 0.9V; or 1V.

As used herein, the "voltage" includes a voltage or a bias applied to or drawn from an electrochemical cell that drives a desired reaction between the anode and the cathode in the electrochemical cell. In some embodiments, the desired reaction may be the electron transfer between the anode and the cathode such that an alkaline solution, water, or hydrogen gas is formed in the cathode electrolyte and the metal ion is oxidized at the anode. In some embodiments, the desired reaction may be the electron transfer between the anode and the cathode such that the metal ion in the higher oxidation state is formed in the anode electrolyte from the metal ion in the lower oxidation state. The voltage may be applied to the electrochemical cell by any means for applying the current across the anode and the cathode of the electrochemical cell. Such means are well known in the art and include, without limitation, devices, such as, electrical power source, fuel cell, device powered by sun light, device powered by wind, and combination thereof. The type of electrical power source to provide the current can be any power source known to one skilled in the art. For example, in some embodiments, the voltage may be applied by connecting the anodes and the cathodes of the cell to an external direct current (DC) power source. The power source can be an alternating current (AC) rectified into DC. The DC power source may have an adjustable voltage and current to apply a requisite amount of the voltage to the electrochemical cell.

In some embodiments, the current applied to the electrochemical cell is at least 50 $mA/cm^2$; or at least 100 $mA/cm^2$; or at least 150 $mA/cm^2$; or at least 200 $mA/cm^2$; or at least 500 $mA/cm^2$; or at least 1000 $mA/cm^2$; or at least 1500 $mA/cm^2$; or at least 2000 $mA/cm^2$; or at least 2500 $mA/cm^2$; or between 100-2500 $mA/cm^2$; or between 100-2000 $mA/cm^2$; or between 100-1500 $mA/cm^2$; or between 100-1000 $mA/cm^2$; or between 100-500 $mA/cm^2$; or between 200-2500 $mA/cm^2$; or between 200-2000 $mA/cm^2$; or between 200-1500 $mA/cm^2$; or between 200-1000 $mA/cm^2$; or between 200-500 $mA/cm^2$; or between 500-2500 $mA/cm^2$; or between 500-2000 $mA/cm^2$; or between 500-1500 $mA/cm^2$; or between 500-1000 $mA/cm^2$; or between 1000-2500 $mA/cm^2$; or between 1000-2000 $mA/cm^2$; or between 1000-1500 $mA/cm^2$; or between 1500-2500 $mA/cm^2$; or between 1500-2000 $mA/cm^2$; or between 2000-2500 $mA/cm^2$.

In some embodiments, the cell runs at voltage of between 0-3V when the applied current is 100-250 $mA/cm^2$ or 100-150 $mA/cm^2$ or 100-200 $mA/cm^2$ or 100-300 $mA/cm^2$ or 100-400 $mA/cm^2$ or 100-500 $mA/cm^2$ or 150-200 $mA/cm^2$ or 200-150 $mA/cm^2$ or 200-300 $mA/cm^2$ or 200-400 $mA/cm^2$ or 200-500 $mA/cm^2$ or 150 $mA/cm^2$ or 200 $mA/cm^2$ or 300 $mA/cm^2$ or 400 $mA/cm^2$ or 500 $mA/cm^2$ or 600 $mA/cm^2$. In some embodiments, the cell runs at between 0-1V. In some embodiments, the cell runs at between 0-1.5V when the applied current is 100-250 $mA/cm^2$ or 100-150 $mA/cm^2$ or 150-200 $mA/cm^2$ or 150 $mA/cm^2$ or 200 $mA/cm^2$. In some embodiments, the cell runs at between 0-1V at an amperic load of 100-250 $mA/cm^2$ or 100-150 $mA/cm^2$ or 150-200 $mA/cm^2$ or 150 $mA/cm^2$ or 200 $mA/cm^2$. In some embodiments, the cell runs at 0.5V at a current or an amperic load of 100-250 $mA/cm^2$ or 100-150 $mA/cm^2$ or 150-200 $mA/cm^2$ or 150 $mA/cm^2$ or 200 $mA/cm^2$.

In some embodiments, the systems and methods provided herein further include a percolator and/or a spacer between the anode and the ion exchange membrane and/or the cathode and the ion exchange membrane. The electrochemical systems containing percolator and/or spacers are described in U.S. Provisional Application No. 61/442,573, filed Feb. 14, 2011, which is incorporated herein by reference in its entirety in the present disclosure.

The systems provided herein are applicable to or can be used for any of one or more methods described herein. In some embodiments, the systems provided herein further include an oxygen gas supply or delivery system operably connected to the cathode chamber. The oxygen gas delivery system is configured to provide oxygen gas to the gas-diffusion cathode. In some embodiments, the oxygen gas delivery system is configured to deliver gas to the gas-diffusion cathode where reduction of the gas is catalyzed to hydroxide ions. In some embodiments, the oxygen gas and water are reduced to hydroxide ions; un-reacted oxygen gas in the system is recovered; and re-circulated to the cathode. The oxygen gas may be supplied to the cathode using any means for directing the oxygen gas from the external source to the cathode. Such means for directing the oxygen gas from the external source to the cathode or the oxygen gas delivery system are well known in the art and include, but not limited to, pipe, duct, conduit, and the like. In some embodiments, the system or the oxygen gas delivery system includes a duct that directs the oxygen gas from the external source to the cathode. It is to be understood that the oxygen gas may be directed to the cathode from the bottom of the cell, top of the cell or sideways. In some embodiments, the oxygen gas is directed to the back side of the cathode where the oxygen gas is not in direct contact with the catholyte. In some embodiments, the oxygen gas may be directed to the cathode through multiple entry ports. The source of oxygen that provides oxygen gas to the gas-diffusion cathode, in the methods and systems provided herein, includes any source of oxygen known in the art. Such sources include, without limitation, ambient air, commercial grade oxygen gas from cylinders, oxygen gas obtained by fractional distillation of liquefied air, oxygen gas obtained by passing air through a bed of zeolites, oxygen gas obtained from electrolysis of water, oxygen obtained by forcing air through ceramic membranes based on zirconium dioxides by either high pressure or electric current, chemical oxygen generators, oxygen gas as a liquid in insulated tankers, or combination thereof. In some embodiments, the source of oxygen may also provide carbon dioxide gas. In some embodiments, the oxygen from the source of oxygen gas may be purified before being administered to the cathode chamber. In some embodiments, the oxygen from the source of oxygen gas is used as is in the cathode chamber.

Alkali in the Cathode Chamber

The cathode electrolyte containing the alkali maybe withdrawn from the cathode chamber. The alkali may be separated from the cathode electrolyte using techniques known in the art, including but not limited to, diffusion dialysis. In some embodiments, the alkali produced in the methods and systems provided herein, is used as is commercially or is used in commercial processes known in the art. The purity of the alkali formed in the methods and systems may vary depending on the end use requirements. For example, methods and systems provided herein that use an electrochemical cell equipped with membranes, may form a membrane quality alkali which may be substantially free of impurities. In some embodiments, a less pure alkali may also be formed by avoiding the use of membranes or by adding the carbon to the cathode electrolyte. In some embodiments, the alkali formed in the cathode electrolyte is more than 2% w/w or more than 5% w/w or between 5-50% w/w.

In some embodiments, the alkali produced in the cathode chamber may be used in various commercial processes, as described herein. In some embodiments, the system appropriate to such uses may be operatively connected to the electrochemical unit, or the alkali may be transported to the appropriate site for use. In some embodiments, the systems include a collector configured to collect the alkali from the cathode chamber and connect it to the appropriate process which may be any means to collect and process the alkali including, but not limited to, tanks, collectors, pipes etc. that can collect, process, and/or transfer the alkali produced in the cathode chamber for use in the various commercial processes.

In some embodiments, the alkali, such as, sodium hydroxide produced in the cathode electrolyte is used as is for commercial purposes or is treated in variety of ways well known in the art. For example, sodium hydroxide formed in the catholyte may be used as a base in the chemical industry, in household, and/or in the manufacture of pulp, paper, textiles, drinking water, soaps, detergents and drain cleaner. In some embodiments, the sodium hydroxide may be used in making paper. Along with sodium sulfide, sodium hydroxide may be a component of the white liquor solution used to separate lignin from cellulose fibers in the Kraft process. It may also be useful in several later stages of the process of bleaching the brown pulp resulting from the pulping process. These stages may include oxygen delignification, oxidative extraction, and simple extraction, all of which may require a strong alkaline environment with a pH>10.5 at the end of the stages. In some embodiments, the sodium hydroxide may be used to digest tissues. This process may involve placing of a carcass into a sealed chamber and then putting the carcass in a mixture of sodium hydroxide and water, which may break chemical bonds keeping the body intact. In some embodiments, the sodium hydroxide may be used in Bayer process where the sodium hydroxide is used in the refining of alumina containing ores (bauxite) to produce alumina (aluminium oxide). The alumina is the raw material that may be used to produce aluminium metal via the electrolytic Hall-Héroult process. The alumina may dissolve in the sodium hydroxide, leaving impurities less soluble at high pH such as iron oxides behind in the form of a highly alkaline red mud. In some embodiments, the sodium hydroxide may be used in soap making process. In some embodiments, the sodium hydroxide may be used in the manufacture of biodiesel where the sodium hydroxide may be used as a catalyst for the trans-esterification of methanol and triglycerides. In some embodiments, the sodium hydroxide may be used as a cleansing agent, such as, but not limited to, degreaser on stainless and glass bakeware.

In some embodiments, the sodium hydroxide may be used in food preparation. Food uses of sodium hydroxide include, but not limited to, washing or chemical peeling of fruits and vegetables, chocolate and cocoa processing, caramel coloring production, poultry scalding, soft drink processing, and thickening ice cream. Olives may be soaked in sodium hydroxide to soften them, while pretzels and German lye rolls may be glazed with a sodium hydroxide solution before baking to make them crisp. In some embodiments, the sodium hydroxide may be used in homes as a drain cleaning agent for clearing clogged drains. In some embodiments, the sodium hydroxide may be used as a relaxer to straighten hair. In some embodiments, the sodium hydroxide may be used in oil refineries and for oil drilling, as it may increase the viscosity and prevent heavy materials from settling. In the chemical industry, the sodium hydroxide may provide fuctions of neutralisation of acids, hydrolysis, condensation, saponification, and replacement of other groups in organic compounds of hydroxyl ions. In some embodiments, the sodium hydroxide may be used in textile industry. Mercerizing of fiber with sodium hydroxide solution may enable greater tensional strength and consistent lustre. It may also remove waxes and oils from fiber to make the fiber more receptive to bleaching and dying. Sodium hydroxide may also be used in the production of viscose rayon. In some embodiments, the sodium hydroxide may be used to make sodium hypochlorite which may be used as a household bleach and disinfectant and to make sodium phenolate which may be used in antiseptics and for the manufacture of Aspirin.

Contact of Carbon Dioxide with Cathode Electrolyte

In one aspect, there are provided methods and systems as described herein, that include contacting carbon dioxide with the cathode electrolyte either inside the cathode chamber or outside the cathode chamber. In one aspect, there are provided methods including contacting an anode with a metal ion in an anode electrolyte in an anode chamber; converting or oxidizing the metal ion from a lower oxidation state to a higher oxidation state in the anode chamber; contacting a cathode with a cathode electrolyte in a cathode chamber; forming an alkali in the cathode electrolyte; and contacting the alkali in the cathode electrolyte with carbon from a source of carbon, such as carbon dioxide from a source of carbon dioxide. In some embodiments, the methods further comprises using the metal in the higher oxidation state formed in the anode chamber as is (as described herein) or use it for reaction with hydrogen gas or reaction with unsaturated or saturated hydrocarbons (as described herein). In some embodiments, there is provided a method comprising contacting an anode with an anode electrolyte; oxidizing metal ion from a lower oxidation state to a higher oxidation state at the anode; contacting a cathode with a cathode electrolyte; producing hydroxide ions in the cathode electrolyte; and contacting the cathode electrolyte with an industrial waste gas comprising carbon dioxide or with a solution of carbon dioxide comprising bicarbonate ions.

In another aspect, there are provided systems including an anode chamber containing an anode in contact with a metal ion in an anode electrolyte, wherein the anode is configured to convert the metal ion from a lower oxidation state to a higher oxidation state; a cathode chamber containing a cathode in contact with a cathode electrolyte wherein the cathode is configured to produce an alkali; and a contactor operably connected to the cathode chamber and configured to contact carbon from a source of carbon such as carbon dioxide from a source of carbon dioxide with the alkali in the cathode electrolyte. In some embodiments, the system further includes a reactor operably connected to the anode chamber and configured to react the metal ion in the higher oxidation state with hydrogen gas or with unsaturated or saturated hydrocarbons (as described herein).

In some embodiments, the carbon from the source of carbon is treated with the cathode electrolyte to form a solution of dissolved carbon dioxide in the alkali of the cathode electrolyte. The alkali present in the cathode electrolyte may facilitate dissolution of carbon dioxide in the solution. The solution with dissolved carbon dioxide includes carbonic acid, bicarbonate, carbonate, or any combination thereof. In such method and system, the carbon from the source of carbon includes gaseous carbon dioxide from an industrial process or a solution of carbon dioxide from a gas/liquid contactor which is in contact with the gaseous carbon dioxide from the industrial process. Such contactor is further defined herein. In some embodiments of the systems including the contactor, the cathode chamber includes bicarbonate and carbonate ions in addition to hydroxide ions.

Figure 12:
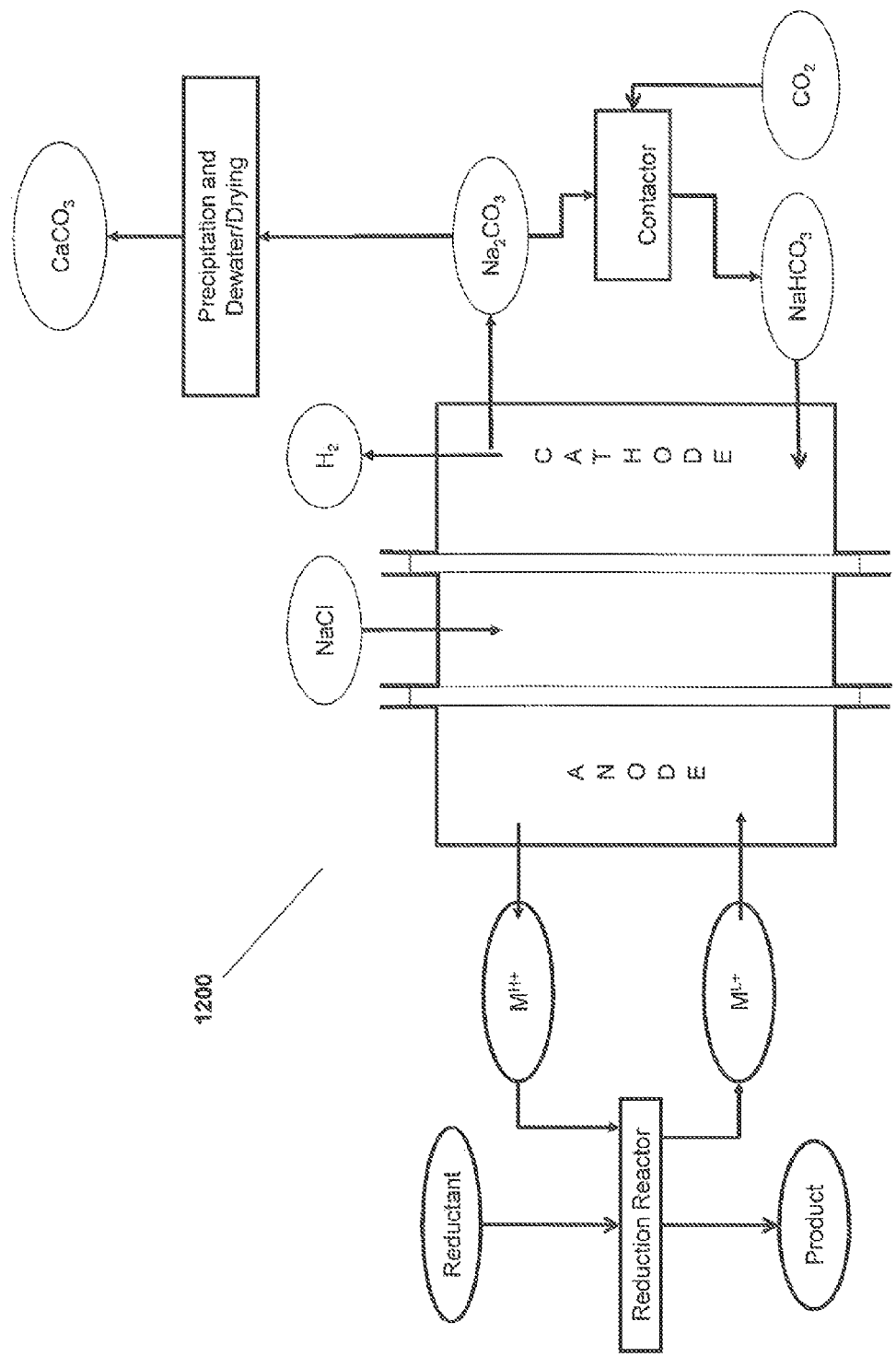
FIG. 12 is an illustration of an embodiment of the invention.

An illustrative example of an electrochemical system integrated with carbon from a source of carbon is as illustrated in FIG. 12. It is to be understood that the system 1200 of FIG. 12 is for illustration purposes only and other metal ions with different oxidations states (e.g., chromium, tin etc.); other electrochemical systems described herein such as electrochemical systems of FIGS. 1A, 1B, 2, 3A, 3B, 4A, 5A, 5C, 6, 8A, 8B, 9, and 11; and the third electrolyte other than sodium chloride such as sodium sulfate, are variations that are equally applicable to this system. The electrochemical system 1200 of FIG. 12 includes an anode and a cathode separated by anion exchange membrane and cation exchange membrane creating a third chamber containing a third electrolyte, NaCl. The metal ion is oxidized in the anode chamber from the lower oxidation state to the higher oxidation state which metal in the higher oxidation state is then used for reactions in a reactor, such as reaction with hydrogen gas or reaction with unsaturated or saturated hydrocarbon. The products formed by such reactions are described herein. The cathode is illustrated as hydrogen gas forming cathode in FIG. 12 although an ODC is equally applicable to this system. The cathode chamber is connected with a gas/liquid contactor that is in contact with gaseous carbon dioxide. The cathode electrolyte containing alkali such as hydroxide and/or sodium carbonate is circulated to the gas/liquid contactor which brings the cathode electrolyte in contact with the gaseous carbon dioxide resulting in the formation of sodium bicarbonate/sodium carbonate solution. This solution of dissolved carbon dioxide is then circulated to the cathode chamber where the alkali formed at the cathode converts the bicarbonate ions to the carbonate ions bringing the pH of the cathode electrolyte to less than 12. This in turn brings the voltage of the cell down to less than 2 V. The sodium carbonate solution thus formed may be re-circulated back to the gas/liquid contactor for further contact with gaseous carbon dioxide or may be taken out for carrying out the calcium carbonate precipitation process as described herein. In some embodiments, the gaseous carbon dioxide is administered directly into the cathode chamber without the intermediate use of the gas/liquid contactor. In some embodiments, the bicarbonate solution from the gas/liquid contactor is not administered to the cathode chamber but is instead used for the precipitation of the bicarbonate product.

The methods and systems related to the contact of the carbon from the source of carbon with the cathode electrolyte (when cathode is either ODC or hydrogen gas producing cathode), as described herein and illustrated in FIG. 12, may result in voltage savings as compared to methods and systems that do not contact the carbon from the source of carbon with the cathode electrolyte. The voltage savings in-turn may result in less electricity consumption and less carbon dioxide emission for electricity generation. This may result in the generation of greener chemicals such as sodium carbonate, sodium bicarbonate, calcium/magnesium bicarbonate or carbonate, halogentated hydrocarbons and/or acids, that are formed by the efficient and energy saving methods and systems of the invention. In some embodiments, the electrochemical cell, where carbon from the source of carbon (such as carbon dioxide gas or sodium carbonate/bicarbonate solution from the gas/liquid contactor) is contacted with the alkali generated by the cathode, has a theoretical cathode half cell voltage saving or theoretical total cell voltage savings of more than 0.1V, or more than 0.2V, or more than 0.5V, or more than 1V, or more than 1.5V, or between 0.1-1.5V, or between 0.1-1V, or between 0.2-1.5V, or between 0.2-1V, or between 0.5-1.5V, or between 0.5-1V as compared to the electrochemical cell where no carbon is contacted with the alkali from the cathode such as, ODC or the hydrogen gas producing cathode. In some embodiments, this voltage saving is achieved with a cathode electrolyte pH of between 7-13, or between 6-12, or between 7-12, or between 7-10, or between 6-13.

Based on the Nernst equation explained earlier, when metal in the lower oxidation state is oxidized to metal in the higher oxidation state at the anode as follows:

$E_{anode}$ based on concentration of copper II species is between 0.159-0.75V.

When water is reduced to hydroxide ions and hydrogen gas at the cathode (as illustrated in FIG. 4A or FIG. 12) and the hydroxide ions come into contact with the bicarbonate ions (such as carbon dioxide gas dissolved directly into the cathode electrolyte or sodium carbonate/bicarbonate solution from the gas/liquid contactor circulated into the cathode electrolyte) to form carbonate, the pH of the cathode electrolyte goes down from 14 to less than 14, as follows:

$$E_{cathode} = -0.059\, pH_c, \text{ where } pH_c \text{ is the pH of the cathode electrolyte} = 10$$

$$E_{cathode} = -0.59$$

The $E_{total}$ then is between 0.749 to 1.29, depending on the concentration of copper ions in the anode electrolyte. The $E_{cathode} = -0.59$ is a saving of more than 200 mV or between 200 mV to 500 mV or between 100-500 mV over the $E_{cathode} = -0.83$ for the hydrogen gas producing cathode that is not in contact with bicarbonate/carbonate ions. The $E_{Total} = 0.749$ to 1.29 is a saving of more than 200 mV or between 200 mV-1.2V or between 100 mV-1.5V over the $E_{Total} = 0.989$ to 1.53 for the hydrogen gas producing cathode that is not in contact with bicarbonate/carbonate ions.

Similarly, when water is reduced to hydroxide ions at ODC (as illustrated in FIG. 5A) and the hydroxide ions come into contact with the bicarbonate ions (such as carbon dioxide gas dissolved directly into the cathode electrolyte or sodium carbonate/bicarbonate solution from the gas/liquid contactor circulated into the cathode electrolyte) to form carbonate, the pH of the cathode electrolyte goes down from 14 to less than 14, as follows:

$$E_{cathode} = 1.224 - 0.059\, pH_c, \text{ where } pH_c = 10$$

$$E_{cathode} = 0.636V$$

$E_{total}$ then is between −0.477 to 0.064V depending on the concentration of copper ions in the anode electrolyte. The $E_{cathode} = 0.636$ is a saving of more than 100 mV or between 100 mV to 200 mV or between 100-500 mV or between 200-500 mV over the $E_{cathode} = 0.4$ for the ODC that is not in contact with bicarbonate/carbonate ions. The $E_{total} = -0.477$ to 0.064V is a saving of more than 200 mV or between 200 mV-1.2V or between 100 mV-1.5V over the $E_{total} = -0.241$ to 0.3 for the ODC that is not in contact with bicarbonate/carbonate ions.

As described above, as the cathode electrolyte is allowed to increase to a pH of 14 or greater, the difference between the anode half-cell potential and the cathode half cell potential would increase. With increased duration of cell operation without $CO_2$ addition or other intervention, e.g., diluting with water, the required cell potential would continue to increase. The operation of the electrochemical cell with the cathode pH between 7-13 or between 7-12 provides a significant energy savings.

Thus, for different pH values in the cathode electrolyte, hydroxide ions, carbonate ions and/or bicarbonate ions are produced in the cathode electrolyte when the voltage applied across the anode and cathode is less than 2.9, or less than 2.5, or less than 2.1, or 2.0, or less than 1.5, or less than 1.0, or less than 0.5, or between 0.5-1.5V, while the pH in the cathode electrolyte is between 7-13 or 7-12 or 6-12 or 7-10.

In some embodiments, the source of carbon is any gaseous source of carbon dioxide and/or any source that provides dissolved form or solution of carbon dioxide. The dissolved form of carbon dioxide or solution of carbon dioxide includes carbonic acid, bicarbonate ions, carbonate ions, or combination thereof. In some embodiments, the oxygen gas and/or carbon dioxide gas supplied to the cathode is from any oxygen source and carbon dioxide gas source known in the art. The source of oxygen gas and the source of carbon dioxide gas may be same or may be different. Some examples of the oxygen gas source and carbon dioxide gas source are as described herein.

In some embodiments, the alkali produced in the cathode chamber may be treated with a gaseous stream of carbon dioxide and/or a dissolved form of carbon dioxide to form carbonate/bicarbonate products which may be used as is for commercial purposes or may be treated with divalent cations, such as, but not limited to, alkaline earth metal ions to form alkaline earth metal carbonates and/or bicarbonates.

As used herein, "carbon from source of carbon" includes gaseous form of carbon dioxide or dissolved form or solution of carbon dioxide. The carbon from source of carbon includes $CO_2$, carbonic acid, bicarbonate ions, carbonate ions, or a combination thereof. As used herein, "source of carbon" includes any source that provides gaseous and/or dissolved form of carbon dioxide. The sources of carbon include, but not limited to, waste streams or industrial processes that provide a gaseous stream of $CO_2$; a gas/liquid contactor that provides a solution containing $CO_2$, carbonic acid, bicarbonate ions, carbonate ions, or combination thereof; and/or bicarbonate brine solution.

The gaseous $CO_2$ is, in some embodiments, a waste stream or product from an industrial plant. The nature of the industrial plant may vary in these embodiments. The industrial plants include, but not limited to, refineries that form unsaturated or saturated hydrocarbons, power plants (e.g., as described in detail in International Application No. PCT/US08/88318, titled, "Methods of sequestering $CO_2$," filed 24 Dec. 2008, the disclosure of which is herein incorporated by reference in its entirety), chemical processing plants, steel mills, paper mills, cement plants (e.g., as described in further detail in U.S. Provisional Application Ser. No. 61/088,340, the disclosure of which is herein incorporated by reference in its entirety), and other industrial plants that produce $CO_2$ as a byproduct. By waste stream is meant a stream of gas (or analogous stream) that is produced as a byproduct of an active process of the industrial plant. The gaseous stream may be substantially pure $CO_2$ or a multi-component gaseous stream that includes $CO_2$ and one or more additional gases. Multi-component gaseous streams (containing $CO_2$) that may be employed as a $CO_2$ source in embodiments of the methods include both reducing, e.g., syngas, shifted syngas, natural gas, and hydrogen and the like, and oxidizing condition streams, e.g., flue gases from combustion, such as combustion of methane. Exhaust gases containing NOx, SOx, VOCs, particulates and Hg would incorporate these compounds along with the carbonate in the precipitated product. Particular multi-component gaseous streams of interest that may be treated according to the subject invention include, but not limited to, oxygen containing combustion power plant flue gas, turbo charged boiler product gas, coal gasification product gas, shifted coal gasification product gas, anaerobic digester product gas, wellhead natural gas stream, reformed natural gas or methane hydrates, and the like. In instances where the gas contains both carbon dioxide and oxygen gas, the gas may be used both as a source of carbon dioxide as well as a source of oxygen. For example, flue gases obtained from the combustion of oxygen and methane may contain oxygen gas and may provide a source of both carbon dioxide gas as well as oxygen gas.

Thus, the waste streams may be produced from a variety of different types of industrial plants. Suitable waste streams for the invention include waste streams, such as, flue gas, produced by industrial plants that combust fossil fuels (e.g., coal, oil, natural gas) or anthropogenic fuel products of naturally occurring organic fuel deposits (e.g., tar sands, heavy oil, oil shale, etc.). In some embodiments, a waste stream suitable for systems and methods of the invention is sourced from a coal-fired power plant, such as a pulverized coal power plant, a supercritical coal power plant, a mass burn coal power plant, a fluidized bed coal power plant. In some embodiments, the waste stream is sourced from gas or oil-fired boiler and steam turbine power plants, gas or oil-fired boiler simple cycle gas turbine power plants, or gas or oil-fired boiler combined cycle gas turbine power plants. In some embodiments, waste streams produced by power plants that combust syngas (i.e., gas that is produced by the gasification of organic matter, for example, coal, biomass, etc.) are used. In some embodiments, waste streams from integrated gasification combined cycle (IGCC) plants are used. In some embodiments, waste streams produced by Heat Recovery Steam Generator (HRSG) plants are used to produce compositions in accordance with systems and methods provided herein.

Waste streams produced by cement plants are also suitable for systems and methods provided herein. Cement plant waste streams include waste streams from both wet process and dry process plants, which plants may employ shaft kilns or rotary kilns, and may include pre-calciners. These industrial plants may each burn a single fuel, or may burn two or more fuels sequentially or simultaneously.

Although carbon dioxide may be present in ordinary ambient air, in view of its very low concentration, ambient carbon dioxide may not provide sufficient carbon dioxide to achieve the formation of the bicarbonate and/or carbonate as is obtained when carbon from the source of carbon is contacted with the cathode electrolyte. In some embodiments of the system and method, the pressure inside the electrochemical system may be greater than the ambient atmospheric pressure in the ambient air and hence ambient carbon dioxide may typically be prevented from infiltrating into the cathode electrolyte.

The contact system or the contactor includes any means for contacting the carbon from the source of carbon to the cathode electrolyte inside a cathode chamber or outside the cathode chamber. Such means for contacting the carbon to the cathode electrolyte or the contactor configured to contact carbon from a source of carbon with the cathode chamber, are well known in the art and include, but not limited to, injection, pipe, duct, conduit, and the like. In some embodiments, the system includes a duct that directs the carbon to the cathode electrolyte inside a cathode chamber. It is to be understood that when the carbon from the source of carbon is contacted with the cathode electrolyte inside the cathode chamber, the carbon may be injected to the cathode electrolyte from the bottom of the cell, top of the cell, from the side inlet in the cell, and/or from all entry ports depending on the amount of carbon desired in the cathode chamber. The amount of carbon from the source of carbon inside the cathode chamber may be dependent on the flow rate of the solution, desired pH of the cathode electrolyte, and/or size of the cell. Such optimization of the amount of the carbon from the source of carbon is well within the scope of the invention. In some embodiments, the carbon from the source of carbon is selected from gaseous carbon dioxide from an industrial process or a solution of carbon dioxide from a gas/liquid contactor in contact with the gaseous carbon dioxide from the industrial process.

In some embodiments, the cathode chamber includes a partition that helps facilitate delivery of the carbon dioxide gas and/or solution of carbon dioxide in the cathode chamber.

In some embodiments, the partition may help prevent mixing of the carbon dioxide gas with the oxygen gas and/or mixing of the carbon dioxide gas in the cathode chamber with the hydrogen gas in the anode chamber. In some embodiments, the partition results in the catholyte with a gaseous form of carbon dioxide as well as dissolved form of carbon dioxide. In some embodiments, the systems provided herein include a partition that partitions the cathode electrolyte into a first cathode electrolyte portion and a second cathode electrolyte portion, where the second cathode electrolyte portion that includes dissolved carbon dioxide contacts the cathode; and where the first cathode electrolyte portion that includes dissolved carbon dioxide and gaseous carbon dioxide, contacts the second cathode electrolyte portion under the partition. In the system, the partition is positioned in the cathode electrolyte such that a gas, e.g., carbon dioxide in the first cathode electrolyte portion is isolated from cathode electrolyte in the second cathode electrolyte portion. Thus, the partition may serve as a means to prevent mixing of the gases on the cathode and/or the gases and or vapor from the anode. Such partition is described in U.S. Publication No. 2010/0084280, filed Nov. 12, 2009, which is incorporated herein by reference in its entirety in the present disclosure.

In some embodiments, the source of carbon is a gas/liquid contactor that provides a dissolved form or solution of carbon dioxide containing $CO_2$, carbonic acid, bicarbonate ions, carbonate ions, or combination thereof. In some embodiments, the solution charged with the partially or fully dissolved $CO_2$ is made by sparging or diffusing the $CO_2$ gaseous stream through slurry or solution to make a $CO_2$ charged water. In some embodiments, the slurry or solution charged with $CO_2$ includes a proton removing agent obtained from the cathode electrolyte of an electrochemical cell, as described herein. In some embodiments, the gas/liquid contactor may include a bubble chamber where the $CO_2$ gas is bubbled through the slurry or the solution containing the proton removing agent. In some embodiments, the contactor may include a spray tower where the slurry or the solution containing the proton removing agent is sprayed or circulated through the $CO_2$ gas. In some embodiments, the contactor may include a pack bed to increase the surface area of contact between the $CO_2$ gas and the solution containing the proton removing agent. For example, the gas/liquid contactor or the absorber may contain a slurry or, solution or pack bed of sodium carbonate. The $CO_2$ is sparged through this slurry or the solution or the pack bed where the alkaline medium facilitates dissolution of $CO_2$ in the solution. After the dissolution of $CO_2$, the solution may contain bicarbonate, carbonate, or combination thereof. In some embodiments, a typical absorber or the contactor fluid temperature is 32-37° C. The absorber or contactor for absorbing $CO_2$ in the solution is described in U.S. application Ser. No. 12/721,549, filed on Mar. 10, 2010, which is incorporated herein by reference in its entirety in the present disclosure. The solution containing the carbonate/bicarbonate species may be withdrawn from the gas/liquid contactor to form bicarbonate/carbonate products. In some embodiments, the carbonate/bicarbonate solution may be transferred to the cathode electrolyte containing the alkali. The alkali may substantially or fully convert the bicarbonate to carbonate to form carbonate solution. The carbonate solution may be re-circulated back to the gas/liquid contactor or may be withdrawn from the cathode chamber and treated with divalent cations to form bicarbonate/carbonate products.

In some embodiments, the alkali produced in the cathode electrolyte may be delivered to the gas/liquid contactor where the carbon dioxide gas comes into contact with the alkali. The carbon dioxide gas after coming into contact with the alkali may result in the formation of carbonic acid, bicarbonate ions, carbonate ions, or combination thereof. The dissolved form of carbon dioxide may be then delivered back to the cathode chamber where the alkali may convert the bicarbonate into the carbonate. The carbonate/bicarbonate mix may be then used as is for commercial purposes or is treated with divalent cations, such as, alkaline earth metal ions to form alkaline earth metal carbonates/bicarbonates.

The system in some embodiments includes a cathode electrolyte circulating system adapted for withdrawing and circulating cathode electrolyte in the system. In some embodiments, the cathode electrolyte circulating system includes a gas/liquid contactor outside the cathode chamber that is adapted for contacting the carbon from the source of carbon with the circulating cathode electrolyte, and for re-circulating the electrolyte in the system. As the pH of the cathode electrolyte may be adjusted by withdrawing and/or circulating cathode electrolyte/carbon from the source of carbon from the system, the pH of the cathode electrolyte compartment can be regulated by regulating an amount of cathode electrolyte removed from the system, passed through the gas/liquid contactor, and/or re-circulated back into the cathode chamber.

In some embodiments, the source of carbon is the bicarbonate brine solution. The bicarbonate brine solution, is as described in U.S. Provisional Application No. 61/433,641, filed on Jan. 18, 2011 and U.S. Provisional Application No. 61/408,325, filed Oct. 29, 2010, which are both incorporated herein by reference in their entirety in the present disclosure. As used herein, the "bicarbonate brine solution" includes any brine containing bicarbonate ions. In some embodiments, the brine is a synthetic brine such as a solution of brine containing the bicarbonate, e.g., sodium bicarbonate, potassium bicarbonate, lithium bicarbonate etc. In some embodiments, the brine is a naturally occurring bicarbonate brine, e.g., subterranean brine such as naturally occurring lakes. In some embodiments, the bicarbonate brine is made from subterranean brines, such as but not limited to, carbonate brines, alkaline brines, hard brines, and/or alkaline hard brines. In some embodiments, the bicarbonate brine is made from minerals where the minerals are crushed and dissolved in brine and optionally further processed. The minerals can be found under the surface, on the surface, or subsurface of the lakes. The bicarbonate brine can also be made from evaporite. The bicarbonate brine may include other oxyanions of carbon in addition to bicarbonate ($HCO_3^-$), such as, but not limited to, carbonic acid ($H_2CO_3$) and/or carbonate ($CO_3^{2-}$).

In some embodiments of the electrochemical cells described herein, the system is configured to produce carbonate ions by a reaction of the carbon such as, $CO_2$, carbonic acid, bicarbonate ions, carbonate ions, or combination thereof, from the source of carbon with an alkali, such as, sodium hydroxide from the cathode electrolyte. In some embodiments (not shown in figures), the carbon from the source of carbon, such as gaseous form of carbon dioxide may be contacted with the catholyte inside the cathode chamber and the catholyte containing hydroxide/carbonate/bicarbonate may be withdrawn from the cathode chamber and contacted with the gas/liquid contactor outside the cathode chamber. In such embodiments, the catholyte from the gas/liquid contactor may be contacted back again with the catholyte inside the cathode chamber.

For the systems where the carbon from the source of carbon is contacted with the cathode electrolyte outside the cathode chamber, the alkali containing cathode electrolyte may be withdrawn from the cathode chamber and may be added to a container configured to contain the carbon from the source of carbon. The container may have an input for the source of carbon such as a pipe or conduit, etc. or a pipeline in communication with the gaseous stream of $CO_2$, a solution containing dissolved form of $CO_2$, and/or the bicarbonate brine. The container may also be in fluid communication with a reactor where the source of carbon, such as, e.g. bicarbonate brine solution may be produced, modified, and/or stored.

For the systems where the carbon from the source of carbon is contacted with the cathode electrolyte inside the cathode chamber, the cathode electrolyte containing alkali, bicarbonate, and/or carbonate may be withdrawn from the cathode chamber and may be contacted with alkaline earth metal ions, as described herein, to form bicarbonate/carbonate products.

Components of Electrochemical Cell

The methods and systems provided herein include one or more of the following components.

In some embodiments, the anode may contain a corrosion stable, electrically conductive base support. Such as, but not limited to, amorphous carbon, such as carbon black, fluorinated carbons like the specifically fluorinated carbons described in U.S. Pat. No. 4,908,198 and available under the trademark SFC™ carbons. Other examples of electrically conductive base materials include, but not limited to, sub-stoichiometric titanium oxides, such as, Magneli phase sub-stoichiometric titanium oxides having the formula $TiO_x$ wherein x ranges from about 1.67 to about 1.9. For example, titanium oxide $Ti_4O_7$. In some embodiments, carbon based materials provide a mechanical support for the GDE or as blending materials to enhance electrical conductivity but may not be used as catalyst support to prevent corrosion.

In some embodiments, the gas-diffusion electrodes or general electrodes described herein contain an electrocatalyst for aiding in electrochemical dissociation, e.g. reduction of oxygen at the cathode. Examples of electrocatalysts include, but not limited to, highly dispersed metals or alloys of the platinum group metals, such as platinum, palladium, ruthenium, rhodium and iridium (e.g. titanium mesh coated with PtIr mixed metal oxide or titanium coated with galvanized platinum); electrocatalytic metal oxides; organometallic macrocyclic compounds, and other electrocatalysts well known in the art for electrochemical reduction of oxygen.

In some embodiments, the electrodes described herein, relate to porous homogeneous composite structures as well as heterogeneous, layered type composite structures wherein each layer may have a distinct physical and compositional make-up, e.g. porosity and electroconductive base to prevent flooding, and loss of the three phase interface, and resulting electrode performance.

The electrodes provided herein may include anodes and cathodes having porous polymeric layers on or adjacent to the anolyte or catholyte solution side of the electrode which may assist in decreasing penetration and electrode fouling. Stable polymeric resins or films may be included in a composite electrode layer adjacent to the anolyte comprising resins formed from non-ionic polymers, such as polystyrene, polyvinyl chloride, polysulfone, etc., or ionic-type charged polymers like those formed from polystyrenesulfonic acid, sulfonated copolymers of styrene and vinylbenzene, carboxylated polymer derivatives, sulfonated or carboxylated polymers having partially or totally fluorinated hydrocarbon chains and aminated polymers like polyvinylpyridine. Stable microporous polymer films may also be included on the dry side to inhibit electrolyte penetration. In some embodiments, the gas-diffusion cathodes includes such cathodes known in the art that are coated with high surface area coatings of precious metals such as gold and/or silver, precious metal alloys, nickel, and the like.

In some embodiments, the electrolyte including the catholyte or the cathode electrolyte and/or the anolyte or the anode electrolyte, or the third electrolyte disposed between AEM and CEM, in the systems and methods provided herein include, but not limited to, saltwater or fresh water. The saltwater includes, but is not limited to, seawater, brine, and/or brackish water. In some embodiments, the cathode electrolyte in the systems and methods provided herein include, but not limited to, seawater, freshwater, brine, brackish water, hydroxide, such as, sodium hydroxide, or combination thereof. "Saltwater" is employed in its conventional sense to refer to a number of different types of aqueous fluids other than fresh water, where the term "saltwater" includes, but is not limited to, brackish water, sea water and brine (including, naturally occurring subterranean brines or anthropogenic subterranean brines and man-made brines, e.g., geothermal plant wastewaters, desalination waste waters, etc), as well as other salines having a salinity that is greater than that of freshwater. Brine is water saturated or nearly saturated with salt and has a salinity that is 50 ppt (parts per thousand) or greater. Brackish water is water that is saltier than fresh water, but not as salty as seawater, having a salinity ranging from 0.5 to 35 ppt. Seawater is water from a sea or ocean and has a salinity ranging from 35 to 50 ppt. The saltwater source may be a naturally occurring source, such as a sea, ocean, lake, swamp, estuary, lagoon, etc., or a man-made source. In some embodiments, the systems provided herein include the saltwater from terrestrial brine. In some embodiments, the depleted saltwater withdrawn from the electrochemical cells is replenished with salt and re-circulated back in the electrochemical cell.

In some embodiments, the electrolyte including the cathode electrolyte and/or the anode electrolyte and/or the third electrolyte, such as, saltwater includes water containing more than 1% chloride content, such as, NaCl; or more than 10% NaCl; or more than 20% NaCl; or more than 30% NaCl; or more than 40% NaCl; or more than 50% NaCl; or more than 60% NaCl; or more than 70% NaCl; or more than 80% NaCl; or more than 90% NaCl; or between 1-99% NaCl; or between 1-95% NaCl; or between 1-90% NaCl; or between 1-80% NaCl; or between 1-70% NaCl; or between 1-60% NaCl; or between 1-50% NaCl; or between 1-40% NaCl; or between 1-30% NaCl; or between 1-20% NaCl; or between 1-10% NaCl; or between 10-99% NaCl; or between 10-95% NaCl; or between 10-90% NaCl; or between 10-80% NaCl; or between 10-70% NaCl; or between 10-60% NaCl; or between 10-50% NaCl; or between 10-40% NaCl; or between 10-30% NaCl; or between 10-20% NaCl; or between 20-99% NaCl; or between 20-95% NaCl; or between 20-90% NaCl; or between 20-80% NaCl; or between 20-70% NaCl; or between 20-60% NaCl; or between 20-50% NaCl; or between 20-40% NaCl; or between 20-30% NaCl; or between 30-99% NaCl; or between 30-95% NaCl; or between 30-90% NaCl; or between 30-80% NaCl; or between 30-70% NaCl; or between 30-60% NaCl; or between 30-50% NaCl; or between 30-40% NaCl; or between 40-99% NaCl; or between 40-95% NaCl; or between 40-90% NaCl; or between 40-80% NaCl; or between 40-70% NaCl; or between 40-60% NaCl; or between 40-50% NaCl; or between 50-99% NaCl; or between 50-95% NaCl; or between 50-90% NaCl; or between 50-80% NaCl; or between 50-70% NaCl; or between 50-60% NaCl; or between 60-99% NaCl; or between 60-95% NaCl; or between 60-90% NaCl; or between 60-80% NaCl; or between 60-70% NaCl; or between 70-99% NaCl; or between 70-95% NaCl; or between 70-90% NaCl; or between 70-80% NaCl; or between 80-99% NaCl; or between 80-95% NaCl; or between 80-90% NaCl; or between 90-99% NaCl; or between 90-95%

NaCl. In some embodiments, the above recited percentages apply to ammonium chloride, ferric chloride, sodium bromide, sodium iodide, or sodium sulfate as an electrolyte. The percentages recited herein include wt % or wt/wt % or wt/v %. It is to be understood that all the electrochemical systems described herein that contain sodium chloride can be replaced with other suitable electrolytes, such as, but not limited to, ammonium chloride, sodium bromide, sodium iodide, sodium sulfate, or combination thereof.

In some embodiments, the cathode electrolyte, such as, saltwater, fresh water, and/or sodium hydroxide do not include alkaline earth metal ions or divalent cations. As used herein, the divalent cations include alkaline earth metal ions, such as but not limited to, calcium, magnesium, barium, strontium, radium, etc. In some embodiments, the cathode electrolyte, such as, saltwater, fresh water, and/or sodium hydroxide include less than 1% w/w divalent cations. In some embodiments, the cathode electrolyte, such as, seawater, freshwater, brine, brackish water, and/or sodium hydroxide include less than 1% w/w divalent cations. In some embodiments, the cathode electrolyte, such as, seawater, freshwater, brine, brackish water, and/or sodium hydroxide include divalent cations including, but not limited to, calcium, magnesium, and combination thereof. In some embodiments, the cathode electrolyte, such as, seawater, freshwater, brine, brackish water, and/or sodium hydroxide include less than 1% w/w divalent cations including, but not limited to, calcium, magnesium, and combination thereof.

In some embodiments, the cathode electrolyte, such as, seawater, freshwater, brine, brackish water, and/or sodium hydroxide include less than 1% w/w; or less than 5% w/w; or less than 10% w/w; or less than 15% w/w; or less than 20% w/w; or less than 25% w/w; or less than 30% w/w; or less than 40% w/w; or less than 50% w/w; or less than 60% w/w; or less than 70% w/w; or less than 80% w/w; or less than 90% w/w; or less than 95% w/w; or between 0.05-1% w/w; or between 0.5-1% w/w; or between 0.5-5% w/w; or between 0.5-10% w/w; or between 0.5-20% w/w; or between 0.5-30% w/w; or between 0.5-40% w/w; or between 0.5-50% w/w; or between 0.5-60% w/w; or between 0.5-70% w/w; or between 0.5-80% w/w; or between 0.5-90% w/w; or between 5-8% w/w; or between 5-10% w/w; or between 5-20% w/w; or between 5-30% w/w; or between 5-40% w/w; or between 5-50% w/w; or between 5-60% w/w; or between 5-70% w/w; or between 5-80% w/w; or between 5-90% w/w; or between 10-20% w/w; or between 10-30% w/w; or between 10-40% w/w; or between 10-50% w/w; or between 10-60% w/w; or between 10-70% w/w; or between 10-80% w/w; or between 10-90% w/w; or between 30-40% w/w; or between 30-50% w/w; or between 30-60% w/w; or between 30-70% w/w; or between 30-80% w/w; or between 30-90% w/w; or between 50-60% w/w; or between 50-70% w/w; or between 50-80% w/w; or between 50-90% w/w; or between 75-80% w/w; or between 75-90% w/w; or between 80-90% w/w; or between 90-95% w/w; of divalent cations including, but not limited to, calcium, magnesium, and combination thereof.

In some embodiments, the cathode electrolyte includes, but not limited to, sodium hydroxide, sodium bicarbonate, sodium carbonate, or combination thereof. In some embodiments, the cathode electrolyte includes, but not limited to, sodium or potassium hydroxide. In some embodiments, the cathode electrolyte includes, but not limited to, sodium hydroxide, divalent cations, or combination thereof. In some embodiments, the cathode electrolyte includes, but not limited to; sodium hydroxide, sodium bicarbonate, sodium carbonate, divalent cations, or combination thereof. In some embodiments, the cathode electrolyte includes, but not limited to, sodium hydroxide, calcium bicarbonate, calcium carbonate, magnesium bicarbonate, magnesium carbonate, calcium magnesium carbonate, or combination thereof. In some embodiments, the cathode electrolyte includes, but not limited to, saltwater, sodium hydroxide, bicarbonate brine solution, or combination thereof. In some embodiments, the cathode electrolyte includes, but not limited to, saltwater and sodium hydroxide. In some embodiments, the cathode electrolyte includes, but not limited to, fresh water and sodium hydroxide. In some embodiments, the cathode electrolyte includes fresh water devoid of alkalinity or divalent cations. In some embodiments, the cathode electrolyte includes, but not limited to, fresh water, sodium hydroxide, sodium bicarbonate, sodium carbonate, divalent cations, or combination thereof.

In some embodiments, the anode electrolyte includes, but not limited to, fresh water and metal ions. In some embodiments, the anode electrolyte includes, but not limited to, saltwater and metal ions. In some embodiments, the anode electrolyte includes metal ion solution.

In some embodiments, the depleted saltwater from the cell may be circulated back to the cell. In some embodiments, the cathode electrolyte includes 1-90%; 1-50%; or 1-40%; or 1-30%; or 1-15%; or 1-20%; or 1-10%; or 5-90%; or 5-50%; or 5-40%; or 5-30%; or 5-20%; or 5-10%; or 10-90%; or 10-50%; or 10-40%; or 10-30%; or 10-20%; or 15-20%; or 15-30%; or 20-30%, of the sodium hydroxide solution. In some embodiments, the anode electrolyte includes 0-5 M; or 0-4.5M; or 0-4M; or 0-3.5M; or 0-3M; or 0-2.5M; or 0-2M; or 0-1.5M; or 0-1M; or 1-5M; or 1-4.5M; or 1-4M; or 1-3.5M; or 1-3M; or 1-2.5M; or 1-2M; or 1-1.5M; or 2-5M; or 2-4.5M; or 2-4M; or 2-3.5M; or 2-3M; or 2-2.5M; or 3-5M; or 3-4.5M; or 3-4M; or 3-3.5M; or 4-5M; or 4.5-5M metal ion solution. In some embodiments, the anode does not form an oxygen gas. In some embodiments, the anode does not form a chlorine gas.

In some embodiments, the cathode electrolyte and the anode electrolyte are separated in part or in full by an ion exchange membrane. In some embodiments, the ion exchange membrane is an anion exchange membrane or a cation exchange membrane. In some embodiments, the cation exchange membranes in the electrochemical cell, as disclosed herein, are conventional and are available from, for example, Asahi Kasei of Tokyo, Japan; or from Membrane International of Glen Rock, N.J., or DuPont, in the USA. Examples of CEM include, but are not limited to, N2030WX (Dupont), F8020/F8080 (Flemion), and F6801 (Aciplex). CEMs that are desirable in the methods and systems of the invention have minimal resistance loss, greater than 90% selectivity, and high stability in concentrated caustic. AEMs, in the methods and systems of the invention are exposed to concentrated metallic salt anolytes and saturated brine stream. It is desirable for the AEM to allow passage of salt ion such as chloride ion to the anolyte but reject the metallic ion species from the anolyte. In some embodiments, metallic salts may form various ion species (cationic, anionic, and/or neutral) including but not limited to, $MCl^+$, $MCl_2^-$, $MCl_2^0$, $M^{2+}$ etc. and it is desirable for such complexes to not pass through AEM or not foul the membranes. Provided in the examples are some of the membranes that have been tested for the methods and systems of the invention that have been found to prevent metal crossover.

Accordingly, provided herein are methods comprising contacting an anode with a metal ion in an anode electrolyte in an anode chamber; converting the metal ion from a lower oxidation state to a higher oxidation state at the anode; contacting a cathode with a cathode electrolyte in a cathode chamber; forming an alkali, water, or hydrogen gas at the cathode; and preventing migration of the metal ions from the anode electrolyte to the cathode electrolyte by using an anion exchange membrane wherein the anion exchange membrane has an ohmic resistance of less than 3 $\Omega cm^2$ or less than 2 $\Omega cm^2$ or less than 1 $\Omega cm^2$. In some embodiments, the anion exchange membrane has an ohmic resistance of between 1-3 $\Omega cm^2$. In some embodiments, there are provided methods comprising contacting an anode with a metal ion in an anode electrolyte in an anode chamber; converting the metal ion from a lower oxidation state to a higher oxidation state at the anode; contacting a cathode with a cathode electrolyte in a cathode chamber; forming an alkali, water, or hydrogen gas at the cathode; and preventing migration of the metal ions from the anode electrolyte to the cathode electrolyte by using an anion exchange membrane wherein the anion exchange membrane rejects more than 80%, or more than 90%, or more than 99%, or about 99.9% of all metal ions from the anode electrolyte.

There are also provided systems comprising an anode in contact with a metal ion in an anode electrolyte in an anode chamber wherein the anode is configured to convert the metal ion from a lower oxidation state to a higher oxidation state in the anode chamber; a cathode in contact with a cathode electrolyte in a cathode chamber wherein the cathode is configured to form an alkali, water, or hydrogen gas in the cathode chamber; and an anion exchange membrane wherein the anion exchange membrane has an ohmic resistance of less than 3 $\Omega cm^2$ or less than 2 $\Omega cm^2$ or less than 1 $\Omega cm^2$. In some embodiments, the anion exchange membrane has an ohmic resistance of between 1-3 $\Omega cm^2$. In some embodiments, there are provided systems comprising contacting an anode in contact with a metal ion in an anode electrolyte in an anode chamber wherein the anode is configured to convert the metal ion from a lower oxidation state to a higher oxidation state in the anode chamber; a cathode in contact with a cathode electrolyte in a cathode chamber wherein the cathode is configured to form an alkali, water, or hydrogen gas in the cathode chamber; and an anion exchange membrane wherein the anion exchange membrane rejects more than 80%, or more than 90%, or more than 99%, or about 99.9% of all metal ions from the anode electrolyte.

Also provided herein are methods comprising contacting an anode with a metal ion in an anode electrolyte in an anode chamber; converting the metal ion from a lower oxidation state to a higher oxidation state at the anode; contacting a cathode with a cathode electrolyte in a cathode chamber; forming an alkali at the cathode; separating the anode electrolyte from a brine compartment with an anion exchange membrane; separating the cathode electrolyte from the brine compartment by a cation exchange membrane; and preventing migration of the metal ions from the anode electrolyte to the brine compartment by using the anion exchange membrane that has an ohmic resistance of less than 3 $\Omega cm^2$ or less than 2 $\Omega cm^2$ or less than 1 $\Omega cm^2$. In some embodiments, the anion exchange membrane has an ohmic resistance of between 1-3 $\Omega cm^2$. In some embodiments, there are provided methods comprising contacting an anode with a metal ion in an anode electrolyte in an anode chamber; converting the metal ion from a lower oxidation state to a higher oxidation state at the anode; contacting a cathode with a cathode electrolyte in a cathode chamber; forming an alkali at the cathode; separating the anode electrolyte from a brine compartment with an anion exchange membrane; separating the cathode electrolyte from the brine compartment by a cation exchange membrane; and preventing migration of the metal ions from the anode electrolyte to the brine compartment by using the anion exchange membrane that rejects more than 80%, or more than 90%, or more than 99%, or about 99.9% of all metal ions from the anode electrolyte.

There are also provided systems comprising an anode in contact with a metal ion in an anode electrolyte in an anode chamber wherein the anode is configured to convert the metal ion from a lower oxidation state to a higher oxidation state in the anode chamber; a cathode in contact with a cathode electrolyte in a cathode chamber wherein the cathode is configured to form an alkali in the cathode chamber; an anion exchange membrane separating the anode electrolyte from a brine compartment; and a cation exchange membrane separating the cathode electrolyte from the brine compartment, wherein the anion exchange membrane has an ohmic resistance of less than 3 $\Omega cm^2$ or less than 2 $\Omega cm^2$ or less than 1 $\Omega cm^2$. In some embodiments, the anion exchange membrane has an ohmic resistance of between 1-3 $\Omega cm^2$. In some embodiments, there are provided systems comprising contacting an anode in contact with a metal ion in an anode electrolyte in an anode chamber wherein the anode is configured to convert the metal ion from a lower oxidation state to a higher oxidation state in the anode chamber; a cathode in contact with a cathode electrolyte in a cathode chamber wherein the cathode is configured to form an alkali in the cathode chamber; an anion exchange membrane separating the anode electrolyte from a brine compartment; and a cation exchange membrane separating the cathode electrolyte from the brine compartment, wherein the anion exchange membrane rejects more than 80%, or more than 90%, or more than 99%, or about 99.9% of all metal ions from the anode electrolyte.

The methods and systems described above comprising the AEM further include the treatment of the anode electrolyte comprising the metal ion in the higher oxidation state with the hydrogen gas, unsaturated hydrocarbon, or saturated hydrocarbon, as described herein.

Examples of cationic exchange membranes include, but not limited to, cationic membrane consisting of a perfluorinated polymer containing anionic groups, for example sulphonic and/or carboxylic groups. However, it may be appreciated that in some embodiments, depending on the need to restrict or allow migration of a specific cation or an anion species between the electrolytes, a cation exchange membrane that is more restrictive and thus allows migration of one species of cations while restricting the migration of another species of cations may be used as, e.g., a cation exchange membrane that allows migration of sodium ions into the cathode electrolyte from the anode electrolyte while restricting migration of other ions from the anode electrolyte into the cathode electrolyte, may be used. Similarly, in some embodiments, depending on the need to restrict or allow migration of a specific anion species between the electrolytes, an anion exchange membrane that is more restrictive and thus allows migration of one species of anions while restricting the migration of another species of anions may be used as, e.g., an anion exchange membrane that allows migration of chloride ions into the anode electrolyte from the cathode electrolyte while restricting migration of hydroxide ions from the cathode electrolyte into the anode electrolyte, may be used. Such restrictive cation and/or anion exchange membranes are commercially available and can be selected by one ordinarily skilled in the art.

In some embodiments, there is provided a system comprising one or more anion exchange membrane, and cation exchange membranes located between the anode and the cathode. In some embodiments, the membranes should be selected such that they can function in an acidic and/or basic electrolytic solution as appropriate. Other desirable characteristics of the membranes include high ion selectivity, low ionic resistance, high burst strength, and high stability in an acidic electrolytic solution in a temperature range of 0° C. to 100° C. or higher, or a alkaline solution in similar temperature range may be used. In some embodiments, it is desirable that the ion exchange membrane prevents the transport of the metal ion from the anolyte to the catholyte. In some embodiments, a membrane that is stable in the range of 0° C. to 90° C.; or 0° C. to 80° C.; or 0° C. to 70° C.; or 0° C. to 60° C.; or 0° C. to 50° C.; or 0° C. to 40° C., or 0° C. to 30° C., or 0° C. to 20° C., or 0° C. to 10° C., or higher may be used. In some embodiments, a membrane that is stable in the range of 0° C. to 90° C.; or 0° C. to 80° C.; or 0° C. to 70° C.; or 0° C. to 60° C.; or 0° C. to 50° C.; or 0° C. to 40° C., but unstable at higher temperature, may be used. For other embodiments, it may be useful to utilize an ion-specific ion exchange membranes that allows migration of one type of cation but not another; or migration of one type of anion and not another, to achieve a desired product or products in an electrolyte. In some embodiments, the membrane may be stable and functional for a desirable length of time in the system, e.g., several days, weeks or months or years at temperatures in the range of 0° C. to 90° C.; or 0° C. to 80° C.; or 0° C. to 70° C.; or 0° C. to 60° C.; or 0° C. to 50° C.; or 0° C. to 40° C.; or 0° C. to 30° C.; or 0° C. to 20° C.; or 0° C. to 10° C., and higher and/or lower. In some embodiments, for example, the membranes may be stable and functional for at least 1 day, at least 5 days, 10 days, 15 days, 20 days, 100 days, 1000 days, 5-10 years, or more in electrolyte temperatures at 100° C., 90° C., 80° C., 70° C., 60° C., 50° C., 40° C., 30° C., 20° C., 10° C., 5° C. and more or less.

The ohmic resistance of the membranes may affect the voltage drop across the anode and cathode, e.g., as the ohmic resistance of the membranes increase, the voltage across the anode and cathode may increase, and vice versa. Membranes that can be used include, but are not limited to, membranes with relatively low ohmic resistance and relatively high ionic mobility; and membranes with relatively high hydration characteristics that increase with temperatures, and thus decreasing the ohmic resistance. By selecting membranes with lower ohmic resistance known in the art, the voltage drop across the anode and the cathode at a specified temperature can be lowered.

Scattered through membranes may be ionic channels including acid groups. These ionic channels may extend from the internal surface of the matrix to the external surface and the acid groups may readily bind water in a reversible reaction as water-of-hydration. This binding of water as water-of-hydration may follow first order reaction kinetics, such that the rate of reaction is proportional to temperature. Consequently, membranes can be selected to provide a relatively low ohmic and ionic resistance while providing for improved strength and resistance in the system for a range of operating temperatures.

In some embodiments, the carbon from the source of carbon, when contacted with the cathode electrolyte inside the cathode chamber, reacts with the hydroxide ions and produces water and carbonate ions, depending on the pH of the cathode electrolyte. The addition of the carbon from the source of carbon to the cathode electrolyte may lower the pH of the cathode electrolyte. Thus, depending on the degree of alkalinity desired in the cathode electrolyte, the pH of the cathode electrolyte may be adjusted and in some embodiments is maintained between 6 and 12; between 7 and 14 or greater; or between 7 and 13; or between 7 and 12; or between 7 and 11; or between 7 and 10; or between 7 and 9; or between 7 and 8; or between 8 and 14 or greater; or between 8 and 13; or between 8 and 12; or between 8 and 11; or between 8 and 10; or between 8 and 9; or between 9 and 14 or greater; or between 9 and 13; or between 9 and 12; or between 9 and 11; or between 9 and 10; or between 10 and 14 or greater; or between 10 and 13; or between 10 and 12; or between 10 and 11; or between 11 and 14 or greater; or between 11 and 13; or between 11 and 12; or between 12 and 14 or greater; or between 12 and 13; or between 13 and 14 or greater. In some embodiments, the pH of the cathode electrolyte may be adjusted to any value between 7 and 14 or greater, a pH less than 12, a pH 7.0, 7.5, 8.0, 8.5, 9.0, 9.5, 10.0, 10.5, 11.0, 11.5, 12.0, 12.5, 13.0, 13.5, 14.0, and/or greater.

Similarly, in some embodiments of the system, the pH of the anode electrolyte is adjusted and is maintained between 0-7; or between 0-6; or between 0-5; or between 0-4; or between 0-3; or between 0-2; or between 0-1. As the voltage across the anode and cathode may be dependent on several factors including the difference in pH between the anode electrolyte and the cathode electrolyte (as can be determined by the Nernst equation well known in the art), in some embodiments, the pH of the anode electrolyte may be adjusted to a value between 0 and 7, including 0, 0.5, 1.0, 1.5, 2.0, 2.5, 3.0, 3.5, 4.0, 4.5, 5.0, 5.5, 6.0, 6.5 and 7, depending on the desired operating voltage across the anode and cathode. Thus, in equivalent systems, where it is desired to reduce the energy used and/or the voltage across the anode and cathode, e.g., as in the chlor-alkali process, the carbon from the source of carbon can be added to the cathode electrolyte as disclosed herein to achieve a desired pH difference between the anode electrolyte and cathode electrolyte.

The system may be configured to produce any desired pH difference between the anode electrolyte and the cathode electrolyte by modulating the pH of the anode electrolyte, the pH of the cathode electrolyte, the concentration of hydroxide in the cathode electrolyte, the withdrawal and replenishment of the anode electrolyte, the withdrawal and replenishment of the cathode electrolyte, and/or the amount of the carbon from the source of carbon added to the cathode electrolyte. By modulating the pH difference between the anode electrolyte and the cathode electrolyte, the voltage across the anode and the cathode can be modulated. In some embodiments, the system is configured to produce a pH difference of at least 4 pH units; at least 5 pH units; at least 6 pH units; at least 7 pH units; at least 8 pH units; at least 9 pH units; at least 10 pH units; at least 11 pH units; at least 12 pH units; at least 13 pH units; at least 14 pH units; or between 4-12 pH units; or between 4-11 pH units; or between 4-10 pH units; or between 4-9 pH units; or between 4-8 pH units; or between 4-7 pH units; or between 4-6 pH units; or between 4-5 pH units; or between 3-12 pH units; or between 3-11 pH units; or between 3-10 pH units; or between 3-9 pH units; or between 3-8 pH units; or between 3-7 pH units; or between 3-6 pH units; or between 3-5 pH units; or between 3-4 pH units; or between 5-12 pH units; or between 5-11 pH units; or between 5-10 pH units; or between 5-9 pH units; or between 5-8 pH units; or between 5-7 pH units; or between 5-6 pH units; or between 6-12 pH units; or between 6-11 pH units; or between 6-10 pH units; or between 6-9 pH units; or between 6-8 pH units; or between 6-7 pH units; or between 7-12 pH units; or between 7-11 pH units; or between 7-10 pH units; or between 7-9 pH units; or between 7-8 pH units; or between 8-12 pH units; or between 8-11 pH units; or between 8-10 pH units; or between 8-9 pH units; or between 9-12 pH units; or between 9-11 pH units; or between 9-10 pH units; or between 10-12 pH units; or between 10-11 pH units; or between 11-12 pH units; between the anode electrolyte and the cathode electrolyte. In some embodiments, the system is configured to produce a pH difference of at least 4 pH units between the anode electrolyte and the cathode electrolyte.

In some embodiments, the anode electrolyte and the cathode electrolyte in the electrochemical cell, in the methods and systems provided herein, are operated at room temperature or at elevated temperatures, such as, e.g., at more than 40° C., or more than 50° C., or more than 60° C., or more than 70° C., or more than 80° C., or between 30-70° C.

Production of Bicarbonate and/or Carbonate Products

In some embodiments, the methods and systems provided herein are configured to process the carbonate/bicarbonate solution obtained after the cathode electrolyte is contacted with the carbon from the source of carbon. In some embodiments, the carbonate and/or bicarbonate containing solution is treated with divalent cations, such as but not limited to, calcium and/or magnesium to form calcium and/or magnesium carbonate and/or bicarbonate. An illustrative embodiment for such processes is provided in FIG. 13.

Figure 13:
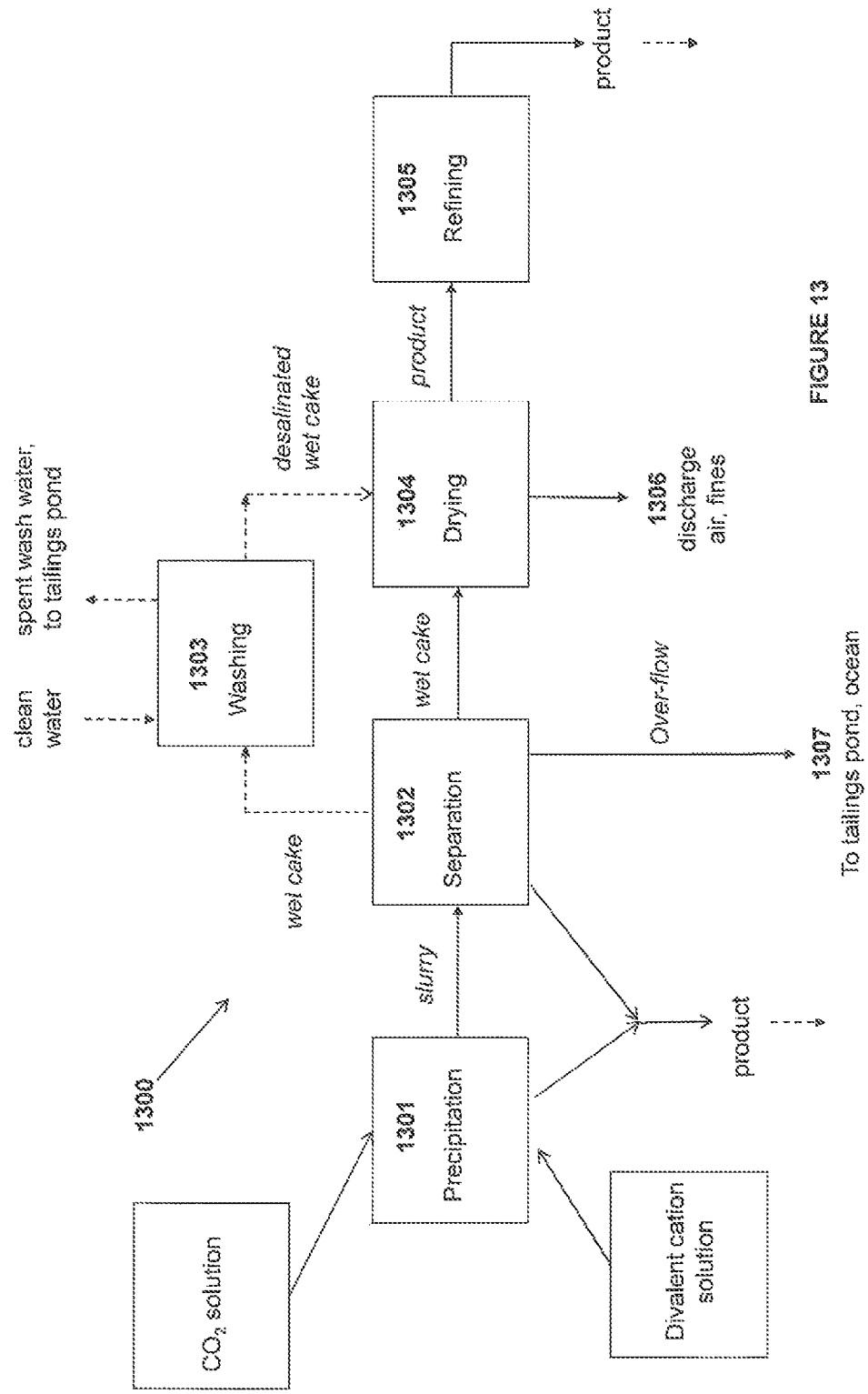
FIG. 13 is an illustration of an embodiment of the invention.

As illustrated in FIG. 13, process 1300 illustrates methods and systems to process the carbonate/bicarbonate solution obtained after the cathode electrolyte is contacted with the carbon from the source of carbon. In some embodiments, the solution is subjected to the precipitation in the precipitator 1301. In some embodiments, the solution includes sodium hydroxide, sodium carbonate, and/or sodium bicarbonate. In some embodiments, the system is configured to treat bicarbonate and/or carbonate ions in the cathode electrolyte with an alkaline earth metal ion or divalent cation including, but not limited to, calcium, magnesium, and combination thereof. The "divalent cation" as used herein, includes any solid or solution that contains divalent cations, such as, alkaline earth metal ions or any aqueous medium containing alkaline earth metals. The alkaline earth metals include calcium, magnesium, strontium, barium, etc. or combinations thereof. The divalent cations (e.g., alkaline earth metal cations such as $Ca^{2+}$ and $Mg^{2+}$) may be found in industrial wastes, seawater, brines, hard water, minerals, and many other suitable sources. The alkaline-earth-metal-containing water includes fresh water or saltwater, depending on the method employing the water. In some embodiments, the water employed in the process includes one or more alkaline earth metals, e.g., magnesium, calcium, etc. In some embodiments, the alkaline earth metal ions are present in an amount of 1% to 99% by wt; 1% to 95% by wt; or 1% to 90% by wt; or 1% to 80% by wt; or 1% to 70% by wt; or 1% to 60% by wt; or 1% to 50% by wt; or 1% to 40% by wt; or 1% to 30% by wt; or 1% to 20% by wt; or 1% to 10% by wt; or 20% to 95% by wt; or 20% to 80% by wt; or 20% to 50% by wt; or 50% to 95% by wt; or 50% to 80% by wt; or 50% to 75% by wt; or 75% to 90% by wt; or 75% to 80% by wt; or 80% to 90% by wt of the solution containing the alkaline earth metal ions. In some embodiments, the alkaline earth metal ions are present in saltwater, such as, seawater. In some embodiments, the source of divalent cations is hard water or naturally occurring hard brines. In some embodiments, calcium rich waters may be combined with magnesium silicate minerals, such as olivine or serpentine.

In some embodiments, gypsum (e.g. from Solvay process) provides a source of divalent cation such as, but not limited to, calcium ions. After the precipitation of the calcium carbonate/bicarbonate using the carbonate/bicarbonate solution from the cathode chamber and the calcium from gypsum, the supernatant containing sodium sulfate may be circulated to the electrochemical systems described herein. The sodium sulfate solution may be used in combination with metal sulfate such as copper sulfate such the Cu(I) ions are oxidized to Cu (II) ions in the anode chamber and are used further for the sulfonation of hydrogen gases or for the sulfonation of unsaturated or saturated hydrocarbons. In such embodiments, the electrochemical system is fully integrated with the precipitation process. Such use of gypsum as a source of calcium is described in U.S. Provisional Application No. 61/514,879, filed Aug. 3, 2011, which is fully incorporate herein by reference in its entirety.

In some locations, industrial waste streams from various industrial processes provide for convenient sources of cations (as well as in some cases other materials useful in the process, e.g., metal hydroxide). Such waste streams include, but are not limited to, mining wastes; fossil fuel burning ash (e.g., fly ash, bottom ash, boiler slag); slag (e.g., iron slag, phosphorous slag); cement kiln waste (e.g., cement kiln dust); oil refinery/petrochemical refinery waste (e.g., oil field and methane seam brines); coal seam wastes (e.g., gas production brines and coal seam brine); paper processing waste; water softening waste brine (e.g., ion exchange effluent); silicon processing wastes; agricultural waste; metal finishing waste; high pH textile waste; and caustic sludge. In some embodiments, the aqueous solution of cations include calcium and/or magnesium in amounts ranging from 10-50,000 ppm; or 10-10,000 ppm; or 10-5,000 ppm; or 10-1,000 ppm; or 10-100 ppm; or 50-50,000 ppm; or 50-10,000 ppm; or 50-1,000 ppm; or 50-100 ppm; or 100-50,000 ppm; or 100-10,000 ppm; or 100-1,000 ppm; or 100-500 ppm; or 1,000-50,000 ppm; or 1,000-10,000 ppm; or 5,000-50,000 ppm; or 5,000-10,000 ppm; or 10,000-50,000 ppm.

Freshwater may be a convenient source of cations (e.g., cations of alkaline earth metals such as $Ca^{2+}$ and $Mg^{2+}$). Any number of suitable freshwater sources may be used, including freshwater sources ranging from sources relatively free of minerals to sources relatively rich in minerals. Mineral-rich freshwater sources may be naturally occurring, including any of a number of hard water sources, lakes, or inland seas. Some mineral-rich freshwater sources such as alkaline lakes or inland seas (e.g., Lake Van in Turkey) also provide a source of pH-modifying agents. Mineral-rich freshwater sources may also be anthropogenic. For example, a mineral-poor (soft) water may be contacted with a source of cations such as alkaline earth metal cations (e.g., $Ca^{2+}$, $Mg^{2+}$, etc.) to produce a mineral-rich water that is suitable for methods and systems described herein. Cations or precursors thereof (e.g., salts, minerals) may be added to freshwater (or any other type of water described herein) using any convenient protocol (e.g., addition of solids, suspensions, or solutions). In some embodiments, divalent cations selected from $Ca^{2+}$ and $Mg^{2+}$ are added to freshwater. In some embodiments, freshwater containing $Ca^{2+}$ is combined with magnesium silicates (e.g., olivine or serpentine), or products or processed forms thereof, yielding a solution comprising calcium and magnesium cations.

The precipitate obtained after the contacting of the carbon from the source of carbon with the cathode electrolyte and the divalent cations includes, but is not limited to, calcium carbonate, magnesium carbonate, calcium bicarbonate, magnesium bicarbonate, calcium magnesium carbonate, or combination thereof. In some embodiments, the precipitate may be subjected to one or more of steps including, but not limited to, mixing, stirring, temperature, pH, precipitation, residence time of the precipitate, dewatering of precipitate, washing precipitate with water, ion ratio, concentration of additives, drying, milling, grinding, storing, aging, and curing, to make the carbonate composition of the invention. In some embodiments, the precipitation conditions are such that the carbonate products are metastable forms, such as, but not limited to vaterite, aragonite, amorphous calcium carbonate, or combination thereof.

The precipitator 1301 can be a tank or a series of tanks. Contact protocols include, but are not limited to, direct contacting protocols, e.g., flowing the volume of water containing cations, e.g. alkaline earth metal ions through the volume of cathode electrolyte containing sodium hydroxide; concurrent contacting means, e.g., contact between unidirectionally flowing liquid phase streams; and countercurrent means, e.g., contact between oppositely flowing liquid phase streams, and the like. Thus, contact may be accomplished through use of infusers, bubblers, fluidic Venturi reactor, sparger, gas filter, spray, tray, or packed column reactors, and the like, as may be convenient. In some embodiments, the contact is by spray. In some embodiments, the contact is through packed column. In some embodiments, the carbon from the source of carbon is added to the source of cations and the cathode electrolyte containing hydroxide. In some embodiments, the source of cations and the cathode electrolyte containing alkali is added to the carbon from the source of carbon. In some embodiments, both the source of cations and the carbon from the source of carbon are simultaneously added to the cathode electrolyte containing alkali in the precipitator for precipitation.

In some embodiments, where the carbon from the source of carbon has been added to the cathode electrolyte inside the cathode chamber, the withdrawn cathode electrolyte including hydroxide, bicarbonate and/or carbonate is administered to the precipitator for further reaction with the divalent cations. In some embodiments, where the carbon from the source of carbon and the divalent cations have been added to the cathode electrolyte inside the cathode chamber, the withdrawn cathode electrolyte including sodium hydroxide, calcium carbonate, magnesium carbonate, calcium bicarbonate, magnesium bicarbonate, calcium magnesium carbonate, or combination thereof, is administered to the precipitator for further processing.

The precipitator 1301 containing the solution of calcium carbonate, magnesium carbonate, calcium bicarbonate, magnesium bicarbonate, calcium magnesium carbonate, or combination thereof is subjected to precipitation conditions. At precipitation step, carbonate compounds, which may be amorphous or crystalline, are precipitated. These carbonate compounds may form a reaction product including carbonic acid, bicarbonate, carbonate, or mixture thereof. The carbonate precipitate may be the self-cementing composition and may be stored as is in the mother liquor or may be further processed to make the cement products. Alternatively, the precipitate may be subjected to further processing to give the hydraulic cement or the supplementary cementitious materials (SCM) compositions. The self-cementing compositions, hydraulic cements, and SCM have been described in U.S. application Ser. No. 12/857,248, filed 16 Aug. 2010, which is incorporated herein by reference in its entirety in the present disclosure.

The one or more conditions or one or more precipitation conditions of interest include those that change the physical environment of the water to produce the desired precipitate product. Such one or more conditions or precipitation conditions include, but are not limited to, one or more of temperature, pH, precipitation, dewatering or separation of the precipitate, drying, milling, and storage. For example, the temperature of the water may be within a suitable range for the precipitation of the desired composition to occur. For example, the temperature of the water may be raised to an amount suitable for precipitation of the desired carbonate compound(s) to occur. In such embodiments, the temperature of the water may be from 5 to 70° C., such as from 20 to 50° C., and including from 25 to 45° C. As such, while a given set of precipitation conditions may have a temperature ranging from 0 to 100° C., the temperature may be raised in certain embodiments to produce the desired precipitate. In certain embodiments, the temperature is raised using energy generated from low or zero carbon dioxide emission sources, e.g., solar energy source, wind energy source, hydroelectric energy source, etc.

The residence time of the precipitate in the precipitator before the precipitate is removed from the solution, may vary. In some embodiments, the residence time of the precipitate in the solution is more than 5 seconds, or between 5 seconds-1 hour, or between 5 seconds-1 minute, or between 5 seconds to 20 seconds, or between 5 seconds to 30 seconds, or between 5 seconds to 40 seconds. Without being limited by any theory, it is contemplated that the residence time of the precipitate may affect the size of the particle. For example, a shorter residence time may give smaller size particles or more disperse particles whereas longer residence time may give agglomerated or larger size particles. In some embodiments, the residence time in the process of the invention may be used to make small size as well as large size particles in a single or multiple batches which may be separated or may remain mixed for later steps of the process.

The nature of the precipitate may also be influenced by selection of appropriate major ion ratios. Major ion ratios may have influence on polymorph formation, such that the carbonate products are metastable forms, such as, but not limited to vaterite, aragonite, amorphous calcium carbonate, or combination thereof. In some embodiments, the carbonate products may also include calcite. Such polymorphic precipitates are described in U.S. application Ser. No. 12/857,248, filed 16 Aug. 2010, which is incorporated herein by reference in its entirety in the present disclosure. For example, magnesium may stabilize the vaterite and/or amorphous calcium carbonate in the precipitate. Rate of precipitation may also influence compound polymorphic phase formation and may be controlled in a manner sufficient to produce a desired precipitate product. The most rapid precipitation can be achieved by seeding the solution with a desired polymorphic phase. Without seeding, rapid precipitation can be achieved by rapidly increasing the pH of the sea water. The higher the pH is, the more rapid the precipitation may be.

In some embodiments, a set of conditions to produce the desired precipitate from the water include, but are not limited to, the water's temperature and pH, and in some instances the concentrations of additives and ionic species in the water. Precipitation conditions may also include factors such as mixing rate, forms of agitation such as ultrasonics, and the presence of seed crystals, catalysts, membranes, or substrates. In some embodiments, precipitation conditions include supersaturated conditions, temperature, pH, and/or concentration gradients, or cycling or changing any of these parameters. The protocols employed to prepare carbonate compound precipitates according to the invention may be batch or continuous protocols. It will be appreciated that precipitation conditions may be different to produce a given precipitate in a continuous flow system compared to a batch system.

Following production of the carbonate precipitate from the water, the resultant precipitated carbonate composition may be separated from the mother liquor or dewatered to produce the precipitate product, as illustrated at step 1302 of FIG. 13. Alternatively, the precipitate is left as is in the mother liquor or mother supernate and is used as a cementing composition.

Separation of the precipitate can be achieved using any convenient approach, including a mechanical approach, e.g., where bulk excess water is drained from the precipitated, e.g., either by gravity alone or with the addition of vacuum, mechanical pressing, by filtering the precipitate from the mother liquor to produce a filtrate, etc. Separation of bulk water produces a wet, dewatered precipitate. The dewatering station may be any number of dewatering stations connected to each other to dewater the slurry (e.g., parallel, in series, or combination thereof).

The above protocol results in the production of slurry of the precipitate and mother liquor. This precipitate in the mother liquor and/or in the slurry may give the self-cementing composition. In some embodiments, a portion or whole of the dewatered precipitate or the slurry is further processed to make the hydraulic cement or the SCM compositions.

Where desired, the compositions made up of the precipitate and the mother liquor may be stored for a period of time following precipitation and prior to further processing. For example, the composition may be stored for a period of time ranging from 1 to 1000 days or longer, such as 1 to 10 days or longer, at a temperature ranging from 1 to 40° C., such as 20 to 25° C.

The slurry components are then separated. Embodiments may include treatment of the mother liquor, where the mother liquor may or may not be present in the same composition as the product. The resultant mother liquor of the reaction may be disposed of using any convenient protocol. In certain embodiments, it may be sent to a tailings pond 1307 for disposal. In certain embodiments, it may be disposed of in a naturally occurring body of water, e.g., ocean, sea, lake or river. In certain embodiments, the mother liquor is returned to the source of feedwater for the methods of invention, e.g., an ocean or sea. Alternatively, the mother liquor may be further processed, e.g., subjected to desalination protocols, as described further in U.S. application Ser. No. 12/163,205, filed Jun. 27, 2008; the disclosure of which is herein incorporated by reference in the present disclosure.

The resultant dewatered precipitate is then dried to produce the carbonate composition of the invention, as illustrated at step 1304 of FIG. 13. Drying can be achieved by air drying the precipitate. Where the precipitate is air dried, air drying may be at a temperature ranging from −70 to 120° C., as desired. In certain embodiments, drying is achieved by freeze-drying (i.e., lyophilization), where the precipitate is frozen, the surrounding pressure is reduced and enough heat is added to allow the frozen water in the material to sublime directly from the frozen precipitate phase to gas. In yet another embodiment, the precipitate is spray dried to dry the precipitate, where the liquid containing the precipitate is dried by feeding it through a hot gas (such as the gaseous waste stream from the power plant), e.g., where the liquid feed is pumped through an atomizer into a main drying chamber and a hot gas is passed as a co-current or counter-current to the atomizer direction. Depending on the particular drying protocol of the system, the drying station may include a filtration element, freeze drying structure, spray drying structure, etc. The drying step may discharge air and fines 1306.

In some embodiments, the step of spray drying may include separation of different sized particles of the precipitate. Where desired, the dewatered precipitate product from 1302 may be washed before drying, as illustrated at step 1303 of FIG. 13. The precipitate may be washed with freshwater, e.g., to remove salts (such as NaCl) from the dewatered precipitate. Used wash water may be disposed of as convenient, e.g., by disposing of it in a tailings pond, etc. The water used for washing may contain metals, such as, iron, nickel, etc.

In some embodiments, the dried precipitate is refined, milled, aged, and/or cured (as shown in the refining step 1305), e.g., to provide for desired physical characteristics, such as particle size, surface area, zeta potential, etc., or to add one or more components to the precipitate, such as admixtures, aggregate, supplementary cementitious materials, etc., to produce the carbonate composition. Refinement may include a variety of different protocols. In certain embodiments, the product is subjected to mechanical refinement, e.g., grinding, in order to obtain a product with desired physical properties, e.g., particle size, etc. The dried precipitate may be milled or ground to obtain a desired particle size.

In some embodiments, the calcium carbonate precipitate formed by the methods and system of the invention, is in a metastable form including but not limited to, vaterite, aragonite, amorphous calcium carbonate, or combination thereof. In some embodiments, the calcium carbonate precipitate formed by the methods and system of the invention, is in a metastable form including but not limited to, vaterite, amorphous calcium carbonate, or combination thereof. The vaterite containing composition of calcium carbonate, after coming into contact with water converts to a stable polymorph form such as aragonite, calcite, or combination thereof with a high compressive strength.

The carbonate composition or the cementitous composition, thus formed, has elements or markers that originate from the carbon from the source of carbon used in the process. The carbonate composition after setting, and hardening has a compressive strength of at least 14 MPa; or at least 16 MPa; or at least 18 MPa; or at least 20 MPa; or at least 25 MPa; or at least 30 MPa; or at least 35 MPa; or at least 40 MPa; or at least 45 MPa; or at least 50 MPa; or at least 55 MPa; or at least 60 MPa; or at least 65 MPa; or at least 70 MPa; or at least 75 MPa; or at least 80 MPa; or at least 85 MPa; or at least 90 MPa; or at least 95 MPa; or at least 100 MPa; or from 14-100 MPa; or from 14-80 MPa; or from 14-75 MPa; or from 14-70 MPa; or from 14-65 MPa; or from 14-60 MPa; or from 14-55 MPa; or from 14-50 MPa; or from 14-45 MPa; or from 14-40 MPa; or from 14-35 MPa; or from 14-30 MPa; or from 14-25 MPa; or from 14-20 MPa; or from 14-18 MPa; or from 14-16 MPa; or from 17-35 MPa; or from 17-30 MPa; or from 17-25 MPa; or from 17-20 MPa; or from 17-18 MPa; or from 20-100 MPa; or from 20-90 MPa; or from 20-80 MPa; or from 20-75 MPa; or from 20-70 MPa; or from 20-65 MPa; or from 20-60 MPa; or from 20-55 MPa; or from 20-50 MPa; or from 20-45 MPa; or from 20-40 MPa; or from 20-35 MPa; or from 20-30 MPa; or from 20-25 MPa; or from 30-100 MPa; or from 30-90 MPa; or from 30-80 MPa; or from 30-75 MPa; or from 30-70 MPa; or from 30-65 MPa; or from 30-60 MPa; or from 30-55 MPa; or from 30-50 MPa; or from 30-45 MPa; or from 30-40 MPa; or from 30-35 MPa; or from 40-100 MPa; or from 40-90 MPa; or from 40-80 MPa; or from 40-75 MPa; or from 40-70 MPa; or from 40-65 MPa; or from 40-60 MPa; or from 40-55 MPa; or from 40-50 MPa; or from 40-45 MPa; or from 50-100 MPa; or from 50-90 MPa; or from 50-80 MPa; or from 50-75 MPa; or from 50-70 MPa; or from 50-65 MPa; or from 50-60 MPa; or from 50-55 MPa; or from 60-100 MPa; or from 60-90 MPa; or from 60-80 MPa; or from 60-75 MPa; or from 60-70 MPa; or from 60-65 MPa; or from 70-100 MPa; or from 70-90 MPa; or from 70-80 MPa; or from 70-75 MPa; or from 80-100 MPa; or from 80-90 MPa; or from 80-85 MPa; or from 90-100 MPa; or from 90-95 MPa; or 14 MPa; or 16 MPa; or 18 MPa; or 20 MPa; or 25 MPa; or 30 MPa; or 35 MPa; or 40 MPa; or 45 MPa. For example, in some embodiments of the foregoing aspects and the foregoing embodiments, the composition after setting, and hardening has a compressive strength of 14 MPa to 40 MPa; or 17 MPa to 40 MPa; or 20 MPa to 40 MPa;

or 30 MPa to 40 MPa; or 35 MPa to 40 MPa. In some embodiments, the compressive strengths described herein are the compressive strengths after 1 day, or 3 days, or 7 days, or 28 days.

The precipitates, comprising, e.g., calcium and magnesium carbonates and bicarbonates in some embodiments may be utilized as building materials, e.g., as cements and aggregates, as described in commonly assigned U.S. patent application Ser. No. 12/126,776, filed on 23 May 2008, herein incorporated by reference in its entirety in the present disclosure.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Various modifications of the invention in addition to those described herein will become apparent to those skilled in the art from the foregoing description and accompanying figures. Such modifications fall within the scope of the appended claims. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

In the examples and elsewhere, abbreviations have the following meanings:

| | |
|---|---|
| AEM = | anion exchange membrane |
| Ag = | silver |
| Ag/AgCl = | silver/silver chloride |
| $cm^2$ = | centimeter square |
| ClEtOH = | chloroethanol |
| CV = | cyclic voltammetry |
| DI = | deionized |
| EDC = | ethylene dichloride |
| g = | gram |
| HCl = | hydrochloric acid |
| hr = | hour |
| Hz = | hertz |
| M = | molar |
| mA = | milliamps |
| $mA/cm^2$ = | milliamps/centimeter square |
| mg = | milligram |
| min. = | minute |
| mmol = | millimole |
| mol = | mole |
| µl = | microliter |
| µm = | micrometer |
| mL = | milliliter |
| ml/min = | milliliter/minute |
| mV = | millivolt |
| mV/s or $mVs^{-1}$ = | millivolt/second |
| NaCl = | sodium chloride |
| NaOH = | sodium hydroxide |
| nm = | nanometer |
| $\Omega cm^2$ = | ohms centimeter square |
| Pd/C = | palladium/carbon |
| Pt = | platinum |
| PtIr = | platinum iridium |
| rpm = | revolutions per minute |
| STY = | space time yield |
| V = | voltage |
| w/v = | weight/volume |
| w/w = | weight/weight |

EXAMPLES

Example 1

Figure 14:
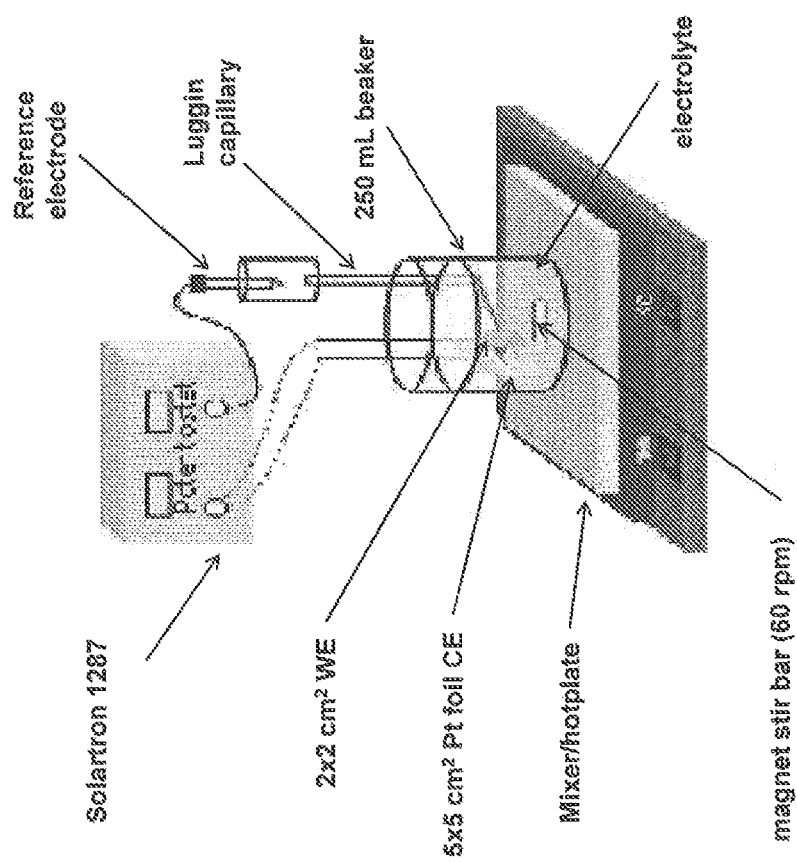
FIG. 14 is an experimental setup as described in Example 1 herein.

This example illustrates an experimental set up and proposed experimental conditions for a half cell reaction. The reaction is carried out in the experimental set up illustrated in FIG. 14. Cyclic voltammetry is performed on metal-salt anolytes (tin (ii) chloride, chromium (II) chloride, iron (II) chloride, and copper (I) chloride).

Example 2

Voltage Savings with $CO_2$ in the Catholyte

This example illustrates the highest current density achieved at 0V in different electrochemical systems. The conditions used for this experiment were: anode: 6 $cm^2$ Pt foil; cathode: 6 $cm^2$ oxygen depolarized cathode; anolyte: 0.5M $Cr^{2+}$ solvated with ultrapure deionized water; brine: 15.6 wt % NaCl solvated with ultrapure deionized water; catholyte: 10 wt % NaOH solvated with ultrapure deionized water. Solution temperatures were held constant at 70° C. and re-circulated in the cell at 400 rpm using an LS16 sized peristaltic tubing. The electrochemical systems used in this experiment were the electrochemical system 500 of FIG. 5A but with 2-compartment system where only one ion exchange membrane was used (System A in FIG. 15); the electrochemical system 500 of FIG. 5A with 2-compartment system and where $CO_2$ was administered to the catholyte (System B in FIG. 15); the electrochemical system 500 of FIG. 5A with 3-compartment system (System C in FIG. 15); and the electrochemical system 500 of FIG. 5A with 3-compartment system and where $CO_2$ was administered to the catholyte (System D in FIG. 15).

Figure 15:
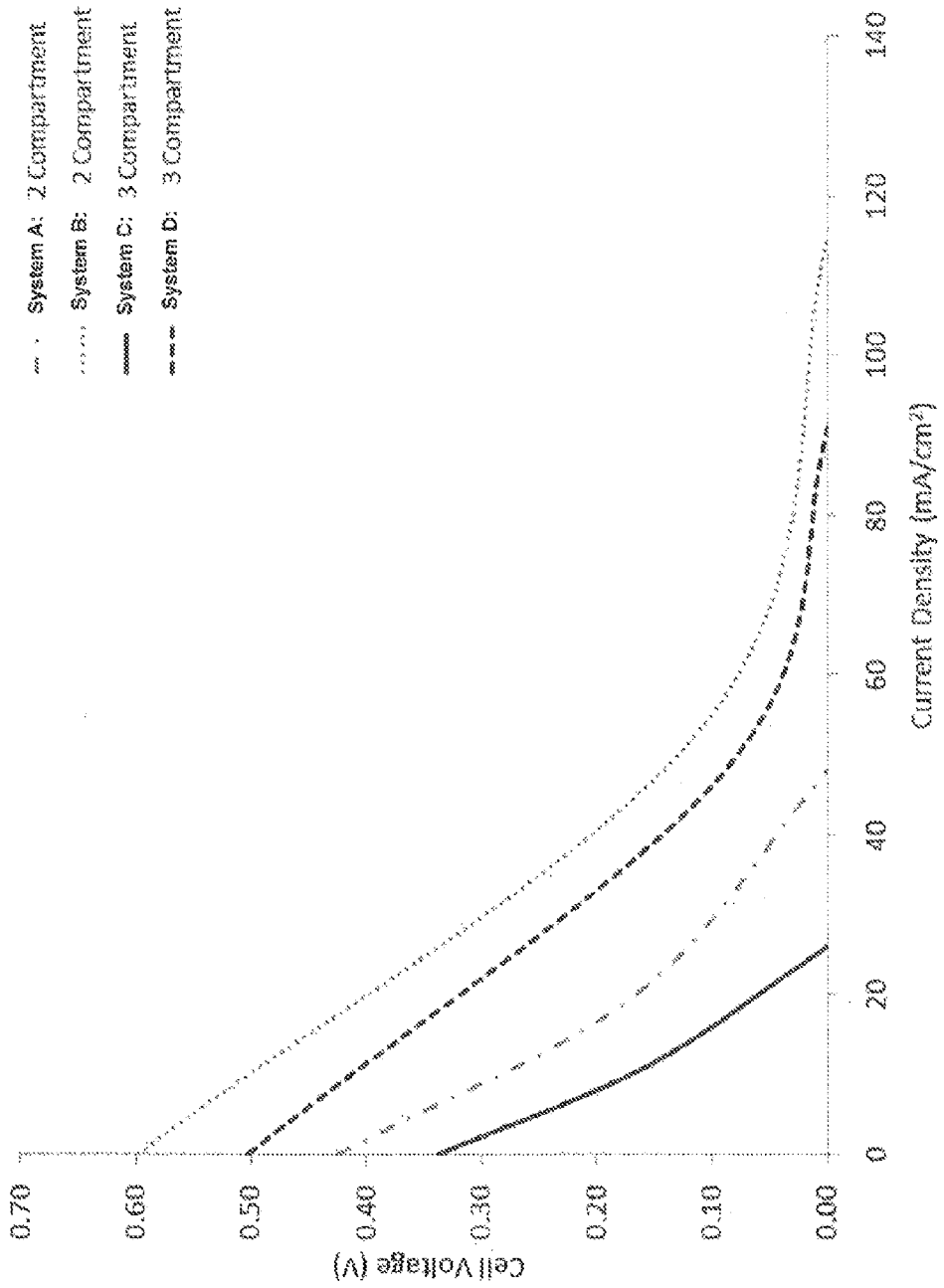
FIG. 15 is an illustrative graph as described in Example 2 herein.

The catholyte was bubbled with $CO_2$ until the pH reached less than 12 and around 10. As illustrated in FIG. 15, adjusting the pH of the catholyte via $CO_2$ injection improved the overall performance as higher current density was achieved at 0V. Also, removing a compartment and cation exchange membrane for the 2-compartment improved results over the 3-compartment system. It is contemplated that there are a reduction of ohmic losses from the membrane and the electrolyte.

Example 3

Voltage Savings with $CO_2$ in the Catholyte

This example illustrates the highest current density achieved at 0V in different electrochemical systems. The conditions used for this experiment were: anode: 6 $cm^2$ Pt foil; cathode: 6 $cm^2$ Pt foil; anolyte: 0.5M $Cr^{2+}$ solvated with ultrapure deionized water; brine: 15.6 wt % NaCl solvated with ultrapure deionized water; catholyte: 10 wt % NaOH solvated with ultrapure deionized water. Solution temperatures were held constant at 70° C. and re-circulated in the cell at 400 rpm using an LS16 sized peristaltic tubing.

Figure 16:
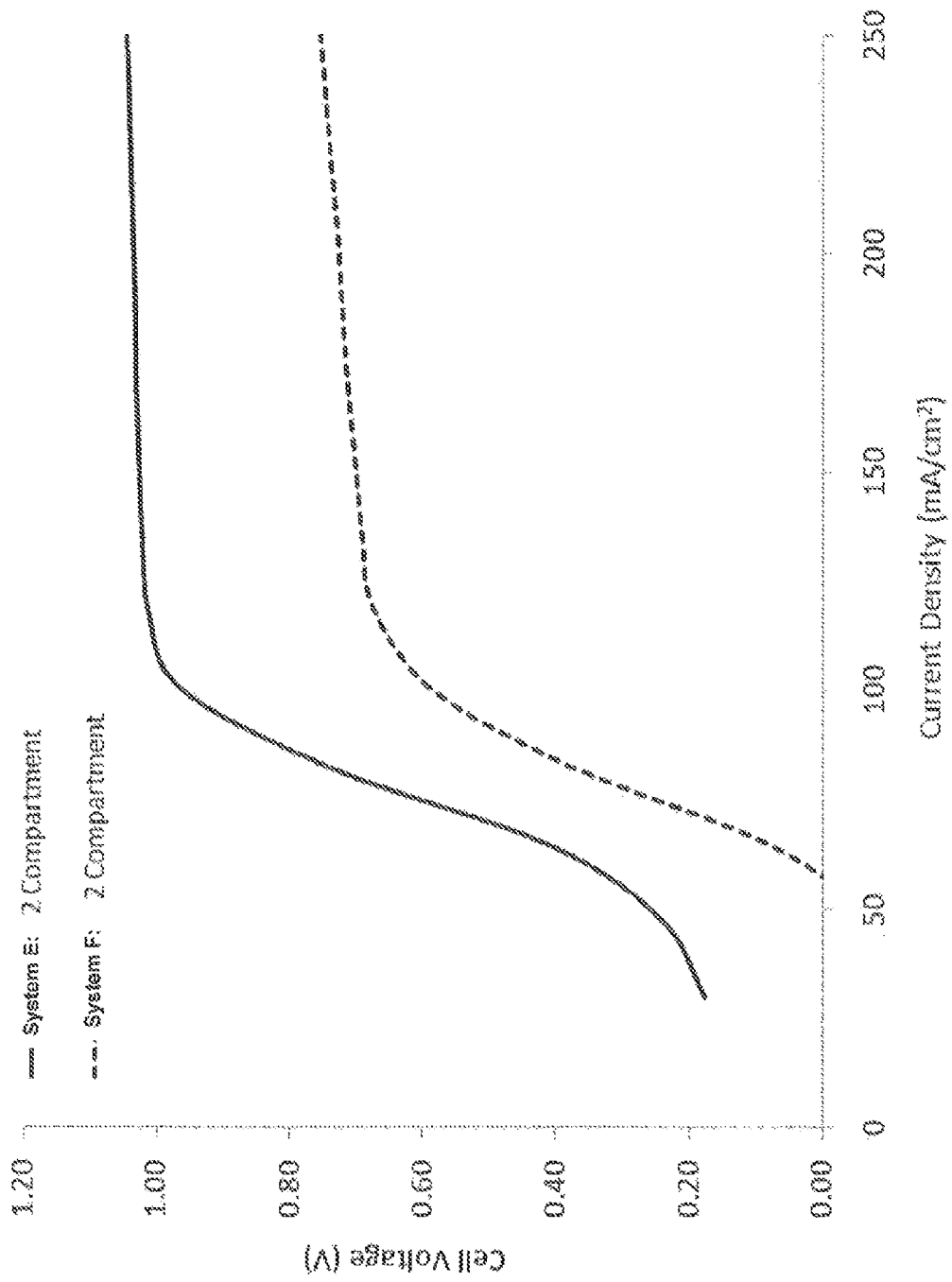
FIG. 16 is an illustrative graph as described in Example 3 herein.

The electrochemical systems used in this experiment were the electrochemical system 400 of FIG. 4A but with 2-compartment system where only one ion exchange membrane was used (System E in FIG. 16); and the electrochemical system 400 of FIG. 4A with 2-compartment system and where $CO_2$ was administered to the catholyte (System F in FIG. 16). It is to be understood that a similar experiment can be set-up for 3-compartment system, as described in Example 2.

The catholyte was bubbled with $CO_2$ until the pH reached less than 12 and around 10. As illustrated in FIG. 16, adjusting the pH of the catholyte via $CO_2$ injection improved the overall performance as it improved the voltage by 300 mV at 150 mA/cm². Here the cathode reaction produced hydrogen that can be used for metal ion regeneration through the use of hydrogenation (as illustrated in FIG. 6). For this test, the current was increased galvanostatically and the resulting cell voltage was recorded.

Example 4

Treatment of Metal with Hydrogen Gas

Experiment 1: Hydrogenation of Chromium

Figure 17A:
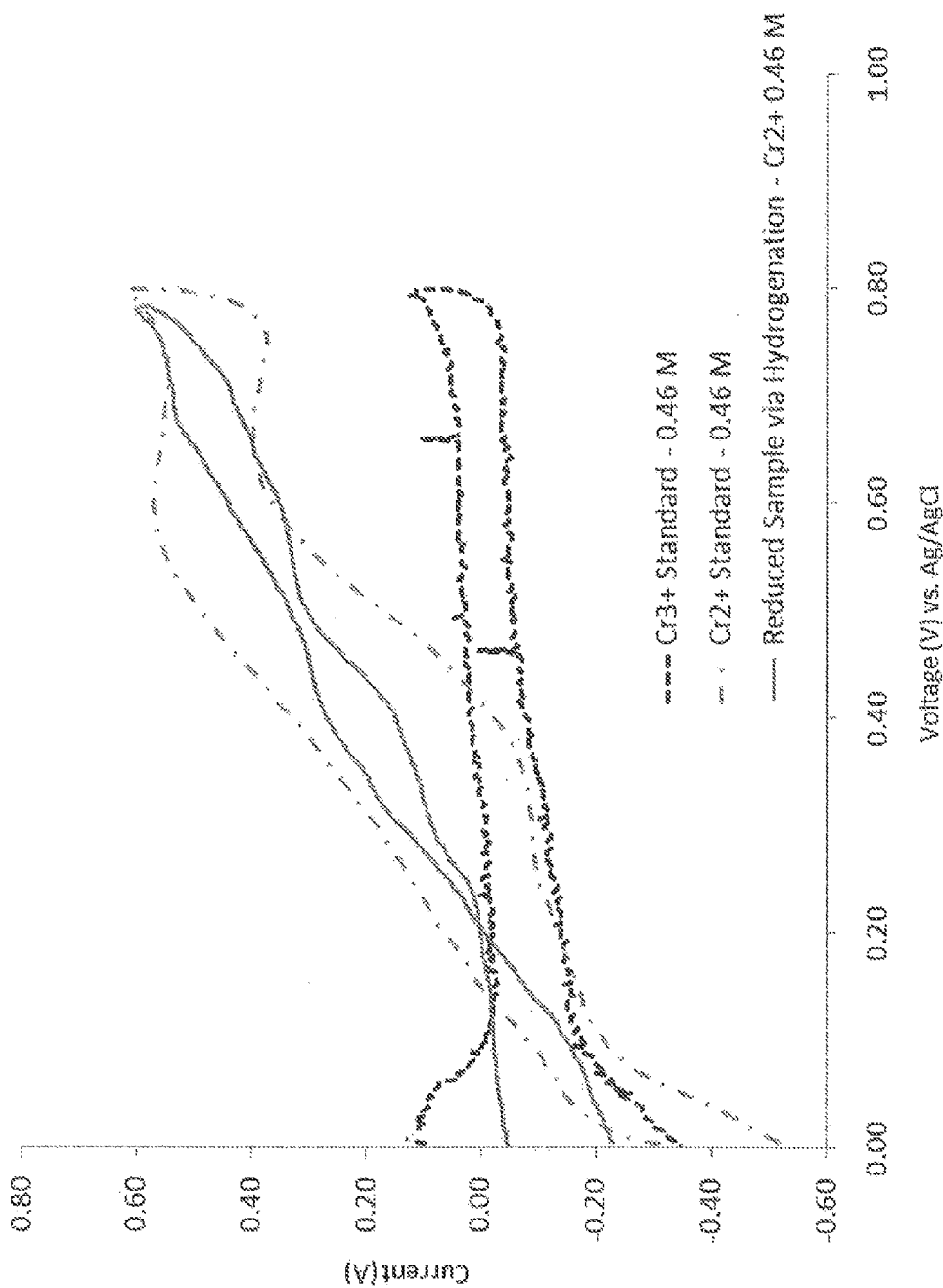
FIG. 17A is an illustrative graph for chromium reduction with hydrogen gas described in Example 4 herein.

This example illustrates the hydrogenation of the chromium ion in the higher oxidation state to form the chromium ion in the lower oxidation state and hydrochloric acid. FIG. 17A is an illustration of electrochemical cyclic voltammograms to detect the presence of $Cr^{2+}$ after reducing a 0.46M solution of $Cr^{3+}$ with hydrogen at 25° C. for 8 hrs. Two standard solutions of 0.46M $Cr^{2+}$ and 0.46M $Cr^{3+}$ were prepared and characterized electrochemically. The conditions used for this experiment were: anode: 6 cm² Pt foil; cathode: 6 cm² Pt foil; anolyte: 0.46M $Cr^{2+}$, 0.46M $Cr^{3+}$, and reduced solution containing $Cr^{3+}$ and $Cr^{2+}$ solvated with ultrapure deionized water. Solution temperatures were held constant at 70°. The voltage was scanned from 0 to 0.8V vs. Ag/AgCl reference electrode at 10 mV/s. It was expected to see $Cr^{2+}$ oxidation with no oxidation signals for the $Cr^{3+}$ standard in this voltage range. Since an oxidation peak for $Cr^{2+}$ standard was seen, the solution that had been reduced from $Cr^{3+}$ to $Cr^{2+}$ was tested using cyclic voltammetry. As illustrated in FIG. 17A, the reduced sample showed the presence of $Cr^{2+}$ indicating a reduction of $Cr^{3+}$ to $Cr^{2+}$ via hydrogenation.

Experiment 2: Hydrogenation of Copper

Figure 17B:
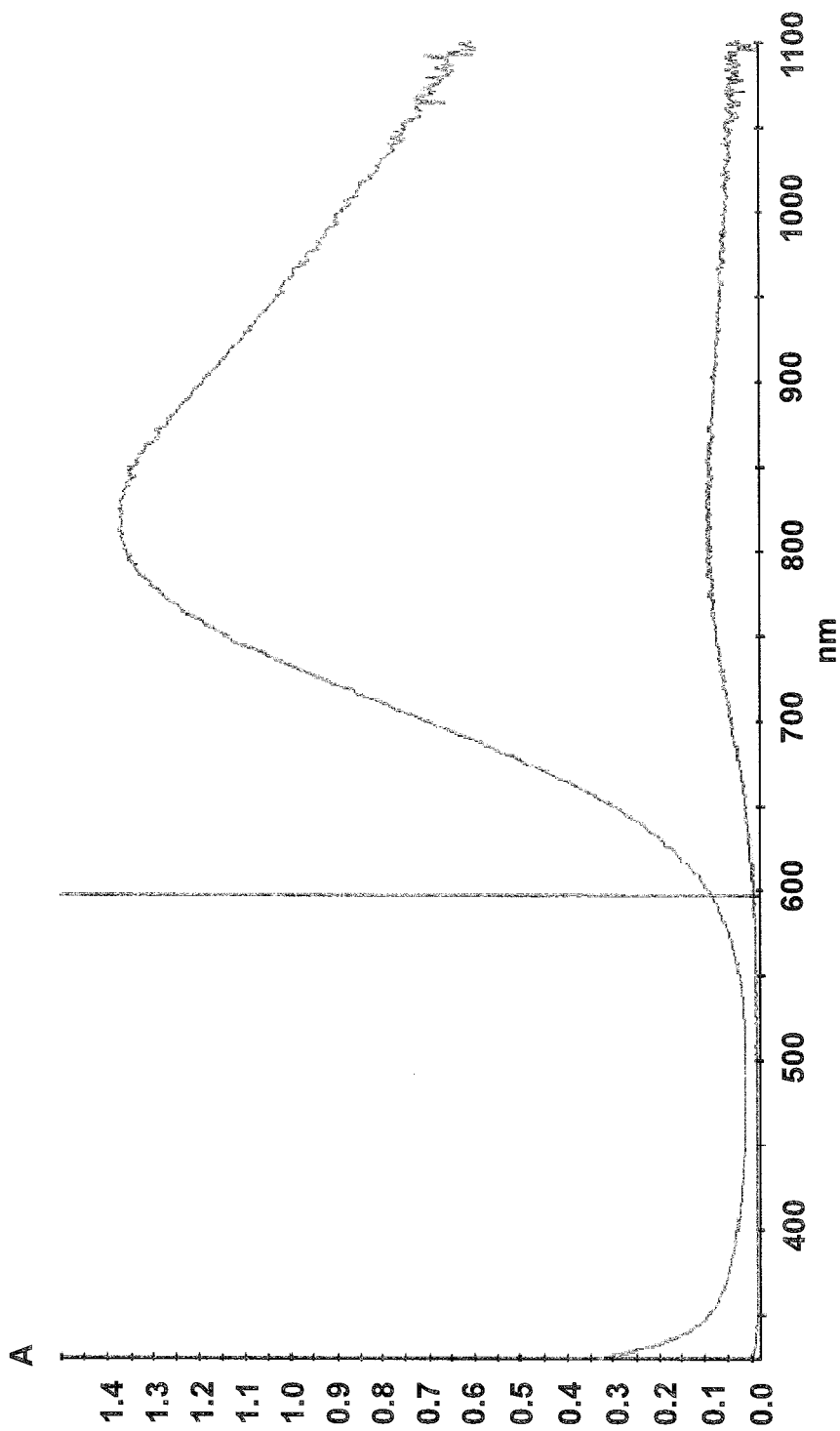
FIG. 17B is an illustrative graph for copper reduction with hydrogen gas described in Example 4 herein.

This example illustrates the hydrogenation of the copper ion in the higher oxidation state to form the copper ion in the lower oxidation state and hydrochloric acid. To a 1-necked 100 ml round bottom flask, was added 100 ml of DI water. Using a t-necked gas inlet adapter, the water was aspirated and filled 5× with nitrogen. To this oxygen free water was then added 1.7 g (0.01 mol) of $CuCl_2·2H_2O$ (0.1M in $CuCl_2·2H_2O$) and magnetic stir bar. To the resulting light blue liquid, was added 300 mg of 1% Pd/C and the mix was rapidly stirred under nitrogen. The mixture was then aspirated 4× with $H_2$ gas from a rubber bladder and finally kept under positive $H_2$ pressure stirring rapidly. After 12 h the stirrer was stopped and a ~2 mL aliquot was removed and filtered through a 0.2 μm filter disk using a 5 ml syringe. The resulting filtrate was clear. As illustrated in FIG. 17B, the UV-VIS showed ~94% conversion of Cu(II) to Cu(I) (top curve is for Cu(II) before reaction and bottom curve is for Cu(II) after reaction) with a notably acidic solution (showing the formation of HCl).

Example 5

Formation of Halohydrocarbon from Unsaturated Hydrocarbon

Formation of EDC from Ethylene Using Copper Chloride

Figure 18:
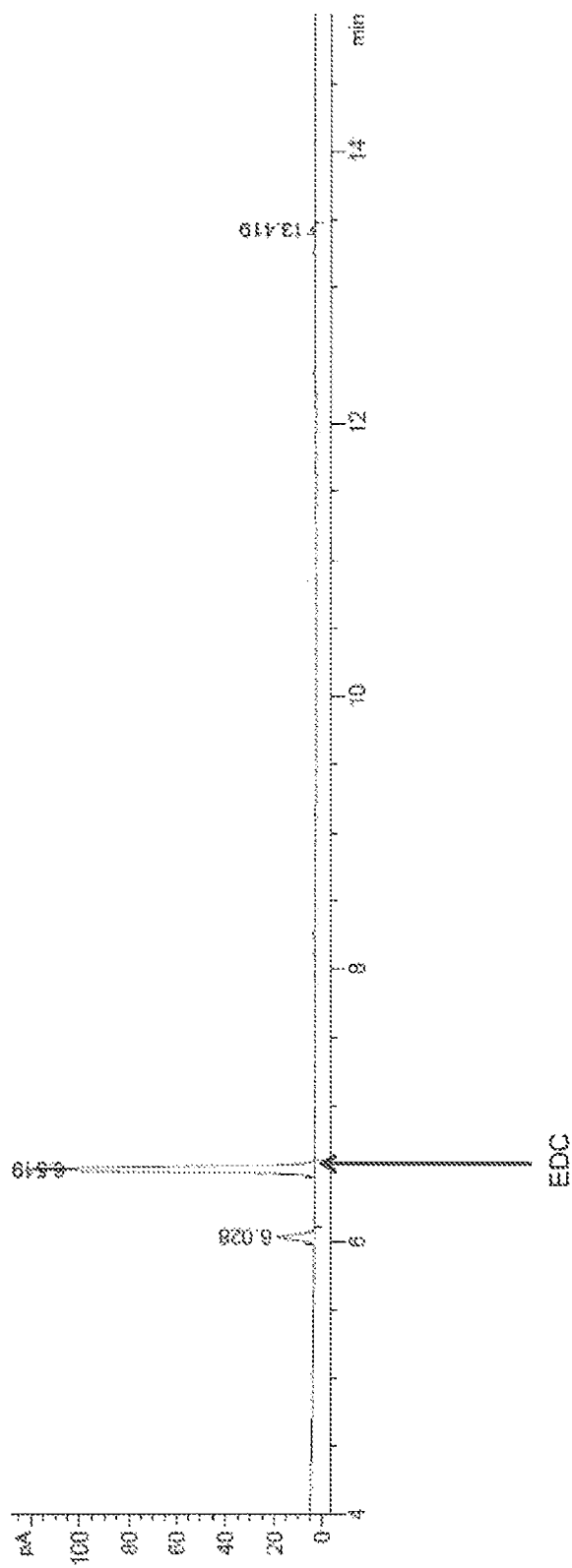
FIG. 18 is an illustrative graph as described in Example 5 herein.
Figure 19:
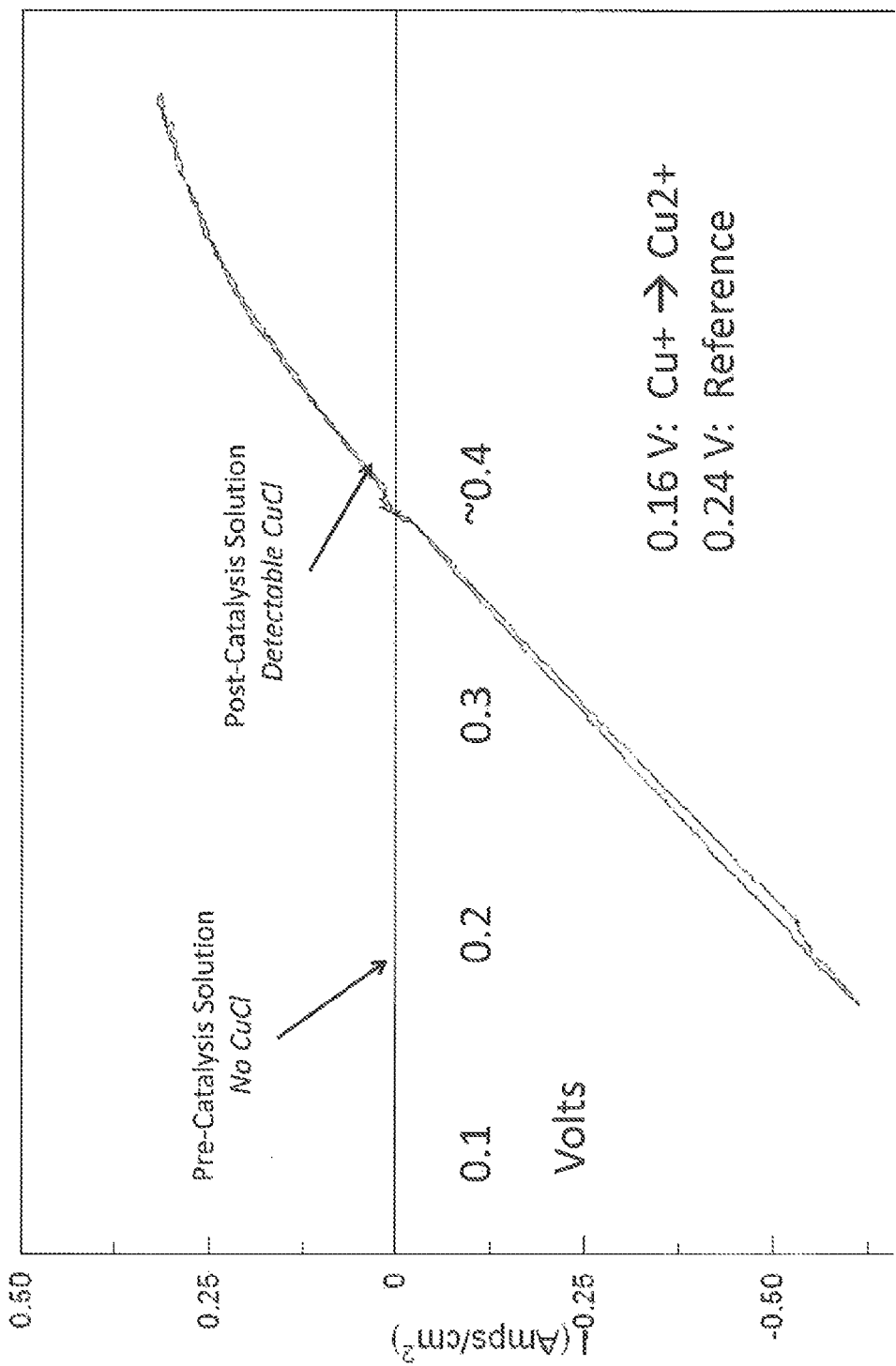
FIG. 19 is an illustrative graph as described in Example 5 herein.

Experiment 1: This experiment is directed to the formation of ethylene dichloride (EDC) from ethylene using cupric chloride. The experiment was conducted in a pressure vessel. The pressure vessel contained an outer jacket containing the catalyst, i.e. cupric chloride solution and an inlet for bubbling ethylene gas in the cupric chloride solution. The catalyst solution used in the experiment was 200 mL of 1M NaCl, 1M $CuCl_2$, and 0.5 mL of 12.1M HCl. This solution was clear and green. The pressure vessel was heated to 160° C. and ethylene gas was passed into the vessel for up to 300 psi for 30 minutes. The solution after reaction was found to be much darker than the starting solution. The product formed in the solution was extracted with 50 mL pentane and was then separated using a separatory funnel. The pentane extract containing the EDC was subjected to gas-chromatography (GC). FIG. 18 illustrates a peak at the retention time for EDC. The other small peaks pertain to pentane. FIG. 19 shows that the CV of a pre-reaction catalyst solution was flat and the CV of a post-reaction solution showed oxidation at 0.4V (for the half cell and the reference electrode). The UV-Vis of the product gave a $Cu^{2+}$ concentration of 0.973M.

Experiment 2: This experiment is directed to the formation of ethylene dichloride (EDC) from ethylene using cupric chloride. The experiment was conducted in a pressure vessel. The pressure vessel contained an outer jacket containing the catalyst, i.e. cupric chloride solution and an inlet for bubbling ethylene gas in the cupric chloride solution. The concentration of the reactants was, as shown in Table II below. The pressure vessel was heated to 160° C. and ethylene gas was passed into the vessel containing 200 mL of the solution at 300 psi for between 30 min.-1 hr in the experiments. The vessel was cooled to 4° C. before venting and opening. The product formed in the solution was extracted with ethyl acetate and was then separated using a separatory funnel. The ethyl acetate extract containing the EDC was subjected to gas-chromatography (GC).

TABLE II

| Time (hrs) | $CuCl_2$ | CuCl | NaCl | HCl (M) | EDC (mg) | Chloro-ethanol (mg) | Cu Utilization (EDC) | STY | Mass Selectivity: EDC/(EDC + ClEtOH) % |
|---|---|---|---|---|---|---|---|---|---|
| 0.5 | 6 | 0.5 | 1 | 0.03 | 3,909.26 | 395.13 | 8.77% | 0.526 | 90.82% |
| 0.5 | 4.5 | 0.5 | 2.5 | 0.03 | 3,686.00 | 325.50 | 11.03% | 0.496 | 91.89% |

Formation of Dichloropropane from Propylene Using Copper Chloride

This experiment is directed to the formation of 1,2-dichloropropane (DCP) from propylene using cupric chloride. The experiment was conducted in a pressure vessel. The pressure vessel contained an outer jacket containing the catalyst, i.e. cupric chloride solution and an inlet for bubbling propylene gas in the cupric chloride solution. A 150 mL solution of 5M $CuCl_2$, 0.5M CuCl, 1M NaCl, and 0.03M HCl was placed into a glass-lined 450 mL stirred pressure vessel. After purging the closed container with $N_2$, it was heated to 160° C. After reaching this temperature, propylene was added to the container to raise the pressure from the autogenous pressure, mostly owing from water vapor, to a pressure of 130 psig. After 15 minutes, more propylene was added to raise the pressure from 120 psig to 140 psig. After an additional 15 minutes, the pressure was 135 psig. At this time, the reactor was cooled to 14° C., depressurized, and opened. Ethyl acetate was used to rinse the reactor parts and then was used as the extraction solvent. The product was analyzed by gas chromatography which showed 0.203 g of 1,2-dichloropropane that was recovered in the ethyl acetate phase.

Example 6

Use of Ligand

In regards to studying a ligated copper system, a sample was made using the ligand N,N,N,N-tetramethylethylenediamine (TMEDA).
TMEDA=

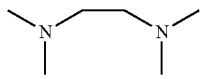

N,N,N,N-tetramethylethylenediamine

Various other examples for the ligand are illustrated in FIG. 20 which have been described herein. Any of the ligands illustrated in FIG. 20 can be used in the catalytic reactions of the invention. Other examples of the ligands are also illustrated in Example 10. The aqueous solution consisted of the following: 2.5M NaCl, 1.0M $CuCl_2$, 0.5M CuCl, and 2.2M TMEDA. Upon mixing the ligand with the rest of the solution, a brownish solution changed quickly to a dark blue solution indicating ligation had occurred. The treatment of the above solution (diluted) with dichloromethane followed by vigorous shaking showed that after phase separation, the complex was not pulled into the extraction solvent. This effect is desirable since this can reduce metal complex contamination when an extraction method is used for isolation of organic products from the metal ions. The pH of the solution changed from acidic to mildly basic (pH 2.6 to 7.8) upon addition of the ligand. This effect of the ligand on the pH can be a benefit to reducing the corrosive nature of the copper chloride catalyst system.

Example 7

Voltage Savings with the Ligand

Figure 21:
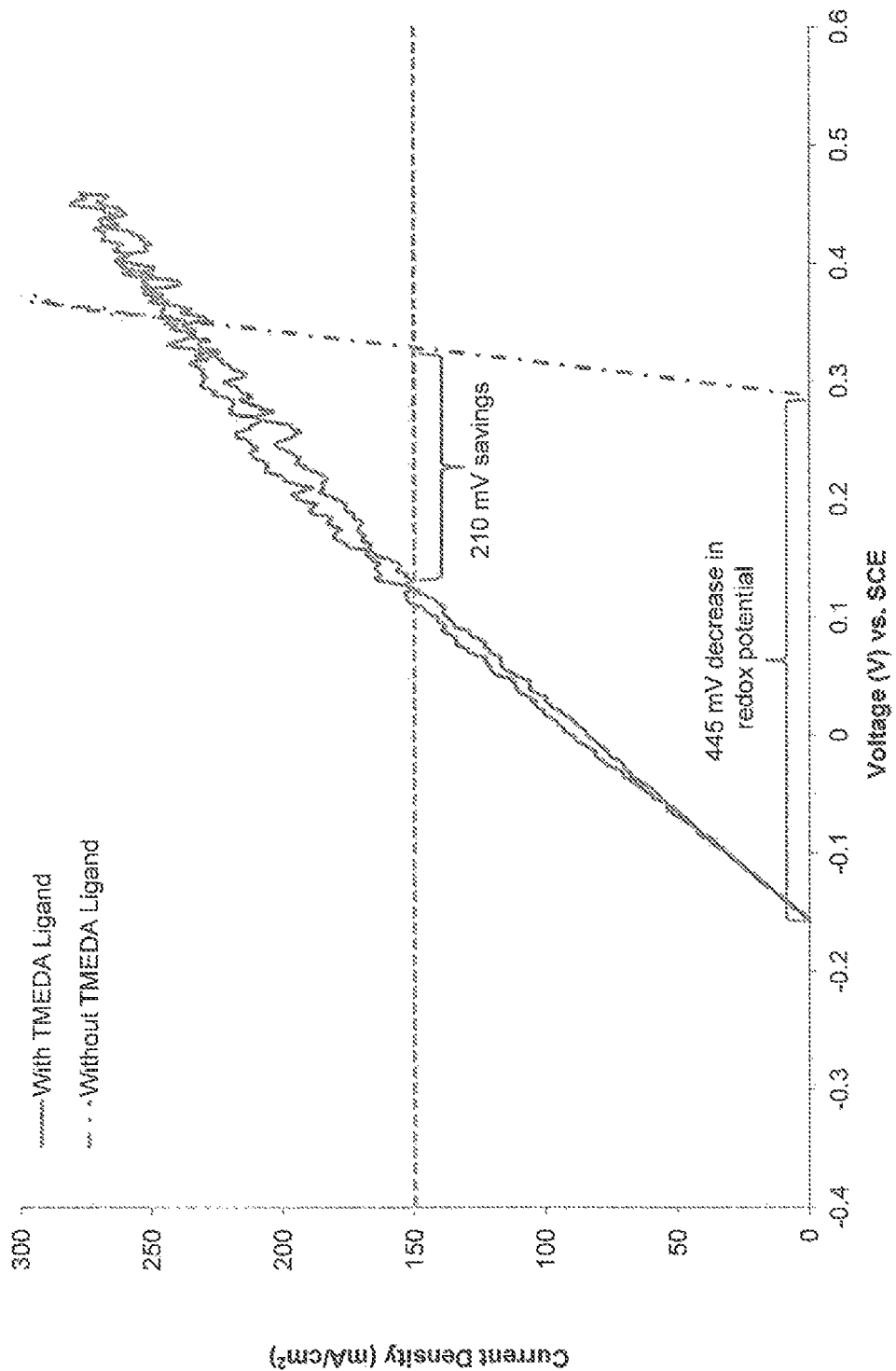
FIG. 21 is an illustrative graph as described in Example 7 herein.

A half cell reaction was carried out using the metal-ligand solution of Example 6 and the set up of Example 1. The working electrode for the half cell reaction was 4 $cm^2$ Pt Gauze 52 mesh anode; the counter electrode was 6 $cm^2$ Pt foil; and the reference electrode was Saturated Calomel electrode (SCE). The solution in the beaker was kept at 70° C. In one experiment, a solution contained 2.5M NaCl, 1.0M $CuCl_2$, and 0.5M CuCl and no ligand. In the other experiment, the solution contained 2.5M NaCl, 1.0M $CuCl_2$, 0.5M CuCl, and 2.2M TMEDA (Example 6). As illustrated in FIG. 21, a voltage savings of about 200 mV was observed at 150 $mA/cm^2$ when the ligand was used in the metal solution.

Example 8

Voltage Savings with the Ligand

Figure 22:
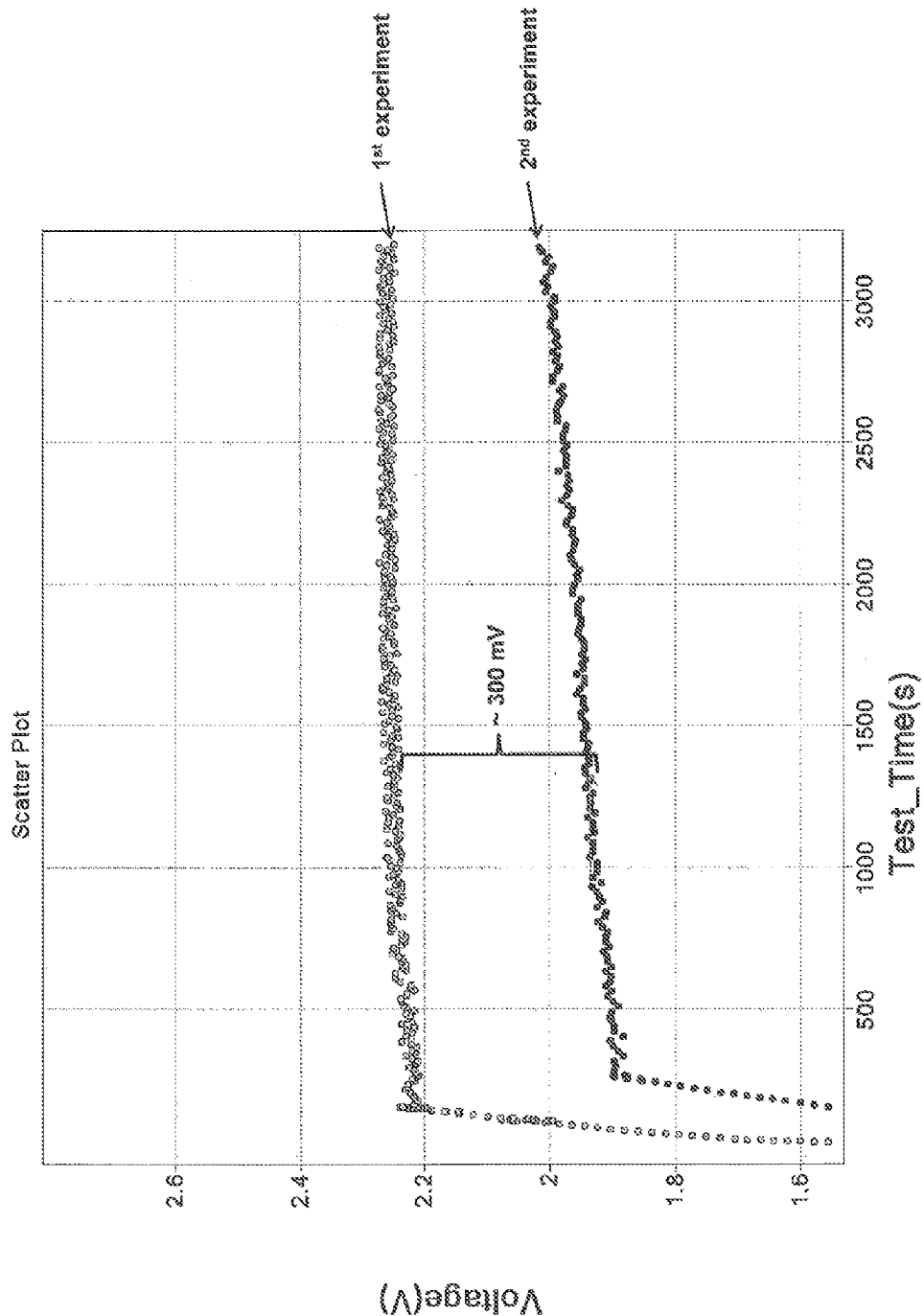
FIG. 22 is an illustrative graph as described in Example 8 herein.

A full cell reaction was carried out using the metal-ligand solution of Example 6 and the cell of FIG. 4A. The components of the cell were commercially available and included Pt guaze anode; fine Ni mesh cathode; anion exchange membrane as AHA; and the cation exchange membrane as 2100. The catholyte was 10 wt % NaOH. In 1st experiment, the anolyte was 2.5M NaCl, 1.0M $CuCl_2$, and 0.5M CuCl and no ligand and in the 2nd experiment, the anolyte was 2.5M NaCl, 1.0M $CuCl_2$, 0.5M CuCl, and 2.2M TMEDA (Example 6). FIG. 22 illustrates that the presence of the ligand reduced the redox potential (about 300 mV in this experiment) which resulted in the decrease in the cell voltage. The color of the ligand solution also changed dramatically which could be due to oxidation of $Cu^+$ to $Cu^{2+}$.

Example 9

Anion Exchange Membrane

This example illustrates effect of selection of AEM on the prevention of the crossover of the metal ions through the AEM to the middle chamber. This example also illustrates the selection of AEM that prevents crossover of metal ions, fouling of the membrane, and increase in resistance.

Direct Current Method

Figure 23:
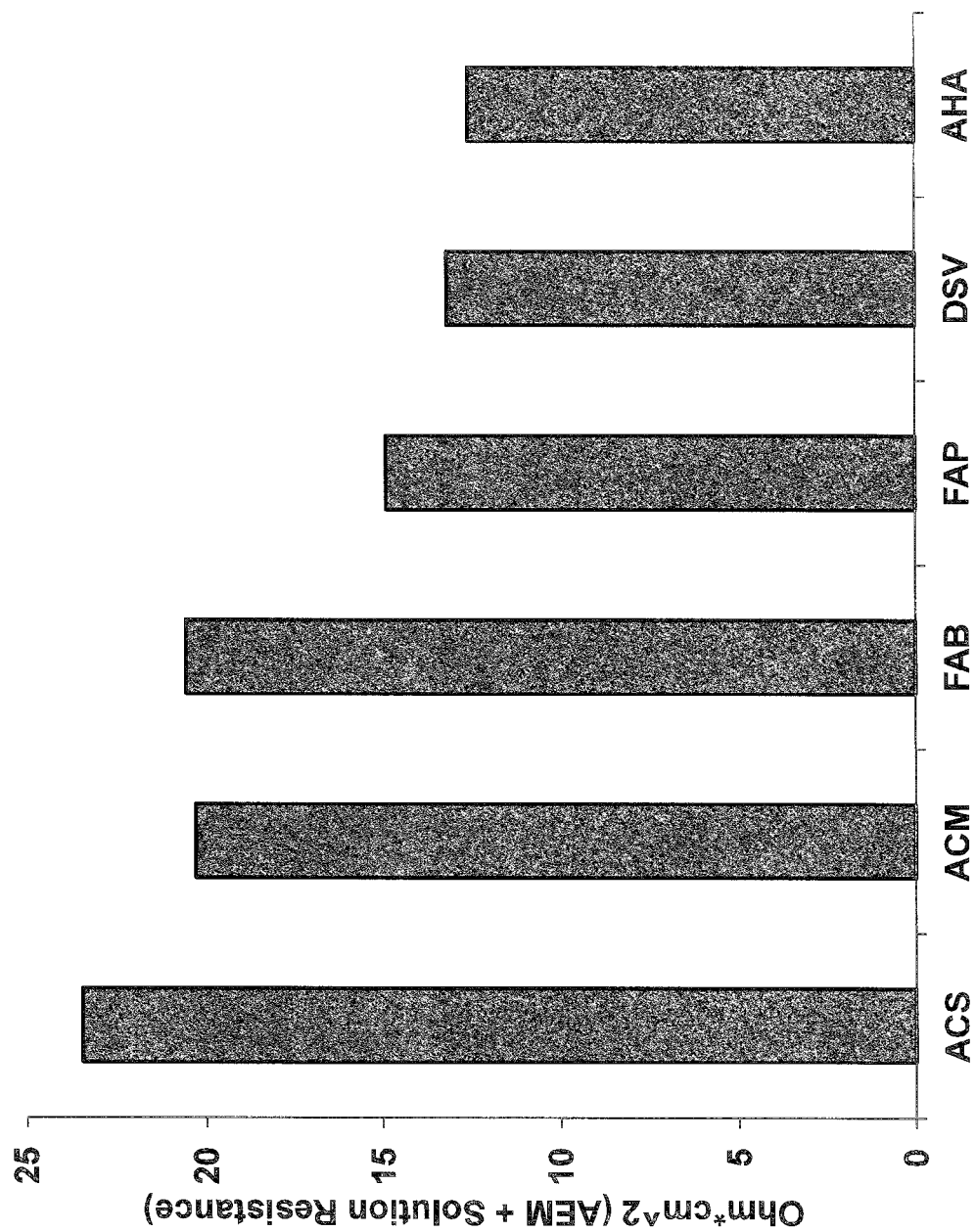
FIG. 23 illustrates a summary of direct current resistance measurements of anion exchange membranes, as described in Example 9.

A series of anion exchange membranes were tested in this experiment including ACS, ACM and AHA from Astom Corporation, FAB and FAP from FuMaTech, and DSV from Asahi Glass. The AEM was sandwiched in between an anolyte containing 3M $CuCl_2$/1M CuCl/4.6M NaCl and a chamber containing 4.6M NaCl electrolyte. A standard three-electrode setup was used including a platinum gauze working/counter electrode and saturated calomel electrode (SCE) reference. An additional two SCE's were placed in a luggin capillary on either side of the membrane. Small current steps of 1, 2, 4, 5, 7.5, 10, and 11 $mA/cm^2$ were applied and a multimeter was used to monitor the change in potential between the two SCEs. The slope of the current density vs voltage change equals the through plane area resistance. The results are illustrated in FIG. 23. The resistance values in FIG. 23 include the AEM and solution resistance. ACS, ACM, and FAB showed the highest resistance. It is contemplated that these AEMs have been designed for enhanced proton blocking and require a highly acidic medium for proper function. FAP, DSV, and AHA had a reduction of over 5 $\Omega cm^2$. FAP and DSV showed significant signs of permeation of Cu-base species. AHA was found to be most effective against crossover and was found to have least resistance.

Impedance Spectroscopy Method

In this experiment, a two Pt-foil electrode setup was used. The AHA membrane was sandwiched in between a saturated brine solution and the Cu-base electrolyte. The frequency range was between 15,000 Hz-0.001 Hz at an amplitude of 20 mA and a DC signal of 150 $mA/cm^2$. The cell was run with and without the AHA and the difference in high frequency x-intercepts represented the AEM area resistance.

The AHA resistance in three different Cu-base electrolytes is summarized in Table III. Solution A is: 4.6M NaCl: solution B is: 0.5M CuCl/2.5M NaCl; solution C is: 4.5M $CuCl_2$/0.5M CuCl/2.5M NaCl; and solution D is: 4.5M $CuCl_2$/0.5M CuCl.

TABLE III

Summary of results for resistance measurements of AHA in different Cu-base solutions

| Chemistry | Ωcm² solution | Ωcm² AHA + solution | Ωcm² AHA | V loss @ 150 mA/cm² |
|---|---|---|---|---|
| A-membrane-A | 1.28 | 3.14 | 1.86 | 0.28 |
| A-membrane-B | 1.28/1.77 | 3.58 | 1.81-2.06 | 0.272-0.308 |
| A-membrane-C | 1.28/2.8 | 4.96 | 2.16-2.92 | 0.324-0.438 |
| A-membrane-D | 1.28/3.14 | 7.51 | 4.37-5.3 | 0.656-0.795 |

It was observed that solution B with no $CuCl_2$ had a resistance similar to plain NaCl with no added CuClx. Solution C showed a voltage loss between 320-430 mV. Adding $CuCl_2$ into the anolyte produced a small increase in resistance. It is contemplated that this could be due to the change in solution resistance through the AEM. Solution D, which is equivalent to solution C with no NaCl, showed over a 2-fold increase in voltage loss. It is contemplated that there may be a change in copper speciation leading to an increase in resistance.

Permeability or Crossover of Cu-Chloride Complexes

Figure 24:
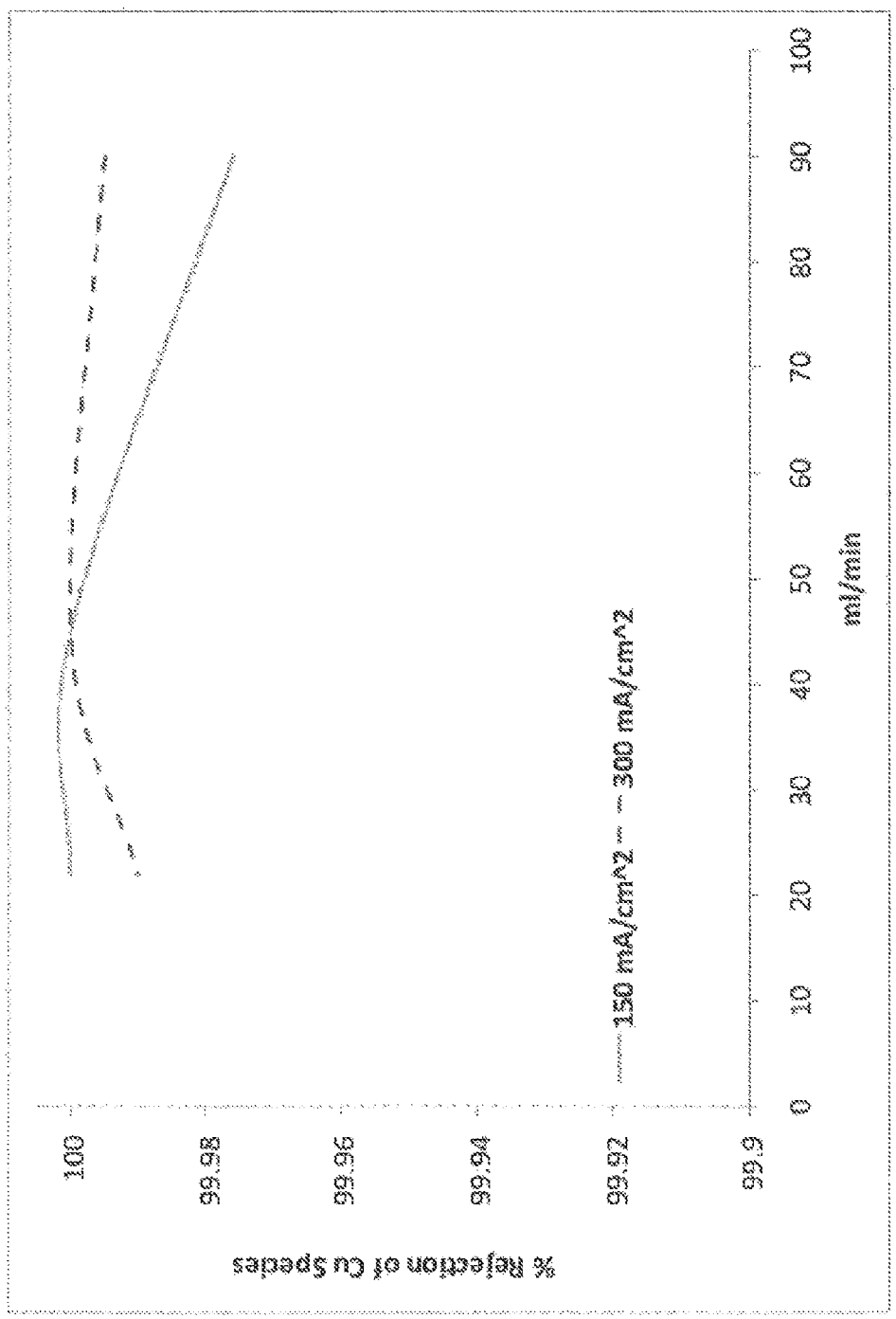
FIG. 24 illustrates rejection of copper ion crossover from anion exchange membranes, as described in Example 9.

A full cell configuration was used to measure the Cu-species transport through the AEM. A solution of 4.5M $CuCl_2$/0.5M CuCl/2.5M NaCl was fed into the anolyte, 4.6M NaCl was fed into the intermediate compartment, and 10 wt % NaOH was fed into the catholyte at 70° C. The cell was operated at 150 mA/cm² and 300 mA/cm² at a series of flow rates. For each flow rate (such as 20 ml/min, 40 ml/min, etc.) the copper ion concentration was measured pre testing and after running the cell for 30 min. UV-VIS was used to measure the total Cu in the brine solution in the intermediate compartment, pre and post testing. This value was then compared to the number of faradaic moles passed to obtain a percent rejection. The results are summarized in FIG. 24. As illustrated in FIG. 24, the AHA membrane provided >99%+/−0.01% rejection of all Cu-species in all cases.

Example 10

Use of a Ligand

To a 4 mL screw cap glass vial, containing a stir bar, was added 49 mg of CuCl (0.5 mmol). To this solution, the ligand together with 100 µl water was added and the reaction mixture was allowed to react for 2-3 hours at room temperature. Next a 2 mL aqueous stock solution of 6M $CuCl_2$ and 1M NaCl, which was heated for complete dissolution, was added. The vial was capped with a pre-slit septa made out of TEF and silicone. The vial was placed in a clam shell pressure reactor on top of a stirring hot plate. The atmosphere inside the reactor was exchanged to $N_2$. The stirring was started at 620 rpm and the reactor was heated to 140° C. After reaching temperature, the reactor with multiple vials inside was pressurized to 350 psi total pressure. After 1 hour, the reactor was cooled to below 30° C. and slowly vented. The reaction mixture was extracted with 1 mL of ethyl acetate. The organic phase was analyzed by GC (gas chromatography) for ethylene dichloride and chloroethanol (ClEtOH) content. FIG. 25A and Table IV illustrate the specific ligand, the amount of the ligand, the reaction conditions, and the amount of main products formed. A comparative example without ligand is included as well. FIG. 25B illustrates other examples of the ligands that can be used in the catalytic reaction. Table IV demonstrates that the ligand not only improves the yield of EDC in the reaction but also improves the selectivity.

TABLE IV

| Ligand # | Ligand amount in mmol | EDC by GC in mg/ml | ClEtOH by GC in mg/ml | Selectivity |
|---|---|---|---|---|
| no ligand | N/A | 10.20 | 1.53 | 0.87 |
| 2 | 0.5 | 6.89 | 1.33 | 0.84 |
| 2 | 2 | 3.87 | 1.15 | 0.77 |
| 3 | 0.5 | 8.20 | 1.48 | 0.85 |
| 3 | 2 | 11.56 | 1.73 | 0.87 |
| 4 | 0.5 | 7.84 | 1.38 | 0.85 |
| 4 | 2 | 1.75 | 0.46 | 0.79 |
| 5 | 0.5 | 7.75 | 1.36 | 0.85 |
| 5 | 2 | 2.11 | 0.70 | 0.75 |
| 6 | 0.5 | 15.49 | 1.78 | 0.90 |
| 6 | 2 | 16.29 | 1.98 | 0.89 |
| 7 | 0.5 | 13.42 | 1.44 | 0.90 |
| 8 | 0.5 | 6.88 | 0.97 | 0.88 |
| 10 | 0.5 | 10.14 | 1.66 | 0.86 |
| 10 | 2 | 15.96 | 1.59 | 0.91 |
| 11 | 0.5 | 11.10 | 1.93 | 0.85 |
| 11 | 2 | 12.22 | 2.01 | 0.86 |
| 12 | 0.5 | 9.75 | 1.50 | 0.87 |
| 12 | 2 | 1.06 | 0.45 | 0.70 |

Example 11

Oxidation of Iron Metal in Electrochemical Cell

Figure 26:
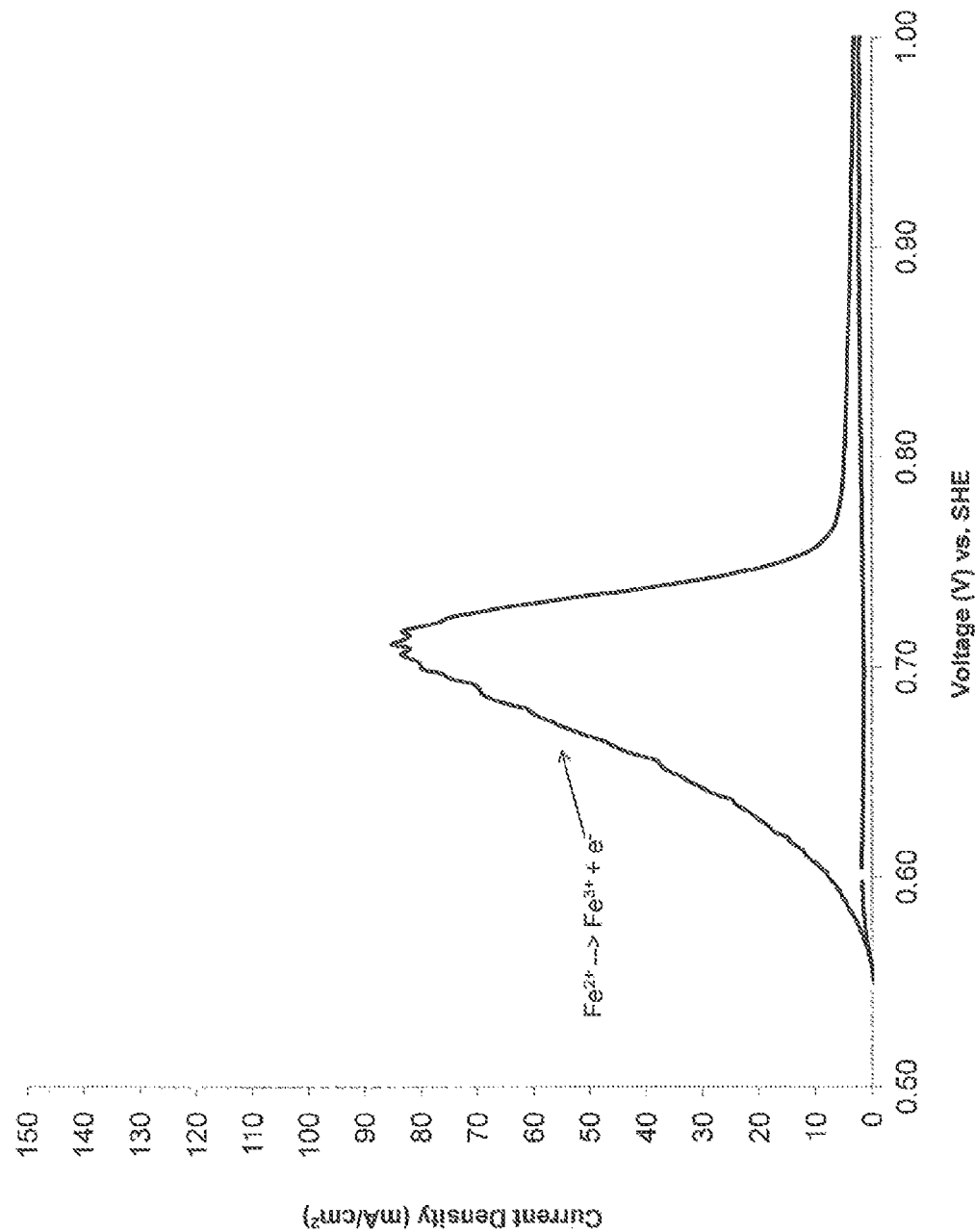
FIG. 26 is an illustrative graph as described in Example 11 herein.

A half cell reaction was carried out using the iron solution with a setup shown in Example 1. The working electrode for the half cell reaction was 6 cm² PtIr 152-mesh gauze; the counter electrode was 8 cm² Pt foil; and the reference electrode was standard hydrogen electrode (SHE) Ag/AgCl. The solution in the beaker was kept at 70° C. In the experiment, a solution contained 1M $FeCl_2$ and 2.5M NaCl. As illustrated in FIG. 26, oxidation of $Fe^{2+}$ to $Fe^{3+}$ at the anode was observed at voltage scan rate of 5 mV/s.

Example 12

Electrolytes in Electrochemical Cell

Figure 27:
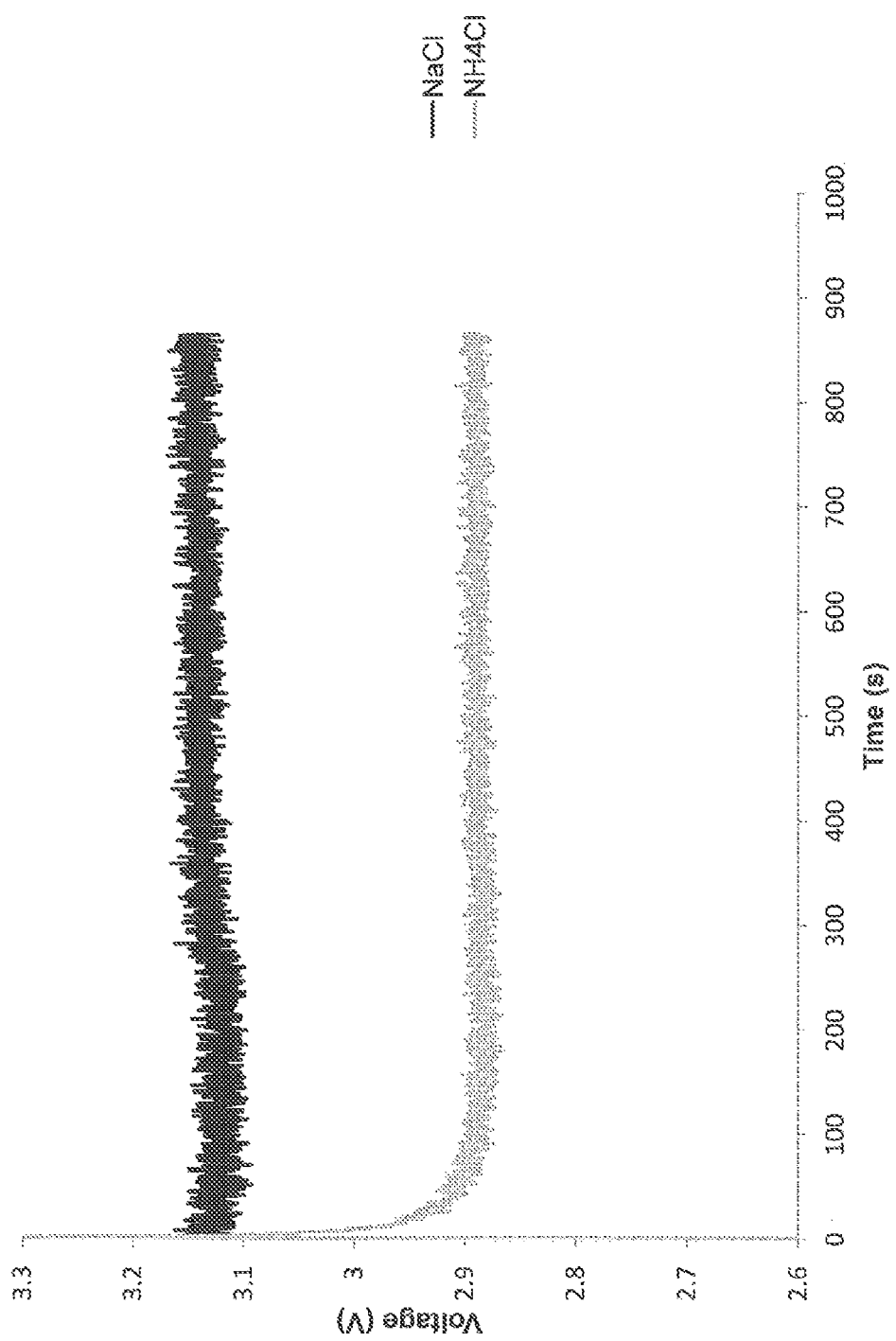
FIG. 27 is an illustrative graph as described in Example 12 herein.

A full cell reaction was carried out using sodium chloride and ammonium chloride as electrolytes. The components of the cell were commercially available and included Pt guaze anode; PGM mesh cathode; anion exchange membrane as AHA from Neosepta; and the cation exchange membrane as Dupont N2100. The catholyte was 10 wt % NaOH. In 1st experiment, the anolyte was 4.5M $CuCl_2$/0.5M CuCl/2.5M NaCl and in the 2nd experiment, the anolyte was 4.5M $CuCl_2$/0.5M CuCl/2.5M $NH_4Cl$. The solution in the cell was kept at 70° C. FIG. 27 illustrates that although both sodium chloride and ammonium chloride electrolytes work well in the electrochemical cell, the $NH_4Cl$ anolyte lowered the operating cell voltage by 200-250 mV at 300 mA/cm². It is contemplated that it may be due to the increased conductivity of the anolyte which resulted in a lower resistance across the AEM.

Example 13

AEM Conditioning at the Start-up of the Electrochemical Cell

Figure 28:
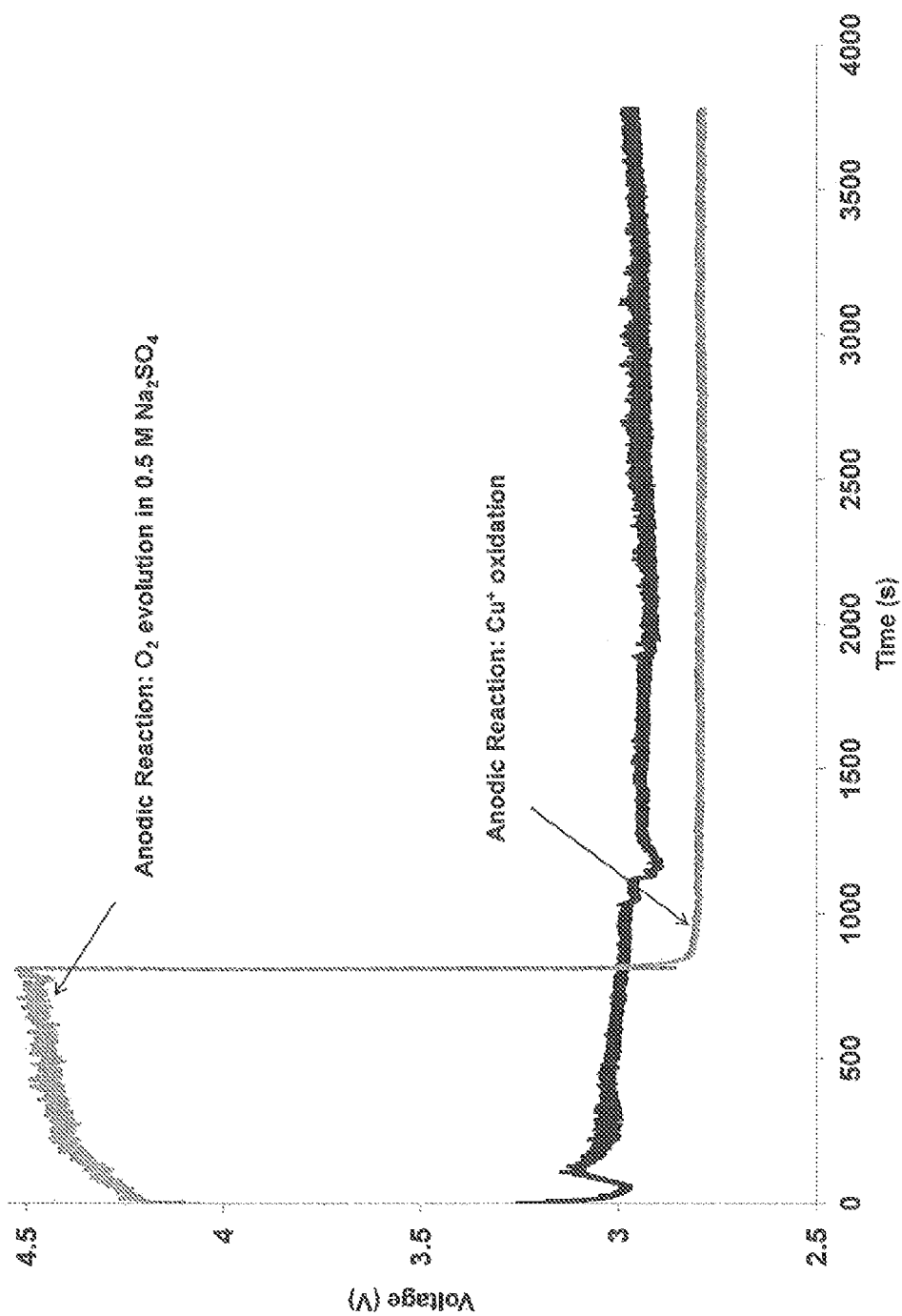
FIG. 28 is an illustrative graph as described in Example 13 herein.

This experiment was related to the conditioning of the AEM before the start of the electrochemical cell. Initial solutions introduced into the full cell were 0.5M $Na_2SO_4$ as the anolyte, 4.6M NaCl into the intermediate compartment, and 10 wt % NaOH as the catholyte. The membranes were FAS from FuMaTech as the anion exchange membrane and N2100 from Dupont as the cation exchange membrane. The cell was then run at 300 mA/cm². At this point, the anodic reaction was oxygen evolution and the cathodic reaction was water reduction. As illustrated in FIG. 28, the initial overall cell voltage of about 4.5V was seen. Once the voltage was stabilized, a valve was switched and the $Na_2SO_4$ was flushed out of the cell and the anolyte (4.5M $CuCl_2$/0.5M CuCl/2.5M NaCl) was then fed into the anode chamber. The cell was constantly held at 300 mA/cm² during this time. The anodic reaction now was copper oxidation, as illustrated in FIG. 28 as the sudden drop in cell voltage. The black curve shows the voltage when the copper electrolyte was introduced into the cell (with no initial voltage stabilization by sodium sulfate) before a voltage was applied. There was about a 200 mV voltage savings when $Na_2SO_4$ was used at the start-up and the voltage was significantly more stable for the duration of the test. The conditioning of the AEM at the operating current density prior to introducing the copper-base electrolyte may be beneficial for voltage and stability.

Example 14

Re-circulation of Aqueous Phase from Catalytic Reactor to Electrochemical System This example illustrates the re-circulation of the Cu(I) solution generated by a catalysis reactor to the electrochemical cell containing a PtIr gauze electrode. A solution containing 4.5M Cu(II), 0.1M Cu(I), and 1.0M NaCl was charged to the Parr bomb reactor for a 60 min. reaction at 160° C. and 330 psi. The same solution was tested via anodic cyclic voltammetry (CV) before and after the catalysis run to look for effects of organic residues such as EDC or residual extractant on anode performance. Each CV experiment was conducted at 70° C. with 10 mVs⁻¹ scan rate for five cycles, 0.3 to 0.8V vs. saturated calomel electrode (SCE).

Figure 29:
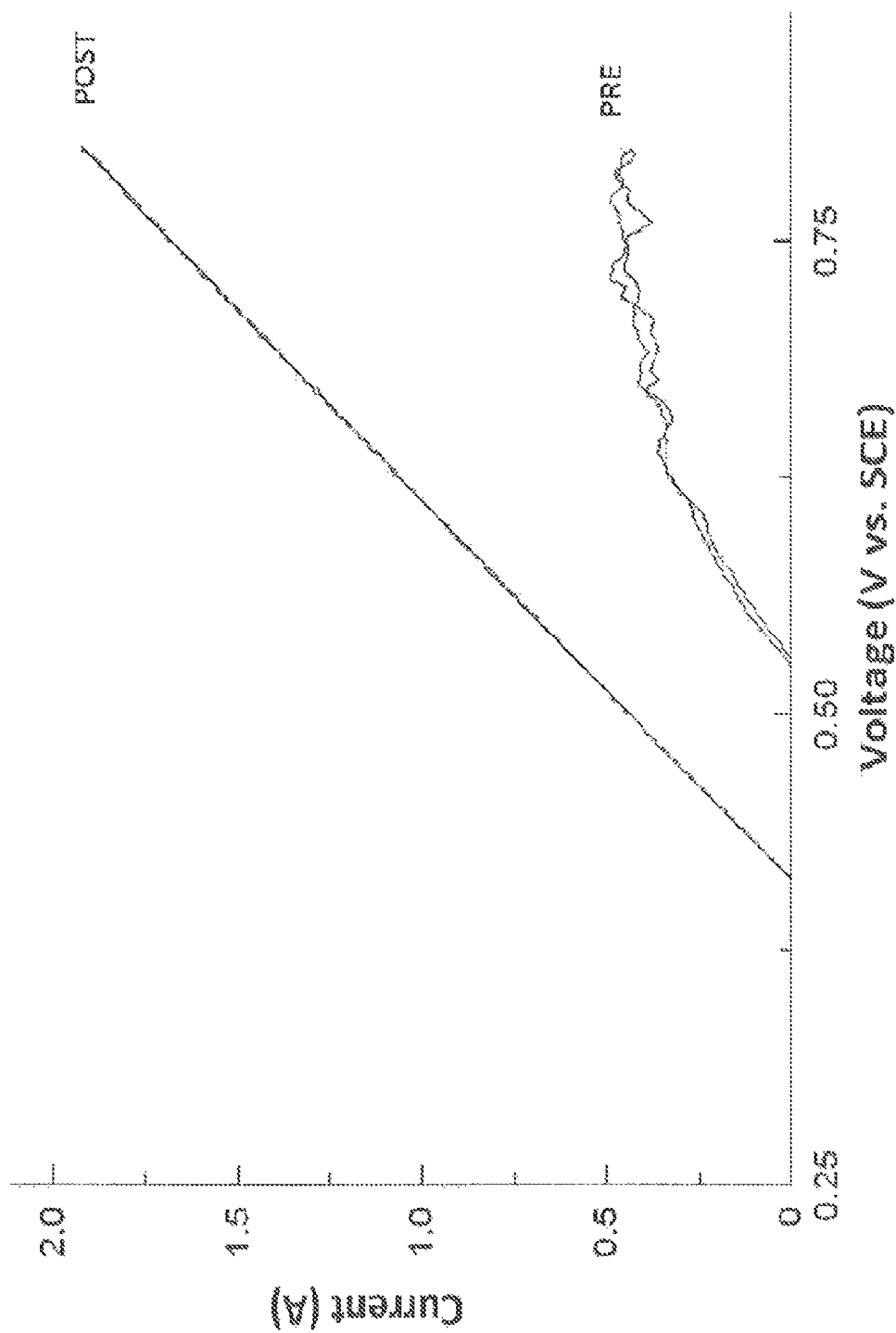
FIG. 29 is an illustrative graph as described in Example 14 herein.

FIG. 29 illustrates the resulting V/I response of a PtIr gauze electrode (6 cm²) in solutions before and after catalysis (labeled pre and post, respectively). As illustrated in FIG. 29, redox potential (voltage at zero current) shifted to lower voltages post-catalysis as expected from the Nernst equation for an increase in Cu(I) concentration. The increase in the Cu(I) concentration was due to EDC production with Cu(I) regeneration during a catalysis reaction. The pre-catalysis CV curve reached a limiting current near 0.5 A due to mass transfer limitations at low Cu(I) concentration. The Cu(I) generation during the catalysis run was signified by a marked improvement in kinetic behavior post-catalysis, illustrated in FIG. 29 as a steeper and linear I/V slope with no limiting current reached. No negative effects of residual EDC or other organics were apparent as indicated by the typical reversible I/V curve obtained in the post-catalysis CV.

Example 15

Re-circulation of Aqueous Phase from Catalytic Reactor Containing Ligand

This example illustrates the re-circulation of the Cu(I) solution containing the ligand from the catalysis reactor to the electrochemical cell. A 2 mL sample of the catalyst solution tested in the catalysis high throughput reactor was sent to a three-electrode micro-cell for electrochemical screening via anodic cyclic voltammetry (CV) to determine if a correlation existed between redox potential and catalysis performance. The ligands were:

Ligand #1=

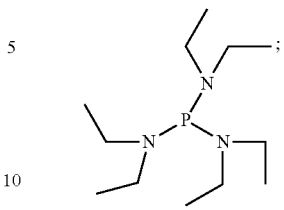

and Ligand #2=

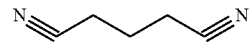

The catalyst solution contained 5.0M Cu(II)/0.5M Cu(I)/ 0.5M or 1M ligand/1M NaCl. These ligand solutions were tested in the anodic micro-half-cell via cyclic voltammetry to measure redox potential. The micro-cell consisted of a PtIr foil working electrode, Pt foil counter electrode, and a capillary bridge to a Ag/AgCl microelectrode as reference. All electrodes were sealed into a 4 mL vial, heated to 70° C. and stirred at 100 rpm. Each CV experiment was conducted at 70° C. with 10 mV s⁻¹ scan rate for five cycles, 0.3 to 0.8 V vs. Ag/AgCl reference electrode.

Table V below shows the voltages obtained for five catalytic re-circulated solutions. The results indicated that ligand enhanced the EDC production and the re-circulated catalytic solution containing the ligand to the electrochemical cell, reduced the electrochemical voltage. Table V shows that the redox potential of samples containing ligand #1 (samples A and B) had a reduced redox potential compared to the equivalent ligand free system E. Samples C and D that contained the ligand #2 had a similar redox potential compared to the ligand free sample E.

TABLE V

| Sample | Ligand # | Concentration | CV |
| --- | --- | --- | --- |
| A | 1 | 0.5 | 0.684 |
| B | 1 | 1 | 0.676 |
| C | 2 | 1 | 0.739 |
| D | 2 | 0.5 | 0.737 |
| E | No ligand | N/A | 0.728 |

What is claimed is:

1. A method comprising:

contacting an anode with an anode electrolyte in an electrochemical cell wherein the anode electrolyte comprises metal halide or metal sulfate;

adding a ligand to the anode electrolyte;

applying a voltage to the anode and cathode and oxidizing the metal halide or the metal sulfate from a lower oxidation state to a higher oxidation state at the anode;

contacting the cathode with a cathode electrolyte in the electrochemical cell; and reacting an unsaturated hydrocarbon or a saturated hydrocarbon with the anode electrolyte comprising the metal halide or the metal sulfate in the higher oxidation state and the ligand wherein the ligand is of formula A:

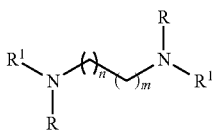

A wherein n and m independently are 0-2 and R and $R^1$ independently are H, alkyl, or substituted alkyl to form halohydrocarbon or sulfohydrocarbon and the metal halide or the metal sulfate in the lower oxidation state.

2. The method of claim 1, further comprising forming an alkali, water, or hydrogen gas at the cathode.

3. The method of claim 1, wherein the cathode electrolyte comprises water and the cathode is an oxygen depolarizing cathode that reduces oxygen and water to hydroxide ions; the cathode electrolyte comprises water and the cathode is a hydrogen gas producing cathode that reduces water to hydrogen gas and hydroxide ions; the cathode electrolyte comprises hydrochloric acid and the cathode is a hydrogen gas producing cathode that reduces hydrochloric acid to hydrogen gas; or the cathode electrolyte comprises hydrochloric acid and the cathode is an oxygen depolarizing cathode that reacts hydrochloric acid and oxygen gas to form water.

4. The method of claim 1, wherein the metal ion of the metal halide or the metal sulfate is selected from the group consisting of iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combination thereof.

5. The method of claim 1, wherein the metal ion of the metal halide or the metal sulfate is selected from the group consisting of iron, chromium, copper, and tin.

6. The method of claim 1, wherein the metal ion of the metal halide or the metal sulfate is copper.

7. The method of claim 1, wherein the lower oxidation state of the metal ion of the metal halide or the metal sulfate is 1+, 2+, 3+, 4+, or 5+.

8. The method of claim 1, wherein the higher oxidation state of the metal ion of the metal halide or the metal sulfate is 2+, 3+, 4+, 5+, or 6+.

9. The method of claim 1, wherein the metal ion of the metal halide or the metal sulfate is copper that is converted from $Cu^+$ to $Cu^{2+}$, the metal ion of the metal halide or the metal sulfate is iron that is converted from $Fe^{2+}$ to $Fe^{3+}$, the metal ion of the metal halide or the metal sulfate is tin that is converted from $Sn^{2+}$ to $Sn^{4+}$, the metal ion of the metal halide or the metal sulfate is chromium that is converted from $Cr^{2+}$ to $Cr^{3+}$, the metal ion of the metal halide or the metal sulfate is platinum that is converted from $Pt^{2+}$ to $Pt^{4+}$, or combination thereof.

10. The method of claim 1, wherein no gas is used or formed at the anode.

11. The method of claim 1, wherein the metal halide or the metal sulfate in the lower oxidation state is re-circulated back to the anode electrolyte.

12. The method of claim 1, wherein the anode electrolyte comprising the metal halide or the metal sulfate in the higher oxidation state further comprises the metal halide or the metal sulfate in the lower oxidation state.

13. The method of claim 1, wherein the unsaturated hydrocarbon is ethylene, propylene, or butylene resulting in ethylene dichloride, propylene dichloride or 1,4-dichlorobutane, respectively.

14. The method of claim 13, further comprising forming vinyl chloride monomer from the ethylene dichloride and forming poly(vinyl chloride) from the vinyl chloride monomer.

15. The method of claim 1, wherein the ligand results in one or more of the properties selected from enhanced reactivity of metal ion of the metal halide or the metal sulfate towards the unsaturated hydrocarbon or the saturated hydrocarbon, enhanced selectivity of metal ion of the metal halide or the metal sulfate towards halogenations of the unsaturated or the saturated hydrocarbon, enhanced transfer of halogen from metal ion of the metal halide or the metal sulfate to the unsaturated hydrocarbon or the saturated hydrocarbon, reduced redox potential of the electrochemical cell, enhanced solubility of metal ion of the metal halide or the metal sulfate in aqueous medium, reduced membrane cross-over of metal ion of the metal halide or the metal sulfate to the cathode electrolyte in the electrochemical cell, reduced corrosion of the electrochemical cell, enhanced separation of metal ion of the metal halide or the metal sulfate from halogenated hydrocarbon solution, and combination thereof.

16. The method of claim 1, wherein the substituted alkyl is alkyl substituted with one or more of a group selected from alkenyl, halogen, amine, and substituted amine.

17. The method of claim 1, wherein concentration of the metal ion of the metal halide or the metal sulfate in the higher oxidation state is between 4.5-7M, concentration of the metal ion of the metal halide or the metal sulfate in the lower oxidation state is between 0.25-1.5M, and concentration of the ligand is between 0.25-6M.

18. The method of claim 17, wherein the anode electrolyte is sodium chloride.

19. The method of claim 18, wherein concentration of the sodium chloride is between 1-3M.

20. The method of claim 1, wherein the saturated hydrocarbon is methane, ethane, or propane.

21. The method of claim 1, wherein the unsaturated hydrocarbon is ethylene and the metal halide is metal chloride.

22. The method of claim 21, wherein the metal chloride is copper chloride.

23. The method of claim 22, wherein the ethylene reacts with the copper chloride in the higher oxidation state and the ligand to form the halohydrocarbon comprising ethylene dichloride.

24. The method of claim 1, wherein the halohydrocarbon comprises ethylene dichloride, chloroethanol, chloral, chloral hydrate, 1,1-dichloroethene, trichloroethylene, tetrachloroethene, 1,1,2,2-tetrachloroethane, or combinations thereof.

25. The method of claim 1, wherein the reaction is in an aqueous medium wherein the aqueous medium comprises more than 5 wt% water.

26. The method of claim 1, wherein the unsaturated hydrocarbon is a C2-C10 alkene or the saturated hydrocarbon is C2-C10 alkane.

* * * * *